United States Patent
Kovalevski-Ishai et al.

(10) Patent No.: US 9,206,206 B2
(45) Date of Patent: Dec. 8, 2015

(54) OXIDIZED LIPID COMPOUNDS AND USES THEREOF

(75) Inventors: Eti Kovalevski-Ishai, Netania (IL); Zeev Ziniuk, Rechovot (IL); Gideon Halperin, Har-Adar (IL); Itzhak Mendel, Rechovot (IL); Erez Feige, Hemed (IL); Niva Yacov, Tel-Aviv (IL); Eyal Breitbart, Hashmoniam (IL)

(73) Assignee: Vascular Biogenics Ltd., Or Yehuda (IL)

(*) Notice: Subject to any disclaimer, the term of this patent is extended or adjusted under 35 U.S.C. 154(b) by 209 days.

(21) Appl. No.: 13/127,717

(22) PCT Filed: Nov. 5, 2009

(86) PCT No.: PCT/IL2009/001049
§ 371 (c)(1),
(2), (4) Date: May 5, 2011

(87) PCT Pub. No.: WO2010/052718
PCT Pub. Date: May 14, 2010

(65) Prior Publication Data
US 2011/0207703 A1    Aug. 25, 2011

Related U.S. Application Data

(60) Provisional application No. 61/193,220, filed on Nov. 6, 2008.

(51) Int. Cl.
| C07C 59/125 | (2006.01) |
| C07C 59/10 | (2006.01) |
| A61K 31/685 | (2006.01) |
| A61K 31/683 | (2006.01) |
| A61K 31/66 | (2006.01) |
| C07F 9/09 | (2006.01) |
| C07F 9/10 | (2006.01) |

(52) U.S. Cl.
CPC ............. *C07F 9/091* (2013.01); *C07C 59/125* (2013.01); *C07F 9/106* (2013.01)

(58) Field of Classification Search
CPC ....... C07F 9/106; C07F 9/091; C07C 59/125; C07C 59/10; A61K 31/685; A61K 31/683; A61K 31/66
See application file for complete search history.

(56) References Cited

U.S. PATENT DOCUMENTS

| 4,329,302 A | 5/1982 | Hanahan et al. |
| 4,450,877 A | 5/1984 | Walker et al. |
| 4,543,258 A | 9/1985 | Urata et al. |
| 4,614,796 A | 9/1986 | Kawamata et al. |
| 4,622,180 A | 11/1986 | Paltauf et al. |
| 4,778,912 A | 10/1988 | Inoue et al. |
| 4,827,011 A | 5/1989 | Wissner et al. |
| 4,970,233 A | 11/1990 | McHugh |
| 4,978,670 A | 12/1990 | Rector et al. |
| 5,061,626 A | 10/1991 | Baldo et al. |
| 5,091,527 A | 2/1992 | Junius et al. |
| 5,561,052 A | 10/1996 | Koike |
| 5,660,855 A | 8/1997 | Malé-Brune |
| 5,962,437 A | 10/1999 | Kucera et al. |
| 5,985,292 A | 11/1999 | Fourneron et al. |
| 6,017,513 A | 1/2000 | Betbeder et al. |
| 6,261,597 B1 | 7/2001 | Kurtz |
| 6,348,583 B1 | 2/2002 | Segev |
| 6,414,168 B1 | 7/2002 | Crivello et al. |
| 6,838,452 B2 * | 1/2005 | Harats et al. ............... 514/114 |
| 7,186,704 B2 | 3/2007 | Harats et al. |
| 7,504,388 B2 | 3/2009 | Harats et al. |
| 7,625,882 B2 * | 12/2009 | Harats et al. ............... 514/114 |
| 7,807,847 B2 * | 10/2010 | Halperin et al. ............... 554/78 |
| 7,893,291 B2 | 2/2011 | Harats et al. |
| 7,902,176 B2 * | 3/2011 | Harats et al. ............... 514/114 |
| 7,973,023 B2 | 7/2011 | Harats et al. |
| 8,124,800 B2 | 2/2012 | Halperin et al. |
| 8,158,611 B2 | 4/2012 | Harats et al. |
| 8,501,715 B2 | 8/2013 | Harats et al. |
| 8,563,534 B2 | 10/2013 | Harats et al. |
| 8,569,529 B2 | 10/2013 | Halperin et al. |
| 2003/0225035 A1 | 12/2003 | Harats et al. |
| 2006/0194765 A1 | 8/2006 | Garcia et al. |
| 2007/0020691 A1 | 1/2007 | Kanter et al. |
| 2007/0099868 A1 | 5/2007 | Harats et al. |
| 2007/0112211 A1 | 5/2007 | Halperin et al. |
| 2007/0264206 A1 | 11/2007 | Boga et al. |
| 2008/0261865 A1 | 10/2008 | Harats et al. |
| 2009/0074720 A1 | 3/2009 | Sabbadini |
| 2009/0149541 A1 | 6/2009 | Stark et al. |

(Continued)

FOREIGN PATENT DOCUMENTS

| AU | 2004243695 A1 | 12/2004 |
| CA | 1102354 | 6/1981 |

(Continued)

OTHER PUBLICATIONS

RN935656-59-0, 2007.*
Halperin et al., caplus an 2008:857961 (2008).*
TyrosineKinase, 2015, https://en.wikipedia.org/wiki/Tyrosine_kinase.*
Supplementary European Search Report and the European Search Opinion Dated Mar. 9, 2012 From the European Patent Office Re. Application No. 09824498.1.
International Preliminary Report on Patentability Dated Apr. 21, 2011 From the International Bureau of WIPO Re. Application No. PCT/2009/000949.

(Continued)

*Primary Examiner* — Sun Jae Yoo
(74) *Attorney, Agent, or Firm* — Sterne, Kessler, Goldstein & Fox P.L.L.C.

(57) ABSTRACT

Novel oxidized lipids are provided herein, as well as methods for producing same, and uses thereof in treating or preventing an inflammation associated with endogenous oxidized lipids and related conditions.

28 Claims, 27 Drawing Sheets
(8 of 27 Drawing Sheet(s) Filed in Color)

(56) References Cited

U.S. PATENT DOCUMENTS

| | | |
|---|---|---|
| 2009/0197242 A1 | 8/2009 | Kaddurah-Daouk et al. |
| 2011/0189212 A1 | 8/2011 | Harats et al. |
| 2011/0195937 A1 | 8/2011 | Breitbar et al. |
| 2011/0207703 A1 | 8/2011 | Kovalevski-Ishai et al. |
| 2012/0130108 A1 | 5/2012 | Halperin et al. |
| 2012/0329757 A1 | 12/2012 | Harats et al. |
| 2012/0329758 A1 | 12/2012 | Cohen et al. |
| 2013/0079540 A1 | 3/2013 | Halperin et al. |
| 2013/0158283 A1 | 6/2013 | Halperin et al. |
| 2013/0172294 A1 | 7/2013 | Cohen et al. |
| 2013/0190523 A1 | 7/2013 | Halperin et al. |
| 2013/0203707 A1 | 8/2013 | Kovalevski-Ishai et al. |
| 2013/0209555 A1 | 8/2013 | Sher et al. |
| 2013/0225525 A1 | 8/2013 | Cohen et al. |
| 2013/0237720 A1 | 9/2013 | Halperin et al. |

FOREIGN PATENT DOCUMENTS

| | | |
|---|---|---|
| CH | 642 665 A5 | 4/1984 |
| EP | 0 121 088 A1 | 10/1984 |
| EP | 0 142 333 A | 5/1985 |
| EP | 0 184 905 A1 | 6/1986 |
| EP | 0 225 129 A1 | 6/1987 |
| EP | 0 331 167 A2 | 9/1989 |
| ES | 2 019 552 A6 | 6/1991 |
| GB | 2 130 206 A | 5/1984 |
| JP | 50004040 A | 1/1975 |
| JP | 54-41807 | 4/1979 |
| JP | 59-93022 | 5/1984 |
| JP | 59-175445 | 10/1984 |
| JP | 60-104066 A | 6/1985 |
| JP | 62-228088 | 11/1986 |
| JP | 62-000094 A | 1/1987 |
| JP | 62-030714 A | 2/1987 |
| JP | 63-054386 A | 3/1988 |
| JP | 63-135395 A | 6/1988 |
| JP | 01-258691 A | 10/1989 |
| JP | 02-006493 | 1/1990 |
| JP | 02-048585 A | 2/1990 |
| JP | 03-258740 | 11/1991 |
| JP | 04-021691 | 1/1992 |
| JP | 05-339387 | 12/1993 |
| JP | 07-258261 A | 10/1995 |
| JP | 08-059545 | 3/1996 |
| JP | 08-208548 | 8/1996 |
| JP | 11-116563 A | 4/1999 |
| JP | 2003-515550 A | 5/2003 |
| JP | 2004-537498 A | 12/2004 |
| JP | 2005-505499 | 2/2005 |
| JP | 2005-507952 A | 3/2005 |
| JP | 2008-037763 | 2/2008 |
| JP | 2008-037763 A | 2/2008 |
| SU | 1400511 A3 | 5/1988 |
| WO | WO 87/05904 A1 | 10/1987 |
| WO | WO 95/23592 | 9/1995 |
| WO | WO 01/39744 A2 | 6/2001 |
| WO | WO 01/75168 A1 | 10/2001 |
| WO | WO 02/41827 A2 | 5/2002 |
| WO | WO 02/087465 A2 | 11/2002 |
| WO | WO 03/040073 A1 | 5/2003 |
| WO | WO 2004/106486 | 12/2004 |
| WO | WO 2004/106486 A2 | 12/2004 |
| WO | WO 2006/006161 | 1/2006 |
| WO | WO 2006/006161 A2 | 1/2006 |
| WO | WO 2008/084472 A2 | 7/2008 |
| WO | WO 2010/041242 | 4/2010 |
| WO | WO 2010/041242 A2 | 4/2010 |
| WO | WO 2010/052718 | 5/2010 |
| WO | WO 2010/052718 A1 | 5/2010 |
| WO | WO 2011/083464 A | 7/2011 |
| WO | WO 2011/083465 A1 | 7/2011 |
| WO | WO 2011/083466 A1 | 7/2011 |
| WO | WO 2011/083467 A1 | 7/2011 |
| WO | WO 2011/083469 A1 | 7/2011 |
| WO | WO 2013/033642 A1 | 3/2013 |

OTHER PUBLICATIONS

International Search Report and the Written Opinion Dated Apr. 12, 2010 From the International Searching Authority Re. Application No. PCT/09/00949.

International Search Report and the Written Opinion Dated Mar. 24, 2010 From the International Searching Authority Re.: Application No. PCT/09/01049.

Bochkov "Inflammatory Profile of Oxidized Phospholipids", Journal of Thrombosis and Hacmastosis, 97: 348-354, Feb. 8, 2007.

Chen et al. "Polyunsaturated Phospholipids Promote the Oxidation and Fragmentation of γ-Hydroxyalkenals: Formation and Reactions of Oxidatively Truncated Ether Phospholipids", Journal of Lipid Research, 49: 832-846, Dec. 29, 2007.

Davies et al. "Oxidized Alkyl Phospholipids Are Specific, High Affinity Peroxisome Proliferator-Activated Receptor γ Ligands and Antagonists", The Journal of Biological Chemisry, 276(19): 16015-16023, May 11, 2001.

International Preliminary Report on Patentability Dated May 19, 2011 From the International Bureau of WIPO Re. Application No. PCT/09/01049.

Invitation Pursuant to Rule 63(1) EPC Dated Feb. 3, 2012 From the European Patent Office Re. Application No. 09818874.1.

Examination Report Dated Nov. 21, 2011 From the Intellectual Property Office of New Zealand Re. Application No. 592357.

Berchtold, R., "Synthesis of Carboxyphospholipids," *Chem. Phys. Lipids* 18(1):55-60, Elsevier, Netherlands (1981).

Bochkov, V.N., "Inflammatory Profile of Oxidized Phospholipids," *Journal of Thrombosis and Haematosis*, 97:348-354, Schattauer GmbH, Germany (2007).

Boullier, A., et al., "The Binding of Oxidized Low Density Lipoprotein to Mouse CD36 Is Mediated in Part by Oxidized Phospholipids That Are Associated With Both the Lipid and Protein Moieties of the Lipoprotein," *Journal of Biological Chemistry*, 275(13):9163-9169, The American Society for Biochemistry and Molecular Biology, Inc., United States (2000).

Chen, X., et al., "Polyunsaturated Phospholipids Promote the Oxidation and Fragmentation of γ-Hydroxyalkenals: Formation and Reactions of Oxidatively Truncated Ehter Phospholipids," *Journal of Lipid Research*, 49:832-846, American Society for Biochemistry and Molecular Biology, United States (2008).

Cooney, S., et al., "Combining site specificities of rabbit antibodies to platelet-activating factor (PAF)," *Mol. Immunol.* 27(5):405-12, Pergamon Press, Great Britain (1990).

Davies, S., et al., "Oxidized Alkyl Phospholipids Are Specific, High Affinity Peroxisome Proliferator-Activated Receptor γ Ligands and Agonists," *Journal of Biological Chemistry* 276(19):16015-16023, The American Society for Biochemistry and Molecular Biology, Inc., United States (2001).

Deigner, H-P. and Dresel, H.A., "Effect of platelet activating factor on the kinetics of LDL oxidation in vitro," *FEBS Lett.* 317(3):202-6, Elsevier Science, Netherlands (1993).

George, J., et al., "Hyperimmunization of Apo-E-Deficient Mice with Homologous Malondialdehyde Low-Density Lipoprotein Suppresses early Atherogenesis," *Atherosclerosis* 138:147-152, Elsevier Science, Ireland (1998).

Hoff, H.F., et al., "Phospholipid Hydroxyalkenals: Biological and Chemical Properties of Specific Oxidized Lipids Present in Atherosclerotic Lesions," *Arterioscler. Thromb. Vasc. Biol.* 23:275-282, The American Heart Association, United States (2003).

Itabe, H., et al. "Oxidized Phosphatidylcholines That Modify Proteins," *Journal of Biological Chemistry* 271(52):33208-33217,The American Socitey for Biochemistry and Molecular Biology, United States (1996).

Itabe, H., et al., "Preparation of radioactive aldehyde-containing phosphatidylcholine," *Anal. Biochem.* 285(1):151-5, Academic Press, United States (2000).

(56) References Cited

OTHER PUBLICATIONS

Kamido, H., et al., "Lipid ester-bound aldehydes among copper-catalyzed peroxidation products of human plasma lipoproteins," *J. Lipid Res.* 36(9):1876-1886, American Society for Biochemistry and Molecular Biologu, United States (1995).

Karasawa, K., et al., "Antibodies to synthetic platelet-activating factor (1-0-alkyl-2-0-acetyl-sn-glycero-3-phosphocholine) analogues with substituents at the sn-2 position," *J. Biochem.* 110(5):683-7, Oxford University Press, England (1991).

Kern, H., "Stimulation of monocytes and platelets by short-chain phosphatidylcholines with and without terminal carboxyl group," *Biochim. Biophys. Acta* 1394(1):33-42, Elsevier, Netherlands (1998).

Leitinger, N., et al., "Structurally Similar Oxidized Phospholipids Differentially Regulate Endothelial Binding of Monocytes and Neutrophils," *Proc. Natl. Acad. Sci.* 96(2):12010-12015, National Academy of Sciences, United States (1999).

MacPherson, J.L., et al., "Production and characterization of antibodies to platelet-activating factor," *J. Lipid. Mediat.* 5(1)49-59, Elsevier Science Publishers, Netherlands (1992).

Mendel, I., et al., "A Lecinoxoid, an oxidized phospholipid small molecule, constrains CNS autoimmune disease," *J. Neuroimmunol.* 226:126-35, Elsevier B.V., Netherlands (2010).

Nitta, T., et al., "Phospholipase $A_2$ Activity of $Fc_{\gamma 2b}$ Receptors of Thioglycollate-Elicited Murine Peritoneal Macrophages," *J. Leuk. Biol.* 36(4):493-504, Wiley Liss, United States (1984).

"The Nomenclature of Lipids," *Journal of Lipid Research* 8:523-528, American Society for Biochemistry and Molecular Biology, United States (1967).

Ota, Y., "Complexes of apoA-1 with phosphatidylcholine suppress dysregulation of arterial tone by oxidized LDL," *Am. J. Physiol.* 273(3), Part 2:H1215-22, The American Physiological Society, United States (1997).

Podrez, E.A., et al., "A Novel Family of Atherogenic Oxidized Phoslipids Promotes Macrophage Foam Cell Formation Via the Scavenger Receptor CD36 and In Enriched in Atherosclerotic Lesions," *J. Biol. Chem.* 277(41): 38517-38523, The American Society for Biochemistry and Molecular Biology, Inc., United States (2002).

Podrez, E.A., et al., "Identification of a Novel Family of Oxidized Phospholipids That Serve as Ligands for the Macrophage Scavenger Receptor CD36," *J. Biol. Chem.* 277(41): 38503-38516, The American Society for Biochemistry and Molecular Biology, Inc., United States (2002).

Pontsler, A.V., et al., "Cyclooxygenase-2 is induced in monocytes by peroxisome proliferator activated receptor gamma and oxidized alkyl phospholipids from oxidized low density lipoprotein," *J. Biol. Chem.* 277(15):13029-36, The American Society for Biochemistry and Molecular Biology, United States (2002).

Shaw, P.X., et al., "Natural antibodies with the T15 idiotype may act in atherosclerosis, apoptotic clearance, and protective immunity," *J. Clin. Invest.* 105(12):1731-1740, American Society for Clinical Investigation, United States (2000).

Smal, M.A., et al., "Production of antibodies to platelet activating factor," *Mol. Immunol.* 26(8):711-19, Pergamon Press, England (1989).

"Study to Assess VB-201 in Patientes with Psoriasis," accessed at: http://clinicaltrialsfeeds.org/clinical-trials/show/NCT01001468, on Oct. 2, 2012.

Subbanagounder, G., et al. "Evidence That Phospholipid Oxidation Products and/or Platelet-Activating Factor Play An Important Role in Early Atherogenesis: In Vitro and In Vivo Inhibition by WEB 2086," *Circulation Research* 85:311-318, American Heart Association, United States (1999).

Subbanagounder, G., et al. "Determinants of Bioactivity of Oxidized Phospholipids: Specific Oxidized Fatty Acyl Groups at the SN-2 Position," *Arteriosclerosis Thromb. Vasc. Biol.* 2248-2254, American Heart Association, United States (2000).

Sun, M., et al., "Novel bioactive phospholipids: practical total syntheses of products from the oxidation of arachidonic and linoleic esters of 2-lysophosphatidylcholine," *J. Org. Chem.* 67(11):3575-84, American Chemical Society, United States (2002).

Tokumura, A., et al., "Cardiovascular Effects of Lysophosphatidic Acid and Its Structural Analogs in Rats," *The Journal of Pharmacology and Experimental Therapeutics* 219:219-224, The American Society of Pharmacology and Experimental Therapeutics, United States (1981).

Wang, C.J. and Tai, H.H., "A facile synthesis of an aldehydic analog of platelet activating factor and its use in the production of specific antibodies," *Chem. Phys. Lipids* 55(3):265-73, Elsevier Science Ireland Ltd., Ireland (1990).

Watson et al. "Structural Identification by Mass Spectrometry of Oxidized Phospholipids in Minimally Oxidized Low Density Lipoprotein That Induce Monocyte/Endothelial Interactions and Evidence for their Presence in Vivo" *J. Biol. Chem.* 272(21):13597-13607, The American Society for Biochemistry and Molecular Biology, Inc., United States (1997).

English language abstract of CH642665 A5, espacenet database, Worldwide, published Apr. 30, 1984.

English language abstract of JP 60-104066, espacenet database, Worldwide, published Jun. 8, 1985.

English language abstract of JP 62-000094 A, espacenet database, Worldwide, published Jan. 6, 1987.

English language abstract of JP 62-030714 A, espacenet database, Worldwide, published Feb. 9, 1987.

English language abstract of JP 63-054386 A, espacenet database, Worldwide, published Mar. 8, 1988.

English language abstract of JP 63-135395 A, espacenet database, Worldwide, published Jun. 7, 1988.

English language abstract of ES 2 019 552 A6, espeacenet database, Worldwide, published Jun. 16, 1991.

English language abstract of JP 11-116563 A, espacenet database, Worldwide, published Apr. 27, 1999.

International Search Report and Written Opinion dated Aug. 24, 2006 from the International Searching Authority Re.: Application No. PCT/IL05/00735.

International Search Report and Written Opinion dated Mar. 13, 2009 from the International Searching Authority Re.: Application No. PCT/IL08/000013.

International Search Report and Written Opinion dated Apr. 18, 2011 from the International Searching Authority Re.: Application No. PCT/IL11/00008.

International Search Report and Written Opinion dated Apr. 18, 2011 from the International Searching Authority Re.: Application No. PCT/IL11/00010.

International Search Report and Written Opinion dated Apr. 18, 2011 from the International Searching Authority Re.: Application No. PCT/IL11/00012.

International Search Report and Written Opinion dated Jul. 11, 2002 and Aug. 12, 2003, respectively, from the International Searching Authority Re.: Application No. PCT/IL01/01080.

International Search Report and Written Opinion dated Nov. 23, 2004 from the International Searching Authority Re.: Application No. PCT/IL2004/000453.

International Search Report and Written Opinion dated Mar. 24, 2010 from the International Searching Authority Re.: Application No. PCT/IL2009/001049.

International Search Report and Written Opinion dated Apr. 6, 2010 from the International Searching Authority Re.: Application No. PCT/IL09/00949.

International Preliminary Report on Patentability dated Jan. 9, 2007 from the International Bureau of WIPO Re.: Application No. PCT/IL05/00735.

International Preliminary Report on Patentability dated Oct. 20, 2009 from the International Bureau of WIPO Re.: Application No. PCT/IL08/000013.

International Preliminary Report on Patentability dated Apr. 12, 2011 from the International Bureau of WIPO Re.: Application No. PCT/IL2009/000949.

International Preliminary Report on Patentability dated Apr. 9, 2005 from the International Bureau of WIPO Re.: Application No. PCT/IL2004/000453.

(56) References Cited

OTHER PUBLICATIONS

International Preliminary Report on Patentability dated May 10, 2011 from the International Bureau of WIPO Re.: Application No. PCT/IL2009/001049.
International Preliminary Report on Patentability dated Jan. 6, 2005 from the International Preliminary Examining Authority Re.: Application No. PCT/IL01/01080.
International Preliminary Report on Patentability dated Jul. 10, 2012 from the International Bureau of WIPO Re.: Application No. PCT/IL11/00012.
International Preliminary Report on Patentability dated Jul. 10. 2012 from the International Bureau of WIPO Re.: Application No. PCT/IL11/00010.
International Preliminary Report on Patentability dated Jul. 10, 2012 from the International Bureau of WIPO Re.: Application No. PCT/IL11/00008.
European Search Report and European Search Opinion dated Feb. 3, 2012 from the European Patent Office Re.: Application No. 11189562.9.
Supplementary Partial European Search Report and European Search Opinion dated Nov. 30, 2009 from the European Patent Office Re.: Application No. 05 75 8938.4.
Supplementary Partial European Search Report dated Mar. 25, 2011 from the European Patent Office Re.: Application No. 08 70 0247.3.
Supplementary European Search Report dated Aug. 3, 2009 from the European Patent Office Re.: Application No. 01997274.4.
Supplementary Partial European Search Report dated Aug. 5, 2009 from the European Patent Office Re.: Application No. 04735088.9.
Supplementary European Search Report and European Search Opinion dated Mar. 9, 2012 from the European Patent Office Re.: Application No. 0982498.1.
Supplementary European Search Report and European Search Opinion dated Oct. 16, 2012 from the European Patent Office Re.: Application No. 12 178 298.1.
Notice of Allowance dated Jun. 10, 2010 from the US Patent and Trademark Office Re.: U.S. Appl. No. 11/650,973.
Office Action dated Dec. 1, 2009 from the US Patent and Trademark Office Re.: U.S. Appl. No. 11/650,973.
Office Action dated May 14, 2009 from the US Patent and Trademark Office Re.: U.S. Appl. No. 11/650,973.
Official Action dated Aug. 19, 2008 from the US Patent and Trademark Office Re.: U.S. Appl. No. 11/650,973.
Notice of Allowance dated Oct. 26, 2011 from the US Patent and Trademark Office Re.: U.S. Appl. No. 12/861,921.
Office Action dated Mar. 17, 2011 from the US Patent and Trademark Office Re.: U.S. Appl. No. 12/861,921.
Notice of Allowance dated Jan. 24, 2011 from the US Patent and Trademark Office Re.: U.S. Appl. No. 12/588,371.
Official Action dated Aug. 23, 2010 from the US Patent and Trademark Office Re.: U.S. Appl. No. 12/588,371.
Official Action dated May 28, 2010 from the US Patent and Trademark Office Re.: U.S. Appl. No. 12/588,371.
Notice of Allowance dated Nov. 3, 2010 from the US Patent and Trademark Office Re.: U.S. Appl. No. 10/567,543.
Official Action dated Jun. 15, 2010 from the US Patent and Trademark Office Re.: U.S. Appl. No. 10/567,543.
Official Action dated Mar. 9, 2010 from the US Patent and Trademark Office Re.: U.S. Appl. No. 10/567,543.
Notice of Allowance dated May 25, 2006 from the US Patent and Trademark Office Re.: U.S. Appl. No. 10/718,596.
Final Official Action dated Mar. 2, 2006 from the US Patent and Trademark Office Re.: U.S. Appl. No. 10/718,596.
Official Action dated Jul. 15, 2005 from the US Patent and Trademark Office Re.: U.S. Appl. No. 10/718,596.
Corrected Notice of Allowance dated Jul. 23, 2009 from the US Patent and Trademark Office Re.: U.S. Appl. No. 11/528,657.
Notice of Allowance dated Jun. 30, 2009 from the US Patent and Trademark Office Re.: U.S. Appl. No. 11/528,657.
Official Action dated Nov. 25, 2008 from the US Patent and Trademark Office Re.: U.S. Appl. No. 11/528,657.
Notice of Allowance dated Nov. 3, 2008 from the US Patent and Trademark Office Re.: U.S. Appl. No. 11/183,884.
Official Action dated Apr. 16, 2008 from the US Patent and Trademark Office Re.: U.S. Appl. No. 11/183,884.
Official Action dated Dec. 7, 2007 from the US Patent and Trademark Office Re.: U.S. Appl. No. 11/183,884.
Notice of Allowance dated Oct. 18, 2010 from the US Patent and Trademark Office Re.: U.S. Appl. No. 12/371,930.
Official Action dated Feb. 24, 2010 from the US Patent and Trademark Office Re.: U.S. Appl. No. 12/371,930.
Official Action dated May 27, 2010 from the US Patent and Trademark Office Re.: U.S. Appl. No. 12/371,930.
Notice of Allowance dated Dec. 15, 2011 from the US Patent and Trademark Office Re.: U.S. Appl. No. 12/985,365.
Notice of Allowance dated Dec. 12, 2011 from the US Patent and Trademark Office Re.: U.S. Appl. No. 12/985,365.
Official Action dated Aug. 5, 2011 from the US Patent and Trademark Office Re.: U.S. Appl. No. 12/985,365.
Notice of Allowance dated Jul. 2, 2004 from the US Patent and Trademark Office Re.: U.S. Appl. No. 10/445,347.
Official Action dated Jan. 7, 2004 from the US Patent and Trademark Office Re.: U.S. Appl. No. 10/445,347.
Official Action dated Nov. 14, 2003 from the US Patent and Trademark Office Re.: U.S. Appl. No. 10/445,347.
Office Action dated Jun. 12, 2012 from the US Patent and Trademark Office Re.: U.S. Appl. No. 13/358,573.
Notice of Allowance dated Oct. 31, 2012 from the US Patent and Trademark Office Re.: U.S. Appl. No. 13/085,542.
Office Action dated Mar. 16, 2012 from the US Patent and Trademark Office Re.: U.S. Appl. No. 13/085,542.
International Search Report dated Sep. 1, 2011 from the International Searching Authority Re: Application No. PCT/IL11/00007.
International Search Report dated May 20, 2011 from the International Searching Authority Re: Application No. PCT/IL11/00009.
International Preliminary Report on Patentability dated Jul. 10, 2012 from the International Bureau of WIPO Re: Application No. PCT/IL2011/0000007.
International Preliminary Report on Patentability dated Jul. 10, 2012 from the International Bureau of WIPO Re: Application No. PCT/IL2011/000009.
International Search Report dated Nov. 13, 2012 from the European Patent Office Re: Application No. PCT/US2012/053533.
Paimela, L., et al., "Clinical significance of antibodies against oxidised low density lipoprotein in early RA," *Ann. Rheum. Dis.* 55(8):558-559, H.K. Lewis, England (1996).
Onorato, J.M., et al., "Immunohistochemical and ELISA assays for Biomarkers of Oxidative Stress in Aging and Disease," *Ann. N. Y. Acad. Sci.* 854:277-290, Blackwell, United States (1998).
Sawai, T., et al., "The effect of phospholipids and fatty acids on tight-junction permeability and bacterial translocation," *Pediatr. Surg. Int.* 17(4):269-274, Springer-Verlag, Germany (2001).
Noguchi, S., et al., "Effect of Extracellular Phosphatidylinositol on C-MYC Gene-Expressed Human Renal Cancer Cell Line," *Biochem. Biophys. Res. Commun.* 182(2):644-650, Academic Press, United States (1992).
Lombardin, P., et al., "Study of thixotropic bases for the filling of hard capsules," *S.T.P Pharma Sciences* 10(6):429-437, Editions de Santé, France (2000).
Notice of Allowance Dated Mar. 8, 2013 From the U.S. Patent and Trademark Office Re.: U.S. Appl. No. 13/085,542, filed Apr. 13, 2011.
Office Action dated Mar. 25, 2013 from the U.S. Patent and Trademark Office Re: U.S. Appl. No. 13/672,811, filed Nov. 9, 2012.
Office Action dated Mar. 15, 2013 from the US Patent and Trademark Office Re: U.S. Appl. No. 13/122,766, filed Apr. 6, 2011.
Co-pending U.S. Appl. No. 13/792,633, filed Mar. 11, 2013, inventors Sher, N., et al.
Co-pending U.S. Appl. No. 13/709,198, filed Dec. 10, 2012, inventors Halperin, G. and Kovaleski-Ishai, E.
Co-pending U.S. Appl. No. 13/796,654, filed Mar. 12, 2013, inventors Halperin, G. and Kovalevski-Ishai, E.
Co-pending U.S. Appl. No. 13/833,940, filed Mar. 15, 2013, inventors Halperin, G. and Kovalevski-Ishai, E.

(56) References Cited

OTHER PUBLICATIONS

Co-pending U.S. Appl. No. 13/828,883, filed Mar. 14, 2013 inventors Kovalevski-Ishai, E., et al.
Co-pending U.S. Appl. No. 13/828,643, filed Mar. 14, 2013 inventors Cohen Y., et al.
Bochkov, V.N., et. al., "Protective role of phospholipid oxidation products in endotoxin induced tissue damage," *Nature*, 419:77-81, Nature Publishing Group, England (Sep. 2002).
Office Action dated Jan. 16, 2013 from the US Patent and Trademark Office Re: U.S. Appl. No. 13/431,262, filed Mar. 27, 2012.
Notice of Allowance dated Jun. 12, 2013 from the US Patent and Trademark Office Re: U.S. Appl. No. 13/431,262, filed Mar. 27, 2012.
English language abstract for JP50004040 A, Derwent World Patents Index, Dialog File No. 351, Accession No. 849902, Accessed on Mar. 25, 2013.
Langan, R.C., et al., "Ulcerative colitis: diagnosis and treatment," *Am. Fam. Physician* 76(9):1323-30, American Academy of Family Physicians, United States (2007).
Anand, S.S. and Yusuf, S., "C-reactive protein is a bystander of cardiovascular disease," *Eur. Heart. J.* 31(17):2092-2097, Oxford University Press, England (2010).
Office Action dated Apr. 10, 2013 from the US Patent and Trademark Office Re: U.S. Appl. No. 13/520,713, filed Jul. 5, 2012.
"Guidance for Industry: Estimating the Maximum Safe Starting Dose in Initial Clinical Trials for Therapeutics in Adult Healthy Volunteers," U.S. Department of Health and Human Services, Food and Drug Administration, Center for Drug Evaluation and Research, pp. 1-27 (Jul. 2005).
Office Action dated Aug. 30, 2013 from the US Patent and Trademark Office Re: U.S. Appl. No. 13/828,643, filed Mar. 14, 2013.
Office Action dated Aug. 7, 2013 from the US Patent and Trademark Office Re: U.S. Appl. No. 13/520,713, § 371(c) date Jul. 5, 2012.
Office Action dated Aug. 22, 2013 from the US Patent and Trademark Office Re: U.S. Appl. No. 13/709,198, filed Dec. 10, 2012.
Office Action dated Aug. 22, 2013 from the US Patent and Trademark Office Re: U.S. Appl. No. 13/796,654, filed Mar. 12, 2013.
Office Action dated Sep. 16, 2013 from the US Patent and Trademark Office Re: U.S. Appl. No. 13/833,940, filed Mar. 15, 2013.
Bhattacharyya, S., et al., "Toll-Like Receptor 4 Signaling Augments Transforming Growth Factor-β Responses: A Novel Mechnanism for Maintaining and Amplifying Fibrosis Scleroderma," *The American Journal of Pathology* 182(1):192-205, Elsevier Inc., United States (2013).
Csak, T., et al., "Deficiency in myeloid differentiation factor-2 and toll-like receptor 4 expression attenuates nonalcoholic steatohepatitis and fibrosis in mice," *Am J Physiol Gastrointest Liver Physiol* 300:G433-G441, American Physiological Society, United States (2011).
Franklin, C., et al., "Design, Synthesis, and Evaluation of Water-Soluble Phospholipid Analogues as Inhibitors of Phospholipase C from *Bacillus cereus*," *Journal of Organic Chemistry* 68(19):7298-7307, American Chemical Society, United States (2003), Caplus AN 2003:643618.
Herre, J., et al., "Allergens as Immunomodulatory Proteins: The Cat Dander Protein Fel d 1 Enhances TLR Activation by Lipid Ligands," *J Immunol* 191:1529-1535, American Association of Immunologists, Inc., United States (2013).

Kwok, S-K., et al., "TLR2 litigation induces the production of IL-23/IL-17 via IL-6, STAT3 and NF-kB pathway in patients with primary Sjogren's syndrome," *Arthritis Research & Therapy* 14(R64):1-13, BioMed Central, England (2012).
Lartigue, A., et al., "Critical Role of TLR2 and TLR4 in Autoantibody Production and Glomerulonephritis in *lpr* Mutation-Induced Mouse Lupus," *J Immunol* 183:6207-6216, American Association of Immunologists, Inc., United States (2009).
Li, J., et al., "Toll-like receptors ad therapeutic targets for autoimmune connective tissue diseases," *Pharmacology & Therapeutics* 138:441-451, Pergamon Press, England (2013).
Millien, V.O., et al., "Cleavage of Fibrinogen by Proteinases Elicits Allergic Responses Through Toll-Like Receptor 4," *Science* 341(6147):792-796, American Association for the Advancement of Science, United States (2013).
Miura, K., et al., "TLR2 and palmitic acid cooperatively contribute to the development of nonalcoholic steatohepatitis through inflammasome activation," *Hepatology* 57(2):577-589, Wiley, United States (2013).
Wen, Z., et al., "Autoantibody Induction by DNA-Containing Immune Complexes Requires HMGB1 with the TLR2/MicroRNA-155 Pathaway," *J Immunol* 190:5411-5422, American Association for the Advancement of Science, United States (2013).
Office Action mailed Mar. 7, 2014, in U.S. Appl. No. 13/833,940, Halperin, G. and Kovalevski-Ishai, E., filed Mar. 15, 2013.
Office Action mailed Jul. 16, 2014, in U.S. Appl. No. 13/833,940, Halperin, G. and Kovalevski-Ishai, E., filed Mar. 15, 2013.
Office Action mailed Apr. 23, 2014, in U.S. Appl. No. 13/122,766, Breitbart, E., et al., § 371(c) date: Apr. 6, 2011.
Office Action mailed Mar. 11, 2014, in U.S. Appl. No. 13/520,713, Cohen, Y., et al., § 371(c) date: Jul. 5, 2012.
Office Action mailed Feb. 25, 2014, in U.S. Appl. No. 13/828,643, Cohen, Y., et al., filed Mar. 14, 2013.
Office Action mailed Jun. 16, 2014, in U.S. Appl. No. 13/520,719, Cohen, Y., et al., filed Mar. 7, 2013.
International Preliminary Report on Patentability for International Application No. PCT/IB2012/002930, International Bureau of WIPO, Geneva, Switzerland, issued Jun. 17, 2014.
Office Action mailed Jul. 21, 2014, in U.S. Appl. No. 13/792,633, inventors Sher, N., et al., filed Mar. 11, 2013.
U.S. Appl. No. 14/364,705, inventors Mendel, I., et al., Int'l Filing Date: Dec. 11, 2012 (Not Published).
Notice of Allowance mailed Nov. 25, 2014, in U.S. Appl. No. 13/833,940, Halperin, G. and Kovalevski-Ishai, E., filed Mar. 15, 2013.
Notice of Allowance mailed Nov. 26, 2014, in U.S. Appl. No. 13/122,766, Breitbart, E., at al., § 371(c) date: Apr. 6, 2011.
Office Action mailed Aug. 26, 2014, in U.S. Appl. No, 13/520,713, Cohen, Y., et al., § 371(c) date: Jul. 5, 2012.
Office Action mailed Aug. 13, 2014, in U.S. Appl. No. 13/828,643, Cohen, Y., et al., filed Mar. 14, 2013.
Office Action mailed Mar. 30, 2015, in U.S. Appl. No. 13/520,719, Cohen, Y., et al., filed Mar. 7, 2013.
Office Action mailed Oct. 24, 2014, in U.S. Appl. No. 13/792,633, Sher, N., et al., filed Mar. 11, 2013.
Office Action mailed Apr. 30, 2015, in U.S. Appl. No. 13/828,883, Kovalevski-Ishai, E., et al., filed Mar. 14, 2013.
Office Action mailed Nov. 13, 2014, in U.S. Appl. No. 13/828,883, Kovalevski-Ishai, E., et al., filed Mar. 14, 2013.
Office Action mailed Apr. 10, 2015, in U.S. Appl. No. 13/792,633, Sher, N., et al., filed Mar. 11, 2013.

* cited by examiner

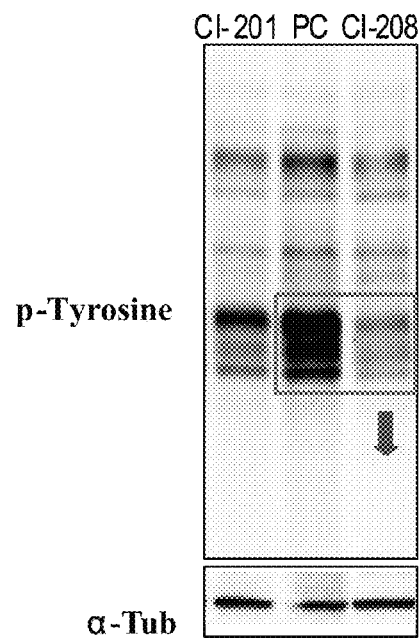
FIG. 23
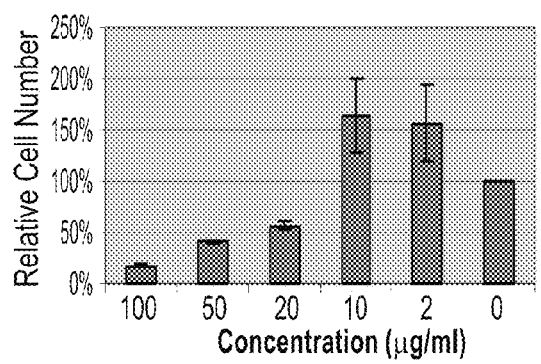 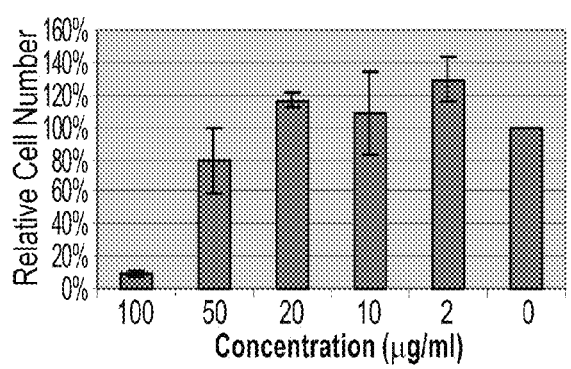
FIG. 24A          FIG. 24B

OXIDIZED LIPID COMPOUNDS AND USES THEREOF

RELATED APPLICATIONS

This application is a National Phase of PCT Patent Application No. PCT/IL2009/001049 having International filing date of Nov. 5, 2009, which claims the benefit of priority of U.S. Provisional Patent Application No. 61/193,220 filed on Nov. 6, 2008. The contents of the above applications are all incorporated herein by reference.

FIELD AND BACKGROUND OF THE INVENTION

The present invention, in some embodiments thereof, relates to novel oxidized lipids and to methods employing oxidized lipids for treating or preventing an inflammation associated with endogenous oxidized lipids. The methods of the present embodiments can be utilized in treating or preventing inflammation associated diseases and disorders such as, for example, atherosclerosis and related disorders, autoimmune diseases or disorders, and proliferative diseases or disorders.

Oxidized phospholipids have been previously described as useful in the treatment of medical conditions such as, for example, cardiovascular diseases, cerebrovascular diseases and inflammatory diseases and disorders.

International Patent Application No. PCT/IL2004/000453 (Publication No. WO 04/106486), by the present assignee, describes oxidized lipids for prevention and treatment of inflammation associated with endogenous oxidized lipids. An exemplary such compound is described and known as CI-201 (also referred to in the art as VB-201).

International Patent Application No. PCT/IL01/01080 (Publication No. WO 02/41827), by the present assignee, describes oxidized lipids for prevention and treatment of atherosclerosis and related diseases.

International Patent Application No. PCT/IL05/000735 (Publication No. WO 06/006161), by the present assignee, describes synthetic routes applicable for industrial preparation of therapeutically beneficial oxidized phospholipids without the use of column chromatography.

Additional background art includes International Patent Application Nos. PCT/IL02/00005 (Publication No. WO 02/053092) and PCT/IL08/000,013 (Publication No. WO 08/084,472), both being also by the present assignee.

All of the above cited publications are incorporated by reference as if fully set forth herein.

All of the above cited publications describe etherified oxidized lipids, which comprise a carbon backbone chain to which an alkyl chain, an alkyl chain substituted by an oxidized moiety and a phosphate-containing group are attached. The alkyl chain which is substituted by an oxidized moiety is preferably attached to the carbon backbone via an ether bond (hence compounds are referred to as "etherified oxidized lipids), as such a bond imparts the compounds desired pharmacological properties, which are described in detail in the above-mentioned publications.

SUMMARY OF THE INVENTION

The present inventors have now designed and successfully prepared and tested novel oxidized phospholipids.

According to an aspect of some embodiments of the present invention there is provided a compound having a formula:

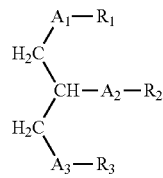

or pharmaceutically acceptable salts thereof, wherein:
(i) $A_1$, $A_2$ and $A_3$ are each independently selected from the group consisting of O and S;
(ii) $R_1$ is selected from the group consisting of an alkyl chain 2-28 carbons in length and

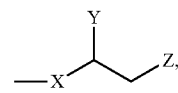

wherein X is a $C_{1-25}$ chain, Y is selected from the group consisting of:

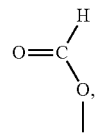

—OH, —H, alkyl, alkoxy, halogen, acetoxy and aromatic functional groups; and
Z is selected from the group consisting of:

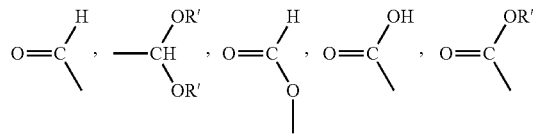

and —OH,
whereas R' is $C_{1-4}$ alkyl; and
(iii) $R_2$ is selected from the group consisting of (4-methylcarboxy)butyl, (3-carboxy)propyl, (6-carboxy)hexanyl, (2-carboxy)ethyl, 5,6-dihydroxyhexanyl, 5,5-diethoxypentyl and 5,5-dimethoxypentyl; and
(iv) $R_3$ is selected from the group consisting of H, acyl, alkyl, phosphate, phosphocholine, phosphoethanolamine, phosphoethanolamine-N-glutaric acid, phosphoserine, and phosphoinositol.

According to an aspect of some embodiments of the present invention there is provided a compound having a formula:

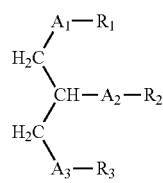

or pharmaceutically acceptable salts thereof, wherein:
(i) $A_1$, $A_2$ and $A_3$ are each independently selected from the group consisting of O and S;

(ii) $R_1$ and $R_2$ are each independently selected from the group consisting of an alkyl chain being 2-28 carbons in length and

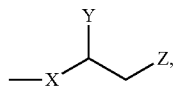

provided that at least one of $R_1$ and $R_2$ is

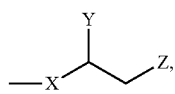

wherein X is a $C_{1-25}$ chain, Y is selected from the group consisting of:

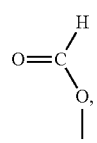

—OH, —H, alkyl, alkoxy, halogen, acetoxy and aromatic functional groups; and

Z is selected from the group consisting of:

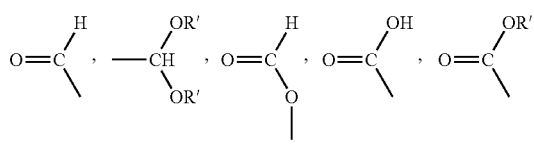

and —OH, whereas R' is $C_{1-4}$ alkyl; and (iii) $R_3$ is selected from the group consisting of H, phosphate, phosphoethanolamine, phosphoethanolamine-N-glutaric acid and phosphoserine.

According to an aspect of some embodiments of the present invention there is provided a compound having a formula:

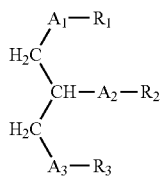

or pharmaceutically acceptable salts thereof, wherein:
 (i) $A_1$, $A_2$ and $A_3$ are each independently selected from the group consisting of O and S;
 (ii) $R_1$ is selected from the group consisting of dodecyl, octadecyl, octyl, eicosanyl, cis-9-hexadecenyl, (2-octyl) dodecyl and (15-carboxy)pentadecyl;
 (iii) $R_2$ is selected from the group consisting of an alkyl chain 2-28 carbons in length and

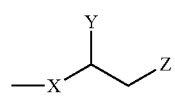

provided that at if $R_1$ is other (15-carboxy)pentadecyl, then $R_2$ is

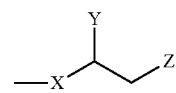

wherein X is a $C_{1-25}$ chain, Y is selected from the group consisting of:

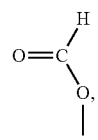

—OH, —H, alkyl, alkoxy, halogen, acetoxy and aromatic functional groups; and

Z is selected from the group consisting of:

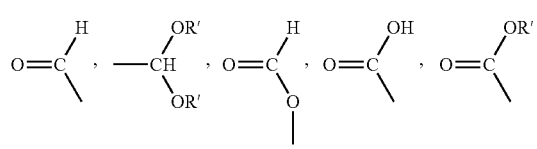

and —OH, whereas R' is $C_{1-4}$ alkyl; and (iv) $R_3$ is selected from the group consisting of H, acyl, alkyl, phosphate, phosphocholine, phosphoethanolamine, phosphoethanolamine-N-glutaric acid, phosphoserine, and phosphoinositol.

According to an aspect of some embodiments of the present invention there is provided a compound having a formula:

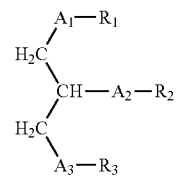

or pharmaceutically acceptable salts thereof, wherein:
 (i) $A_1$ is S and $A_2$ and $A_3$ are each O;
 (ii) $R_1$ and $R_2$ are each independently selected from the group consisting of an alkyl chain 2-28 carbons in length and

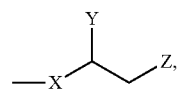

provided that at least one of $R_1$ and $R_2$ is

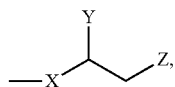

wherein X is a $C_{1-25}$ chain, Y is selected from the group consisting of:

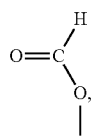

—OH, —H, alkyl, alkoxy, halogen, acetoxy and aromatic functional groups; and
Z is selected from the group consisting of:

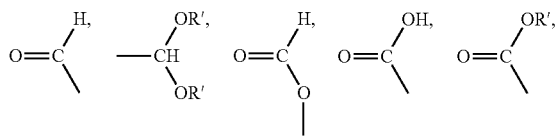

and —OH,
whereas R' is $C_{1-4}$ alkyl; and
(iii) $R_3$ is selected from the group consisting of H, acyl, alkyl, phosphate, phosphocholine, phosphoethanolamine, phosphoethanolamine-N-glutaric acid, phosphoserine, and phosphoinositol.

According to an aspect of some embodiments of the present invention there is provided a compound selected from the group consisting of:
1-hexadecyl-2-(4-carboxy)butyl-glycero-3-phosphate (CI-201-PA);
1-hexadecyl-2-(4-methylcarboxy)butyl-glycero-3-phosphoethanolamine;
1-hexadecyl-2-(4-methylcarboxy)butyl-glycero-3-phosphocholine (CI-208);
1-hexadecyl-2-(4-carboxy)butyl-glycero-3-phosphoethanolamine (CI-202);
1-hexadecyl-2-(3-carboxy)propyl-glycero-3-phosphoethanolamine (CI-206);
1-hexadecyl-2-(3-carboxy)propyl-glycero-3-phosphocholine (CI-205);
1-hexadecyl-2-(6-carboxy)hexanyl-glycero-3-phosphocholine (CI-203);
1-dodecyl-2-(4-carboxy)butyl-glycero-3-phosphocholine (CI-209);
1-hexadecyl-2-(4-carboxy)butyl-glycero-3-phosphoethanolamine-N-glutaric acid (CI-210);
1-(15'-carboxy)pentadecyl-2-(4-carboxy)butyl-glycero-3-phosphocholine (CI-213);
1-(15'-carboxy)pentadecyl-2-(4-carboxy)butyl-glycero-3-phosphoethanolamine (CI-214);
1-octadecyl-2-(4-carboxy)butyl-glycero-3-phosphocholine (CI-215);
1-octadecyl-2-(4-carboxy)butyl-glycero-3-phosphoethanolamine (CI-216);
1-hexadecyl-2-(2-carboxy)ethyl-glycero-3-phosphocholine (CI-217);
1-S-hexadecyl-2-(4-carboxy)butyl-glycero-3-phosphocholine (1-S-CI-201);
1-S-hexadecyl-2-(4-carboxy)butyl-glycero-3-phosphoethanolamine (1-S-CI-202);
1-hexadecyl-2-(5,6-dihydroxy)hexanyl-glycero-3-phosphocholine (di-OH);
1-(cis-9-hexadecenyl)-2-(4-carboxy)butyl-glycero-3-phosphocholine;
1-hexadecyl-2-(4-carboxy)butyl-glycerol;
1-hexadecyl-2-(5',5'-diethoxypentyl)-glycero-3-phosphocholine (diEtAc);
1-hexadecyl-2-(5',5'-dimethoxypentyl)-glycero-3-phosphocholine (diMeAc);
1-octyl-2-(4-carboxy)butyl-glycero-3-phosphocholine (CI-207);
1-octyl-2-(4-carboxy)butyl-glycero-3-phosphoethanolamine;
1-eicosanyl-2-(4-carboxy)butyl-glycero-3-phosphocholine (CI-219);
1-eicosanyl-2-(4-carboxy)butyl-glycero-3-phosphoethanolamine (CI-220);
1-(2-octyl)dodecyl-2-(4-carboxy)butyl-glycero-3-phosphocholine (VB-221);
1-(2-octyl)dodecyl-2-(4-carboxy)butyl-glycero-3-phosphoethanolamine (VB-222); and
1-hexadecyl-2-(4-carboxy)butyl-glycero-3-phosphoserine (VB-223).

According to an aspect of some embodiments of the present invention there is provided a pharmaceutical composition comprising, as an active ingredient, a compound herein, and a pharmaceutically acceptable carrier.

According to an aspect of some embodiments of the present invention there is provided a method of treating or preventing an inflammation associated with an endogenous oxidized lipid, the method comprising administering to a subject in need thereof a therapeutically effective amount of a compound described herein, thereby treating or preventing the inflammation associated with an endogenous oxidized lipid in the subject.

According to an aspect of some embodiments of the present invention there is provided a method of decreasing a level of a cytokine selected from the group consisting of interleukin-12 and interleukin-23 in a subject, the method comprising administering to the subject an effective amount of a compound described herein.

According to an aspect of some embodiments of the present invention there is provided a method of treating a disease or disorder in which decreasing a level of a cytokine selected from the group consisting of interleukin-12 and interleukin-23 is beneficial, the method comprising administering to a subject in need thereof an effective amount of a compound described herein.

According to an aspect of some embodiments of the present invention there is provided a use of the compound described herein in the manufacture of a medicament for treating or preventing an inflammation associated with an endogenous oxidized lipid.

According to an aspect of some embodiments of the present invention there is provided a use of the compound described herein in the manufacture of a medicament for decreasing a level of a cytokine selected from the group consisting of interleukin-12 and interleukin-23 in a subject.

According to an aspect of some embodiments of the present invention there is provided a use of the compound described herein in the manufacture of a medicament for treating a disease or disorder in which decreasing a level of a cytokine selected from the group consisting of interleukin-12 and interleukin-23 is beneficial.

According to some embodiments of the invention, $R_1$ is an alkyl chain 2-28 carbons in length.

According to some embodiments of the invention, the compound described herein is identified for use in a method of treating or preventing an inflammation associated with an endogenous oxidized lipid.

According to some embodiments of the invention, the compound described herein is identified for use in a method for decreasing of a level of a cytokine selected from the group consisting of interleukin-12 and interleukin-23.

According to some embodiments of the invention, the compound described herein is identified for use in a method of treating a disease or disorder in which decreasing of a level of a cytokine selected from the group consisting of interleukin-12 and interleukin-23 is beneficial.

According to some embodiments of the invention, the pharmaceutical composition is packaged in a packaging material and identified in print, in or on the packaging material, for use in the treatment or prevention of an inflammation associated with an endogenous oxidized lipid.

According to some embodiments of the invention, the pharmaceutical composition is packaged in a packaging material and identified in print, in or on the packaging material, for decreasing of a level of a cytokine selected from the group consisting of interleukin-12 and interleukin-23.

According to some embodiments of the invention, the pharmaceutical composition is packaged in a packaging material and identified in print, in or on the packaging material, for use in the treatment of a disease or disorder in which decreasing of a level of a cytokine selected from the group consisting of interleukin-12 and interleukin-23 is beneficial.

According to some embodiments of the invention, the inflammation is associated with a disease or disorder selected from the group consisting of an idiopathic inflammatory disease or disorder, a chronic inflammatory disease or disorder, an acute inflammatory disease or disorder, an autoimmune disease or disorder, an infectious disease or disorder, an inflammatory malignant disease or disorder, an inflammatory transplantation-related disease or disorder, an inflammatory degenerative disease or disorder, a disease or disorder associated with a hypersensitivity, an inflammatory cardiovascular disease or disorder, an inflammatory cerebrovascular disease or disorder, a peripheral vascular disease or disorder, an inflammatory glandular disease or disorder, an inflammatory gastrointestinal disease or disorder, an inflammatory cutaneous disease or disorder, an inflammatory hepatic disease or disorder, an inflammatory neurological disease or disorder, an inflammatory musculo-skeletal disease or disorder, an inflammatory renal disease or disorder, an inflammatory reproductive disease or disorder, an inflammatory systemic disease or disorder, an inflammatory connective tissue disease or disorder, an inflammatory tumor, necrosis, an inflammatory implant-related disease or disorder, an inflammatory aging process, an immunodeficiency disease or disorder and an inflammatory pulmonary disease or disorder.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a graph showing IL12/23 p40 production in cells treated with various doses of CI-202 (each bar represents 3 samples); $P<0.004$ for each dose in comparison with the control (0 μg/ml);

FIG. 2 is a graph showing IL12/23 p40 mRNA expression in cells treated with CI-201, CI-202 and phosphatidyl choline (PC) at 2, 3 and 4 hours after treatment;

Figure 3:
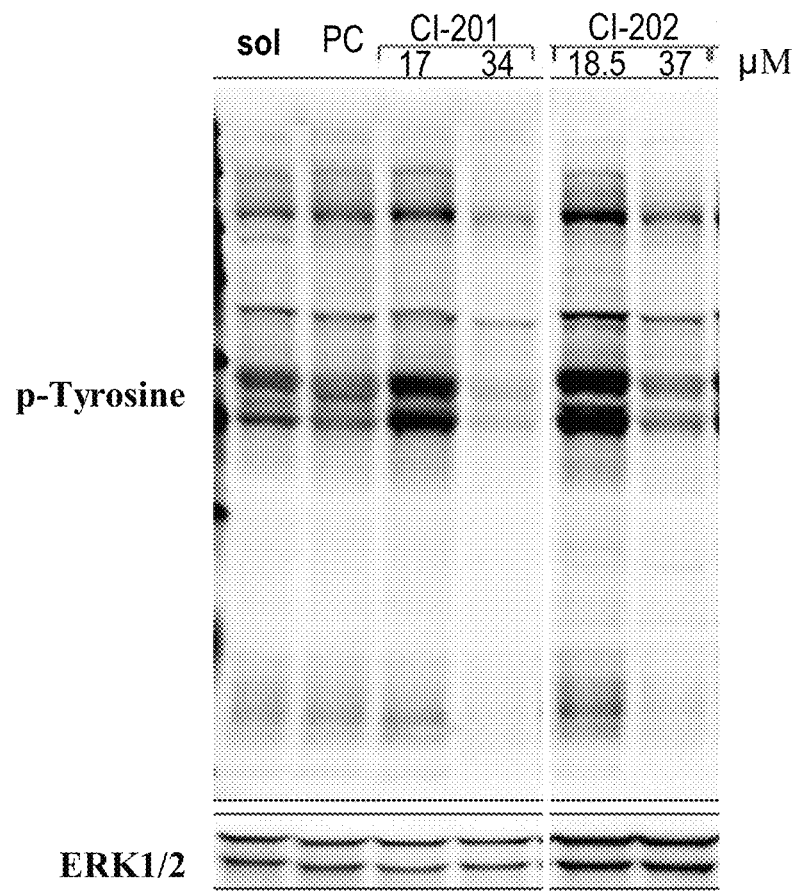
Figure 4A:
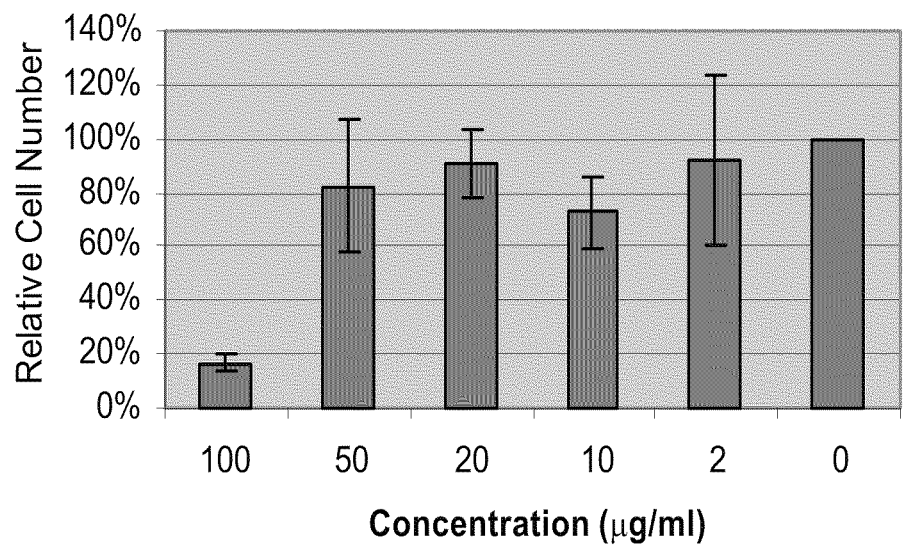
Figure 4B:
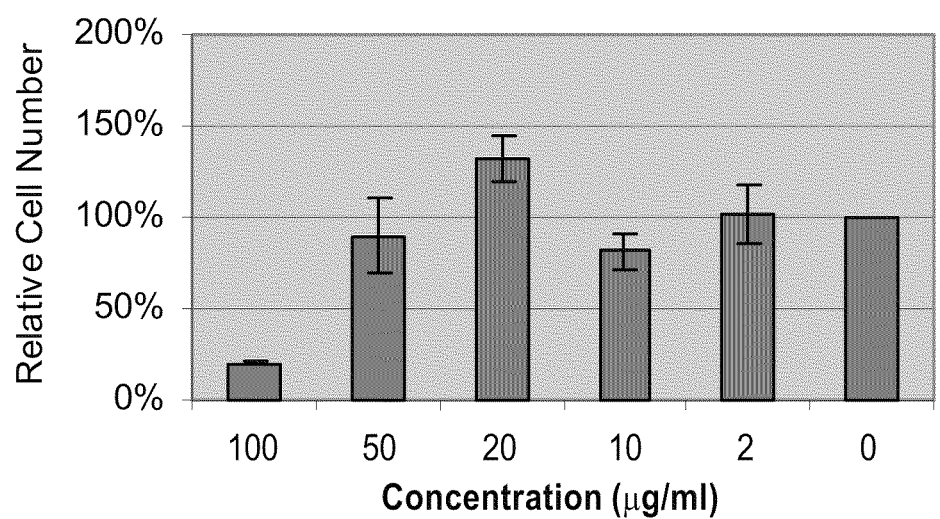
Figure 5:
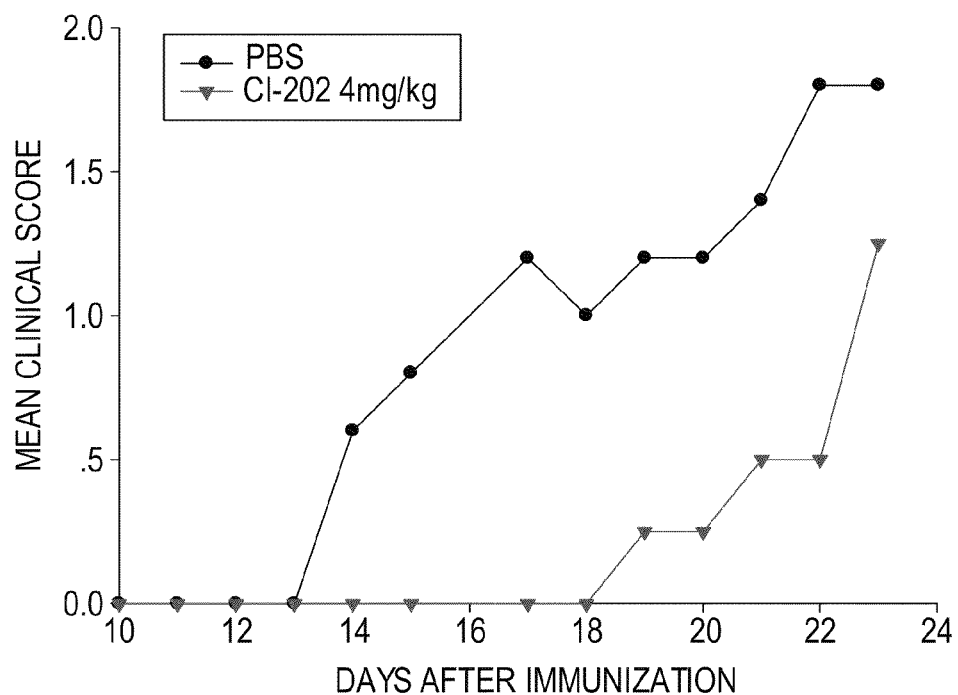
Figure 6:
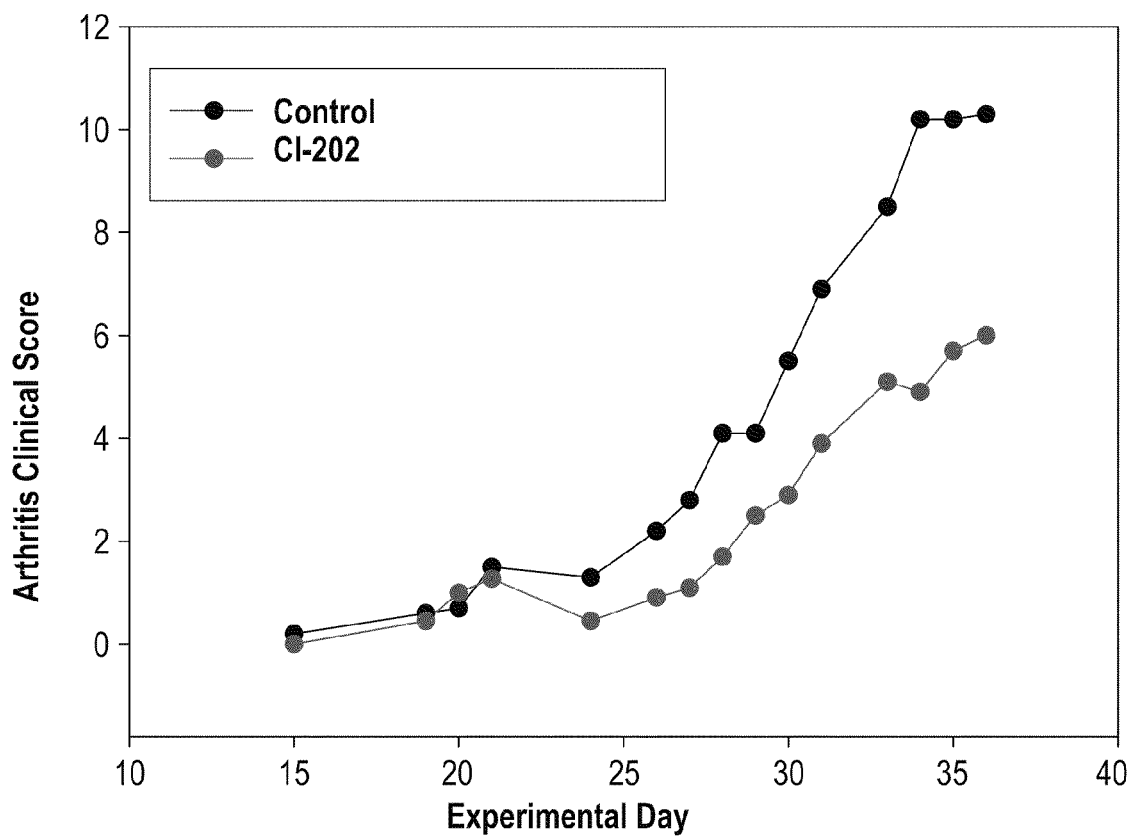
Figure 7:
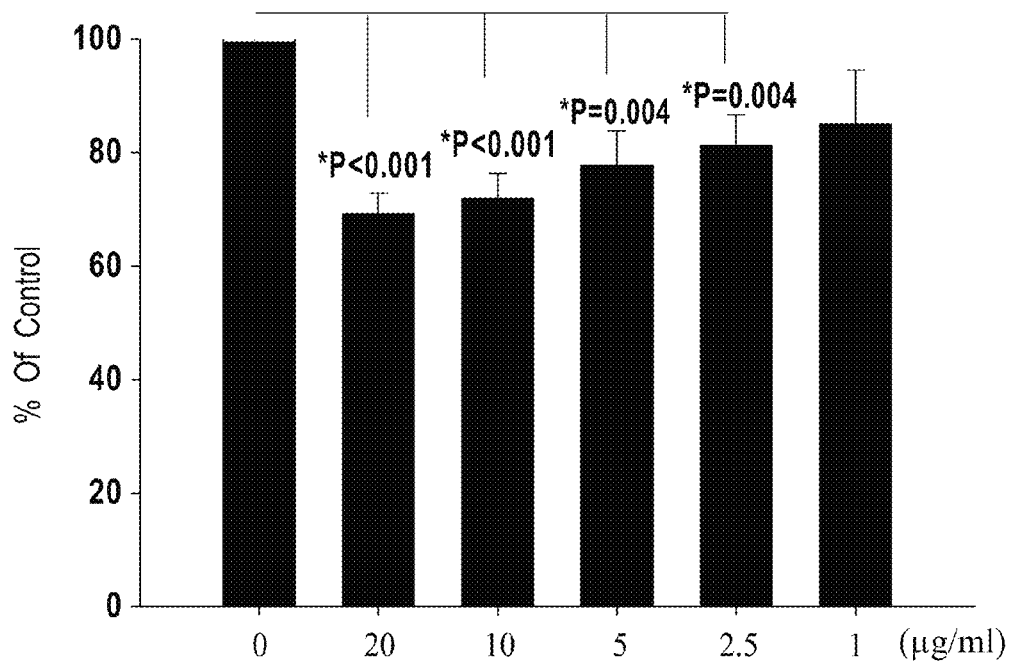
Figure 8:
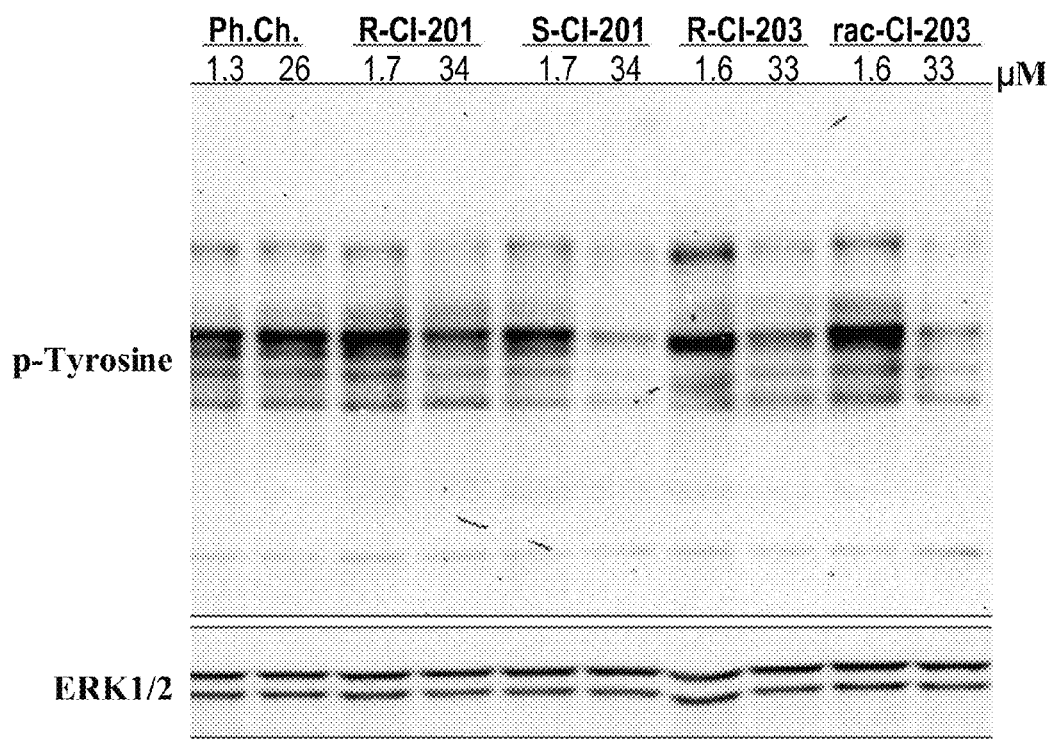
Figure 9A:
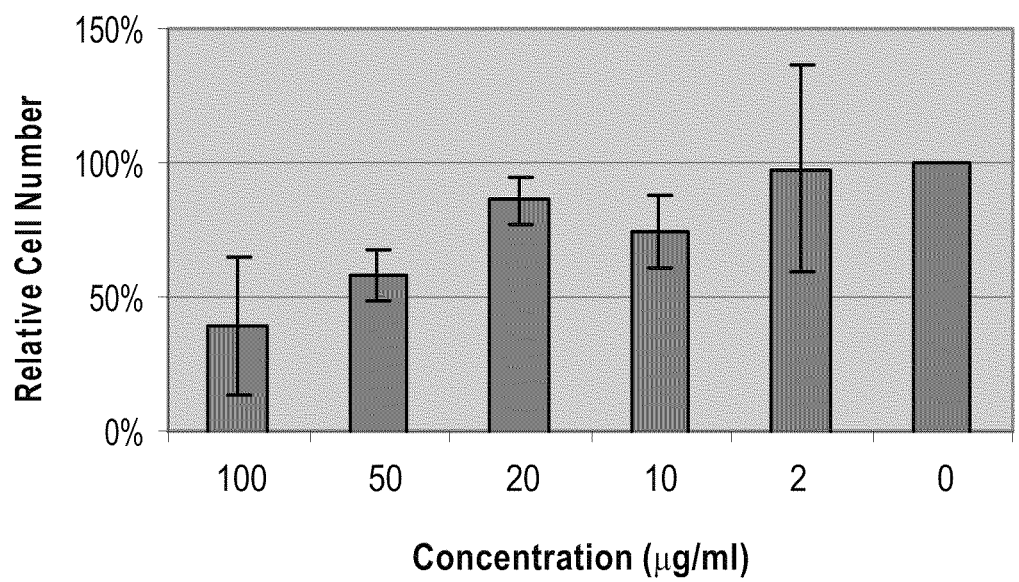
Figure 9B:
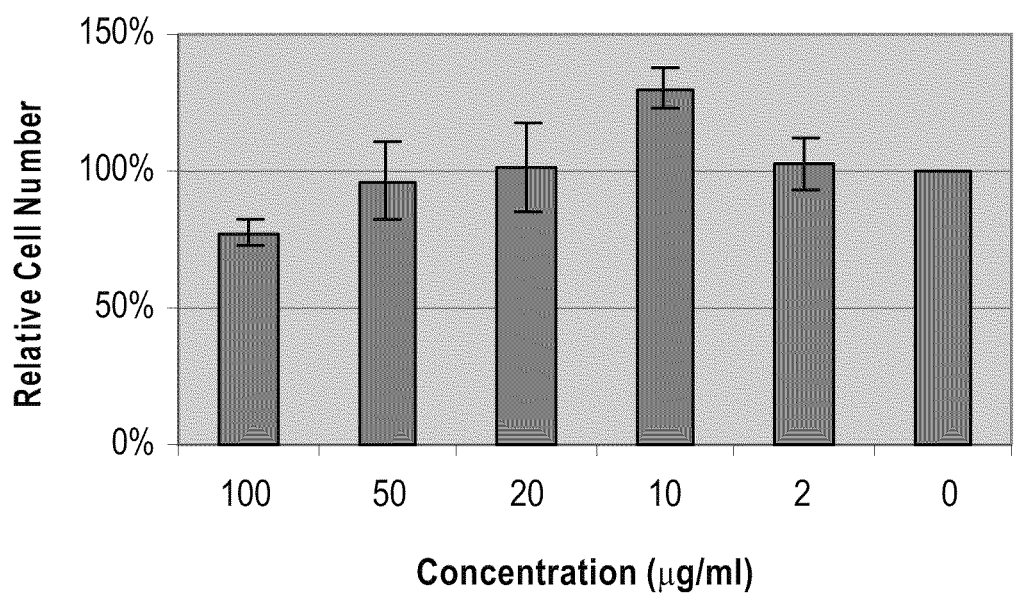
Figure 10:
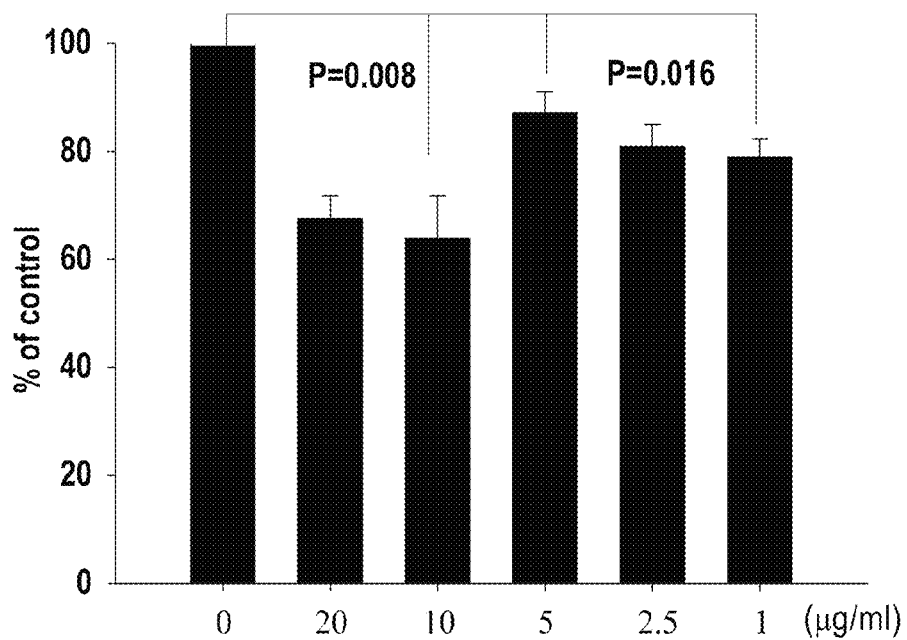
Figure 11:
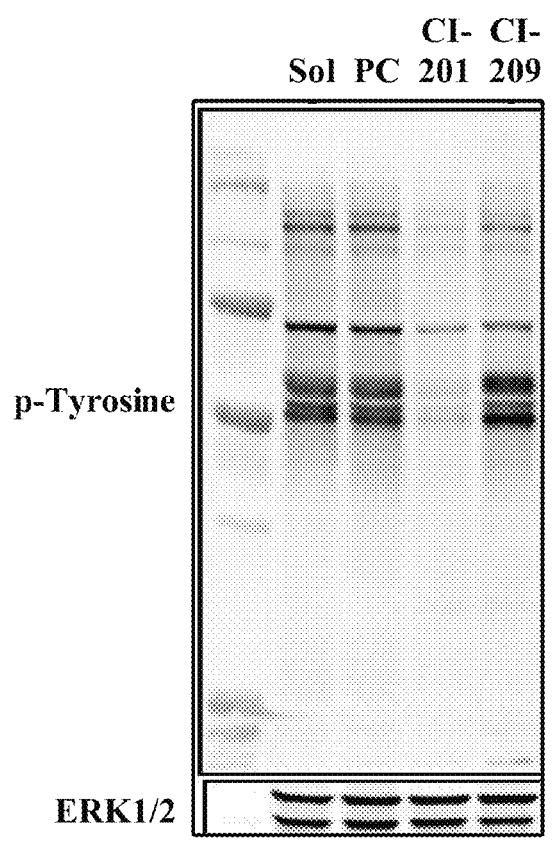
Figure 12A:
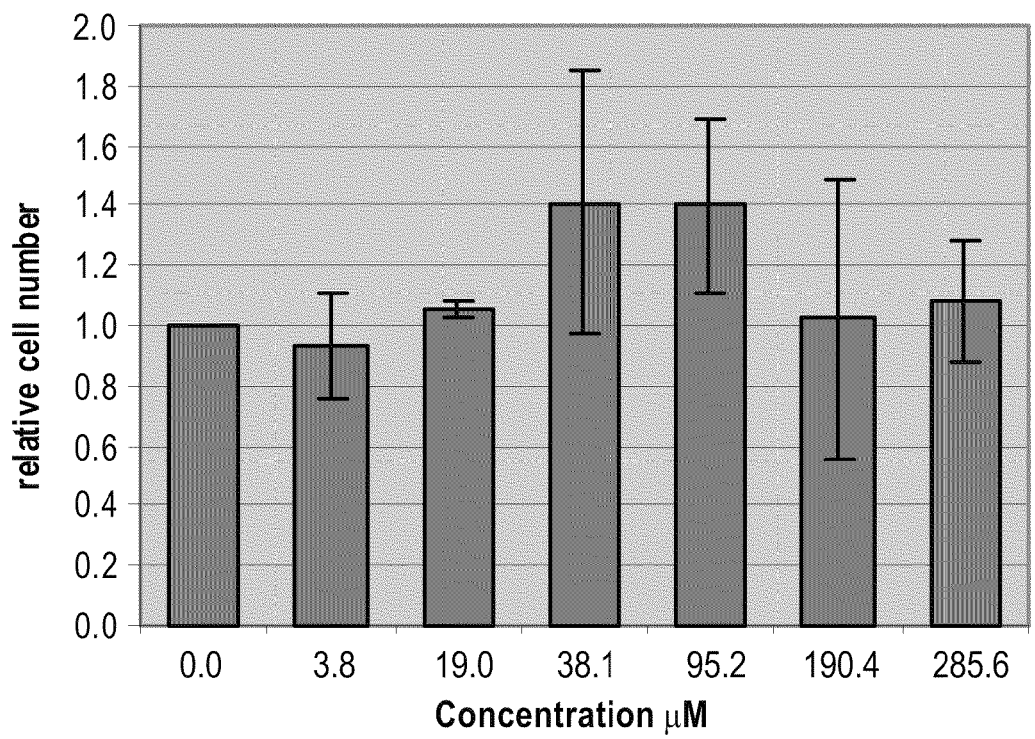
Figure 12B:
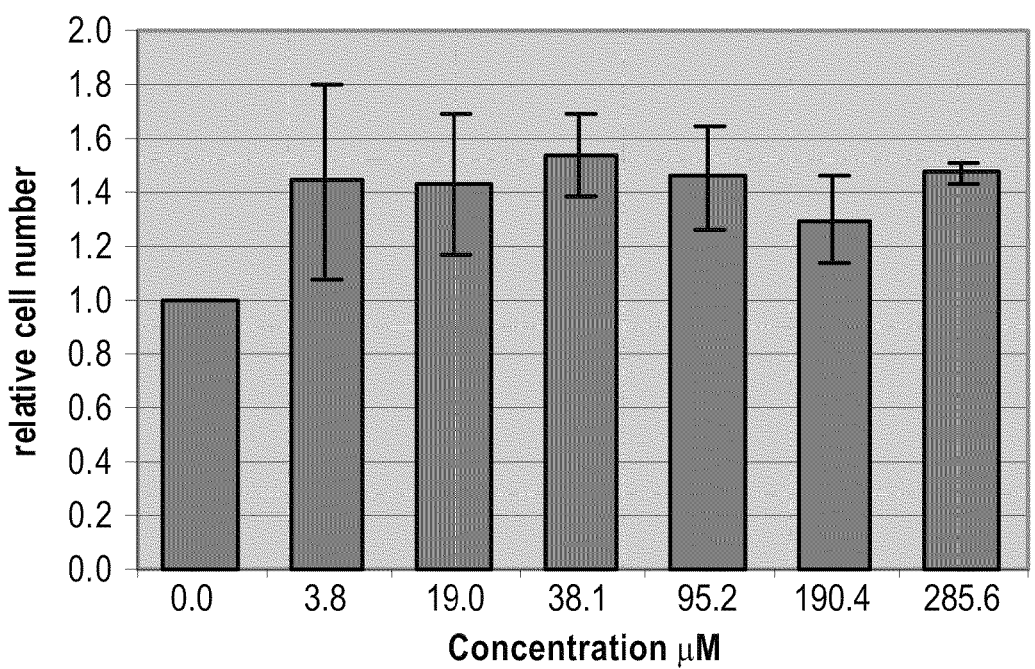
Figure 13:
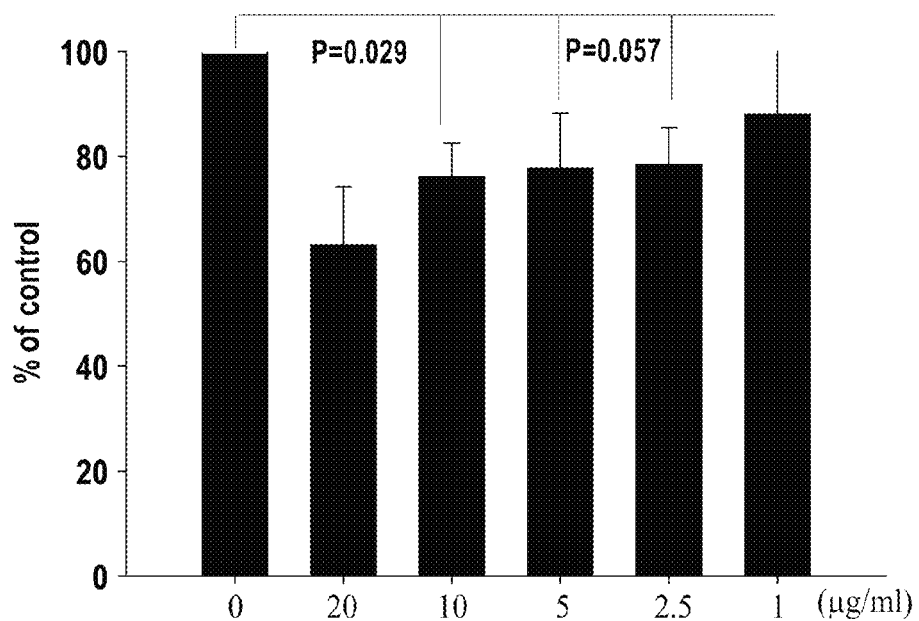
Figure 14:
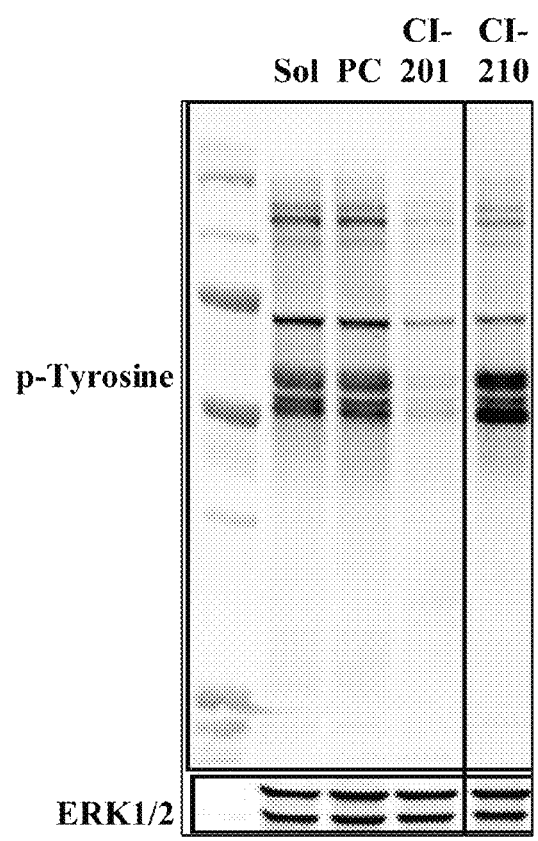
Figure 15A:
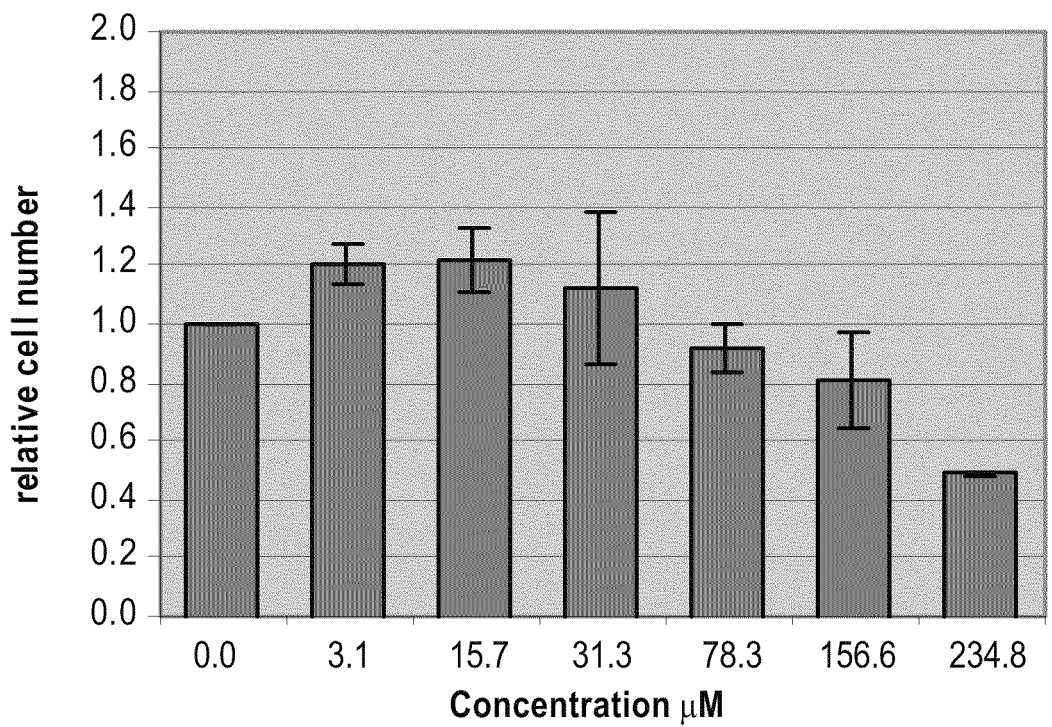
Figure 15B:
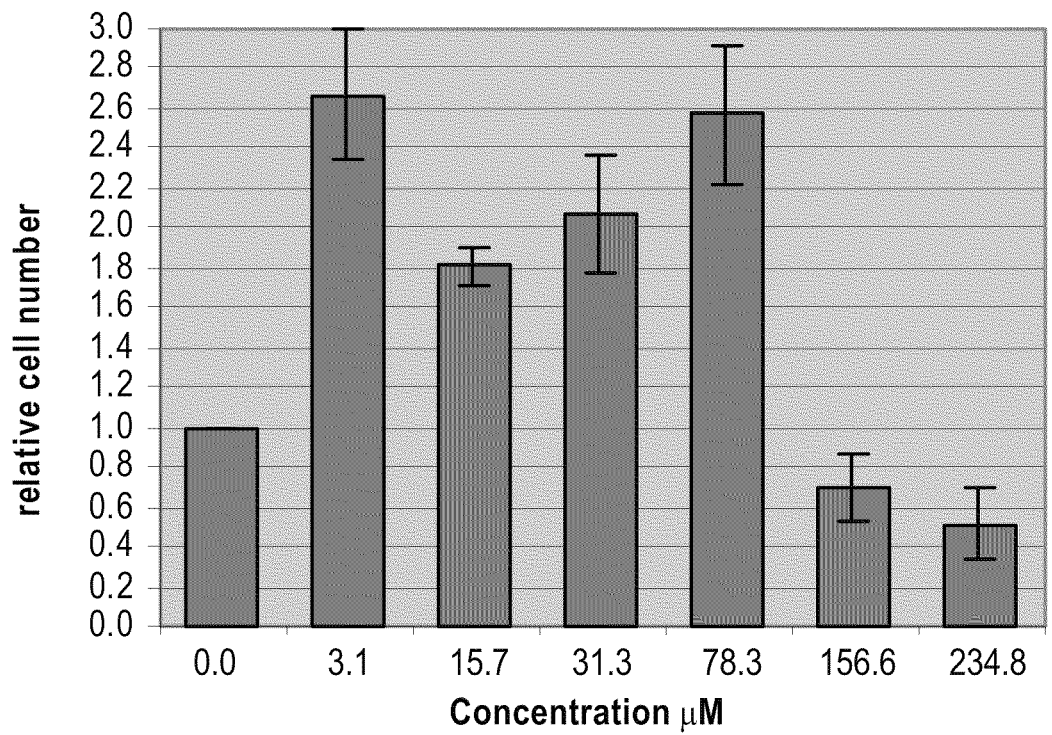
Figure 16:
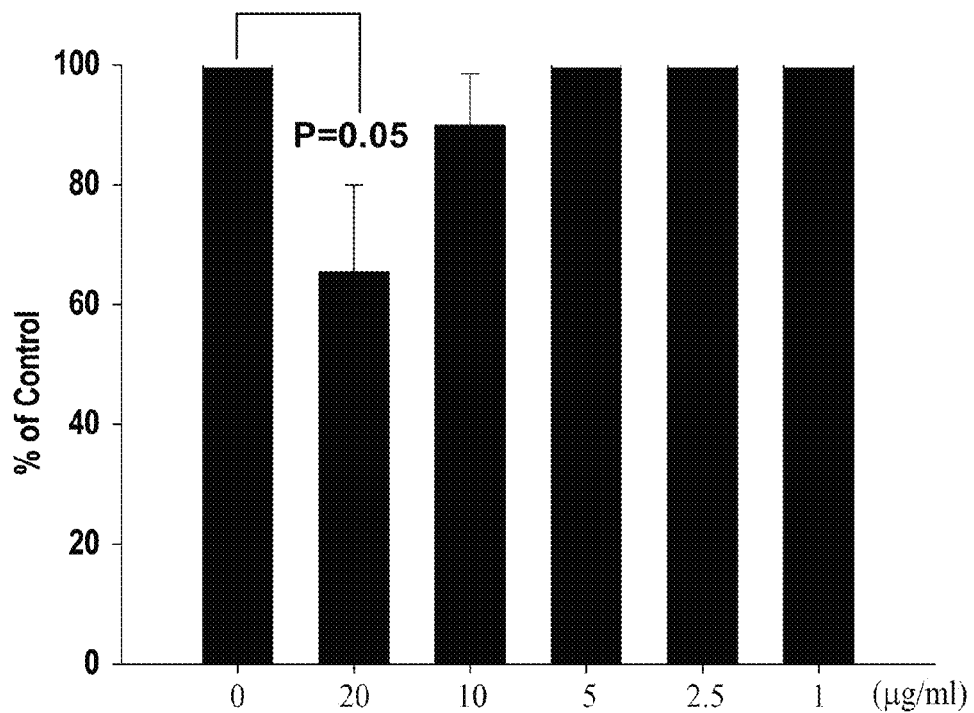
Figure 17:
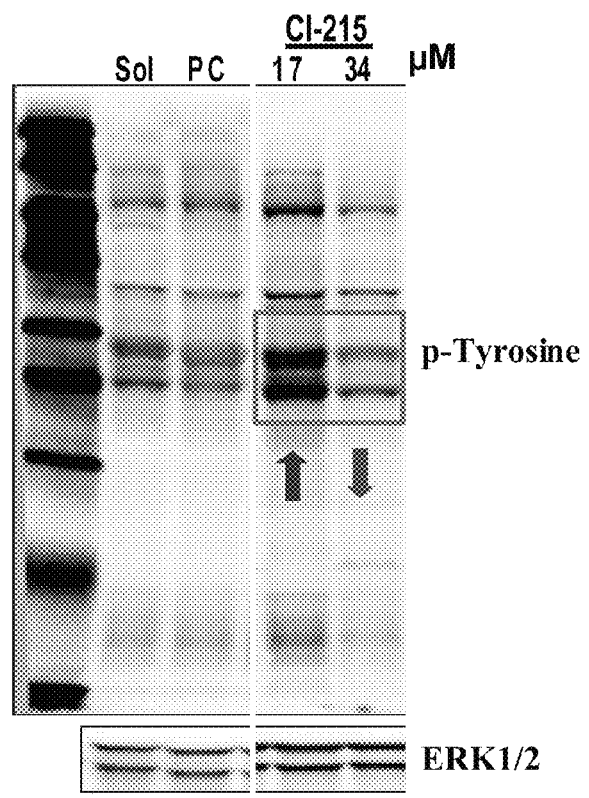
Figure 18:
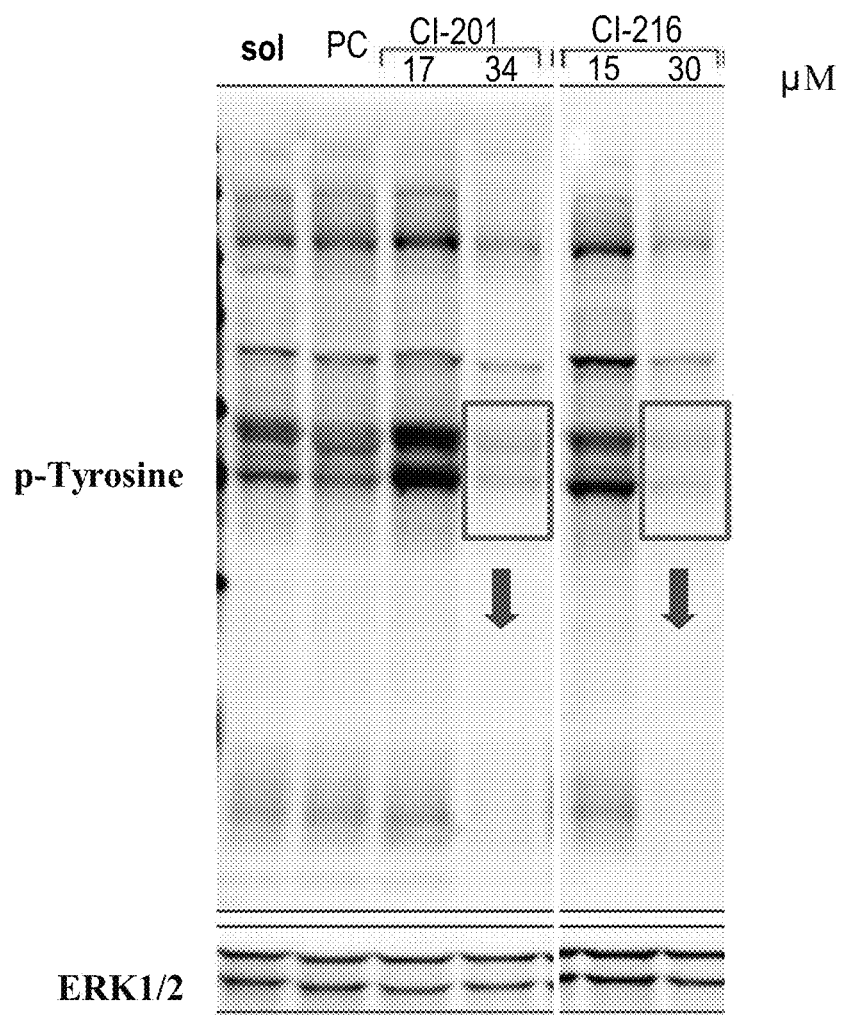
Figure 19:
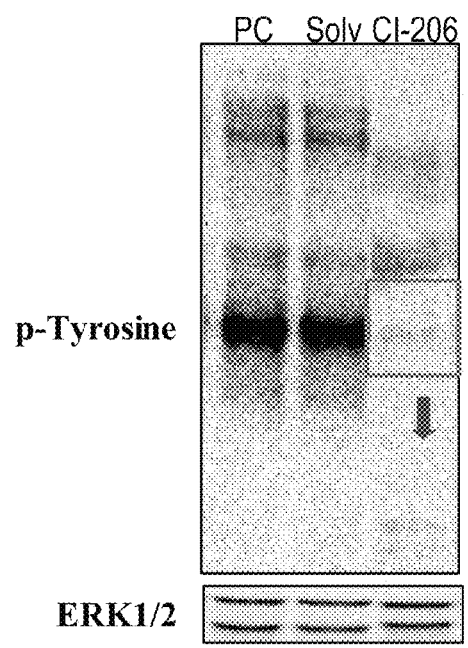
Figure 20:
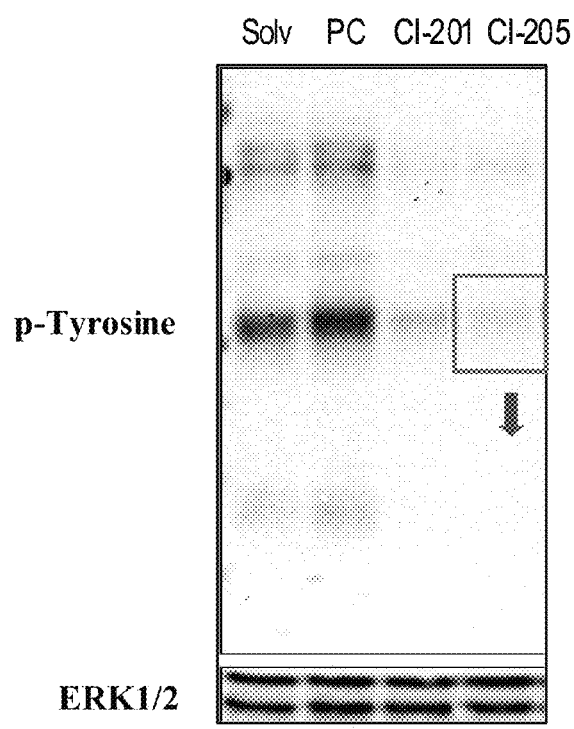
Figure 21A:
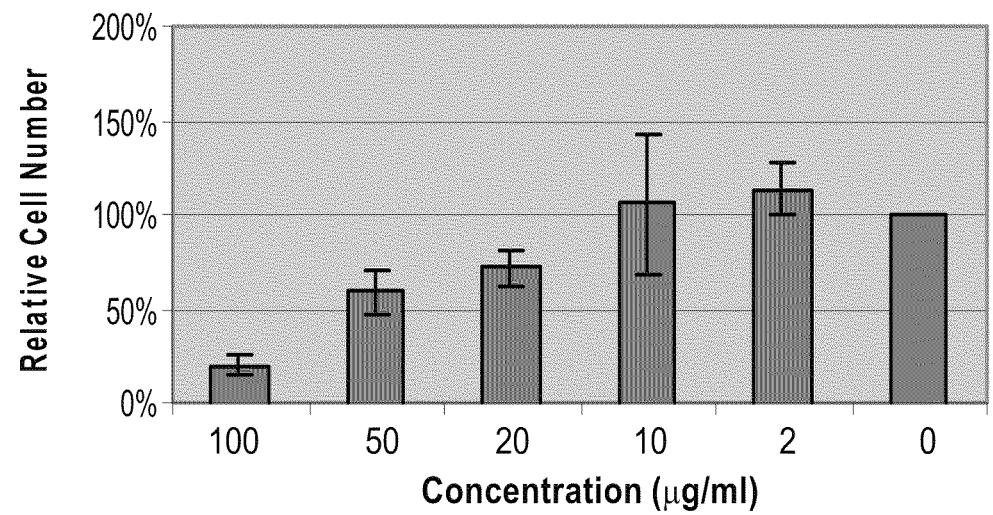
Figure 21B:
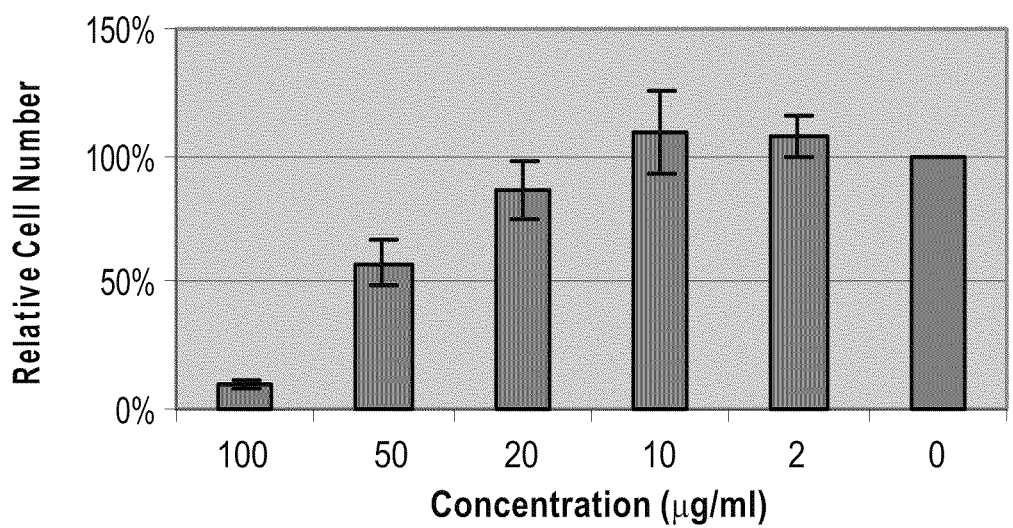
Figure 22A:
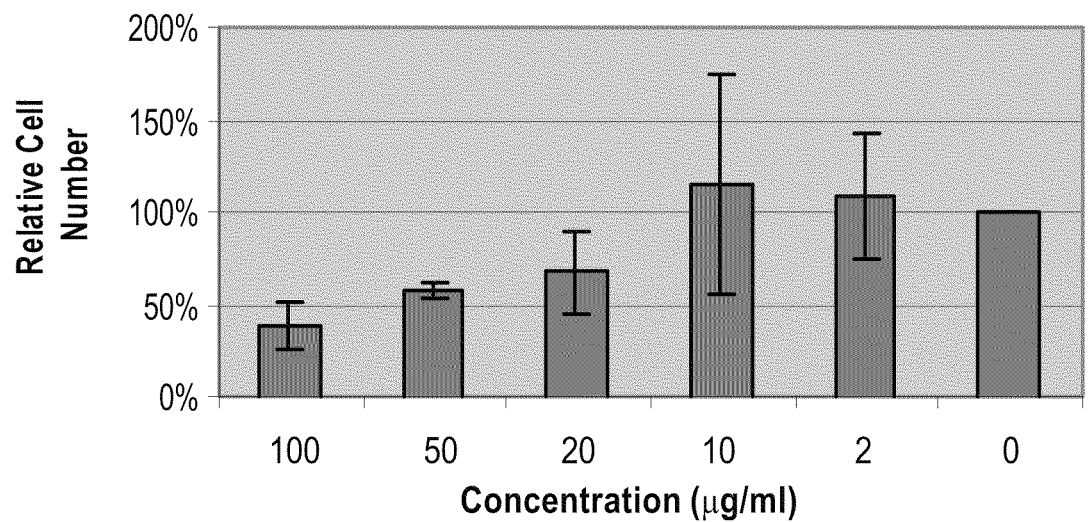
Figure 22B:
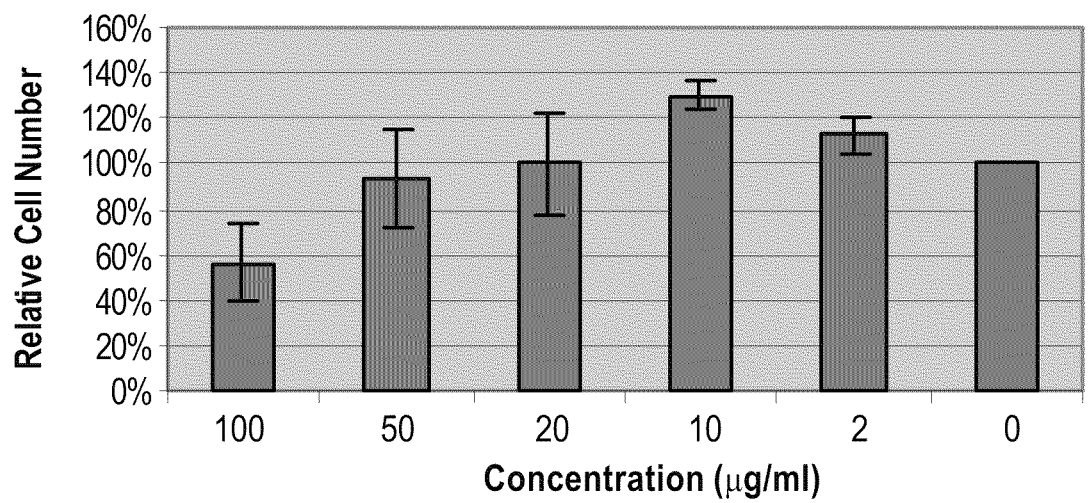
Figure 25A:
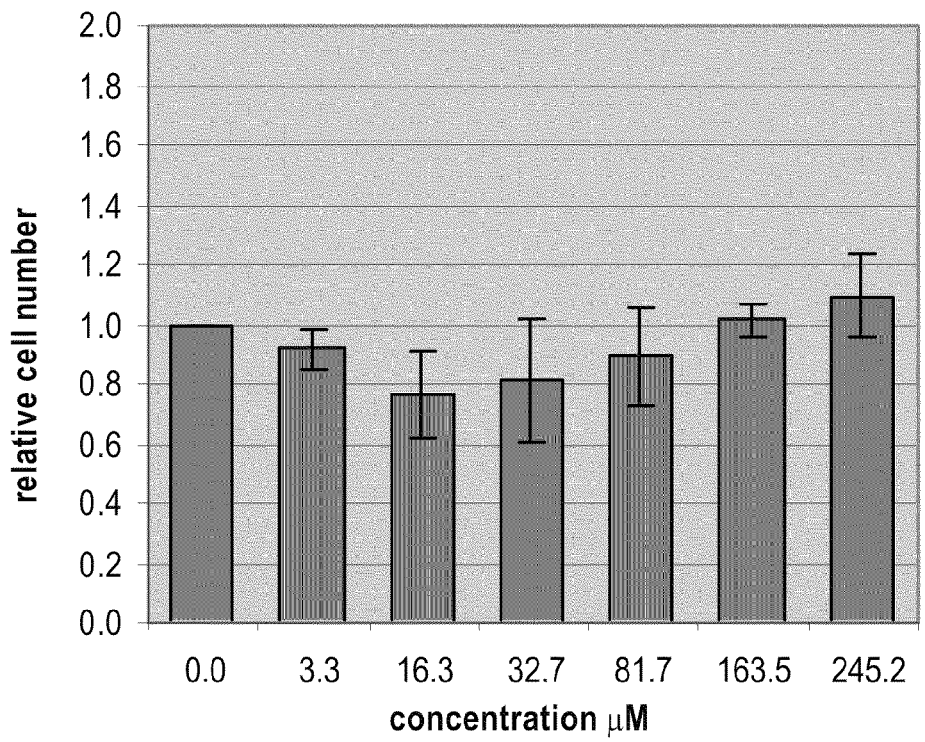
Figure 25B:
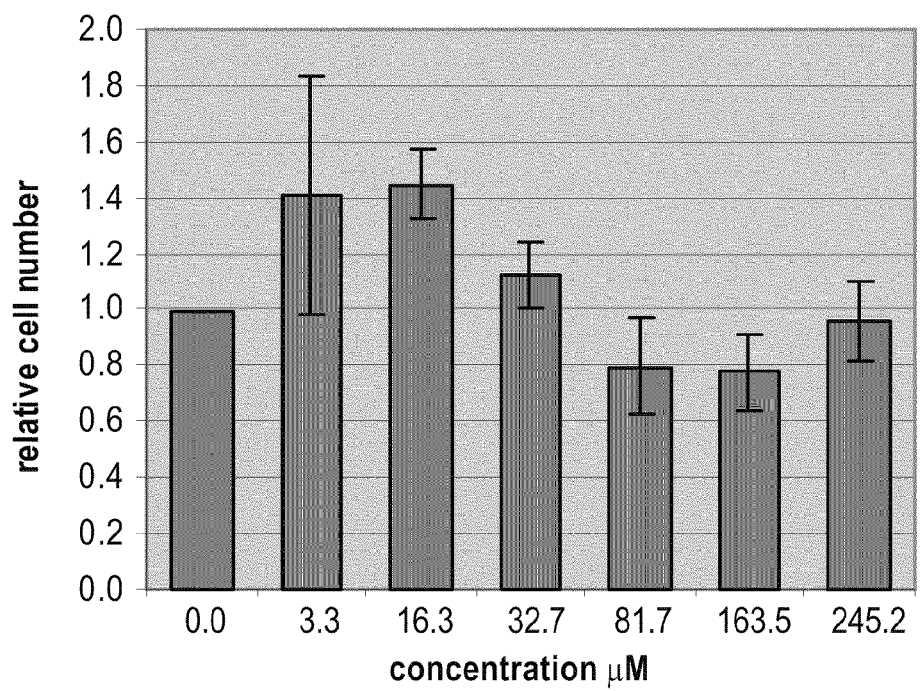
Figure 26A:
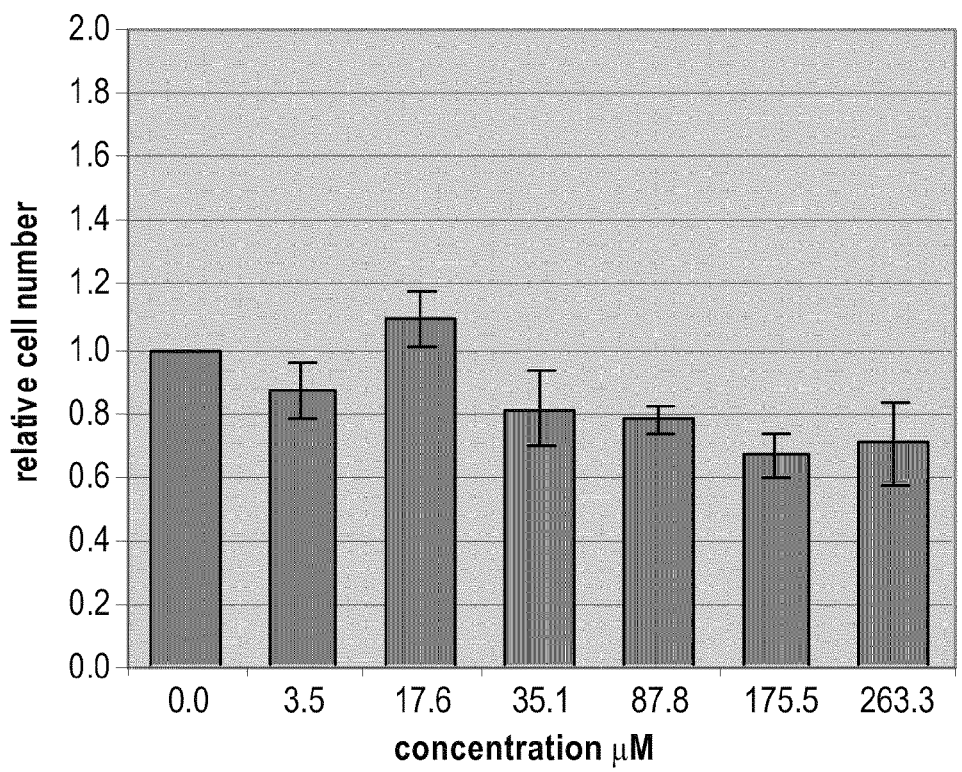
Figure 26B:
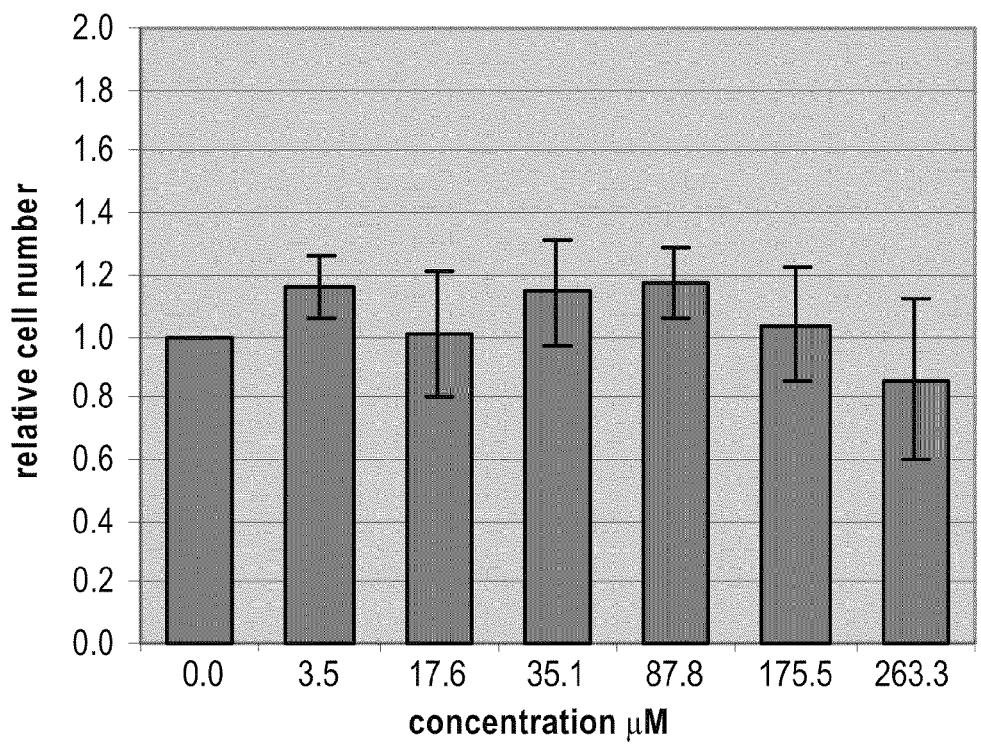
Figure 27:
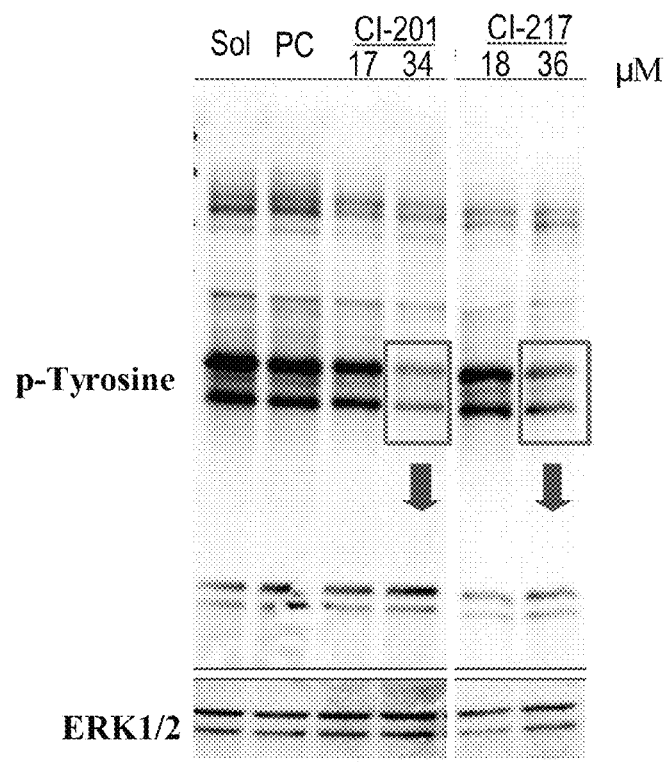
Figure 28:
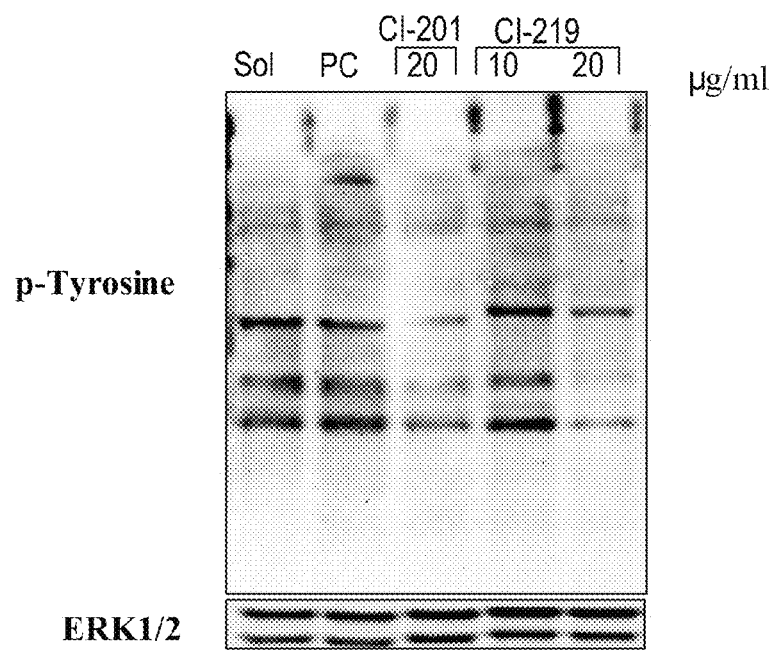
Figure 29:
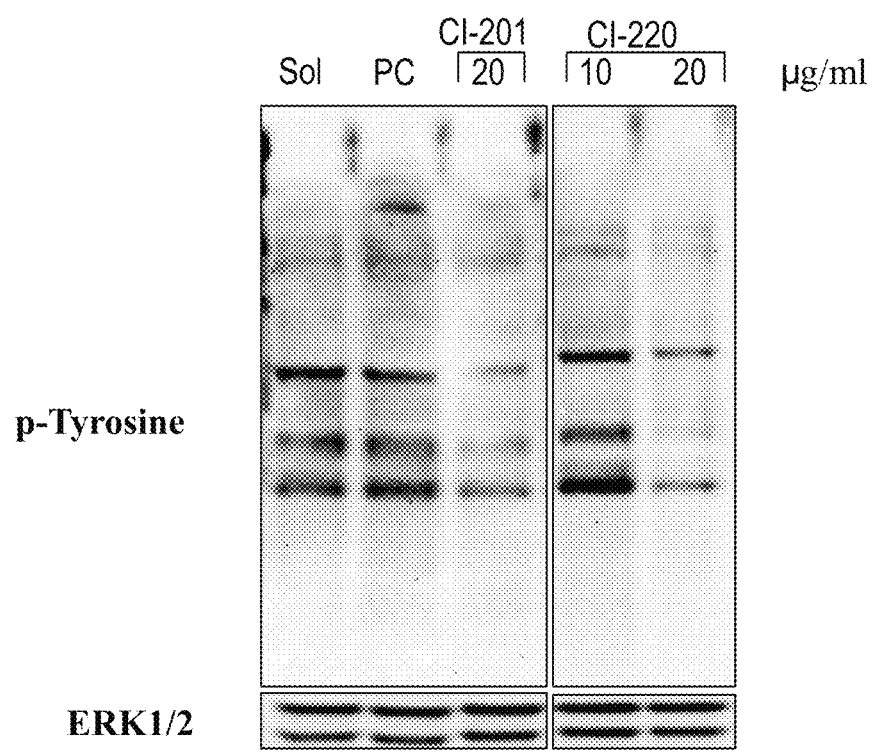
Figure 30A:
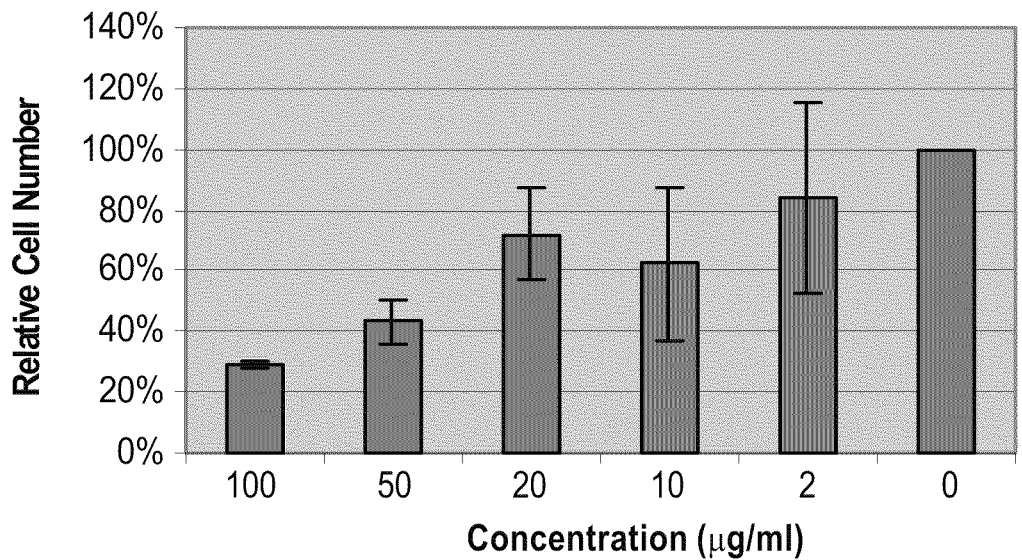
Figure 30B:
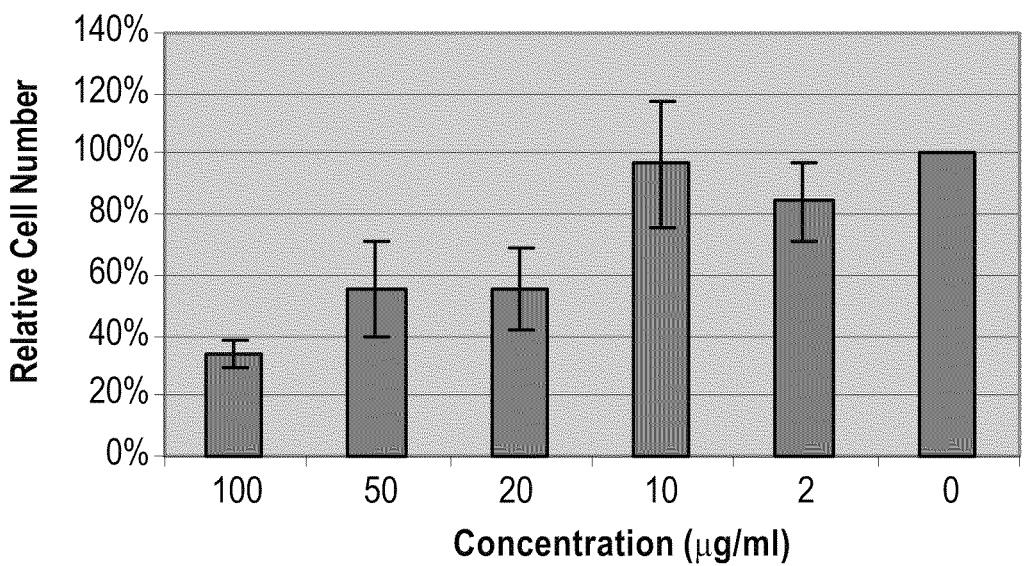
Figure 31:
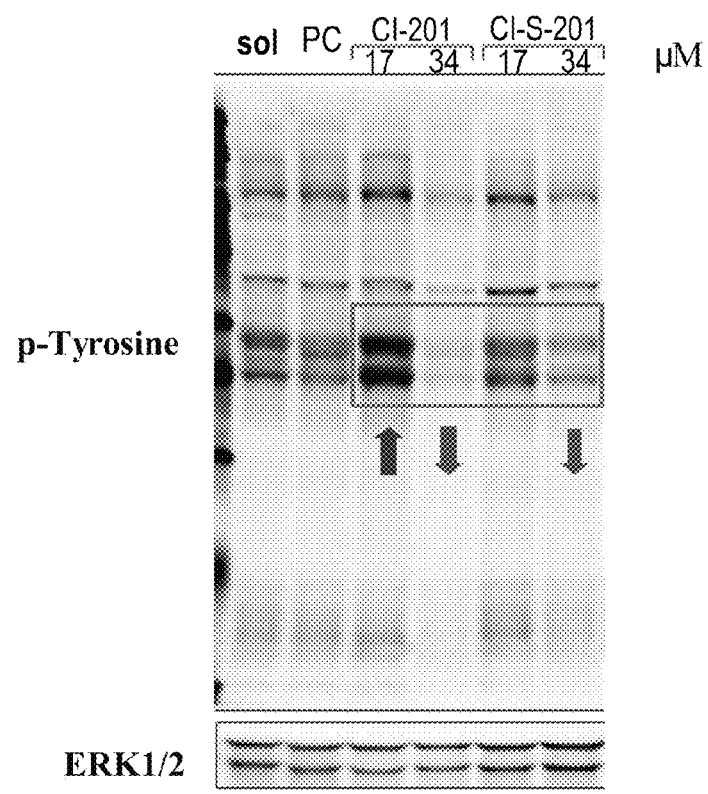
Figure 32:
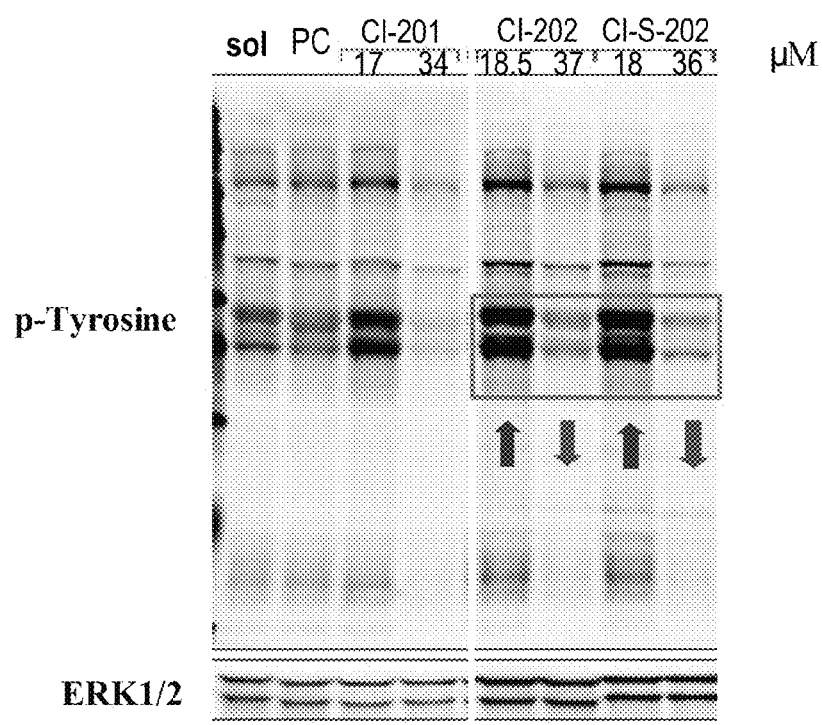
Figure 33A:
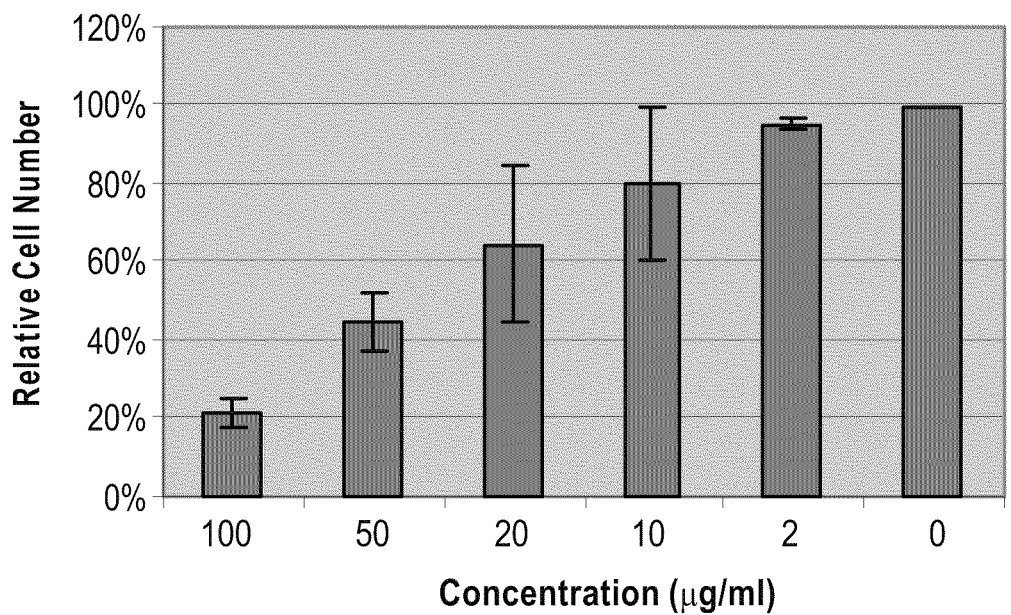
Figure 33B:
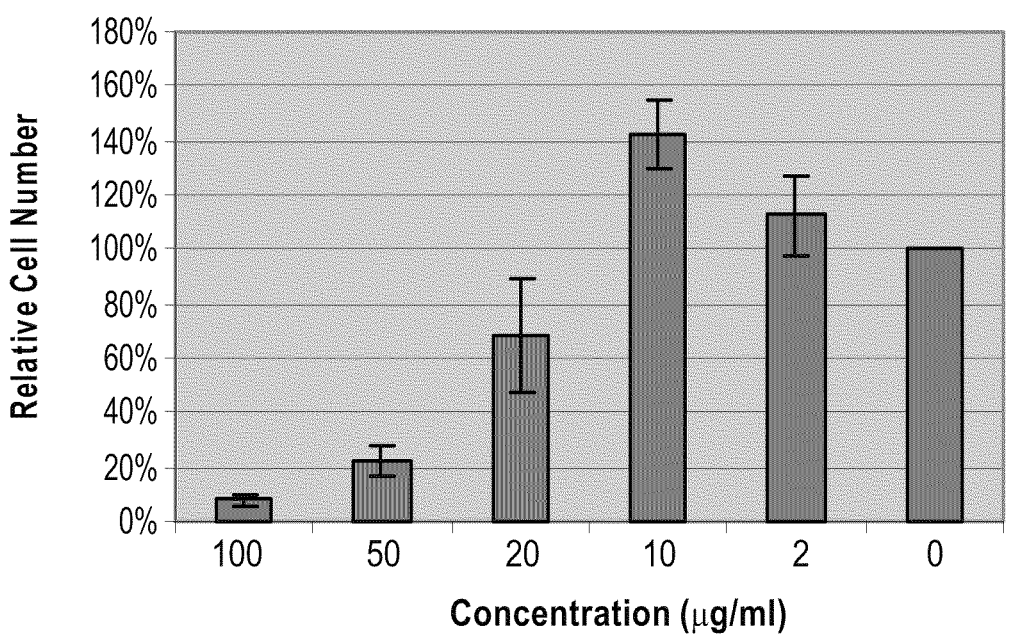
Figure 34:
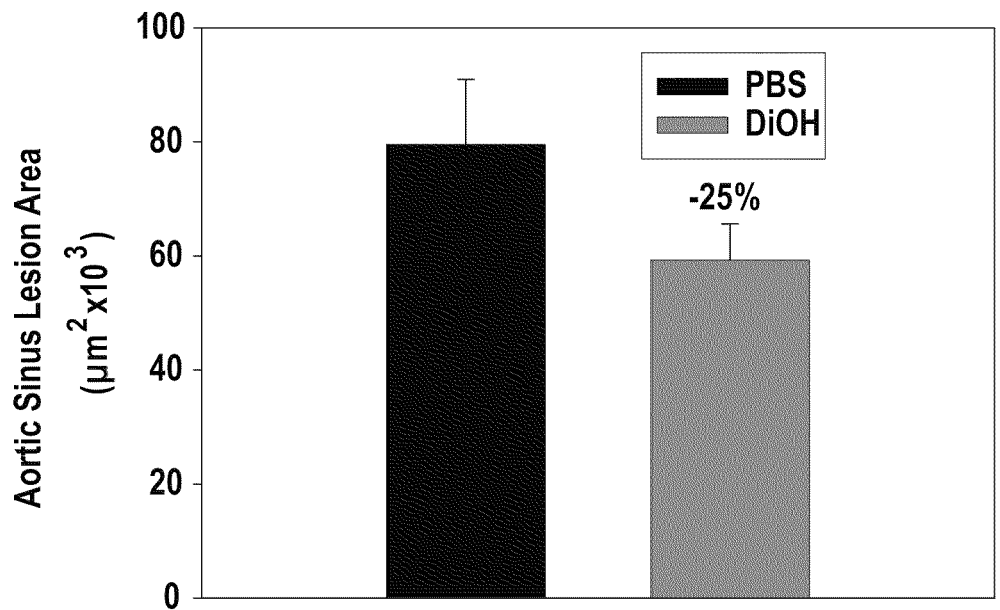
Figure 35:
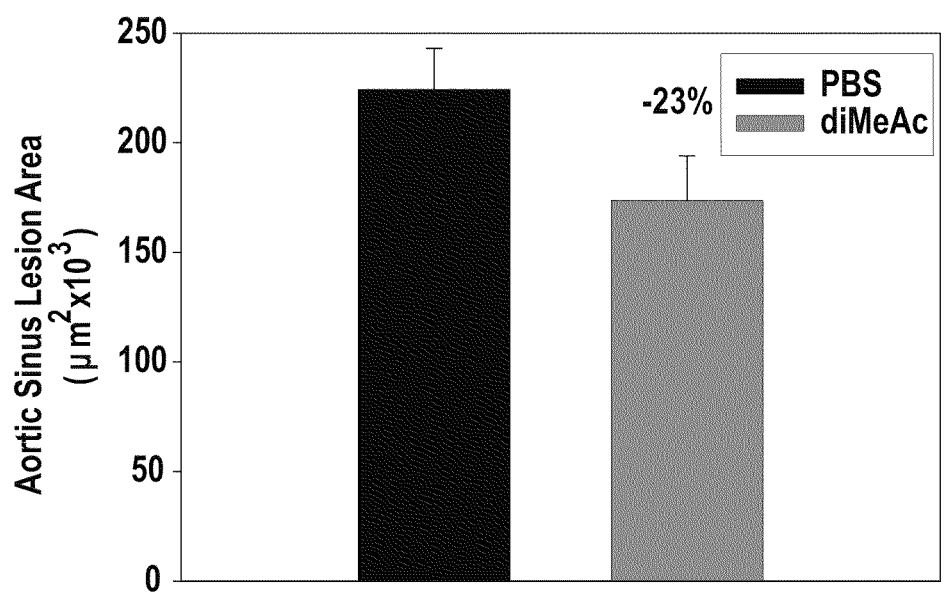
Figure 36A:
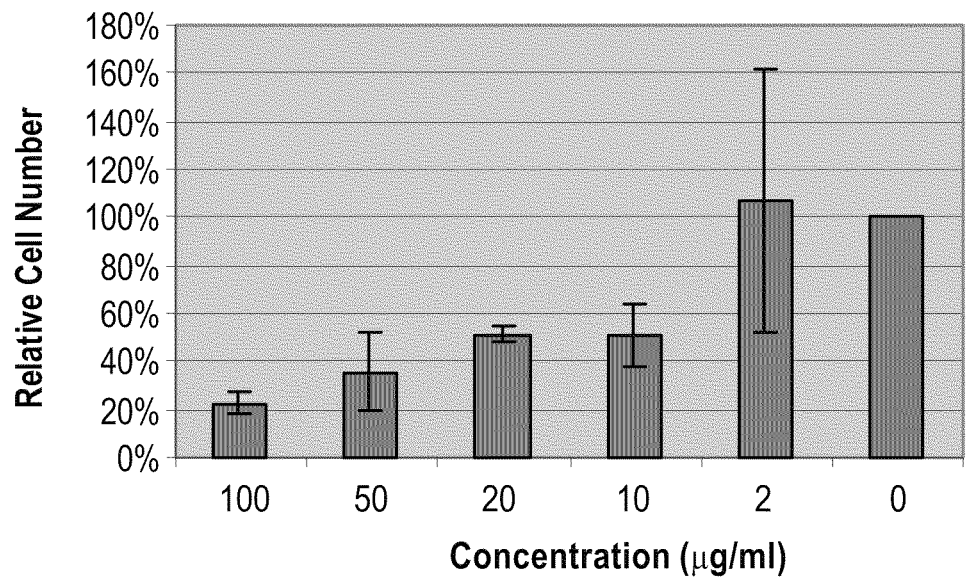
Figure 36B:
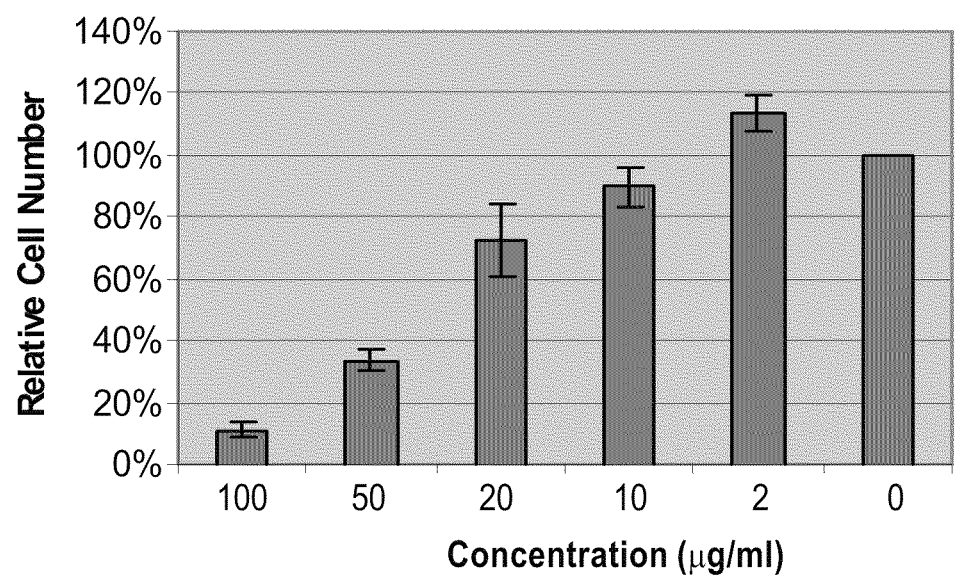
Figure 37:
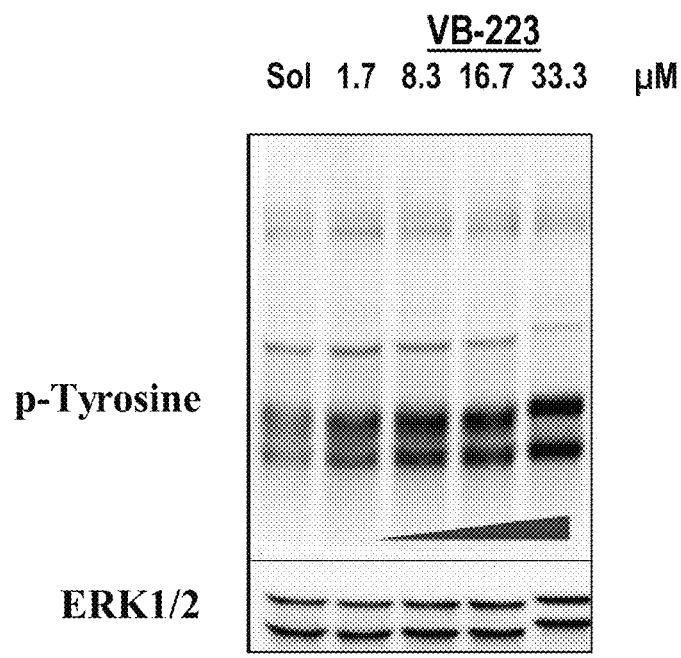
Figure 38:
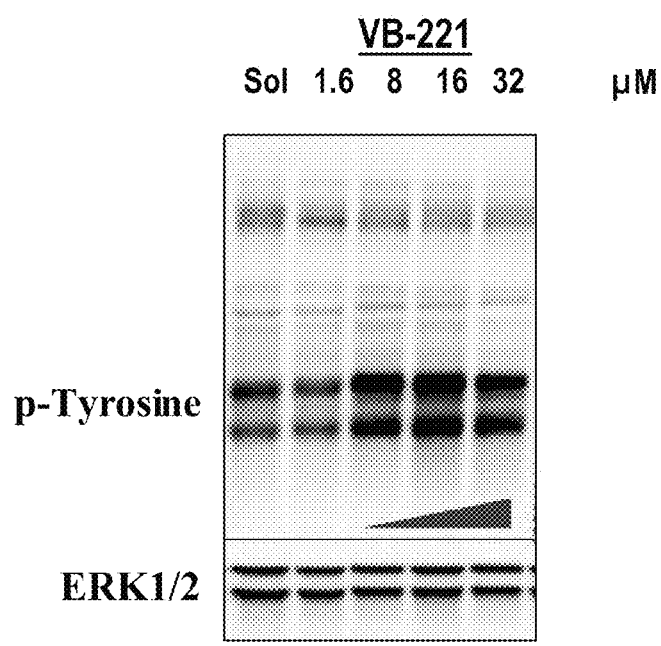
Figure 39:
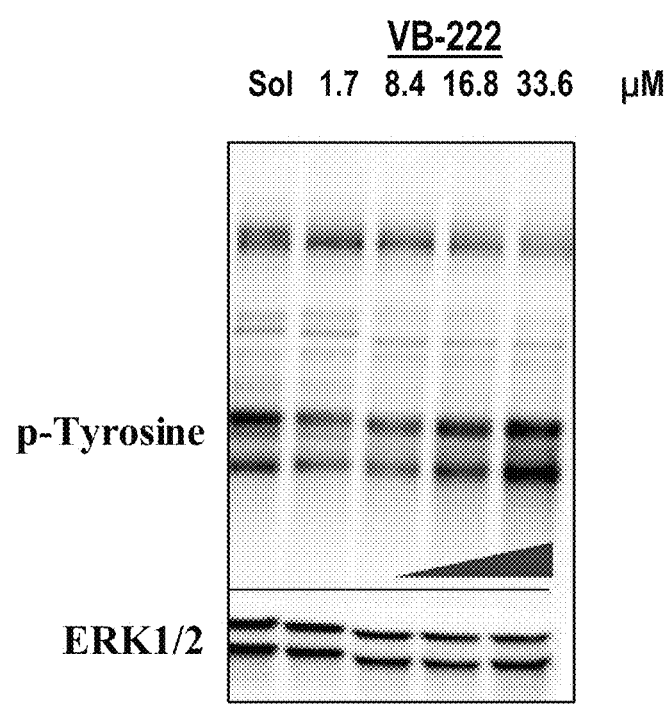

FIG. 3 presents a photograph of a Western blot showing phosphotyrosine (p-Tyrosine) in samples treated with 10 or 20 μg/ml (18.5 or 37 μM) CI-202, 10 or 20 μg/ml (17 or 34 μM) CI-201, phosphatidyl choline (PC) and PBS/1% ethanol (sol); ERK1/2 is shown as a control for protein loading;

FIGS. 4A and 4B are each graphs showing results of an individual experiment testing toxicity of various doses of CI-202;

FIG. 5 is a graph showing the development of MOG-induced experimental autoimmune encephalomyelitis in mice treated with PBS or 4 mg/kg CI-202;

FIG. 6 is a graph showing development of collagen-induced arthritis in mice treated with CI-202 (ethanolamine analog of CI-201) and in control mice;

FIG. 7 is a graph showing IL12/23 p40 production in cells treated with various doses of CI-203 (each bar represents 6 samples) and P values in comparison with the control (0 μg/ml);

FIG. 8 presents a photograph of a Western blot showing phosphotyrosine (p-Tyrosine) in samples treated with 1 or 20 μg/ml (1.6 or 33 μM) of (R)-CI-203 (R-CI-203), and racemic CI-203 (rac-CI-203), 1 or 20 μg/ml (1.7 or 34 μM) of (R)-CI-201 (R-CI-201) and (S)-CI-201 (S-CI-201), and 1 or 20 μg/ml (1.3 or 26 μM) of phosphatidyl choline (Ph.Ch.); ERK1/2 is shown as a control for protein loading;

FIGS. 9A and 9B are each graphs showing results of an individual experiment testing toxicity of various doses of CI-203;

FIG. 10 is a graph showing IL12/23 p40 production in cells treated with various doses of CI-209 (each bar represents 5 samples) and P values ($P<0.008$ for doses of 10 and 20 μg/ml, and $P<0.016$ for doses of 1, 2.5 and 5 μg/ml) in comparison with the control (0 μg/ml);

FIG. 11 presents a photograph of a Western blot showing phosphotyrosine (p-Tyrosine) in samples treated with 20 μg/ml (38 μM) CI-209, CI-201 or phosphatidyl choline (PC) or with PBS/1% ethanol (Sol); ERK1/2 is shown as a control for protein loading;

FIGS. 12A and 12B are each graphs showing results of an individual experiment testing toxicity of various doses of CI-209;

FIG. 13 is a graph showing IL12/23 p40 production in cells treated with various doses of CI-210 (each bar represents 4 samples) and P values (P<0.029 for doses of 10 and 20 μg/ml, and P<0.057 for doses of 2.5 and 5 μg/ml) in comparison with the control (0 μg/ml);

FIG. 14 presents a photograph of a Western blot showing phosphotyrosine (p-Tyrosine) in samples treated with 20 μg/ml (31 μM) CI-210, CI-201 or phosphatidyl choline (PC) or with PBS/1% ethanol (Sol); ERK1/2 is shown as a control for protein loading;

FIGS. 15A and 15B are each graphs showing results of an individual experiment testing toxicity of various doses of CI-210;

FIG. 16 is a graph showing IL12/23 p40 production in cells treated with various doses of CI-216 (each bar represents 4 samples) and P values in comparison with the control (0 μg/ml);

FIG. 17 presents a photograph of a Western blot showing phosphotyrosine (p-Tyrosine) in samples treated with 10 or 20 μg/ml (17 or 34 μM) CI-215, or with phosphatidyl choline (PC) or PBS/1% ethanol (Sol); ERK1/2 is shown as a control for protein loading;

FIG. 18 presents a photograph of a Western blot showing phosphotyrosine (p-Tyrosine) in samples treated with 10 or 20 μg/ml (15 or 30 μM) CI-216, 10 or 20 μg/ml (17 or 34 μM) CI-201, phosphatidyl choline (PC) or PBS/1% ethanol (sol); ERK1/2 is shown as a control for protein loading;

FIG. 19 presents a photograph of a Western blot showing phosphotyrosine (p-Tyrosine) in samples treated with 20 μg/ml (38 μM) of CI-206 or phosphatidyl choline (PC) or with PBS/1% ethanol (Sol); ERK1/2 is shown as a control for protein loading;

FIG. 20 presents a photograph of a Western blot showing phosphotyrosine (p-Tyrosine) in samples treated with 20 μg/ml (35 μM) of CI-205, CI-201 or phosphatidyl choline (PC) or with PBS/1% ethanol (Sol); ERK1/2 is shown as a control for protein loading;

FIGS. 21A and 21B are each graphs showing results of an individual experiment testing toxicity of various doses of CI-206;

FIGS. 22A and 22B are each graphs showing results of an individual experiment testing toxicity of various doses of CI-205;

FIG. 23 presents a photograph of a Western blot showing phosphotyrosine (p-Tyrosine) in samples treated with 20 μg/ml (34 μM) of CI-208, CI-201 or phosphatidyl choline (PC); α-tubulin (α-Tub) is shown as a control for protein loading;

FIGS. 24A and 24B are each graphs showing results of an individual experiment testing toxicity of various doses of CI-208;

FIGS. 25A and 25B are each graphs showing results of an individual experiment testing toxicity of various doses of CI-213;

FIGS. 26A and 26B are each graphs showing results of an individual experiment testing toxicity of various doses of CI-214;

FIG. 27 presents a photograph of a Western blot showing phosphotyrosine (p-Tyrosine) in samples treated with 10 or 20 μg/ml (18 or 36 μM) CI-217, 10 or 20 μg/ml (17 or 34 μM) CI-201, phosphatidyl choline (PC) or PBS/1% ethanol (Sol); ERK1/2 is shown as a control for protein loading;

FIG. 28 presents a photograph of a Western blot showing phosphotyrosine (p-Tyrosine) in samples treated with 10 or 20 μg/ml (31 μM) of CI-219 and 20 μg/ml (34 μM) of CI-201 or phosphatidyl choline (PC), or with PBS/1% ethanol (Sol); ERK1/2 is shown as a control for protein loading;

FIG. 29 presents a photograph of a Western blot showing phosphotyrosine (p-Tyrosine) in samples treated with 10 or 20 μg/ml (34 μM) of CI-220 and 20 μg/ml (34 μM) of CI-201 or phosphatidyl choline (PC), or with PBS/1% ethanol (Sol); ERK1/2 is shown as a control for protein loading;

FIGS. 30A and 30B are each graphs showing results of an individual experiment testing toxicity of various doses of CI-201-PA;

FIG. 31 presents a photograph of a Western blot showing phosphotyrosine (p-Tyrosine) in samples treated with 10 or 20 μg/ml (17 or 34 μM) 1-S-CI-201 (CI-201), 10 or 20 μg/ml (17 or 34 μM) CI-201, phosphatidyl choline (PC) or PBS/1% ethanol (Sol); ERK1/2 is shown as a control for protein loading;

FIG. 32 presents a photograph of a Western blot showing phosphotyrosine (p-Tyrosine) in samples treated with 10 or 20 μg/ml (18 or 36 μM) 1-S-CI-202 (CI-202), 10 or 20 μg/ml (18.5 or 37 μM) CI-202, 10 or 20 μg/ml (17 or 34 μM) CI-201, phosphatidyl choline (PC) or PBS/1% ethanol (sol); ERK1/2 is shown as a control for protein loading;

FIGS. 33A and 33B are each graphs showing results of an individual experiment testing toxicity of various doses of di-OH;

FIG. 34 is a graph showing the area of atherosclerotic lesions in mice treated with di-OH and in control mice;

FIG. 35 is a graph showing the area of atherosclerotic lesions in mice treated with diMeAc and in control mice;

FIGS. 36A and 36B are each graphs showing results of an individual experiment testing toxicity of various doses of diEtAc;

FIG. 37 presents a photograph of a Western blot showing phosphotyrosine (p-Tyrosine) in samples treated with 1, 5, 10 or 20 μg/ml (1.7, 8.3, 16.7 or 33.3 μM) VB-223 or PBS/1% ethanol (Sol); ERK1/2 is shown as a control for protein loading;

FIG. 38 presents a photograph of a Western blot showing phosphotyrosine (p-Tyrosine) in samples treated with 1, 5, 10 or 20 μg/ml (1.6, 8, 16 or 32 μM) VB-221 or PBS/1% ethanol (Sol); ERK1/2 is shown as a control for protein loading; and FIG. 39 presents a photograph of a Western blot showing phosphotyrosine (p-Tyrosine) in samples treated with 1, 5, 10 or 20 μg/ml (1.7, 8.4, 16.8 or 33.6 μM) VB-222 or PBS/1% ethanol (Sol); ERK1/2 is shown as a control for protein loading.

DESCRIPTION OF SPECIFIC EMBODIMENTS OF THE INVENTION

The present invention, in some embodiments thereof, relates to novel oxidized lipids and to methods employing oxidized lipids for treating or preventing an inflammation associated with endogenous oxidized lipids. The oxidized lipids described herein can be utilized in treating or preventing inflammation associated diseases and disorders such as, for example, atherosclerosis and related disorders, autoimmune diseases or disorders, and proliferative diseases or disorders.

The principles and operation of the present invention may be better understood with reference to the figures and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Experimental and clinical evidence indicates a causative role for oxidized LDL (ox LDL) and LDL components in the etiology of an excessive inflammatory response in atherosclerosis. Both cellular and humoral immune reactivity to plaque related oxidized LDL has been demonstrated, suggesting an important anti-oxidized LDL autoimmune component in atherogenesis. Thus, LDL, oxidized LDL and components thereof, have been the targets of numerous therapies for prevention and treatment of heart disease, cerebral-vascular disease and peripheral vascular disease.

A role of oxidized phospholipids in treating inflammation is disclosed, for example, in International Patent Application No. PCT/IL2004/000453 (Publication No. WO 04/106486) and U.S. patent application Ser. No. 11/528,657 (Publication No. 2007-0099868) by the present assignee, both of which are incorporated by reference as if fully set forth herein.

CI-201 (also referred to herein and in the art as VB-201) is a promising oxidized phospholipid which is currently in advanced clinical trials for treatment of inflammatory conditions such as atherosclerosis.

In an attempt to improve treatment of inflammation and diseases and disorders associated with oxidized lipids, the present inventors have prepared novel oxidized phospholipids and structurally related compounds, which are designed to exhibit an improved anti-inflammatory effect and/or improved pharmacological performance.

Improved anti-inflammatory effect can be readily determined by known in vitro and in vivo models for inflammatory processes, and can be exhibited by improved therapeutic effect for a disease to be treated, as further detailed hereinbelow. Improved pharmacological performance includes improved biostability, bioavailability, reduced toxicity and further, improved stability in production, formulation and/or storage. These features can also be determined by experimentations readily recognized by those skilled in the art, and as is further detailed hereinbelow.

As is demonstrated in the Examples section that follows, while reducing the present invention to practice, it was indeed confirmed that newly designed oxidized lipids described herein modulate a cytokine production associated with immune and/or inflammatory response to endogenous oxidized LDL, thereby exhibiting a capability to reduce an inflammatory response in inflammatory diseases such as, but not limited to, atherosclerosis and rheumatoid arthritis.

As is further demonstrated in the Examples section that follows, newly designed oxidized lipids described herein modulate tyrosine phosphorylation, similarly to CI-201, thereby indicating that these newly designed oxidized lipids share biological effects (e.g., anti-inflammatory effects) previously shown to be exhibited by CI-201.

As is further demonstrated in the Examples section that follows, the compounds described herein exhibit minor toxicity, and exhibit biological effects at doses at which the compounds are substantially non-toxic.

Figure 1:
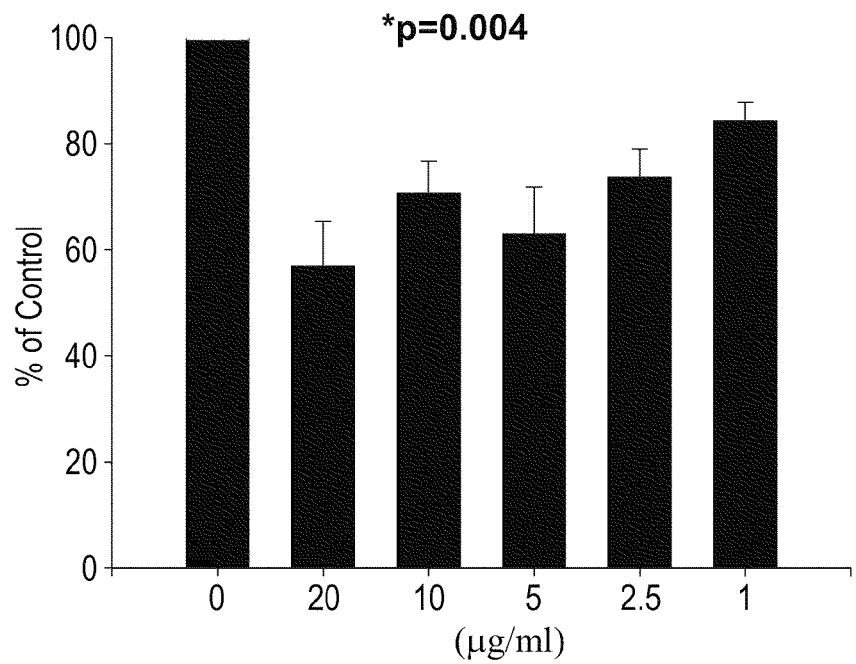
Figure 2:
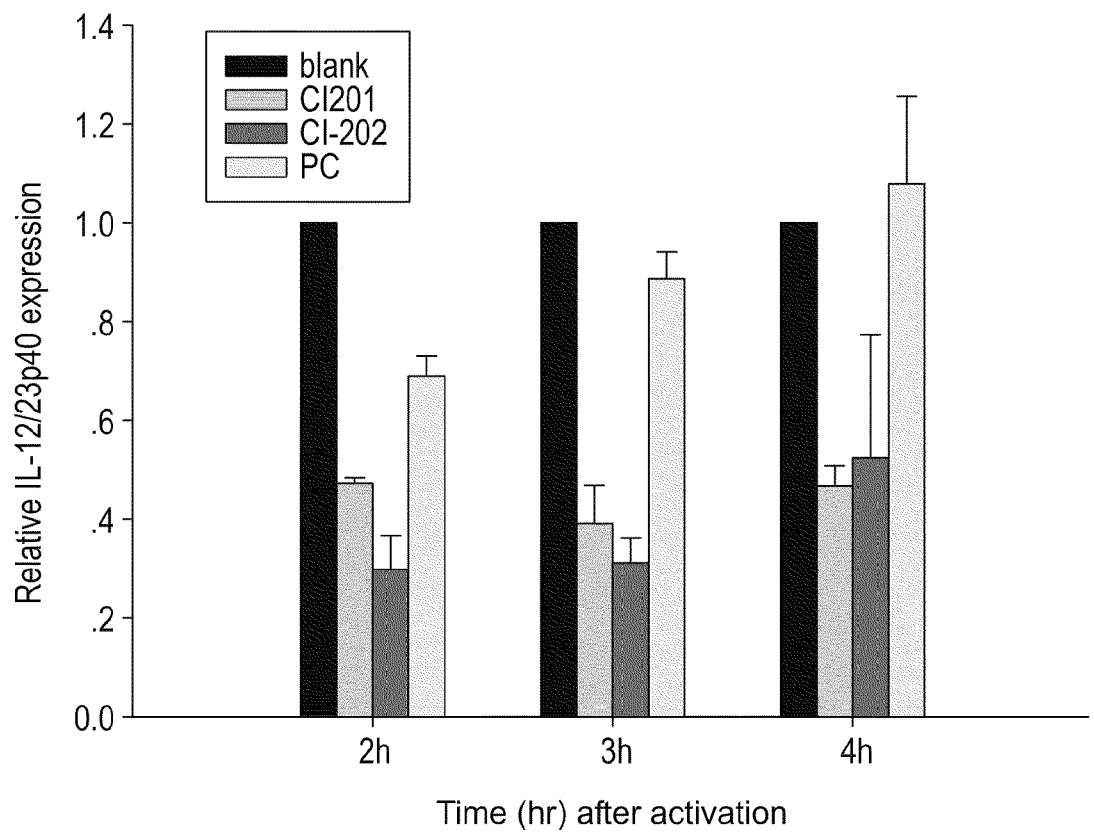

FIGS. 1 and 2 show inhibition by the exemplary compound CI-202 of production of the p40 subunit of the pro-inflammatory cytokines interleukin-12 and interleukin-23. FIG. 3 shows tyrosine phosphorylation modulation by CI-202 as being similar to that exhibited by CI-201. FIGS. 4A and 4B show toxicity profiles of CI-202. FIG. 5 shows that CI-202 is therapeutically effective in a mouse autoimmune encephalomyelitis model (an experimental model of human multiple sclerosis and acute disseminated encephalomyelitis). FIG. 6 shows that CI-202 is therapeutically effective in a mouse arthritis model.

FIG. 7 shows inhibition by the exemplary compound CI-203 of production of the p40 subunit of the pro-inflammatory cytokines interleukin-12 and interleukin-23. FIG. 8 shows tyrosine phosphorylation modulation by CI-203 as being similar to that exhibited by CI-201. FIGS. 9A and 9B show toxicity profiles of CI-203.

FIG. 10 shows inhibition by the exemplary compound CI-209 of production of the p40 subunit of the pro-inflammatory cytokines interleukin-12 and interleukin-23. FIG. 11 shows tyrosine phosphorylation modulation by CI-209. FIGS. 12A and 12B show toxicity profiles of CI-209.

FIG. 13 shows inhibition by the exemplary compound CI-210 of production of the p40 subunit of the pro-inflammatory cytokines interleukin-12 and interleukin-23. FIG. 14 shows tyrosine phosphorylation modulation by CI-210. FIGS. 15A and 15B show toxicity profiles of CI-210.

FIG. 16 shows inhibition by the exemplary compound CI-216 of production of the p40 subunit of the pro-inflammatory cytokines interleukin-12 and interleukin-23. FIG. 18 shows tyrosine phosphorylation modulation by CI-216 as being similar to that exhibited by CI-201.

FIG. 17 shows tyrosine phosphorylation modulation by CI-215.

FIG. 19 tyrosine phosphorylation modulation by the exemplary compound CI-206. FIGS. 21A and 21B show toxicity profiles of CI-206.

FIG. 20 shows tyrosine phosphorylation modulation by the exemplary compound CI-205 as being similar to that exhibited by CI-201. FIGS. 22A and 22B show toxicity profiles of CI-205.

FIG. 23 shows tyrosine phosphorylation modulation by the exemplary compound CI-208 as being similar to that exhibited by CI-201. FIGS. 24A and 24B show toxicity profiles of CI-208.

FIGS. 25A and 25B, and 26A and 26B, show toxicity profiles of the exemplary compounds CI-213 and CI-214, respectively.

FIG. 27 shows tyrosine phosphorylation modulation by the exemplary compound CI-217 as being similar to that exhibited by CI-201.

FIG. 28 shows tyrosine phosphorylation modulation by the exemplary compound CI-219 as being similar to that exhibited by CI-201.

FIG. 29 shows tyrosine phosphorylation modulation by the exemplary compound CI-220 as being similar to that exhibited by CI-201.

FIGS. 30A and 30B show toxicity profiles of the exemplary compound CI-201-PA.

FIG. 31 shows tyrosine phosphorylation modulation by the exemplary compound 1-S-CI-201 as being similar to that exhibited by CI-201.

FIG. 32 shows tyrosine phosphorylation modulation by the exemplary compound 1-S-CI-202 as being similar to that exhibited by CI-201.

FIG. 34 shows that the exemplary compound di-OH is therapeutically effective an a mouse atherosclerosis model. FIGS. 33A and 33B show toxicity profiles of di-OH.

FIG. 35 shows that the exemplary compound diMeAc is therapeutically effective an a mouse atherosclerosis model. FIGS. 36A and 36B show toxicity profiles of diEtAc, a compound closely related to diMeAc.

FIGS. 37-39 shows tyrosine phosphorylation modulation by the exemplary compounds VB-223, VB-221 and VB-222, respectively.

Thus, exemplary compounds described herein have been shown to be biologically active by in vitro tests, and some of the compounds have been confirmed to be therapeutically effective in vivo. The performance of the oxidized lipid which have not yet been tested in vivo can be further tested in suitable animal models such as, for example, those described in the Examples section hereinbelow, in International Patent Application No. PCT/IL2004/000453 (Publication No. WO 04/106486) and U.S. patent application Ser. No. 11/528,657 (Publication No. 2007-0099868), and in models designed as described, for example, in Singh et al., Clinical Chemistry 51:12, 2252-2256 (2005), which is incorporated by reference as if fully set forth herein.

The biostability of the oxidized lipids described herein is improved due to the presence of ether and/or sulfide bonds instead of the ester bonds present in most lipids. Biostability typically improves the therapeutic effect of a compound. The biostability of the oxidized lipids can be determined, for example, by assaying its enzymatic degradation by phospholipase-C, using ELISA or absorbance measurements.

The oxidized lipids described herein can therefore be advantageously recognized as exhibiting an improved effect in treating or preventing inflammation associated with endogenous oxidized lipids, in terms of improved therapeutic and/or pharmacokinetic parameters.

Hence, according to an aspect of embodiments of the present invention there are provided novel oxidized lipids (e.g., oxidized phospholipids) as described herein.

According to an exemplary embodiment, the oxidized lipid is 1-hexadecyl-2-(4-carboxy)butyl-glycero-3-phosphate (also referred to herein as "CI-201-PA"). According to an exemplary embodiment, the oxidized lipid is 1-hexadecyl-2-(4-methylcarboxy)butyl-glycero-3-phosphoethanolamine. According to an exemplary embodiment, the oxidized lipid is 1-hexadecyl-2-(4-methylcarboxy)butyl-glycero-3-phosphocholine (also referred to herein as "CI-208"). According to an exemplary embodiment, the oxidized lipid is 1-hexadecyl-2-(4-carboxy)butyl-glycero-3-phosphoethanolamine (also referred to herein as "CI-202"). According to an exemplary embodiment, the oxidized lipid is 1-hexadecyl-2-(3-carboxy)propyl-glycero-3-phosphoethanolamine (also referred to herein as "CI-206"). According to an exemplary embodiment, the oxidized lipid is 1-hexadecyl-2-(3-carboxy)propyl-glycero-3-phosphocholine (also referred to herein as "CI-205"). According to an exemplary embodiment, the oxidized lipid is 1-hexadecyl-2-(6-carboxy)hexanyl-glycero-3-phosphocholine (also referred to herein as "CI-203"). According to an exemplary embodiment, the oxidized lipid is 1-dodecyl-2-(4-carboxy)butyl-glycero-3-phosphocholine (also referred to herein as "CI-209"). According to an exemplary embodiment, the oxidized lipid is 1-hexadecyl-2-(4-carboxy)butyl-glycero-3-phosphoethanolamine-N-glutaric acid (also referred to herein as "CI-210"). According to an exemplary embodiment, the oxidized lipid is 1-(15'-carboxy)pentadecyl-2-(4 carboxy)butyl-glycero-3-phosphocholine (also referred to herein as "CI-213"). According to an exemplary embodiment, the oxidized lipid is 1-(15'-carboxy)pentadecyl-2-(4 carboxy)butyl-glycero-3-phosphoethanolamine (also referred to herein as "CI-214"). According to an exemplary embodiment, the oxidized lipid is 1-octadecyl-2-(4-carboxy)butyl-glycero-3-phosphocholine (also referred to herein as "CI-215"). According to an exemplary embodiment, the oxidized lipid is 1-octadecyl-2-(4-carboxy)butyl-glycero-3-phosphoethanolamine (also referred to herein as "CI-216"). According to an exemplary embodiment, the oxidized lipid is 1-hexadecyl-2-(2-carboxy)ethyl-glycero-3-phosphocholine (also referred to herein as "CI-217"). According to an exemplary embodiment, the oxidized lipid is 1-S-hexadecyl-2-(4-carboxy)butyl-glycero-3-phosphocholine (also referred to herein as "1-S-CI-201"). According to an exemplary embodiment, the oxidized lipid is 1-S-hexadecyl-2-(4-carboxy)butyl-glycero-3-phosphoethanolamine (also referred to herein as "1-S-CI-202"). According to an exemplary embodiment, the oxidized lipid is 1-hexadecyl-2-(5,6-dihydroxy)hexanyl-glycero-3-phosphocholine (also referred to herein as "di-OH"). According to an exemplary embodiment, the oxidized lipid is 1-(cis-9-hexadecenyl)-2-(4-carboxy)butyl-glycero-3-phosphocholine. According to an exemplary embodiment, the oxidized lipid is 1-hexadecyl-2-(4-carboxy)butyl-glycerol. According to an exemplary embodiment, the oxidized lipid is 1-hexadecyl-2-(5',5'-diethoxypentyl)-glycero-3-phosphocholine (also referred to herein as "diEtAc"). According to an exemplary embodiment, the oxidized lipid is 1-hexadecyl-2-(5',5'-dimethoxypentyl)-glycero-3-phosphocholine (also referred to herein as "diMeAc"). According to an exemplary embodiment, the oxidized lipid is 1-octyl-2-(4-carboxy)butyl-glycero-3-phosphocholine (also referred to herein as "CI-207"). According to an exemplary embodiment, the oxidized lipid is 1-octyl-2-(4-carboxy)butyl-glycero-3-phosphoethanolamine. According to an exemplary embodiment, the oxidized lipid is 1-eicosanyl-2-(4-carboxy)butyl-glycero-3-phosphocholine (also referred to herein as "CI-219"). According to an exemplary embodiment, the oxidized lipid is 1-eicosanyl-2-(4-carboxy)butyl-glycero-3-phosphoethanolamine (also referred to herein as "CI-220"). According to an exemplary embodiment, the oxidized lipid is 1-(2-octyl)dodecyl-2-(4 carboxy)butyl-glycero-3-phosphocholine (also referred to herein as "VB-221"). According to an exemplary embodiment, the oxidized lipid is 1-(2-octyl)dodecyl-2-(4-carboxy)butyl-glycero-3-phosphoethanolamine (also referred to herein as "VB-222"). According to an exemplary embodiment, the oxidized lipid is 1-hexadecyl-2-(4-carboxy)butyl-glycero-3-phosphoserine (also referred to herein as "VB-223").

As used herein, the prefix "1-S-" refers to a compound wherein the oxygen atom at the 1-position of the glycerol backbone (sn-1) is replaced by a sulfur atom, such that the compound is a derivative of 1-thioglycerol instead of a derivative of glycerol.

The prefixes "CI-" and "VB-" are used herein interchangeably.

Depending on the substituents, some carbon atoms in each of the compounds described herein, can be chiral or non-chiral. Thus, in the exemplary compounds described hereinabove, the carbon atom at the 2-position of the glycerol backbone is chiral. Any chiral carbon atom that is present in the compounds described herein can be either in an R-configuration, an S-configuration or as a racemate. Thus present embodiments encompass any combination of chiral and racemic carbon atoms, including all the possible stereoisomers, optical isomers, and enantiomers.

As is demonstrated in the Examples section that follows, the compounds of embodiments of the present invention can be synthesized while retaining a configuration of the starting material. The compounds of the present embodiments can be further selectively synthesized in terms of the stereochemistry of the oxidized group. Hence, by selecting the appropriate starting materials and the appropriate syntheses conditions, the optical purity (e.g., the inclusion of chiral and/or racemic carbons) and the obtained stereoisomers of the resulting compounds can be determined. In cases where racemic mixtures are obtained, known techniques can be used to separate the optical or stereo-isomers. Such techniques are described, for example, in "Organic chemistry, fourth Edition by Paula Yurkanis Bruice, page 180-185 and page 214, Prentice Hall, Upper Sadde River, N.J. 07458".

The above compounds may be characterized according to certain novel structural elements thereof.

Thus, some of the above oxidized lipids comprise a glycerol backbone to which an oxidized side chain is attached at the 2-position thereof, wherein the oxidized side chain is selected from the group consisting of (4-methylcarboxy)butyl, (3-carboxy)propyl, (6-carboxy)hexanyl, (2-carboxy)ethyl, 5,6-dihydroxyhexanyl, 5,5-diethoxypentyl and 5,5-dimethoxypentyl.

Hence, according to some embodiments of the present invention, there are provided compounds collectively represented by a formula:

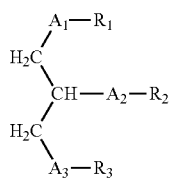

or pharmaceutically acceptable salts thereof, wherein:
(i) $A_1$, $A_2$ and $A_3$ are each independently selected from the group consisting of O and S;
(ii) $R_1$ is selected from the group consisting of an alkyl chain 2-28 carbons in length and

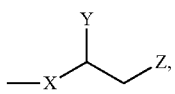

wherein X is a $C_{1-25}$ chain, Y is selected from the group consisting of:

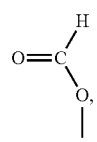

—OH, —H, alkyl, alkoxy, halogen, acetoxy and aromatic functional groups; and
Z is selected from the group consisting of:

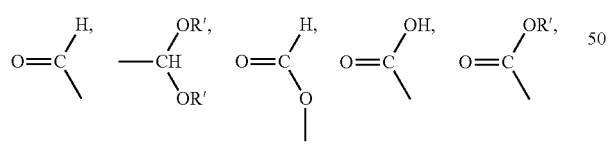

and —OH,
whereas R' is $C_{1-4}$ alkyl; and
(iii) $R_2$ is selected from the group consisting of (4-methylcarboxy)butyl, (3-carboxy)propyl, (6-carboxy)hexanyl, (2-carboxy)ethyl, 5,6-dihydroxyhexanyl, 5,5-diethoxypentyl and 5,5-dimethoxypentyl; and
(iv) $R_3$ is selected from the group consisting of H, acyl, alkyl, phosphate, phosphocholine, phosphoethanolamine, phosphoethanolamine-N-glutaric acid, phosphoserine, and phosphoinositol.

According to some embodiments, $R_1$ is an alkyl chain 2-28 carbons in length.

Some of the oxidized lipids described hereinabove may be characterized in that they comprise a phosphoryl moiety at the 3-position thereof selected from the group consisting of phosphate, phosphoethanolamine, phosphoethanolamine-N-glutaric acid and phosphoserine, or as being non-phosphorylated and non-substituted at the 3-position (i.e., a hydrogen atom is present at the 3-position).

Hence, according to some embodiments of the present invention, there are provided compounds collectively represented by a formula:

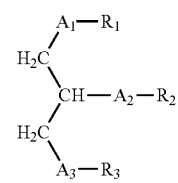

or pharmaceutically acceptable salts thereof, wherein:
(i) $A_1$, $A_2$ and $A_3$ are each independently selected from the group consisting of O and S;
(ii) $R_1$ and $R_2$ are each independently selected from the group consisting of an alkyl chain being 2-28 carbons in length and

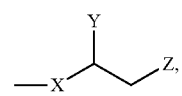

provided that at least one of $R_1$ and $R_2$ is

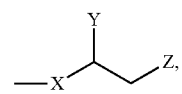

wherein X is a $C_{1-25}$ chain, Y is selected from the group consisting of:

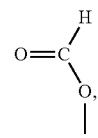

—OH, —H, alkyl, alkoxy, halogen, acetoxy and aromatic functional groups; and
Z is selected from the group consisting of:

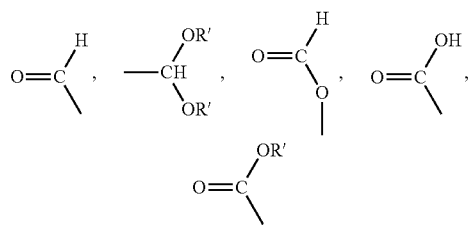

and —OH,
whereas R' is $C_{1-4}$ alkyl; and
(iii) $R_3$ is selected from the group consisting of H, phosphate, phosphoethanolamine, phosphoethanolamine-N-glutaric acid and phosphoserine.

According to some embodiments, $R_1$ is an alkyl chain 2-28 carbons in length. It is to be appreciated that in such embodiments, $R_2$ is

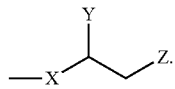

Some of the oxidized lipids described hereinabove may be characterized in that they comprise a side chain at the 1-position thereof selected from the group consisting of dodecyl, octadecyl, octyl, eicosanyl, cis-9-hexadecenyl, (2-octyl) dodecyl and (15-carboxy)pentadecyl.

Hence, according to some embodiments of the present invention, there are provided compounds collectively represented by a formula:

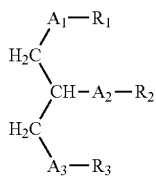

or pharmaceutically acceptable salts thereof, wherein:
(i) $A_1$, $A_2$ and $A_3$ are each independently selected from the group consisting of O and S;
(ii) $R_1$ is selected from the group consisting of dodecyl, octadecyl, octyl, eicosanyl, cis-9-hexadecenyl, (2-octyl) dodecyl and (15-carboxy)pentadecyl;
(iii) $R_2$ is selected from the group consisting of an alkyl chain 2-28 carbons in length and

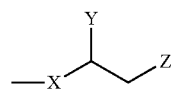

provided that at if $R_1$ is other (15-carboxy)pentadecyl, then $R_2$ is

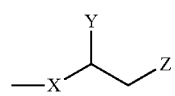

wherein X is a $C_{1-25}$ chain, Y is selected from the group consisting of:

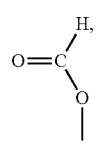

—OH, —H, alkyl, alkoxy, halogen, acetoxy and aromatic functional groups; and

Z is selected from the group consisting of:

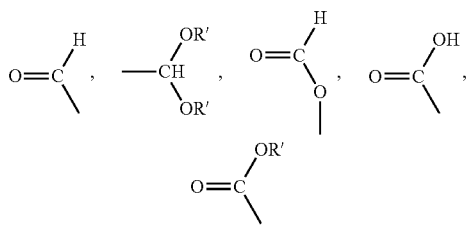

and —OH,
whereas R' is $C_{1-4}$ alkyl; and
(iv) $R_3$ is selected from the group consisting of H, acyl, alkyl, phosphate, phosphocholine, phosphoethanolamine, phosphoethanolamine-N-glutaric acid, phosphoserine, and phosphoinositol.

It is to be appreciated that a (15-carboxy)pentadecyl group described herein corresponds to the

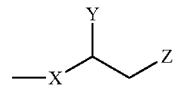

moiety described herein, wherein X is a 13-carbon alkyl chain, Y is hydrogen, and Z is —C(=O)OH.

Similarly, (4-methylcarboxy)butyl, (3-carboxy)propyl, (6-carboxy)hexanyl, (2-carboxy)ethyl, 5,6-dihydroxyhexanyl, 5,5-diethoxypentyl and 5,5-dimethoxypentyl, correspond to the

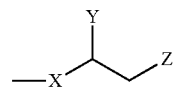

moiety wherein Z is —C(=O)OH (as for (3-carboxy)propyl, (6-carboxy)hexanyl and (2-carboxy)ethyl), wherein Z is —CH(OR')$_2$ (as for 5,5-diethoxypentyl and 5,5-dimethoxypentyl), or wherein Z is —OH (as for 5,6-dihydroxyhexanyl).

Some of the oxidized lipids described hereinabove may be characterized in that they comprise a sulfur atom at the 1-position thereof and oxygen atoms at the 2- and 3-positions thereof.

Hence, according to some embodiments of the present invention, there are provided compounds represented by a formula:

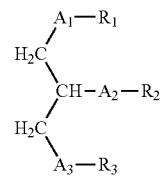

or pharmaceutically acceptable salts thereof, wherein:
(i) $A_1$ is S and $A_2$ and $A_3$ are each O;
(ii) $R_1$ and $R_2$ are each independently selected from the group consisting of an alkyl chain 2-28 carbons in length and

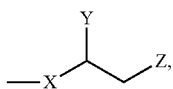

provided that at least one of $R_1$ and $R_2$ is

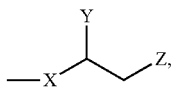

wherein X is a $C_{1-25}$ chain, Y is selected from the group consisting of:

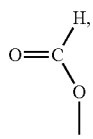

—OH, —H, alkyl, alkoxy, halogen, acetoxy and aromatic functional groups; and

Z is selected from the group consisting of:

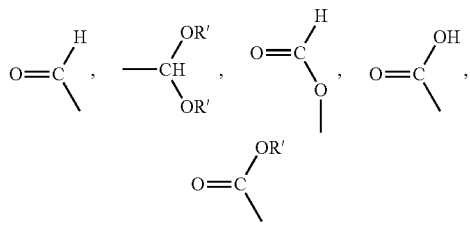

and —OH, whereas R' is $C_{1-4}$ alkyl; and (iii) $R_3$ is selected from the group consisting of H, acyl, alkyl, phosphate, phosphocholine, phosphoethanolamine, phosphoethanolamine-N-glutaric acid, phosphoserine, and phosphoinositol.

According to some embodiments, $R_1$ is an alkyl chain 2-28 carbons in length.

According to some embodiments of the present invention, the variable Z described hereinabove is selected from the group consisting of:

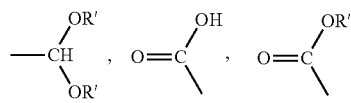

and —OH.

According to optional embodiments of the present invention, the variable Y is selected from the group consisting of H and —OH. In some embodiments, Y is —OH when Z is —OH and/or —O—C(=O)H. In some embodiments, Y is H when Z is —C(=O)H, —CH(OR')$_2$, —C(=O)OH and/or —C(=O)OR'.

According to exemplary embodiments, R' is a saturated, non-substituted $C_{1-4}$ alkyl. Optionally, R' is selected from the group consisting of ethyl and methyl.

According to optional embodiments, the alkyl chain 2-28 carbons in length described herein is saturated, unless specifically indicated otherwise. Optionally, the alkyl chain is non-substituted, unless specifically indicated otherwise.

According to optional embodiments, the variable X described herein a saturated alkyl chain 1 to 25 carbon atoms in length, unless specifically indicated otherwise. Optionally, the alkyl chain is non-substituted, unless specifically indicated otherwise.

As used herein throughout, the term "alkyl" refers to a saturated or unsaturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or non-substituted. When substituted, the substituent group can be, for example, cycloalkyl, aryl, heteroaryl, heteroalicyclic, halo, hydroxy, alkoxy, aryloxy, thiohydroxy, thioalkoxy, thioaryloxy, cyano, nitro, azide, sulfonyl, sulfinyl, sulfonamide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, and amino, as these terms are defined herein. In some embodiments, the alkyl is non-substituted.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, aryl, heteroaryl, heteroalicyclic, halo, hydroxy, alkoxy, aryloxy, thiohydroxy, thioalkoxy, thioaryloxy, cyano, nitro, azide, sulfonyl, sulfinyl, sulfonamide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, and amino, as these terms are defined herein.

An "aryl" group, also referred to herein as "aromatic functional group", refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, cycloalkyl, aryl, heteroaryl, heteroalicyclic, halo, hydroxy, alkoxy, aryloxy, thiohydroxy, thioalkoxy, thioaryloxy, cyano, nitro, azide, sulfonyl, sulfinyl, sulfonamide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, cycloalkyl, aryl, heteroaryl, heteroalicyclic, halo, hydroxy, alkoxy, aryloxy, thiohydroxy, thioalkoxy, thioaryloxy, cyano, nitro, azide, sulfonyl, sulfinyl, sulfonamide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, cycloalkyl, aryl, heteroaryl, heteroalicyclic, halo, hydroxy, alkoxy, aryloxy, thiohydroxy, thioalkoxy, thioaryloxy, cyano, nitro, azide, sulfonyl, sulfinyl, sulfonamide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, and amino, as these terms are defined herein. Representative examples are piperidine, piperazine, tetrahydrofuran, tetrahydropyrane, morpholine and the like.

A "hydroxy" group refers to an —OH group.

An "azide" group refers to a —N=N group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "carbonyl" or "acyl" group refers to a —C(=O)—R group, where R is hydrogen, alkyl, alkenyl, cycloalkyl, aryl, heteroaryl (bonded through a ring carbon) or heteroalicyclic (bonded through a ring carbon) as defined herein.

An "aldehyde" group refers to a carbonyl group, where R is hydrogen.

A "thiocarbonyl" group refers to a —C(=S)—R group, where R is as defined herein.

A "C-carboxy" group refers to a —C(=O)—O—R groups, where R is as defined herein.

An "O-carboxy" group refers to an RC(=O)—O— group, where R is as defined herein.

An "acetoxy" group refers to $CH_3C(=O)—O—$.

An "oxo" group refers to a =O group.

A "carboxylic acid" group refers to a C-carboxyl group in which R is hydrogen.

A "halo" or "halogen" group refers to fluorine, chlorine, bromine or iodine.

A "sulfinyl" group refers to an —S(=O)—R group, where R is as defined herein.

A "sulfonyl" group refers to an —S(=O)$_2$—R group, where R is as defined herein.

A "sulfonamide" group refers to a S(=O)$_2$NR$_2$ group or RS(=O)$_2$—NR— group, with each of R as is defined herein.

An "O-carbamyl" group refers to an —OC(=O)—NR$_2$ group, where each of R is as defined herein.

An "N-carbamyl" group refers to an ROC(=O)—NR— group, where each of R is as defined herein.

An "O-thiocarbamyl" group refers to an —OC(=S)—NR$_2$ group, where each of R is as defined herein.

An "N-thiocarbamyl" group refers to an ROC(=S)NR— group, where each of R is as defined herein.

An "amino" group refers to an —NR$_2$ group where each of R is as defined herein.

A "C-amido" group refers to a —C(=O)—NR$_2$ group, where each of R is as defined herein.

An "N-amido" group refers to an RC(=O)—NR— group, where each of R is as defined herein.

An "urea" group refers to an —NRC(=O)—NR$_2$ group, where each of R is as defined herein.

A "nitro" group refers to an —NO$_2$ group.

A "cyano" group refers to a —C≡N group.

The term "phosphonyl" or "phosphonate" describes a —P(=O)(OR)$_2$ group, with R as defined hereinabove.

The term "phosphinyl" describes a —PR$_2$ group, with each of R as defined hereinabove.

The term "thiourea" describes a —NR—C(=S)—NR— group, with each of R as defined hereinabove.

The present embodiments further encompass any pharmaceutically acceptable salts, prodrugs, hydrates and solvates of the compounds described hereinabove.

The term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. The prodrug may also have improved solubility as compared with the parent drug in pharmaceutical compositions. Prodrugs are also often used to achieve a sustained release of the active compound in vivo. An example, without limitation, of a prodrug would be a compound as described herein, having one or more carboxylic acid moieties, which is administered as an ester (the "prodrug"). Such a prodrug is hydrolysed in vivo, to thereby provide the free compound (the parent drug). The selected ester may affect both the solubility characteristics and the hydrolysis rate of the prodrug.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. An example, without limitation, of a pharmaceutically acceptable salt would be a carboxylate anion and a cation such as, but not limited to, ammonium, sodium, potassium and the like.

The term "solvate" refers to a complex of variable stoichiometry (e.g., di-, tri-, tetra-, penta-, hexa-, and so on), which is formed by a solute (the compound of present embodiments) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

As is detailed hereinbelow, the newly designed compounds of present embodiments exert a highly beneficial immunomodulation activity and therefore can be utilized in various therapeutic applications. Utilizing these compounds in therapeutic application involves administration thereof either per se, or as a part of a pharmaceutical composition where it is mixed with suitable carriers or excipients.

Thus, according to another aspect of embodiments of the present invention, there is provided a pharmaceutical composition, which comprises, as an active ingredient, any of the compounds described herein, and a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the compounds (oxidized lipids) described hereinabove accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

In an optional embodiment of the present invention, the pharmaceutical compositions are designed for modulating an immune and/or inflammatory response via mucosal administration.

In another optional embodiment of the present invention, the pharmaceutical compositions are designed for modulating an immune and/or inflammatory response via oral administration.

Optionally, the pharmaceutical compositions of embodiments of the present invention are designed for nasal, or intraperitoneal administration, as is detailed hereinafter.

Pharmaceutical compositions of embodiments of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with present embodiments thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, for example, in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to embodiments of the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of embodiments of the present invention may also be formulated in rectal compositions such as suppositories or retention enemas, using, e.g., conventional suppository bases such as cocoa butter or other glycerides.

Pharmaceutical compositions suitable for use in context of the present embodiments include compositions wherein the active ingredients are contained in an amount effective to achieve the intended purpose. More specifically, a therapeutically effective amount means an amount of active ingredients effective to prevent, alleviate or ameliorate symptoms of a disorder (e.g., atherosclerosis) or prolong the survival of the subject being treated.

Determination of a therapeutically effective amount is well within the capability of those skilled in the art, especially in light of the detailed disclosure provided herein.

For any preparation used in the methods of embodiments of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or in experimental animals (e.g., as exemplified hereinbelow in the Examples section). The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See, e.g., Fingl, et al., 1975, in "The Pharmacological Basis of Therapeutics", Ch. 1 p. 1).

Dosage amount and interval may be adjusted individually to provide plasma or brain levels of the active ingredient (minimal effective concentration, MEC) that are sufficient to induce or suppress an inflammation (e.g., angiogenesis). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of embodiments of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation described herein formulated in a compatible pharmaceutical carrier may also be prepared, placed in an appropriate container, and labeled for treatment of an indicated condition, as is further detailed hereinbelow.

Thus, in an optional embodiment of the present invention, the pharmaceutical composition is packaged in a packaging material and identified in print, on or in the packaging material, for use in the treatment or prevention of an inflammation associated with an endogenous oxidized lipid. A list of representative examples of diseases and disorders associated with such an inflammation is provided hereinbelow.

Alternatively or additionally, the pharmaceutical composition is packaged in a packaging material and identified in print, on or in the packaging material, for use in decreasing of a level of a cytokine selected from the group consisting of interleukin-12 and interleukin-23, and/or for use in the treatment of a disease or disorder in which decreasing a level of a cytokine selected from the group consisting of interleukin-12 and interleukin-23 is beneficial.

As is further described in detail hereinbelow, the pharmaceutical composition of present embodiments can further include an additional compound, which is useful in the treatment or prevention of the inflammation described herein.

As is described in detail in the Examples section that follows, representative examples of the newly designed compounds of embodiments of the present invention have been found effective in modulating a level of cytokines associated with an immune response and with inflammation. These results indicate that these compounds are effective for inhibiting an immune response and inflammation associated with an endogenous oxidized lipid.

Hence, according to another aspect of embodiments of the present invention there is provided a method of treating or preventing an inflammation associated with an endogenous oxidized lipid. The method according to this aspect of the present embodiments is effected by administering to a subject in need thereof a therapeutically effective amount of one or more oxidized lipids as described herein.

As used herein, the phrase "an endogenous oxidized lipid" refers to one or more oxidized lipids that are present or formed in vivo, as a result of inflammatory and other cell- or humoral-mediated processes.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the phrase "treating or preventing" includes abrogating, substantially inhibiting, slowing or reversing the progression of a disease, substantially ameliorating clinical symptoms of a disease or substantially preventing the appearance of clinical symptoms of a disease.

Examples of subjects suitable for such treatment include subjects suffering from a disease or disorder associated with an inflammation, as is detailed hereinbelow. Suitable individual subjects according to present embodiments include mammals such as canines, felines, ovines, porcines, equines, and bovines. Optionally, the individual subjects according to the present embodiments are humans.

As used herein, the phrase "inflammation associated with an endogenous oxidized lipid" describes an inflammation that is associated with the in vivo formation or presence of one or more oxidized lipids (e.g., oxidized LDL, oxidized membrane lipids, etc.).

Inflammation is a protective response of the body to an injury. Several cytokines play key roles in mediating inflammatory reactions amongst which are interleukins 12 and 23 (IL-12 and IL-23). Excessive inflammation is oftentimes deleterious, involving or leading to a myriad of diseases and disorders. As is explained in detail hereinabove, excessive inflammatory response is typically associated with oxidized lipid epitopes.

Hence, according to optional embodiments of the present invention, there is provided a method of decreasing a level of a cytokine selected from the group consisting of interleukin-12 and interleukin-23 in a subject.

According to additional optional embodiments of the present invention, there is provided a method for treating a disease or disorder in which decreasing a level of a cytokine selected from the group consisting of interleukin-12 and interleukin-23 is beneficial.

The above methods are effected by administering to a subject in need thereof a therapeutically effective amount of one or more oxidized lipids as described herein.

According to another aspect of embodiments of the present invention, there is provided a use of at least one oxidized lipid described herein in the manufacture of a medicament. Optional formulations for a medicament are described herein.

In some embodiments, the medicament is for treating or preventing an inflammation associated with an endogenous oxidized lipid, as described in further detail herein.

In some embodiments, the medicament is for decreasing a level of a cytokine selected from the group consisting of interleukin-12 and interleukin-23 in a subject In some embodiments, the medicament is for treating a disease or disorder in which decreasing a level of a cytokine selected from the group consisting of interleukin-12 and interleukin-23 is beneficial.

The anti-inflammatory effect of oxidized lipids described herein may be utilized in treating or preventing inflammation-associated disease or disorders in which endogenous oxidized LDL or any other endogenous oxidized lipid is implicated. Such diseases and disorders include, for example, diseases or disorders associated with plaque formation, including but not limited to atherosclerosis, atherosclerotic cardiovascular disease, cerebrovascular disease, peripheral vascular disease, stenosis, restenosis and in-stent-stenosis, as well as autoimmune diseases or disorders, neurodegenerative diseases or disorders, proliferative disease or disorders and aging processes.

Thus, representative examples of diseases or disorders associated with an inflammation, which in turn is associated with an endogenous oxidized lipids, and are therefore treatable by the method of embodiments of the present invention include, for example, idiopathic inflammatory diseases or disorders, chronic inflammatory diseases or disorders, acute inflammatory diseases or disorders, autoimmune diseases or disorders, infectious diseases or disorders, inflammatory malignant diseases or disorders, inflammatory transplantation-related diseases or disorders, inflammatory degenerative diseases or disorders, diseases or disorders associated with a hypersensitivity, inflammatory cardiovascular diseases or disorders, inflammatory cerebrovascular diseases or disorders, peripheral vascular diseases or disorders, inflammatory glandular diseases or disorders, inflammatory gastrointestinal diseases or disorders, inflammatory cutaneous diseases or disorders, inflammatory hepatic diseases or disorders, inflammatory neurological diseases or disorders, inflammatory musculo-skeletal diseases or disorders, inflammatory renal diseases or disorders, inflammatory reproductive diseases or disorders, inflammatory systemic diseases or disorders, inflammatory connective tissue diseases or disorders, inflammatory tumors, necrosis, inflammatory implant-related diseases or disorders, inflammatory aging processes, immunodeficiency diseases or disorders, proliferative diseases and disorders and inflammatory pulmonary diseases or disorders, as is detailed hereinbelow.

Non-limiting examples of hypersensitivities include Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity, delayed type hypersensitivity, helper T lymphocyte mediated hypersensitivity, cytotoxic T lymphocyte mediated hypersensitivity, TH1 lymphocyte mediated hypersensitivity, and TH2 lymphocyte mediated hypersensitivity.

Non-limiting examples of inflammatory cardiovascular disease or disorder include occlusive diseases or disorders, atherosclerosis, a cardiac valvular disease, stenosis, restenosis, in-stent-stenosis, myocardial infarction, coronary arterial disease, acute coronary syndromes, congestive heart failure, angina pectoris, myocardial ischemia, thrombosis, Wegener's granulomatosis, Takayasu's arteritis, Kawasaki syndrome, anti-factor VIII autoimmune disease or disorder, necrotizing small vessel vasculitis, microscopic polyangiitis, Churg and Strauss syndrome, pauci-immune focal necrotizing glomerulonephritis, crescentic glomerulonephritis, antiphospholipid syndrome, antibody induced heart failure, thrombocytopenic purpura, autoimmune hemolytic anemia, cardiac autoimmunity, Chagas' disease or disorder, and anti-helper T lymphocyte autoimmunity.

Stenosis is an occlusive disease of the vasculature, commonly caused by atheromatous plaque and enhanced platelet activity, most critically affecting the coronary vasculature.

Restenosis is the progressive re-occlusion often following reduction of occlusions in stenotic vasculature. In cases where patency of the vasculature requires the mechanical support of a stent, in-stent-stenosis may occur, re-occluding the treated vessel.

Non-limiting examples of cerebrovascular diseases or disorders include stroke, cerebrovascular inflammation, cerebral hemorrhage and vertebral arterial insufficiency.

Non-limiting examples of peripheral vascular diseases or disorders include gangrene, diabetic vasculopathy, ischemic bowel disease, thrombosis, diabetic retinopathy and diabetic nephropathy.

Non-limiting examples of autoimmune diseases or disorders include all of the diseases caused by an immune response such as an autoantibody or cell-mediated immunity to an autoantigen and the like. Representative examples are chronic rheumatoid arthritis, juvenile rheumatoid arthritis, systemic lupus erythematosus, scleroderma, mixed connective tissue disease, polyarteritis nodosa, polymyositis/dermatomyositis, Sjogren's syndrome, Bechet's disease, multiple sclerosis, autoimmune diabetes, Hashimoto's disease, psoriasis, primary myxedema, pernicious anemia, myasthenia gravis, chronic active hepatitis, autoimmune hemolytic anemia, idiopathic thrombocytopenic purpura, uveitis, vasculitides and heparin induced thrombocytopenia.

Non-limiting examples of inflammatory glandular diseases or disorders include pancreatic diseases or disorders, Type I diabetes, thyroid diseases or disorders, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome.

Non-limiting examples of inflammatory gastrointestinal diseases or disorders include colitis, ileitis, Crohn's disease, chronic inflammatory intestinal disease, inflammatory bowel syndrome, chronic inflammatory bowel disease, celiac disease, ulcerative colitis, an ulcer, a skin ulcer, a bed sore, a gastric ulcer, a peptic ulcer, a buccal ulcer, a nasopharyngeal ulcer, an esophageal ulcer, a duodenal ulcer and a gastrointestinal ulcer.

Non-limiting examples of inflammatory cutaneous diseases or disorders include acne, an autoimmune bullous skin disease, pemphigus vulgaris, bullous pemphigoid, pemphigus foliaceus, contact dermatitis and drug eruption.

Non-limiting examples of inflammatory hepatic diseases or disorders include autoimmune hepatitis, hepatic cirrhosis, and biliary cirrhosis.

Non-limiting examples of inflammatory neurological diseases or disorders include multiple sclerosis, Alzheimer's disease, Parkinson's disease, myasthenia gravis, motor neuropathy, Guillain-Barre syndrome, autoimmune neuropathy, Lambert-Eaton myasthenic syndrome, paraneoplastic neurological disease or disorder, paraneoplastic cerebellar atrophy, non-paraneoplastic stiff man syndrome, progressive cerebellar atrophy, Rasmussen's encephalitis, amyotrophic lateral sclerosis, Sydeham chorea, Gilles de la Tourette syndrome, autoimmune polyendocrinopathy, dysimmune neuropathy, acquired neuromyotonia, arthrogryposis multiplex, Huntington's disease, AIDS associated dementia, amyotrophic lateral sclerosis (AML), multiple sclerosis, stroke, an inflammatory retinal disease or disorder, an inflammatory ocular disease or disorder, optic neuritis, spongiform encephalopathy, migraine, headache, cluster headache, and stiff-man syndrome.

Non-limiting examples of inflammatory connective tissue diseases or disorders include autoimmune myositis, primary Sjogren's syndrome, smooth muscle autoimmune disease or disorder, myositis, tendinitis, a ligament inflammation, chondritis, a joint inflammation, a synovial inflammation, carpal tunnel syndrome, arthritis, rheumatoid arthritis, osteoarthritis, ankylosing spondylitis, a skeletal inflammation, an autoimmune ear disease or disorder, and an autoimmune disease or disorder of the inner ear.

Non-limiting examples of inflammatory renal diseases or disorders include autoimmune interstitial nephritis and/or renal cancer.

Non-limiting examples of inflammatory reproductive diseases or disorders include repeated fetal loss, ovarian cyst, or a menstruation associated disease or disorder.

Non-limiting examples of inflammatory systemic diseases or disorders include systemic lupus erythematosus, systemic sclerosis, septic shock, toxic shock syndrome, and cachexia.

Non-limiting examples of infectious disease or disorder include chronic infectious diseases or disorders, a subacute infectious disease or disorder, an acute infectious disease or disorder, a viral disease or disorder, a bacterial disease or disorder, a protozoan disease or disorder, a parasitic disease or disorder, a fungal disease or disorder, a mycoplasma disease or disorder, gangrene, sepsis, a prion disease or disorder, influenza, tuberculosis, malaria, acquired immunodeficiency syndrome, and severe acute respiratory syndrome.

Non-limiting examples of inflammatory transplantation-related diseases or disorders include graft rejection, chronic graft rejection, subacute graft rejection, acute graft rejection hyperacute graft rejection, and graft versus host disease or disorder. Exemplary implants include a prosthetic implant, a breast implant, a silicone implant, a dental implant, a penile implant, a cardiac implant, an artificial joint, a bone fracture repair device, a bone replacement implant, a drug delivery implant, a catheter, a pacemaker, an artificial heart, an artificial heart valve, a drug release implant, an electrode, and a respirator tube.

Non-limiting examples of inflammatory tumors include a malignant tumor, a benign tumor, a solid tumor, a metastatic tumor and a non-solid tumor.

Non-limiting examples of inflammatory pulmonary diseases or disorders include asthma, allergic asthma, emphysema, chronic obstructive pulmonary disease or disorder, sarcoidosis and bronchitis.

An example of a proliferative disease or disorder is cancer.

The implication of phospholipids and phospholipid metabolites in treating of preventing diseases and syndromes such as, for example, oxidative stress of aging (Onorato J M, et al, Annal N Y Acad Sci 1998 Nov. 20; 854:277-90), rheumatoid arthritis (RA) (Paimela L, et al. Ann Rheum Dis 1996 August; 55(8):558-9), juvenile rheumatoid arthritis (Savolainen A, et al, 1995; 24(4):209-11), inflammatory bowel disease (IBD) (Sawai T, et al, Pediatr Surg Int 2001 May; 17(4): 269-74) and renal cancer (Noguchi S, et al, Biochem Biophys Res Commun 1992 Jan. 31; 182(2):544-50), has been reported, and thus further support the beneficial use of oxidized lipid analogs of oxidized phospholipids in the treatment or prevention of these diseases or disorders.

According to the method of embodiments of the present invention, the oxidized lipids can be administered to a subject by various routes, including, for example, the oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular routes. However, as is described in detail herein throughout and is further demonstrated in the Examples section that follows, preferred routes of administration include the oral, mucosal, nasal, intradermal (subcutaneous) and intraperitoneal routes.

Hence, in one embodiment, 0.1-100 mg/kg of an oxidized lipid as described herein is administered intraperitoneally, in a suitable carrier such as but not limited to PBS or glycerol, one to three times, every week, on a chronic or alternate regiment.

In another embodiment, 0.1-100 mg/kg of an oxidized lipid as described herein is administered nasally, in a suitable carrier such as but not limited to PBS or glycerol, one to three times, every week, on a chronic or alternate regiment.

In still another embodiment, 0.1-100 mg/kg of an oxidized lipid as described herein is administered subcutaneously, in a suitable carrier such as but not limited to PBS or glycerol, one to three times, every week, on a chronic or alternate regiment.

In yet another embodiment, 0.1-100 mg/kg of an oxidized lipid as described herein is administered orally, in a suitable carrier such as but not limited to PBS or glycerol, one to three times, every week, on a chronic or alternate regiment.

The pharmaceutical compositions and the methods described herein may further involve the administration of one or more additional compounds that are capable of treating or preventing an inflammation associated with endogenous oxidized lipid as delineated hereinabove.

The methods according to embodiments of the present invention can therefore involve co-administering, prior to, concomitant with or after the administration of the oxidized lipids, a therapeutically effective amount of one or more of such additional compounds, while the pharmaceutical composition according to the present embodiments may include, in addition to the compounds as described herein, such additional compounds.

Representative examples of additional compounds that are capable of treating or preventing an inflammation associated with endogenous oxidized lipid delineated hereinabove, and are therefore usable is the context of this embodiment of the present invention include, without limitation, HMGCoA reductase inhibitors (statins), mucosal adjuvants, corticosteroids, steroidal anti-inflammatory drugs, non-steroidal anti-inflammatory drugs, analgesics, growth factors, toxins, cholesteryl ester transfer protein (CETP) inhibitors, peroxisomes, proliferative activated receptor (PPAR) agonists, anti-atherosclerosis drugs, anti-proliferative agents, ezetimide, nicotinic acid, squalene inhibitors, an ApoE Milano, HSPs, Beta-2-glycoprotein-I and any derivative and analog thereof.

HMGCoA reductase inhibitors (statins) are well known drugs that effectively reduce LDL-cholesterol levels by inhibiting the enzyme that regulates the rate of cholesterol production and increasing the clearance of LDL-cholesterol present in the blood by the liver. Non-limiting examples of commonly prescribed statins include Atorvastatin, Fluvastatin, Lovastatin, Pravastatin and Simvastatin.

Ezetimibe is the first of a new class of cholesterol absorption inhibitors that potently and selectively inhibits dietary and biliary cholesterol absorption at the brush border of the intestinal epithelium, without affecting the absorption of triglyceride or fat-soluble vitamins. Ezetimibe thus reduces overall cholesterol delivery to the liver, secondarily inducing increased expression of LDL receptors, resulting in an increased removal of LDL-C from the plasma.

Peroxisome is a single-membrane organelle present in nearly all eukaryotic cells. One of the most important metabolic processes of the peroxisome is the β-oxidation of long and very long chain fatty acids. The peroxisome is also involved in bile acid synthesis, cholesterol synthesis, plasmalogen synthesis, amino acid metabolism, and purine metabolism.

Nicotinic acid is a known agent that lowers total cholesterol, LDL-cholesterol, and triglyceride levels, while raising HDL-cholesterol levels. There are three types of nicotinic acid drugs: immediate release, timed release, and extended release. Nicotinic acid or niacin, the water-soluble B vitamin, improves all lipoproteins when given in doses well above the vitamin requirement.

Squalene, an isoprenoid compound structurally similar to beta-carotene, is an intermediate metabolite in the synthesis of cholesterol. In humans, about 60 percent of dietary squalene is absorbed. It is transported in serum generally in association with very low density lipoproteins and is distributed ubiquitously in human tissues, with the greatest concentration in the skin, where it is one of the major components of skin surface lipids. Squalene inhibitors (e.g., monooxygenase and synthase) serve as cholesterol biosynthesis inhibitors.

Proliferative Activated Receptor (PPAR) agonists, e.g., fibrates, are fatty acid-activated members of the nuclear receptor superfamily that play important roles in lipid and glucose metabolism, and have been implicated in obesity-related metabolic diseases such as hyperlipidemia, insulin resistance, and coronary artery disease. Fibrates are generally effective in lowering elevated plasma triglycerides and cholesterol and act as PPAR agonists. The most pronounced effect of fibrates includes a decrease in plasma triglyceride-rich lipoproteins (TRLs). Levels of LDL cholesterol (LDL-C) generally decrease in individuals with elevated baseline plasma concentrations, and HDL cholesterol (HDL-C) levels are usually increased when baseline plasma concentrations are low. Non-limiting examples of commonly prescribed fibrates include bezafibrate, gemfibrozil and fenofibrate.

Cholesteryl Ester Transfer Protein (CETP) inhibitors play a major role in atherogenesis, by reducing cholesteryl ester accumulation within macrophages and the arterial wall, and thus reducing foam cell formation and affecting the cholesterol absorption. The most promising presently known CETP inhibitor is avisimibe.

ApoA-I Milano is typically used as a recombinant complex with phospholipid (ETC-216) and produces significant regression of coronary atherosclerosis.

Co-administration of mucosal adjuvants has been shown to be highly beneficial for preventing the invasion of infectious agents through mucosal surfaces. In the early stages of induction of mucosal immune response, the uptake of orally or nasally administered antigens is achieved through a unique set of antigen-sampling cells, M cells located in follicle-associated epithelium (FAE) of inductive sites. After successful uptake, the antigens are immediately processed and presented by the underlying dendritic cells (DCs).

Non-limiting examples of non-steroidal anti-inflammatory drugs include oxicams, such as piroxicam, isoxicam, tenoxicam, sudoxicam, and CP-14,304; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acemetacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone.

Non-limiting examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Non-limiting examples of analgesics (pain relievers) include aspirin and other salicylates (such as choline or magnesium salicylate), ibuprofen, ketoprofen, naproxen sodium, and acetaminophen.

Growth factors are hormones which have numerous functions, including regulation of adhesion molecule production, altering cellular proliferation, increasing vascularization, enhancing collagen synthesis, regulating bone metabolism and altering migration of cells into given area. Non-limiting examples of growth factors include insulin-like growth factor-1 (IGF-1), transforming growth factor-β (TGF-β), a bone morphogenic protein (BMP) and the like.

Non-limiting examples of toxins include the cholera toxin, which also serves as an adjuvant.

Non-limiting examples of anti-proliferative agents include an alkylating agent such as a nitrogen mustard, an ethylenimine and a methylmelamine, an alkyl sulfonate, a nitrosourea, and a triazene; an antimetabolite such as a folic acid analog, a pyrimidine analog, and a purine analog; a natural product such as a vinca alkaloid, an epipodophyllotoxin, an antibiotic, an enzyme, a taxane, and a biological response modifier; miscellaneous agents such as a platinum coordination complex, an anthracenedione, an anthracycline, a substituted urea, a methyl hydrazine derivative, or an adrenocortical suppressant; or a hormone or an antagonist such as an adrenocorticosteroid, a progestin, an estrogen, an antiestrogen, an androgen, an antiandrogen, or a gonadotropin-releasing hormone analog. Specific examples of chemotherapeutic agents include, for example, a nitrogen mustard, an epipodophyllotoxin, an antibiotic, a platinum coordination complex, bleomycin, doxorubicin, paclitaxel, etoposide, 4-OH cyclophosphamide, and cisplatinum.

The HSP family consists of approximately 25 proteins discerned by their molecular weights with highly conserved structures. Almost all humans have cellular and humoral immune reactions against microbial heat-shock protein 60 (HSP60). Because a high degree of antigenic homology exists between microbial (bacterial and parasitic) and human HSP60, the 'cost' of immunity to microbes might be the danger of cross-reactivity with human HSP60 expressed by the endothelial cells of stressed arteries. Genuine autoimmunity against altered autologous HSP60 might trigger this process also (Wick et al. Atherosclerosis as an autoimmune disease: an update. TRENDS in Immunology. 2001; 22(12):665-669). HSP has been implicated as a target autoantigen in several experimental autoimmune diseases (arthritis, type I diabetes). Anti-HSP65 as well as anti-HSP60 antibodies have been demonstrably associated with atheromatous lesions in humans. Studies conducted in rabbits and mice show that the generation of an HSP65-induced immune response by immunization with the recombinant protein or with an HSP65-rich preparation of *Mycobacterium tuberculosis* enhances atherogenesis. As autoimmune processes pointing to HSP65 as a possible antigenic candidate, creating a state of unresponsiveness by induction of mucosal "tolerization" has been employed in order to block these responses, our group reported that early atherosclerosis was attenuated in HSP65-fed mice, compared with either BSA or PBS fed mice (Harats et al. Oral tolerance with heat shock protein 65 attenuates *mycobacterium tuberculosis* induced and high fat diet driven atherosclerosis lesions. J Am Coll Cardiol. 2002; 40:1333-1338), this was further supported by Maron who demonstrated that nasal vaccination with HSP reduces the inflammatory process associated with atherosclerosis (Maron et al. Mucosal administration of heat shock protein-65 decreases atherosclerosis and inflammation in aortic arch of low density lipoprotein receptor-deficient mice. Circulation. 2002; 106: 1708-1715).

Beta-2-glycoprotein I (beta2GPI) is a phospholipid binding protein shown to serve as a target for prothrombotic antiphospholipid antibodies. It has recently been demonstrated to drive an immune mediated reaction and enhance murine atherosclerosis. β-Antibodies to beta-2-GPI have the ability to activate monocytes and endothelial cells and can induce an immune response to beta2GPI in atherosclerosis-prone mice accelerated atherosclerosis. When beta2GPI-reactive lymph node and spleen cells were transferred to LDL-receptor-deficient mice they promoted fatty streak formation, proving a direct proatherogenic role for beta2GPI-specific lymphocytes. Inducing immunological tolerance to beta2GPI by prior oral feeding with the antigen resulted in a significant reduction in the extent of atherosclerotic lesions. Thus, beta2GPI is a candidate player in the atherosclerotic plaque, and can possibly be employed as an immunomodulator of plaque progression. Oral feeding with of beta2GPI inhibited lymph node cell reactivity to beta2GPI in mice immunized against the human protein. IL-4 and IL-10 production was upregulated in lymph node cells of beta2GPI-tolerant mice immunized against beta2GPI, upon priming with the respective protein. Thus, oral administration of beta2GPI is an effective means of suppressing atherogenesis in mice (George et al. Suppression of early atherosclerosis in LDL-receptor deficient mice by oral tolerance with beta2-glycoprotein I. Cardiovasc Res. 2004; 62(3):603-9).

The oxidized lipids described herein may be prepared according to any suitable method know in the chemical arts. For example, phospholipids described herein may be prepared according to procedures described in International Patent Application No. PCT/IL05/000735 (Publication No. WO 06/006161) or U.S. patent application Ser. No. 11/650, 973 (Publication No. 2007-0112211).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials:
Acetic acid (glacial) was obtained from Bio-Lab;
Crystal violet was obtained from Sigma;
Dithiothreitol (DTT) was obtained from Bio-Lab;
Fetal bovine serum (heat inactivated) was obtained from Biological Industries (Israel);

Methanol (absolute) was obtained from Bio-Lab;

MOG peptide 35-55 was obtained from Sigma-Aldrich;

Mouse GM-CSF (granulocyte-macrophage colony-stimulating factor) was obtained from Peprotech (Israel);

Penicillin/streptomycin solution was obtained from Biological Industries (Israel);

Red blood cell lysis buffer was obtained from Biological Industries (Israel); and RPMI-1640 medium with L-glutamine was obtained from Biological Industries (Israel).

COSTAR® Sterile 24-well tissue culture treated plates were obtained from Corning.

Phosphate buffered saline (PBS) was prepared by diluting Dulbecco's phosphate buffered saline 10× concentrate without calcium or magnesium (Biological Industries, Israel) with double-distilled water.

Cells were incubated at 37° C. in an atmosphere with 5% $CO_2$.

Spectrometric measurements were performed using a Tecan SUNRISE plate reader and Magellan Version 6.3 data acquisition software. Absorption at 595 nm was determined using a Tecan SpectraFluor 595 nm band-pass filter.

For in vitro studies, the tested compounds were dissolved in ethanol to a concentration of 100 mg/ml and then diluted in PBS to a concentration of 1 mg/ml.

Tyrosine Phosphorylation Assay:

Tyrosine phosphorylation in macrophages or bone marrow-derived cells (BMDCs) of mice was assayed.

Mouse primary macrophages were isolated from the peritoneum of 7-8 week old C57BL/6 female mice following thioglycollate stimulation. Cells were pre-starved with 0.5% fetal bovine serum (FBS) in RPMI-1640 medium overnight. Mouse primary bone marrow-derived cells were isolated by flushing bone marrow out of the femur and tibia of female SJL mice using cold RPMI-1640. A cell suspension was prepared and erythrocytes were removed using red blood cell lysis buffer, and incubated at 4° C. for 15 minutes in a buffer containing phosphate buffered saline (PBS) and 0.5% bovine serum albumin (BSA) with mouse B220 and CD90 microbeads (Miltenyi Biotech). Cells were then washed, resuspended in the same buffer and depleted of B and T cells on a Midi-Macs separation unit through a LD or LS column (Miltenyi Biotech). The depleted bone marrow cells were counted, washed and seeded at a concentration of $10^6$ cells per ml in RPMI-1640 medium with L-glutamine, β-mercaptoethanol, 10% fetal bovine serum, antibiotics (penicillin/streptomycin) and 2 ng/ml of mouse granulocyte-macrophage colony-stimulating factor (GM-CSF). The medium was replaced every other day. On days 5-6 post-culturing, the cells were collected, counted and seeded ($10^6$ cells/ml) in the medium for 24 hours, followed by starvation with 0.5% fetal bovine serum (FBS) in RPMI-1640 medium overnight.

The macrophages or BMDCs were then treated for 10 minutes with 1, 10 or 20 μg/ml of the tested compound in phosphate buffered saline (PBS) with 1% ethanol. Treatment with either 1 or 20 μg/ml of phosphatidylcholine or solvent (PBS with 1% ethanol) was used as a negative control. Treatment with 1, 10 or 20 μg/ml CI-201 (1-hexadecyl-2-(4-carboxy)butyl-sn-glycero-3-phosphocholine) was used as a positive control.

Proteins with phosphorylated tyrosine were then observed by Western blot, using a monoclonal anti-phosphotyrosine antibody. Western blotting for ERK1/2 or α-tubulin was performed as a control for protein loading.

In Vitro Toxicity Assay:

Thioglycollate-elicited mouse peritoneal macrophages were washed, counted and seeded ($2 \times 10^5$ to $3 \times 10^5$ cells per well in 24-well plates) in triplicate wells in medium containing RPMI-1640, L-glutamine, 10% FBS and antibiotics (penicillin/streptomycin). After a recovery period of 24 hours, the tested compound (or controls) was added to the cell medium at doses of 2, 10, 20, 50, 100 or 150 μg/ml, keeping the added volume equal in all treatments by complementing the volume with solvent.

Following addition of the compounds, the cells were incubated for an additional 24 hours, after which the cells were washed, fixed with a solution of 10% methanol/10% acetic acid and stained with crystal violet (0.4% in 20% ethanol). Cell numbers were measured by determining optical density at 595 nm. Cells incubated with vehicle (PBS with 1% ethanol) were used as a control, to which cell numbers in treated samples were normalized.

Data are presented as mean±standard deviation. Statistical significance relative to vehicle-treated cells was calculated using a student's t-test, with p-values of less than 0.05 being considered as indicating statistical significance.

In Vitro IL12/23p40 Production Assay:

Bone marrow derived cells (BMDCs) were obtained from the femur and tibia of female C57BL mice, cultured, and seeded at a concentration of $10^6$ cells/ml 5-6 days post-culturing, as described hereinabove for the tyrosine phosphorylation assay.

The tested compound was then added to the cells for 1 hour at a concentration of 1, 2.5, 5, 10 or 20 μg/ml. The cells were activated for IL12/23p40 production by incubation for 24 hours with 10 μg/ml peptidoglycan (PGN). Cytokine production from the supernatant was measured by ELISA. Activated cells without the tested compound were used as the control.

In Vitro IL12/23 p40 mRNA Expression Assay:

Bone marrow-derived cell cultures were prepared as described hereinabove. On days 5-6 post culturing, the cell cultures were enriched for CD11c+ dendritic cells (>90%) with mouse CD11c microbeads over MS or LS columns (Miltenyi Biotech). CD11c+ dendritic cells were stimulated for 1, 2 and 3 hours with 10 μg/ml peptidoglycan alone or in the presence of 20 μg/ml of the tested compound added 1 hour before activation. RNA was extracted from cells using RNeasy mini kit (Qiagen, Valencia, Calif.). For cDNA preparation, 1 μg of RNA was combined with Oligo dT for 10 minutes at 70° C., $1^{st}$ strand buffer. Dithiothreitol and dNTP and super-script reverse transcriptase (Invitrogen, Carlsbad, Calif.) were added for 50 minutes at 42° C. and the reaction was ended by incubation for an additional 15 minutes at 70° C. All real time PCR reactions were performed using LightCycler Taqman master (Roche Diagnostics, Mannheim, Germany) and run on the LightCycler machine (Roche). Ready sets of probe with primers were used for IL12/23 p40 and GAPDH assays (Applied Biosystems, assays #Mm01288992_m1 and Mm99999915_g1, respectively) with the latter served to normalize RNA levels. 20 μg/ml CI-201 and phosphatidylcholine (PC) were used as positive and negative controls respectively.

In Vivo Myelin Oligodendrocyte Glycoprotein (MOG)-Induced Experimental Autoimmune Encephalomyelitis (EAE) Assay:

C57BL/6 mice were orally administered with the indicated amount of the tested compound in a final volume of 200 μl for 5 consecutive days starting 5 days before immunization.

For EAE induction, mice were immunized subcutaneously with an emulsion containing 1.5 mg/ml MOG peptide 35-55 (MEVGWYRSPFSRVVHLYRNGK) and 2.5 mg/ml CFA (complete Freund's adjuvant), 100 μl emulsion being injected into each flank. Pertussis toxin (500 ng in 500 μl PBS) was administered intraperitoneally immediately and 48 hours after the immunization.

Onset of EAE was evaluated by a mean clinical score.

In Vivo Collagen-Induced Arthritis (CIA) Assay:

DBA/1 male mice were immunized to induce arthritis by a collagen injection containing complete Freund's adjuvant (CFA) in the base of the tail (day 0) and a booster shot in the flank (day 21). Mice were followed for arthritis development until day 36. Administration by gavage of the tested compound and control substances began on day 22 and was carried out on a daily basis (6 times per week).

Onset of arthritis was evaluated by an arthritis clinical score.

In Vivo Atherosclerotic Lesion Assay:

12-16-week old LDL-RD male mice were orally administered with 0.2 ml of PBS or PBS with an indicated amount of the tested compound, once a day, every other day, for 5 treatments. The mice were challenged with western diet for 5 weeks and then sacrificed.

Alternatively, 14-16-week old ApoE KO mouse were orally administered with 0.2 ml of PBS or PBS with an indicated amount of the tested compound, once a day, every other day, for 5 treatments, and sacrificed by the end of 8 weeks.

The quantification of atherosclerotic lesions was done by calculating the lesion size in the aortic sinus as previously described [Paigen et al., Quantitative assessment of atherosclerotic lesions in mice. Atherosclerosis 1987; 68:231-240] with a few modifications. Briefly, the heart and the aorta were removed from the animals, and the peripheral fat was cleaned carefully. The hearts were embedded in Optimal Cutting Temperature (OCT) gel and frozen. Aortic sinus lesion was determined from 3-8 Oil red O-stained serial sections (10 μm thick), throughout the aortic sinus (400 μm). The lesion area was calculated using a computer analyzing method (Image Pro Plus software [version 4.5.1.29], Medical Cybernetics Corporation).

Example 1

1-Hexadecyl-2-(4-carboxy)butyl-glycero-3-phosphoethanolamine (CI-202) and 1-hexadecyl-2-(4-methylcarboxy)butyl-glycero-3-phosphoethanolamine (R)-1-hexadecyl-2-(4-carboxy)butyl-sn-glycero-3-phosphoethanolamine and (R)-1-hexadecyl-2-(4-methylcarboxy)butyl-sn-glycero-3-phosphoethanolamine were synthesized as described hereinbelow using (R)-(−)-2,2-dimethyl-1,3-dioxolane-4-methanol as a starting material. (S)-1-hexadecyl-2-(4-carboxy)butyl-glycero-3-phosphoethanolamine and (S)-1-hexadecyl-2-(4-methylcarboxy)butyl-glycero-3-phosphoethanolamine are synthesized using the same procedures, but with (S)-(+)-2,2-dimethyl-1,3-dioxolane-4-methanol as the starting material.

Synthesis of (S)-1-hexadecyl-glycerol 11 grams of (R)-(−)-2,2-dimethyl-1,3-dioxolane-4-methanol, 20 grams of powdered potassium hydroxide and 27.96 grams of hexadecyl bromide were stirred in 150 ml toluene and refluxed for 6 hours, while removing the water formed by azeotropic distillation. The volume of the solvent was gradually reduced to about 40 ml. The reaction mixture was cooled to room temperature, 100 ml water was added, and the reaction mixture was extracted thrice with 75 ml dichloromethane. The combined organic phase was washed with 50 ml water and the solvent was removed under reduced pressure. The residue was dissolved in 200 ml of a mixture of 90:10:5 (volume/volume) methanol:water:concentrated hydrochloric acid, and the resulting solution was refluxed for 2 hours. After cooling to room temperature, 100 ml of water was added. The product was extracted thrice with 100 ml dichloromethane, washed consecutively with 100 ml water, 100 ml saturated aqueous solution of sodium carbonate and again with 100 ml water. The solvent was then removed under reduced pressure, and the product was crystallized from hexane (200 ml) to give 21.69 grams pure (S)-1-hexadecyl-glycerol, which was dried in a desiccator under reduced pressure. The yield was 82%.

Synthesis of (R)-1-hexadecyl-3-trityl-glycerol 20 grams of (S)-1-hexadecyl-glycerol and 21.29 grams of triphenylchloromethane were dissolved in 369 ml dry tetrahydrofuran (THF) and 93 ml dry acetonitrile. 17.75 ml triethylamine was added and the reaction mixture was refluxed for 17 hours. The reaction mixture was cooled to room temperature, poured on ice (100 grams), transferred to a separatory funnel and extracted with methyl tert-butyl ether. The organic phase was washed consecutively with 200 ml water, twice with 200 ml dilute (1.5%) sulfuric acid, 200 ml water, 200 ml saturated aqueous sodium bicarbonate, and again with 200 ml water. The organic phase was dried over anhydrous sodium sulfate and the solvent was removed under reduced pressure to give 36.86 grams of crude product as a residue. This residue was dissolved in hot hexane (200 ml) and the resulting solution was cooled at 4° C. overnight. The precipitated product was filtered, yielding 30.71 grams of (R)-1-hexadecyl-3-trityl-glycerol.

Synthesis of (R)-1-hexadecyl-2-(5'-hexenyl)-3-trityl-glycerol 19.94 grams of 1-hexadecyl-3-trityl-glycerol, 6.98 grams of 6-bromo-1-hexene and 15 grams of powdered potassium hydroxide were stirred in 350 ml hexane and refluxed for 8 hours, while removing the water formed by azeotropic distillation. The reaction mixture was cooled to room temperature, transferred to a separatory funnel, washed twice with 200 ml water, and the solvent was then removed under reduced pressure. The residue was dissolved in 150 ml hexane and washed again twice with 200 ml water. The organic solution was kept at 4° C. overnight, during which precipitation of byproducts occurred. Filtration and removal of the solvent under reduced pressure gave 19.86 grams of (R)-1-hexadecyl-2-(5'-hexenyl)-3-trityl-glycerol. The yield was 86.6%.

Synthesis of (S)-1-hexadecyl-2-(4-carboxy)butyl-sn-glycerol 150.16 grams (702 mmol) sodium periodate was suspended in 500 ml of water in a three-neck round-bottom flask equipped with a thermometer and dropping funnel. 7.21 grams (85.8 mmol) sodium bicarbonate and 2.47 grams (15.6 mmol) potassium permanganate were added, and the suspension was heated to a temperature of 40° C. 50 grams (78 mmol) of (R)-1-hexadecyl-2-(5'-hexenyl)-3-trityl-glycerol was dissolved in 500 ml tert-butanol, and this solution was added to the mixture of sodium periodate and potassium permanganate during the course of 1 hour. After adding (R)-1-hexadecyl-2-(5'-hexenyl)-3-trityl-glycerol to the sodium periodate and potassium permanganate, the reaction mixture was heated at a temperature of 40° C. for 3 hours. After 1.5 hours, an additional 0.62 gram (3.9 mmol) of potassium permanganate was added to maintain the pink color of the reaction mixture. At the end of the 3 hour period, the reaction mixture was cooled to room temperature, transferred to a separation funnel and extracted with 200 ml hexane. The organic phase was washed with a solution of 15 grams $Na_2S_2O_5$ in 100 ml water. Dilute hydrochloric acid (0.65 ml concentrated HCl in 13 ml water) was added to the organic phase and 200 ml of the solvent was distilled under reduced pressure. The remaining clear solution was heated to a temperature of 80° C. for 6 hours, and an additional volume of 250 ml of solvent was distilled off. The residue was treated with 100 ml water and 10 ml of a 30% NaOH solution, giving a pH of 12. The precipitated triphenylmethanol was filter off and washed 4 times with 10 ml water. The filtrate was extracted with a mixture of 50 ml hexane and 50 ml ethyl acetate to remove remaining triphenylmethanol and other impurities. In the aqueous phase, the sodium salt of 1-hexadecyl-2-(4-carboxy)butyl-sn-glycerol was protonated with 8.45 ml (101.4 mmol) concentrated hydrochloric acid. The resulting free carboxylic acid was extracted with 100 ml hexane. Evaporation to dryness and co-evaporation with 100 ml hexane gave 27.00 grams of crude (S)-1-hexadecyl-2-(4 carboxy)butyl-sn-glycerol. The crude product was crystallized by dissolving in a mixture of 7 ml acetone and 68 ml hexane, and cooling to 0° C. The precipitate was filtered, washed twice with 7 ml of cold hexane and dried. 20.90 grams of (S)-1-hexadecyl-2-(4 carboxy)butyl-sn-glycerol was obtained as an off-white solid. The yield was 64.3%.

Synthesis of (S)-1-hexadecyl-2-(4-methylcarboxy) butyl-sn-glycerol 15.0 grams (36.0 mmol) of (S)-1-Hexadecyl-2-(4-carboxy)butyl-sn-glycerol was dissolved in 100 ml methanol, and 3 ml of concentrated hydrochloric acid was added. The reaction mixture was stirred at room temperature overnight. Triethylamine was added until the pH of the reaction mixture reached 7. The solution was transferred to a separation funnel and extracted twice with 200 ml hexane. The organic phase was washed with water. Evaporation to dryness and co-evaporation with 100 ml hexane yielded 14.92 grams of (S)-1-hexadecyl-2-(4-methylcarboxy)butyl-sn-glycerol. The yield was 96.2%.

Synthesis of (R)-1-hexadecyl-2-(4-methylcarboxy) butyl-sn-glycero-3-phosphoethanolamine 2.88 grams of (S)-1-hexadecyl-2-(4-methylcarboxy)butyl-sn-glycerol and 3 ml of triethylamine were dissolved in 30 ml THF. This solution was added dropwise over the course of 15 minutes to an ice-cooled solution of 2 ml $POCl_3$ in 20 ml tetrahydrofuran while stirring. The stirring was continued for additional 10 minutes with cooling and at room temp for an additional 45 minutes. The reaction mixture was ice-cooled and a solution of 1.21 ml ethanolamine and 5.6 ml triethylamine in 50 ml THF was added dropwise over the course of 20 minutes. The stirring was continued for 10 minutes with cooling and at room temperature overnight. The reaction mixture was filtered and the solvent was removed under reduced pressure. The obtained residue was dissolved in a mixture of 24 ml acetic acid and 10 ml water and heated to 70° C. for 1 hour. The mixture was extracted thrice with 50 ml chloroform, the organic phase washed twice with 50 ml water, and the solvent was removed under reduced pressure to give 4.0 grams of (R)-1-hexadecyl-2-(4-methylcarboxy)butyl-sn-glycero-3-phosphoethanolamine as a yellow wax.

NMR characterization of 1-hexadecyl-2-(4-methylcarboxy)butyl-glycero-3-phosphoethanolamine A sample of 1-hexadecyl-2-(4-methylcarboxy)butyl-glycero-3-phosphoethanolamine was dissolved in deuterated chloroform ($CDCl_3$). The spectra were then measured at 300 MHz. Samples were measured by both $^1H$ and $^{13}C$ NMR spectroscopy.

The results showed the expected signals for the structural elements of 1-hexadecyl-2-(4-methylcarboxy)butyl-glycero-3-phosphoethanolamine and thus fully supported the structure.

The assignment of the observed $^1H$ peaks according to the structure of 1-hexadecyl-2-(4-methylcarboxy)butyl-glycero-3-phosphoethanolamine was as follows.

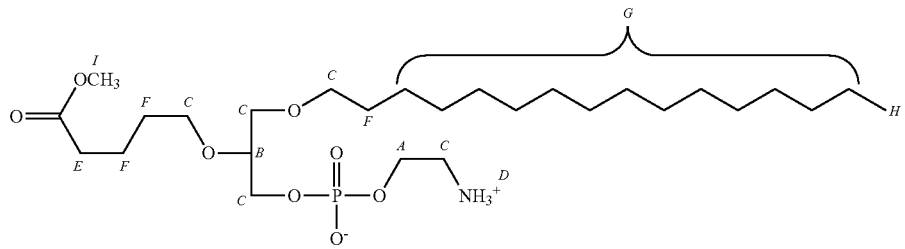

$^1H$ NMR (300 MHz, reference solvent ($CDCl_3$)=7.28 ppm)

| δ [ppm] | Description | Assignment (see formula above) |
|---|---|---|
| 6.905 | 3 H, br, s | D |
| 4.200 | 2 H, br, s | A |
| 3.594 | 3H, s | I |
| 3.336-3.562 | 10 H, m, 5 × CH2 | C |
| 3.291-3.313 | 1 H, m | B |
| 2.250-2.299 | 2 H, t, J = 7.35 Hz | E |
| 1.454-1.620 | 6 H, m, 3 × CH2 | F |
| 1.185 | 26 H, m, 13 × CH2 | G |
| 0.807 | 3 H, t, 1 × CH3, J = 6.75 Hz | H |

The assignment of the observed $^{13}C$ peaks according to the structure of 1-hexadecyl-2-(4-methylcarboxy)butyl-glycero-3-phosphoethanolamine was as follows:

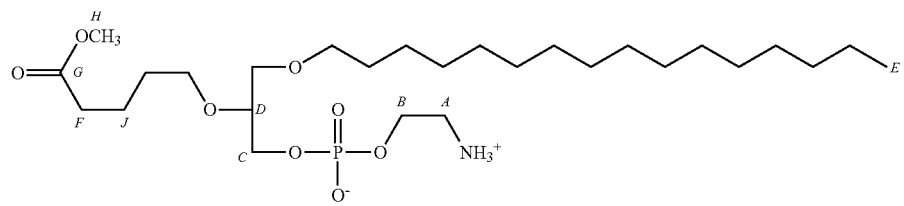

$^{13}$C NMR (300 MHz, reference solvent (CDCl$_3$)=77.0 ppm)

| δ [ppm] | Assignment (see formula above) |
|---|---|
| 174.08 | G |
| 79.00 | D |
| 72.01 | |
| 70.38 | |
| 70.13 | |
| 66.25-66.34 | C |
| 62.34-62.43 | B |
| 51.61 | H |
| 40.42-40.51 | A |
| 33.87 | F |
| 32.05 | |
| 29.81 | |
| 29.65 | |
| 29.47 | |
| 26.20 | |
| 22.77 | |
| 21.74 | J |
| 20.74 | |
| 14.00 | E |

Mass spectrometry characterization of 1-hexadecyl-2-(4-methylcarboxy)butyl-glycero-3-phosphoethanolamine The calculated mass for 1-hexadecyl-2-(4-methylcarboxy)butyl-glycero-3-phosphoethanolamine (C$_{27}$H$_{56}$NO$_8$P) was 553.7092.

The mass spectrum obtained using Electrospray Ionization Mass Spectrometry (ESI+-MS), showed a molecular ion with m/z=554, corresponding to the protonated molecular ion [M+H]$^+$. The mass spectrometry spectrum is thus in agreement with the chemical structure of 1-hexadecyl-2-(4-methylcarboxy)butyl-glycero-3-phosphoethanolamine.

Synthesis of (R)-1-hexadecyl-2-(4-carboxy)butyl-sn-glycero-3-phosphoethanolamine (CI-202)

3.5 grams of (R)-1-hexadecyl-2-(4-methylcarboxy)butyl-sn-glycero-3-phosphoethanolamine was dissolved in 100 ml of a mixture of 8:2 (v/v) methanol: 10% sodium hydroxide solution. The mixture was stirred at room temperature for 5 hours. The pH of the reaction was adjusted to 4 by adding sodium dihydrogen phosphate and formic acid. Water (100 ml) and chloroform (100 ml) were added. After extraction, the phases were separated and the solvent from the organic phase was removed under reduced pressure. The obtained residue was dissolved in chloroform, dried over sodium sulfate and filtered, and the solvent was removed under reduced pressure to give 3.0 grams of crude (R)-1-hexadecyl-2-(4-carboxy)butyl-sn-glycero-3-phosphoethanolamine. The crude product was purified by chromatography on silica gel (120 grams). The product was eluted with mixture of chloroform:methanol and water at a 60:35:5 volumetric ratio. The solvent from fractions containing the desirable product was removed under reduced pressure, the residue dissolved in chloroform and dried over sodium sulfate, and the solvent removed reduced pressure to give 2.11 grams of pure (R)-1-hexadecyl-2-(4-carboxy)butyl-sn-glycero-3-phosphoethanolamine as a wax. The wax was dried under reduced pressure over phosphorus pentoxide.

NMR Characterization of CI-202:

A sample of CI-202 was dissolved in deuterated chloroform (CDCl$_3$). The spectra were then measured at 300 MHz. Samples were measured by both $^1$H and $^{13}$C NMR spectroscopy.

The results showed the expected signals for the structural elements of 1-hexadecyl-2-(4-carboxy)butyl-glycero-3-phosphoethanolamine (CI-202) and thus fully supported the structure.

The assignment of the observed $^1$H peaks according to the structure of 1-hexadecyl-2-(4-carboxy)butyl-glycero-3-phosphoethanolamine was as follows.

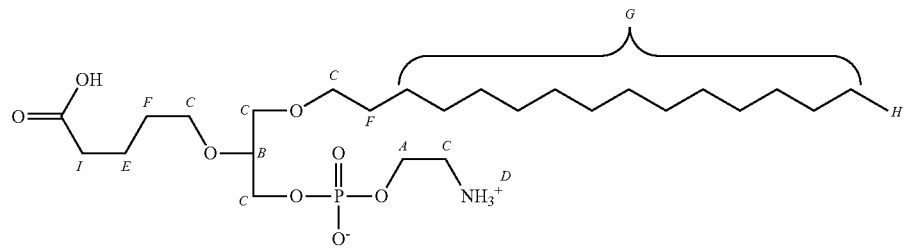

$^1$H NMR (300 MHz, reference solvent (CDCl$_3$)=7.26 ppm)

| δ [ppm] | Description | Assignment (see formula above) |
|---|---|---|
| 8.140 | 3 H, br, s | D |
| 4.144 | 2 H, br, s | A |
| 3.838-4.037 | 2H, m | C |
| 3.612-3.697 | 2H, m | C |

-continued

| δ [ppm] | Description | Assignment (see formula above) |
|---|---|---|
| 3.385-3.530 | 6 H, m, 3 × CH2 | C |
| 3.256 | 1 H, br, s | B |
| 2.302-2.348 | 2H, t, CH2, J = 6.9 Hz | I |
| 1.672-1710 | 2 H, m | E |
| 1.518-1.606 | 4 H, m, 2 × CH2 | F |
| 1.254 | 26 H, m, 13 × CH2 | G |
| 0.879 | 3 H, t, 1 × CH3, J = 6.75 Hz | H |

The assignment of the observed $^{13}$C peaks according to the structure of 1-hexadecyl-2-(4-carboxy)butyl-glycero-3-phosphoethanolamine was as follows:

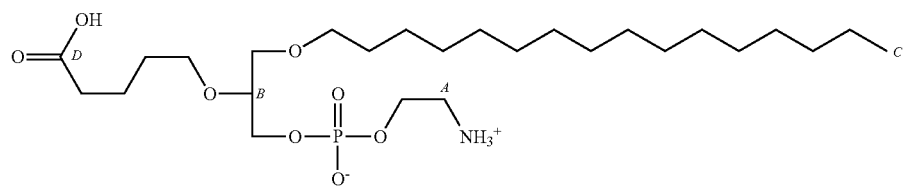

$^{13}$C NMR (300 MHz, reference solvent (CDCl$_3$)=77.004 ppm)

| δ [ppm] | Assignment (see formula above) |
|---|---|
| 177.16 | D |
| 77.868 | B |
| 71.776 | |
| 70.218 | |
| 69.814 | |
| 66.161 | |
| 62.205 | |
| 40.533 | A |
| 33.818 | |
| 31.916 | |
| 29.714 | |
| 29.664 | |
| 29.549 | |
| 29.359 | |
| 29.156 | |
| 26.080 | |
| 22.679 | |
| 21.732 | |
| 14.109 | C |

Mass Spectrometry Characterization of CI-202:

The calculated mass for 1-hexadecyl-2-(4-carboxy)butyl-glycero-3-phosphoethanolamine ($C_{26}H_{54}NO_8P$) was 539.36.

The mass spectrum obtained using Electrospray Ionization Mass Spectrometry (ESI$^-$-MS) showed a molecular ion with m/z=538 corresponding to the deprotonated molecular ion $[M-H]^-$. The mass spectrometry spectrum is thus in agreement with the chemical structure of 1-hexadecyl-2-(4-carboxy)butyl-glycero-3-phosphoethanolamine (CI-202).

In Vitro IL12/23 p40 Production:

The effect of CI-202 on in vitro production of IL12/23 p40 was determined as described hereinabove in the Materials and Methods section.

As shown in FIG. 1, CI-202 inhibited production of IL12/23 p40 by bone marrow-derived cells in a dose-dependent manner.

IL12/23p40 mRNA Expression:

The effect of CI-202 on in vitro IL12/23 p40 mRNA expression was determined as described hereinabove in the Materials and Methods section.

As shown in FIG. 2, CI-202 inhibited IL12/23 p40 mRNA expression during the whole tested time period (2-4 hours following administration of CI-202), and the inhibition by CI-202 was comparable to the inhibition by CI-201.

Tyrosine Phosphorylation:

The effect of CI-202 on in vitro tyrosine phosphorylation in primary macrophages was determined as described hereinabove in the Materials and Methods section.

As shown in FIG. 3, treatment with 10 μg/ml (18.5 μM) CI-202 results in induction of tyrosine phosphorylation, whereas exposure to 20 μg/ml (37 μM) CI-202 causes reduction in phosphotyrosine levels. These changes are very similar to the effect induced respectively by 10 μg/ml (17 μM) and 20 μg/ml (34 μM) of the positive control CI-201.

Toxicity of CI-202:

The toxicity of CI-202 was evaluated as described hereinabove in the Materials and Methods section.

As shown in FIGS. 4A and 4B, significant toxicity of CI-202 was detected only at doses above 50 μg/ml, and the $LD_{50}$ of CI-202 lies between 50 and 100 μg/ml.

Development of Myelin Oligodendrocyte Glycoprotein (MOG)-Induced Experimental Autoimmune Encephalomyelitis (EAE):

The effect of CI-202 on development of in vivo myelin oligodendrocyte glycoprotein (MOG)-induced experimental autoimmune encephalomyelitis (EAE) in mice was determined as described hereinabove in the Materials and Methods section.

As shown in FIG. 5, administration of 4 mg/kg of CI-202 delayed disease onset and reduced clinical manifestation of EAE.

Development of Collagen-Induced Arthritis (CIA):

The effect of CI-202 on development of in vivo collagen induced arthritis in mice was determined as described hereinabove in the Materials and Methods section.

As shown in FIG. 6, administration of 0.4 mg/kg of CI-202 significantly decreased arthritis severity throughout the study period. The peak arthritis clinical score was decreased by 42% relative to the control mice.

Example 2

1-Hexadecyl-2-(6-carboxy)hexanyl-glycero-3-phosphocholine (CI-203)

(R)-1-hexadecyl-2-(6-carboxy)hexanyl-sn-glycero-3-phosphocholine was synthesized as described hereinbelow using (R)-(−)-2,2-dimethyl-1,3-dioxolane-4-methanol as a starting material. (S)-1-hexadecyl-2-(6-carboxy)hexanyl-glycero-3-phosphocholine is synthesized using the same procedures, but with (S)-(+)-2,2-dimethyl-1,3-dioxolane-4-methanol as the starting material.

Synthesis of (R)-1-hexadecyl-3-trityl-glycerol (R)-1-hexadecyl-3-trityl-glycerol was prepared as described in Example 1, by first preparing (S)-1-hexadecylglycerol using (R)-(–)-2,2-dimethyl-1,3-dioxolane-4-methanol.

Synthesis of (R)-1-hexadecyl-2-(6-ethylcarboxy) hexanyl-3-trityl-glycerol 5 grams of (R)-1-hexadecyl-3-trityl-glycerol and 2 ml of ethyl 7-bromo-heptanoate were dissolved in 70 ml benzene. 23 grams of powdered KOH was added and the reaction mixture was stirred and refluxed for 14 hours, while removing the water formed in the reaction by azeotropic distillation. The reaction mixture was cooled to room temperature, washed thrice with 70 ml water, and dried over sodium sulfate. The solvent was removed under reduced pressure, the obtained residue was dissolved in 25 ml hot hexane, and the solution was cooled to 4° C. overnight. The precipitated byproduct was filtered and the solvent removed under reduced pressure to give 5 grams (R)-1-hexadecyl-2-(6 ethylcarboxy)hexanyl-3-trityl-glycerol as a white solid.

Synthesis of (S)-1-hexadecyl-2-(6-ethylcarboxy)hexanyl-glycerol 5 grams of (R)-1-hexadecyl-2-(6-ethylcarboxy)hexanyl-3-trityl-glycerol was dissolved in 90 ml ethanol. 20 ml of concentrated hydrochloric acid was added slowly, and the mixture was stirred and refluxed for 4 hours. The reaction mixture was cooled to room temperature, poured on ice and extracted thrice with 100 ml diethyl ether. The organic phase was washed with 100 ml water, 100 ml saturated sodium bicarbonate solution, and again with 100 ml water, and dried over sodium sulfate. After filtration of the sodium sulfate, the solvent was removed under reduced pressure. The obtained residue was dissolved in hot n-hexane and the mixture was then kept at 4° C. overnight. After filtration of the precipitate, the solvent was removed under reduced pressure to give 3.1 grams of a yellow oil. The residue was purified by chromatography on a silica gel column (140 grams). The product was eluted with 300 ml of CHCl$_3$:ethyl acetate (6:4 v/v). Removal of the solvent under reduced pressure gave 1.34 gram of a colorless oil. Drying under reduced pressure over phosphorus pentoxide gave (S)-1-hexadecyl-2-(6-ethylcarboxy)hexanyl-glycerol as a colorless solid.

Synthesis of (R)-1-hexadecyl-2-(6-ethylcarboxy) hexanyl-sn-glycero-3-phosphoethanolamine 1.34 gram of (S)-1-hexadecyl-2-(6-ethylcarboxy)hexanyl-glycerol and 1.2 ml of triethylamine were dissolved in 15 ml THF. This solution was added dropwise during the course of 15 minutes to an ice-cooled solution of 0.8 ml POCl$_3$ in 10 ml THF. The solution was stirred for an additional 10 minutes with cooling and for an additional 45 minutes at room temperature. The reaction mixture was cooled in ice and a solution of 0.52 ml ethanolamine and 2.4 ml triethylamine in 25 ml THF was added dropwise over the course of 15 minutes. Stirring of the reaction mixture was continued for 10 minutes while being cooled in an ice bath and then overnight at room temperature. The reaction mixture was filtered, and the solvent was removed under reduced pressure. The obtained residue was dissolved in a mixture of 24 ml acetic acid and 10 ml water, and then heated to a temperature of 70° C. for 1 hour. The mixture was then extracted thrice with 50 ml chloroform and washed twice with 50 ml water. Removal of the solvent under reduced pressure gave 1.87 gram of (R)-1-hexadecyl-2-(6-ethylcarboxy)hexanyl-sn-glycero-3-phosphoethanolamine as a yellow oil.

Synthesis of (R)-1-hexadecyl-2-(6-ethylcarboxy) hexanyl-sn-glycero-3-phosphocholine 1.87 gram of (R)-1-hexadecyl-2-(6-ethylcarboxy)hexanyl-sn-glycero-3-phosphoethanolamine was dissolved in a mixture of 50 ml isopropanol and 18 ml dichloromethane. A solution of 2.17 grams potassium carbonate in 10 ml water was added dropwise over the course of 5 minutes while the reaction was kept at a temperature of 35-40° C. A solution of 1.52 ml dimethylsulfate in 10 ml isopropanol was added dropwise at a temperature of 40° C. over the course of 10 minutes. The reaction was kept at a temperature of 40° C. for 90 minutes, and then water was added and the mixture was extracted twice with 50 ml chloroform. The organic phase washed with 50 ml water, and the solvent was removed under reduced pressure to give 1.8 gram of (R)-1-hexadecyl-2-(6 ethylcarboxy)hexanyl-sn-glycero-3-phosphocholine as a wax.

Synthesis of (R)-1-hexadecyl-2-(6-carboxy)hexanyl-sn-glycero-3-phosphocholine (CI-203)

1.8 gram of (R)-1-hexadecyl-2-(6-ethylcarboxy)hexanyl-sn-glycero-3-phosphocholine was dissolved in 50 ml methanol. A solution of 10% sodium hydroxide was added, and the reaction mixture was stirred at room temperature for 5 hours. The pH of the reaction was adjusted to a range of 4-5 by adding sodium dihydrogen phosphate. 70 ml water and 70 ml chloroform were added. The aqueous and organic phases were separated, and the solvent from the organic phase was removed under reduced pressure. The obtained residue was dissolved in chloroform, dried over sodium sulfate and filtered, and the solvent was removed under reduced pressure to give 1.29 gram of a white wax. The residue was purified by chromatography on silica gel (62 grams). The product was eluted with CHCl$_3$:methanol:H$_2$O at a 60:35:5 volumetric ratio. After removal of the solvent under reduced pressure, the residue was dissolved in chloroform, dried over sodium sulfate and the solvent was removed under reduced pressure to give 1.0 gram of (R)-1-hexadecyl-2-(6-carboxy)hexanyl-sn-glycero-3-phosphocholine as a white wax.

NMR characterization of 1-hexadecyl-2-(6-carboxy) hexanyl-glycero-3-phosphocholine The sample was dissolved in deuterated chloroform (CDCl$_3$). $^1$H NMR and $^{13}$C NMR spectra were measured at 300 MHz.

The results showed the expected signals for the structural elements of 1-hexadecyl-2-(6-carboxy)hexanyl-glycero-3-phosphocholine and thus fully supported the structure.

The assignment of the observed $^1$H peaks according to the structure of 1-hexadecyl-2-(6-carboxy)hexanyl-glycero-3-phosphocholine was as follows:

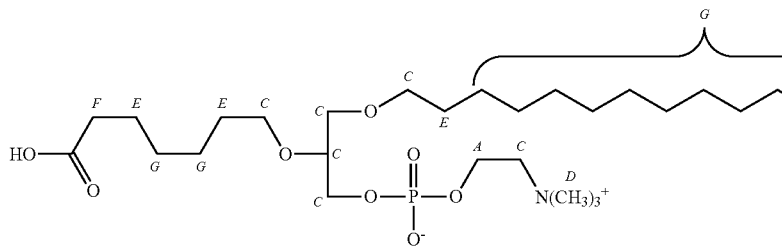

¹H NMR (300 MHz, reference solvent (CDCl₃)=7.260 ppm)

| δ [ppm] | Description | Assignment (see formula above) |
|---|---|---|
| 4.279 | 2H, br, s | A |
| 3.375-3.539 | 11 H, m, 5 × CH₂ + CH | C |
| 3.242 | 9H, s, 3 × CH₃ | D |
| 2.302 | 2 H, t, CH₂, J = 6.15 Hz | F |
| 1.543-1556 | 6H, m | E |
| 1.256-1374 | 30 H, m, 15 × CH₂ | G |
| 0.879 | 3 H, t, 1 × CH₃, J = 6.75 Hz | H |

The assignment of the observed $^{13}$C peaks according to the structure of 1-hexadecyl-2-(6-carboxy)hexanyl-glycero-3-phosphocholine was as follows:

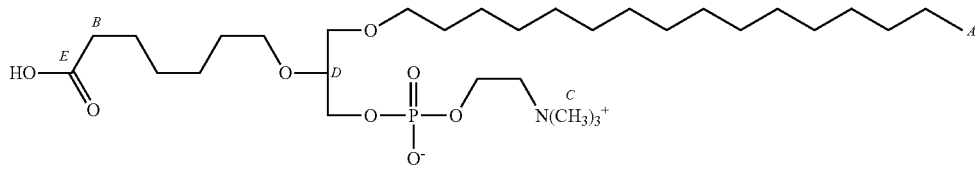

$^{13}$C NMR (300 MHz, reference solvent (CDCl₃)=77.002 ppm)

| δ [ppm] | Assignment (see formula above) |
|---|---|
| 176.60 | E |
| 78.166 | D |
| 71.749 | |
| 70.368 | |
| 70.116 | |
| 65.972 | |
| 59.777 | |
| 54.390 | C |
| 34.120 | B |
| 31.925 | |
| 29.732 | |
| 29.597 | |
| 29.526 | |
| 29.368 | |
| 28.412 | |
| 26.109 | |
| 25.373 | |
| 24.665 | |
| 22.685 | |
| 14.111 | A |

Mass spectrometry characterization of 1-hexadecyl-2-(6-carboxy)hexanyl-glycero-3-phosphocholine The calculated mass for 1-hexadecyl-2-(6-carboxy)hexanyl-glycero-3-phosphocholine ($C_{31}H_{64}NO_8P$) was 609.82.

The mass spectrum obtained using Electrospray Ionization Mass Spectrometry (ESI-MS), showed a molecular ion with m/z=609 corresponding to the deprotonated molecular ion $[M-H]^-$. The mass spectrometry spectrum is thus in agreement with the chemical structure of 1-hexadecyl-2-(6-carboxy)hexanyl-glycero-3-phosphocholine.

In Vitro IL12/23 p40 Production:

The effect of CI-203 on in vitro production of IL12/23 p40 was determined as described hereinabove in the Materials and Methods section.

As shown in FIG. 7, CI-203 inhibited production of IL12/23 p40 by bone marrow-derived cells in a dose-dependent manner.

Tyrosine Phosphorylation:

The effect of CI-203 on in vitro tyrosine phosphorylation in bone marrow-derived cells was determined as described hereinabove in the Materials and Methods section. Both the R enantiomer of CI-203 and racemic CI-203 were tested. Both the R enantiomer and the S enantiomer of CI-201 were used as controls.

As shown in FIG. 8, treatment with 20 µg/ml (33 µM) of both (R)-CI-203 and racemic CI-203 caused a reduction in phosphotyrosine levels, whereas treatment with 1 µg/ml (1.7 µM) CI-203 had no apparent effect. The effect of (R)-CI-203 and racemic CI-203 was similar to the effect induced by both the R and S enantiomers of CI-201.

Toxicity of CI-203:

The toxicity of CI-203 was evaluated as described hereinabove in the Materials and Methods section.

As shown in FIGS. 9A and 9B, significant toxicity of CI-203 was observed only at a dose of 100 µg/ml, and the $LD_{50}$ of CI-203 lies between 50 and 100 µg/ml.

Example 3

1-dodecyl-2-(4-carboxy)butyl-glycero-3-phosphocholine (CI-209)

(R)-1-dodecyl-2-(4-carboxy)butyl-sn-glycero-3-phosphocholine was synthesized as described hereinbelow using (R)-(−)-2,2-dimethyl-1,3-dioxolane-4-methanol as a starting material. (S)-1-dodecyl-2-(4-carboxy)butyl-glycero-3-phosphocholine is synthesized using the same procedures, but with (S)-(+)-2,2-dimethyl-1,3-dioxolane-4-methanol as the starting material.

Synthesis of (S)-1-dodecyl-glycerol 11 grams of (R)-(−)-2,2-dimethyl-1,3-dioxolane-4-methanol, 20.6 grams of powdered potassium hydroxide and 24.08 grams of dodecyl bromide were stirred in 300 ml benzene and refluxed for 14 hours, while removing the water formed by azeotropic distillation. The reaction mixture was then cooled to room temperature and 150 ml water was added. The reaction mixture was then extracted thrice with 150 ml methyl tert-butyl ether (MTBE), the combined organic phase was washed with 100 ml water, and the solvent was then removed under reduced pressure, yielding 29.71 grams of a light brown oil. This residue was dissolved in 100 ml methanol. 6 ml of concentrated hydrochloric acid was added, and the resulting solution was refluxed until a clear solution was obtained, followed by cooling to room temperature and addition of 100 ml water. The product was extracted with 150 ml chloroform, washed consecutively with 150 ml water, 150 ml of a saturated aqueous solution of sodium bicarbonate, and again with 150 ml water. The solvent was dried over anhydrous $Na_2SO_4$, filtered, and removed under reduced pressure, yielding 23.77 grams of the crude product. The crude product was recrystallized from 200 ml hexane at 4° C. to give 19.83 grams of pure (S)-1-dodecyl-glycerol as white crystals.

Synthesis of (R)-1-dodecyl-3-trityl-glycerol 19.83 grams of (S)-1-dodecyl-glycerol and 21.0 grams of triphenylchloromethane were added to a mixture of 250 ml dry tetrahydrofuran (THF) and 60 ml dry acetonitrile. 22 ml of dry triethylamine was added and the reaction mixture was refluxed for 17 hours under nitrogen. The reaction mixture was then cooled to room temperature, and 5 ml triethylamine and 10 grams of ice were added. The mixture was transferred to a separatory funnel and extracted with 100 ml MTBE. The organic phase was washed consecutively with 150 ml water, 150 ml of dilute (1.5%) $H_2SO_4$, 150 ml water, 150 ml of concentrated aqueous sodium bicarbonate, and again with 150 ml water. The solution was then dried over anhydrous $Na_2SO_4$ and the solvent was removed under reduced pressure. The residue, 40.63 grams of a brown oil, was dissolved in 200 ml ethyl acetate and cooled to −20° C. for a couple of days. The mixture was centrifuged at a temperature of −10° C. and the mother liquid was poured off. The solid melted at room temperature and was purified by chromatography on a silica gel column (195 grams). 18.57 grams of pure (R)-1-dodecyl-3-trityl-glycerol was eluted by mixtures of chloroform and hexane followed by a mixture of 9:1 (v/v) chloroform:ethyl acetate. The yield was 48.5%.

Synthesis of (S)-1-dodecyl-2-(5'-hexenyl)-glycerol 18.57 grams of (R)-1-dodecyl-3-trityl-glycerol, 4 ml of 6-bromo-1-hexene and 22.57 grams of powdered potassium hydroxide were stirred in 100 ml benzene and refluxed for 9 hours, while removing the water formed by azeotropic distillation. The reaction mixture was cooled to room temperature, 100 ml water added, and the solution was transferred to a separatory funnel. The solution was extracted four times with 50 ml diethyl ether and the solvent from the combined organic phase was removed under reduced pressure, yielding 19.31 grams of a residue. The residue was dissolved in 100 ml methanol and 6 ml of concentrated HCl (37%) was then added. The reaction mixture was refluxed for 4 hours, cooled to room temperature and stirred at this temperature for over 96 hours. The reaction mixture was concentrated to about 50 ml by removal of the solvent under reduced pressure, and 50 ml water was added. The solution was transferred to a separatory funnel and extracted twice with 100 ml MTBE. The solvent was then removed under reduced pressure. The residue (18.85 grams) was dissolved in hexane and the obtained solution was cooled in an ice-bath for 30 minutes. The precipitate was filtered off, washed with cooled hexane, and the solvent from the filtrate was removed under reduced pressure. The residue (15.23 grams) was dissolved again in hot hexane, and cooled to 4° C. overnight. After filtration and removal of the solvent from the filtrate, the filtrate was purified by chromatography over silica gel (77.34 grams). The elution was performed with a 1:1 (v/v) mixture of chloroform and ethyl acetate, followed by pure chloroform and then chloroform with 3% acetone. 10.03 grams of pure (S)-1-dodecyl-2-(5'-hexenyl)-glycerol was obtained. The yield was 78.1%.

Synthesis of (R)-1-dodecyl-2-(5'-hexenyl)-sn-glycero-3-phosphoethanolamine 5.75 grams of (S)-1-dodecyl-2-(5'-hexenyl)-sn-glycerol (which was dried in a desiccator over $P_2O_5$) and 3.11 ml of triethylamine were dissolved in 50 ml THF. This solution was added dropwise during the course of 30 minutes to an ice-cooled solution of 1.7 ml $POCl_3$ in 20 ml THF. The stirring was continued for an additional 30 minutes with cooling and then for an additional 45 minutes at room temperature. The reaction mixture was then cooled in an ice-bath, and a solution of 1.3 ml ethanolamine and 3.3 ml triethylamine in 30 ml THF was then added dropwise over the course of 15 minutes. The stirring was continued for 30 minutes in the ice-bath and then at room temperature overnight. The reaction mixture was filtered, and the solvent from the filtrate was removed under reduced pressure. The residue was dissolved in a mixture of 36 ml acetic acid and 15 ml water, heated to 70° C. for 1 hour, and cooled to room temperature. The solution was extracted twice with 50 ml of a 2:1 (v/v) mixture of chloroform:methanol, washed with dilute sodium bicarbonate solution, and the solvent was removed under reduced pressure, yielding 8.54 grams of a crude product. This crude product was purified by chromatography over silica gel (55 grams). 4.99 grams of pure (R)-1-dodecyl-2-(5'-hexenyl)-sn-glycero-3-phosphoethanolamine was eluted with chloroform followed by mixtures of chloroform with 2.5-40% methanol. The yield was 63.85%.

Synthesis of (R)-1-dodecyl-2-(5'-hexenyl)-sn-glycero-3-phosphocholine 4.99 grams of (R)-1-dodecyl-2-(5'-hexenyl)-sn-glycero-3-phosphoethanolamine was dissolved in a mixture of 35 ml methanol and 100 ml dichloromethane. A solution of 10 grams potassium carbonate in 20 ml water was added. 2.5 ml of dimethylsulfate was then added dropwise during the course of 1 hour, and the reaction was stirred at room temperature overnight. As determined by thin layer chromatography, there was still some starting material in the reaction mixture. An additional 1 ml of dimethylsulfate was added, and the reaction mixture was heated to 40° C. for 5 hours. The reaction mixture was then cooled to room temperature, 100 ml water added, followed by extraction of the mixture thrice with 100 ml of a 2:1 (v/v) mixture of chloroform:methanol. The solvent from the organic phase was removed under reduced pressure, yielding 5.8 grams of crude (R)-1-dodecyl-2-(5'-hexenyl)-sn-glycero-3-phosphocholine.

Synthesis of (R)-1-dodecyl-2-(4-carboxy)butyl-sn-glycero-3-phosphocholine (CI-209)

2.76 grams of sodium bicarbonate was added to a solution of 5.18 grams (R)-1-dodecyl-2-(5'-hexenyl)-sn-glycero-3-phosphocholine in 100 ml water. A solution of 20.4 grams sodium periodate in 100 ml water was then added. A solution of 270 mg potassium permanganate in 82 ml water was placed in a dropping funnel and added dropwise as needed to maintain a pink color of the reaction mixture. A total of 58 ml of permanganate solution was added during the reaction. The reaction mixture was stirred at room temperature overnight. The pH of the reaction was adjusted to approximately 4 by addition of 20 grams of sodium dihydrogen phosphate and then 3 ml of 80% phosphoric acid. The reaction mixture was extracted thrice with 50 ml of a 2:1 mixture of chloroform:methanol, and the solvent from the organic phase was removed under reduced pressure. The residue was dissolved in chloroform and washed with water. The organic solution was dried over anhydrous $Na_2SO_4$ and the solvent was removed under reduced pressure, yielding 4.89 grams of the crude product. The crude product was purified by chromatography over silica gel (58.2 grams). 1.81 grams of pure (R)-1-dodecyl-2-(4-carboxy)butyl-sn-glycero-3-phosphocholine was eluted with chloroform followed by mixtures of chloroform with 10%-60% methanol. The yield was 33.76%.

An additional synthetic pathway for synthesis of CI-209 was performed as follows:

Synthesis of (R)-1-dodecyl-2-(5'-hexenyl)-3-acetyl-glycerol (R)-1-dodecyl-3-trityl-glycerol (67 grams), prepared as described hereinabove, 6-bromo-1-hexene (26.14 grams) and powdered KOH (35 grams) were stirred in benzene (200 ml) and refluxed for 9 hours while removing the water formed by azeotropic distillation. The volume of the solvent was gradually reduced to about 100 ml. The reaction mixture was cooled to room temperature and water (150 ml) added. The solution was transferred to a separatory funnel and extracted with diethyl ether (3×150 ml). The combined organic phase was washed with water (3×150 ml) and then the solvent removed under reduced pressure. The residue (78 grams) was dissolved in acetic acid (200 ml) and the solution was cooled in an ice bath. To this cooled solution, a mixture of 40 ml acetic anhydride (40 ml) and 1 ml 70% perchloric acid were added. The reaction mixture was allowed to reach room temperature and was then stirred at room temperature overnight. Ice was added, and then diethyl ether (400 ml) and water (400 ml) were added. The organic phase was separated and the solvent was removed under reduced pressure. The residue was dissolved in hot hexane and the solution was stored overnight at a temperature of 4° C. The precipitated by-products were filtered off and the solvent from the filtrate was removed under reduced pressure to give 55 grams of an oily brown product. The crude product was purified by chromatography on silica gel column (350 grams). The pure (R)-1-dodecyl-2-(5'-hexenyl)-3-acetyl-glycerol was eluted with mixture of 1:1 (v/v) chloroform:hexane (1500 ml) followed by chloroform (1500 ml). Removal of solvent from fractions containing the product yielded 52 grams of the product.

Synthesis of (S)-1-dodecyl-2-(4-carboxy)butyl-glycerol

Sodium periodate (150 grams), potassium permanganate (2.5 grams) and sodium hydrogen carbonate (10 grams) were suspended in water (500 ml). A solution of (R)-1-dodecyl-2-(5'-hexenyl)-3-acetyl-glycerol (52 grams) in tert-butanol (500 ml) was added to the aqueous suspension over 1 hour and the reaction mixture was then stirred at room temperature overnight. The mixture was filtered through a pad of Celite which was further washed with tert-butanol. The solution was extracted with hexane (3×100 ml). The combined organic phase was washed twice with aqueous sodium bisulfite (15 grams in 100 ml water) and then with water (100 ml). The solvent was concentrated under reduced pressure and treated with 100 ml water and 10 ml of 30% NaOH to reach a pH of 12. The mixture was stirred at room temperature overnight. The mixture was extracted with an 8:2 (v/v) mixture of hexane: MTBE (200 ml) in order to remove remaining impurities. The aqueous basic solution was acidified with HCl (6 ml) to pH 1 and then extracted with a 7:3 (v/v) mixture of hexane: ethyl acetate (3×100 ml). The combined organic phase was dried over sodium sulfate and the solvent was removed under reduced pressure. The residue (30 grams of a yellow oil) was purified by chromatography on a silica gel column (500 grams). Pure (S)-1-dodecyl-2-(4 carboxy)butyl-glycerol was eluted with a 1:1 (v/v) mixture of chloroform:hexane (1000 ml) followed by chloroform (1000 ml) and then mixtures of chloroform:ethyl acetate (9:1 to 1:1, v/v). Removal of the solvent from fractions containing the product yielded 13.4 grams of the product.

Synthesis of (S)-1-dodecyl-2-(4-methylcarboxy)butyl-sn-glycerol (S)-1-dodecyl-2-(4-carboxy)butyl-sn-glycerol (13.38 grams) was dissolved in 100 ml methanol, and 2 ml of concentrated hydrochloric acid was added. The reaction mixture was stirred at room temperature for 5 hours. Water (50 ml) was added, and the solution was transferred to a separation funnel and extracted with chloroform (3×100 ml). The combined organic phase was washed with water (100 ml), concentrated sodium bicarbonate (100 ml) and again with water (100 ml). Drying over anhydrous $Na_2SO_4$ and evaporation of the solvent under reduced pressure yielded 13.9 grams of crude product as a residue. The residue was purified by chromatography on a silica gel column (200 grams). Pure (S)-1-dodecyl-2-(4 methylcarboxy)butyl-glycerol was eluted with chloroform followed by mixtures of chloroform:ethyl acetate (9:1 to 7:3, v/v). Removal of solvent from fractions containing the product yielded 10.7 grams of pure product.

Synthesis of (R)-1-dodecyl-2-(4-methylcarboxy)butyl-sn-glycero-3-phosphocholine 10.7 grams of (S)-1-dodecyl-2-(4-methylcarboxy)butyl-sn-glycerol (which was dried by azeotropic distillation with benzene) and 5.2 ml of dry triethylamine were dissolved in THF (50 ml). This solution was added dropwise during the course of 90 minutes to an ice-cooled solution of $POCl_3$ (3.2 ml) in 50 ml THF while stirring. The stirring was continued for an additional 15 minutes with cooling and then for an additional 45 minutes at room temperature. The reaction mixture was then cooled in an ice-bath, and a solution of ethanolamine (22 ml) and triethylamine (7.2 ml) in 50 ml THF was then added dropwise over the course of 60 minutes while stirring. The stirring was continued for 30 minutes in the ice-bath and then at room temperature overnight. The reaction mixture was filtered, and the solvent from the filtrate was removed under reduced pressure. The residue (14 grams of a yellow oil) was dissolved in a mixture of acetic acid (120 ml) and water (50 ml), heated to 70° C. for 1 hour, and cooled to room temperature. The solution was extracted with a 2:1 (v/v) mixture of chloroform:methanol (3×100 ml), the combined organic phase washed with water (2×100 ml) and the solvent was removed under reduced pressure, yielding 15 grams of (R)-1-dodecyl-2-(4-methylcarboxy)butyl-sn-glycero-3-phosphoethanolamine as an orange oil. (R)-1-dodecyl-2-(4-methylcarboxy)butyl-sn-glycero-3-phosphoethanolamine (14 grams) was dissolved in mixture of isopropanol (100 ml) and dichloromethane (55 ml). A solution of potassium carbonate (22 grams) in water (100 ml) was added dropwise while the reaction mixture was kept at 35-40° C. A solution of dimethylsulfate (14 ml) in isopropanol (50 ml) was added dropwise at 40° C. The mixture was stirred at 40° C. for 2 hours, cooled to room temperature, and stirred at room temperature overnight. Water (80 ml) was added and the mixture was extracted with chloroform (3×100 ml). The combined organic phase was washed with water (100 ml) and the solvent was removed under reduced pressure, yielding crude (R)-1-dodecyl-2-(4 methylcarboxy)butyl-sn-glycero-3-phosphocholine (14.6 grams) as an orange wax.

Synthesis of (R)-1-dodecyl-2-(4-carboxy)butyl-sn-glycero-3-phosphocholine (CI-209)

(R)-1-dodecyl-2-(4-methylcarboxy)butyl-sn-glycero-3-phosphocholine (14.6 grams) was dissolved in 8:2 (v/v) methanol: 10% NaOH solution (100 ml) and the reaction mixture was stirred at room temperature for 5 hours. The pH of the reaction was adjusted to 5 by addition of sodium dihydrogen phosphate and formic acid. Water (150 ml), chloroform (150 ml) and methanol (50 ml) were added. The aqueous and organic phases were separated, and the solvent from the organic phase was removed under reduced pressure. The obtained residue was dissolved in chloroform, dried over sodium sulfate and filtered, and the solvent was removed under reduced pressure, yielding 15 grams as a wax. The wax was purified by chromatography on silica gel (224 grams). The product was eluted with chloroform (600 ml) followed by an 8:2 (v/v) mixture of chloroform:methanol (600 ml) and then by a mixture of chloroform:methanol:$H_2O$ (60:35:5, v/v). After removal of the solvent under reduced pressure from the fractions containing the desired product, the residue was dissolved in chloroform, dried over sodium sulfate and the solvent was removed under reduced pressure, yielding 10.5 grams of (R)-1-dodecyl-2-(4 carboxy)butyl-sn-glycero-3-phosphocholine as a white wax.

NMR characterization of 1-dodecyl-2-(4-carboxy)butyl-glycero-3-phosphocholine

The sample was dissolved in deuterated chloroform (CDCl$_3$) with a few drops of deuterated methanol. $^1$H NMR and $^{13}$C NMR spectra were measured at 300 MHz.

The results showed the expected signals for the structural elements of 1-dodecyl-2-(4-carboxy)butyl-glycero-3-phosphocholine and thus fully supported the structure.

The assignment of the observed $^1$H peaks according to the structure of 1-dodecyl-2-(4-carboxy)butyl-glycero-3-phospcholine was as follows:
$^1$H NMR

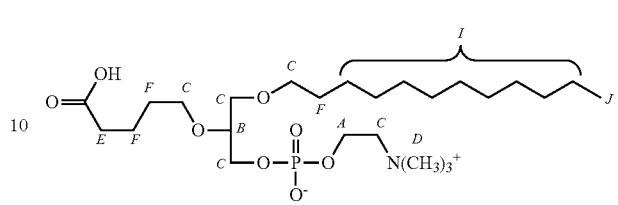

$^1$H NMR (300 MHz, reference solvent (CDCl$_3$)=7.282 ppm)

| δ [ppm] | Description | Assignment (see formula above) |
|---|---|---|
| 4.264 | 2 H, br, s | A |
| 3.775 | 1 H, m | B |
| 3.381-3.671 | 10 H, m, 5 × CH$_2$ | C |
| 3.251 | 9 H, s, 3 × CH$_3$ | D |
| 2.261 | 2 H, t, | E |
| 1.535-1.582 | 6 H, m 3 × CH$_2$ | F |
| 1.258 | 18 H, m, 9 × CH$_2$ | I |
| 0.880 | 3 H, t, 1 × CH$_3$, J = 6.6 Hz | J |

The assignment of the observed $^{13}$C peaks according to the structure of 1-dodecyl-2-(4-carboxy)butyl-glycero-3-phosphocholine was as follows:
$^{13}$C NMR

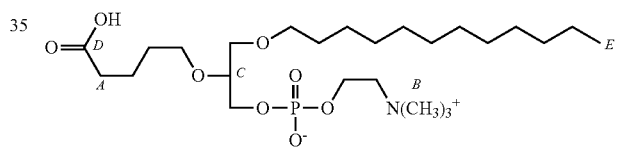

$^{13}$C NMR (300 MHz, reference solvent (CDCl$_3$)=78.020 ppm)

| δ [ppm] | Assignment (see formula above) |
|---|---|
| 178.51 | D |
| 78.446 | C |
| 72.200 | |
| 70.535-70.642 | |
| 66.805-66.812 | |
| 65.997-66.070 | |
| 59.515-59.580 | |
| 54.419 | B |
| 35.578 | A |
| 32.310 | |
| 30.015 | |
| 29.892 | |
| 29.730 | |
| 26.449 | |
| 23.037 | |
| 22.685 | |
| 14.224 | E |

Mass spectrometry characterization of 1-dodecyl-2-(4-carboxy)butyl-glycero-3-phosphocholine The calculated mass for 1-dodecyl-2-(4-carboxy)butyl-glycero-3-phosphocholine (C$_{25}$H$_{52}$NO$_8$P) was 525.3431.

The mass spectrum obtained using Electrospray Ionization Mass Spectrometry (ESI-MS), showed a molecular ion with m/z=524 corresponding to the deprotonated molecular ion [M−H]⁻. The mass spectrometry spectrum is thus in agreement with the chemical structure of 1-dodecyl-2-(4-carboxy) butyl-glycero-3-phosphocholine.

In Vitro IL12/23 p40 Production:

The effect of CI-209 on in vitro production of IL12/23 p40 was determined as described hereinabove in the Materials and Methods section.

As shown in FIG. 10, CI-209 inhibited production of IL12/23 p40 by bone marrow-derived cells in a dose-dependent manner.

Tyrosine Phosphorylation:

The effect of CI-209 on in vitro tyrosine phosphorylation in primary macrophages cells was determined as described hereinabove in the Materials and Methods section.

As shown in FIG. 11, treatment with 20 μg/ml of CI-209 induced an increase in phosphotyrosine levels, whereas treatment with 20 μg/ml of CI-201 caused a decrease in phosphotyrosine levels.

Toxicity of CI-209:

The toxicity of CI-209 was evaluated as described hereinabove in the Materials and Methods section.

As shown in FIGS. 9A and 9B, in two experiments which were conducted, toxicity of CI-209 was not observed at any of the tested doses. Thus, the $LD_{50}$ of CI-209 was above 150 μg/ml (286 μM).

Example 4

1-hexadecyl-2-(4-carboxy)butyl-glycero-3-phosphoethanolamine-N-glutaric acid (CI-210)

(R)-1-hexadecyl-2-(4-carboxy)butyl-sn-glycero-3-phosphoethanolamine-N-glutaric acid was synthesized as described hereinbelow using (R)-1-hexadecyl-2-(4 methylcarboxy)butyl-sn-glycero-3-phosphoethanolamine as a starting material. (S)-1-hexadecyl-2-(4-carboxy)butyl-glycero-3-phosphoethanolamine-N-glutaric acid is synthesized using the same procedures, but with (S)-1-hexadecyl-2-(4 methylcarboxy)butyl-glycero-3-phosphoethanolamine as the starting material.

The synthesis of (R)- and (S)-1-hexadecyl-2-(4 methylcarboxy)butyl-glycero-3-phosphoethanolamine is described hereinabove in Example 1.

1.85 grams (3.33 mmol) of (R)-1-hexadecyl-2-(4-methylcarboxy)butyl-sn-glycero-3-phosphoethanolamine was dissolved in 175 ml of dichloromethane, and 1.39 ml of triethylamine was added. This solution was added dropwise during the course of 15 minutes to a solution of 0.42 gram glutaric anhydride in 175 ml of dichloromethane. After completing the addition, the reaction mixture was stirred at room temperature for 1 hour. A solution of 20 grams sodium hydrogen phosphate in 100 ml water was added and the reaction mixture was stirred vigorously for 20 minutes. The reaction mixture was transferred to a separatory funnel, the phases separated, and the aqueous phase was extracted twice with 100 ml chloroform. The combined organic phase was dried over anhydrous $Na_2SO_4$ and the solvent was removed under reduced pressure. 1.16 gram of the crude product was obtained, which was purified over silica gel (60 grams). The product was eluted from the column with 200 ml of chloroform followed by mixtures of chloroform:methanol at ratios of 9:1, 8:2 and 7:3 (v/v), and then 200 ml of chloroform:methanol (1:1 by volumetric ratio). The solvent from fractions containing the product was removed under reduced pressure, the residue was dissolved in chloroform and dried over anhydrous $Na_2SO_4$, and the solvent was removed under reduced pressure to give 131.4 mg of pure (R)-1-hexadecyl-2-(4-carboxy)butyl-sn-glycero-3-phosphoethanolamine-N-glutaric acid (CI-210) as an off-white wax.

NMR characterization of 1-hexadecyl-2-(4-carboxy) butyl-glycero-3-phosphoethanolamine-N-glutaric acid The sample was dissolved in deuterated chloroform ($CDCl_3$) with a few drops of deuterated methanol. ¹H NMR and ¹³C NMR spectra were measured at 300 MHz.

The results showed the expected signals for the structural elements of 1-hexadecyl-2-(4-carboxy)butyl-glycero-3-phosphoethanolamine-N-glutaric acid and thus fully supported the structure.

The assignment of the observed ¹H peaks according to the structure of 1-hexadecyl-2-(4-carboxy)butyl-glycero-3-phosphoethanolamine-N-glutaric acid was as follows:

¹H NMR

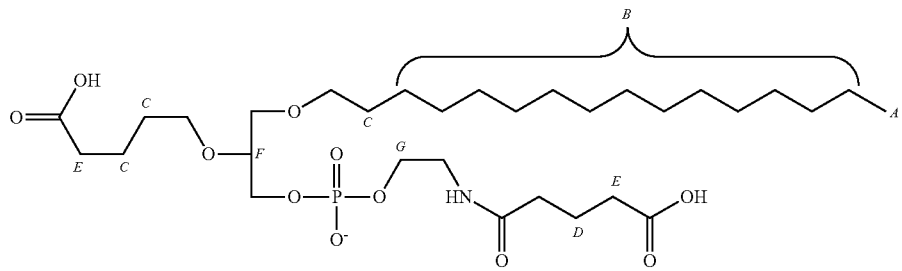

¹H NMR (300 MHz, reference solvent ($CDCl_3$)=7.28 ppm)

| δ [ppm] | Description | Assignment (see formula above) |
|---|---|---|
| 3.945 | 2 H, br, s | G |
| 3.896 | 1 H, br, s | F |
| 3.585-3.608 | 4 H, m, 2 × $CH_2$ | |
| 3.385-3.431 | 4 H, m, 2 × $CH_2$ | |
| 3.058-3.130 | 2 H, m, $CH_2$ | |
| 2.332 | 4 H, m, 2 × $CH_2$ | E |
| 1.933 | 2 H, m, $CH_2$ | D |
| 1.533-1.673 | 6 H, m, 3 × $CH_2$ | C |
| 1.255 | 26 H, m, 13 × $CH_2$ | B |
| 0.879 | 3 H, t, 1 × $CH_3$, J = 6.45 Hz | A |

The assignment of the observed $^{13}$C peaks according to the structure of 1-hexadecyl-2-(4-carboxy)butyl-glycero-3-phosphoethanolamine-N-glutaric acid was as follows:

$^{13}$C NMR

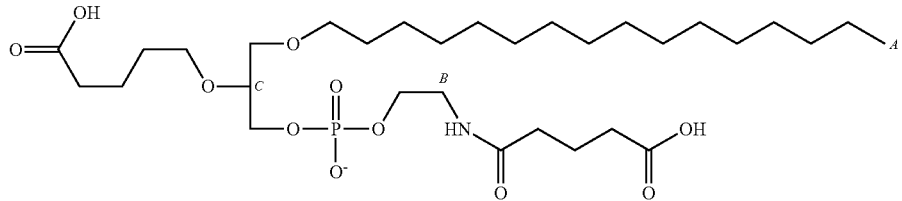

$^{13}$C NMR (300 MHz, reference solvent (CDCl$_3$)=77.062 ppm)

| δ [ppm] | Assignment (see formula above) |
| --- | --- |
| 177.78 | |
| 177.37 | |
| 174.31 | |
| 78.656 | C |
| 71.836 | |
| 70.343 | |
| 69.841 | |
| 65.463-65.790 | |
| 64.541-64.861 | |
| 45.732 | B |
| 35.075 | |
| 33.872 | |
| 33.213 | |
| 31.951 | |
| 30.938 | |
| 29.748 | |
| 29.698 | |
| 29.572 | |
| 29.391 | |
| 29.084 | |
| 26.142 | |
| 22.710 | |
| 21.566 | |
| 20.985 | |
| 14.128 | A |

Mass spectrometry characterization of 1-hexadecyl-2-(4-carboxy)butyl-glycero-3-phosphoethanolamine-N-glutaric acid The calculated mass for 1-hexadecyl-2-(4-carboxy)butyl-glycero-3-phosphoethanolamine-N-glutaric acid (C$_{31}$H$_{59}$NO$_{11}$P) was 652.7746.

The mass spectrum obtained using Electrospray Ionization Mass Spectrometry (ESI-MS), showed a molecular ion with m/z=652 corresponding to the deprotonated molecular ion [M–H]$^-$. The mass spectrometry spectrum is thus in agreement with the chemical structure of 1-hexadecyl-2-(4-carboxy)butyl-glycero-3-phosphoethanolamine-N-glutaric acid (CI-210).

In Vitro IL12/23 p40 Production:

The effect of CI-210 on in vitro production of IL12/23 p40 was determined as described hereinabove in the Materials and Methods section.

As shown in FIG. 13, CI-210 inhibited production of IL12/23 p40 by bone marrow-derived cells in a dose-dependent manner.

Tyrosine Phosphorylation:

The effect of CI-210 on in vitro tyrosine phosphorylation in primary macrophages cells was determined as described hereinabove in the Materials and Methods section.

As shown in FIG. 14, treatment with 20 μg/ml of CI-210 induced an increase in phosphotyrosine levels, whereas treatment with 20 μg/ml of CI-201 caused a decrease in phosphotyrosine levels.

Toxicity of CI-210:

The toxicity of CI-210 was evaluated as described hereinabove in the Materials and Methods section.

As shown in FIGS. 15A and 15B, significant toxicity of CI-210 was observed at a dose of 100 μg/ml (156.6 μM) or higher, and the LD$_{50}$ of CI-210 was approximately 150 μg/ml (235 μM).

Example 5

1-octadecyl-2-(4-carboxy)butyl-glycero-3-phosphoethanolamine (CI-216) and 1-octadecyl-2-(4-carboxy)butyl-glycero-3-phosphocholine (CI-215)

(R)-1-octadecyl-2-(4-carboxy)butyl-sn-glycero-3-phosphoethanolamine and (R)-1-octadecyl-2-(4-carboxy)butyl-sn-glycero-3-phosphocholine were synthesized as described hereinbelow using (R)-(−)-2,2-dimethyl-1,3-dioxolane-4-methanol as a starting material. (S)-1-octadecyl-2-(4-carboxy)butyl-glycero-3-phosphoethanolamine and (S)-1-hexadecyl-2-(4-carboxy)butyl-glycero-3-phosphocholine are synthesized using the same procedures, but with (S)-(+)-2,2-dimethyl-1,3-dioxolane-4-methanol as the starting material.

Synthesis of (S)-1-octadecyl-glycerol 20 ml of (R)-(−)-2,2-dimethyl-1,3-dioxolane-4-methanol, 27 grams of powdered potassium hydroxide and 59 grams of 1-bromooctadecane were stirred in 250 ml benzene and refluxed for 6 hours, while removing the water formed by azeotropic distillation. The volume of the solvent was gradually reduced to about 200 ml. The reaction mixture was then cooled to room temperature and stirred at this temperature overnight. 200 ml water was added, the reaction mixture extracted twice with 200 ml diethyl ether, the combined organic phase was washed with 200 ml water, and the solvent was then removed under reduced pressure. The obtained residue was dissolved in 100 ml of a mixture of 90:10:5 (v/v) methanol:water:concentrated hydrochloric acid, and the resulting solution was refluxed for 1 hour, followed by cooling to room temperature and addition of 200 ml water. The product was extracted twice with 200 ml chloroform, washed consecutively with 200 ml water, 200 ml of a saturated aqueous solution of sodium carbonate, and again with 200 ml water. The solvent was then removed under reduced pressure, and the crude product was crystallized from 500 ml hexane to give 39.5 grams of pure (S)-1-octadecyl-glycerol, which was dried in a desiccator under reduced pressure with phosphorus oxide.

Synthesis of (R)-1-octadecyl-3-trityl-glycerol 39 grams (113 mmol) of (S)-1-octadecyl-glycerol and 40 grams (137 mmol) of triphenylchloromethane were added to a mixture of 500 ml of dry THF and 130 ml of dry acetonitrile. 32 ml of dry triethylamine was added and the reaction mixture was refluxed for 17 hours. The reaction mixture was then cooled to room temperature, poured on ice (1 kilogram), transferred to a separatory funnel and extracted twice with 200 ml diethyl ether. The organic phase was washed consecutively with 200 ml water, twice with 100 ml dilute (1.5%) $H_2SO_4$, 200 ml water, 200 ml concentrated aqueous sodium bicarbonate, and again with 200 ml water. The solution was then dried over anhydrous sodium sulfate and the solvent was removed under reduced pressure. The residue, a brown oil, was dissolved in 250 ml ethyl acetate and cooled to −20° C. overnight. The mixture was centrifuged (3,500 rotations per minute) at a temperature of −10° C. (3500 RPM), and the mother liquid was then poured off. The remaining solid was dissolved in hexane and refrigerated (5±3° C.) overnight. Filtration of the precipitate yielded 50 grams of pure (R)-1-octadecyl-3-trityl-glycerol.

Synthesis of (R)-1-octadecyl-2-(5'-hexenyl)-3-trityl-glycerol 50 grams (89.2 mmol) of (R)-1-octadecyl-3-trityl-glycerol and 18 grams (102 mmol) of 5-hexenyl-1-methane sulfonate were dissolved in 150 ml benzene. 20 grams of powdered KOH were added, and the reaction mixture was stirred and refluxed for 6 hours while removing the water formed in the reaction by azeotropic distillation. The volume of the solvent was gradually reduced to about 50 ml. The reaction mixture was cooled to room temperature and 200 ml water was added. The mixture was extracted thrice with 200 ml diethyl ether, the combined organic phase was washed thrice with 200 ml water, and the solvent was removed under reduced pressure, yielding 50 grams of (R)-1-octadecyl-2-(5'-hexenyl)-3-trityl-glycerol as an orange oil.

Synthesis of (S)-1-octadecyl-2-(4-carboxy)butyl-glycerol 145 grams of $NaIO_4$ was dissolved in 500 ml water. To this solution, 14 grams of $K_2CO_3$ and 2.4 grams of $KMnO_4$ were added, and the suspension was heated to a temperature of 40° C. A solution of 50 grams of (R)-1-octadecyl-2-(5'-hexenyl)-3-trityl-glycerol in 500 ml of tert-butanol was added dropwise during the course of 1.5 hours, and the mixture was heated for an additional 4 hours. Additional amounts of $KMnO_4$ solution were added as needed to maintain a pink color. The reaction mixture was cooled to room temperature and stirred at this temperature overnight. Sodium bisulfite was added portionwise until the pink color and then brown color disappeared and the reaction mixture turned yellow. After stirring this solution for 30 minutes at room temperature, 100 ml of 10% sulfuric acid was added dropwise, and the solution was transferred to a separatory funnel and extracted thrice with 200 ml hexane. The organic phase was washed twice with a solution of 15 grams of $Na_2S_2O_5$ in 100 ml water and then with 200 ml water. The organic phase was concentrated by removal of about 500 ml of solvent under reduced pressure. To the remaining solution, 15 ml of water and 1.5 ml concentrated hydrochloric acid were added, and the obtained mixture was refluxed for 6 hours, then cooled to room temperature and concentrated again by removal of solvent under reduced pressure. The pH of the residue was adjusted to 12 by addition of 100 ml water and 10 ml of a 30% NaOH solution. The precipitate was filtered off and washed four times with 10 ml water. The filtrate was extracted with 100 ml of a 1:1 (v/v) mixture of hexane:ethyl acetate. The aqueous phase was acidified to a pH of 1 by adding 8 ml of concentrated hydrochloric acid, and then extracted with 100 ml hexane. Drying over anhydrous $NaSO_4$, removal of the solvent under reduced pressure and overnight recrystallization of the crude product from a 1:9 (v/v) acetone:hexane mixture at 5±3° C. yielded 19 grams of pure (S)-1-octadecyl-2-(4-carboxy)butyl-sn-glycerol as an off-white solid.

Synthesis of (S)-1-octadecyl-2-(4-methylcarboxy)butyl-glycerol 17 grams of (S)-1-octadecyl-2-(4-carboxy)butyl-sn-glycerol was dissolved in 100 ml of methanol. 2 ml of concentrated HCl (37%) was added, and the reaction mixture was stirred at room temperature overnight. The solvent was removed under reduced pressure and 100 ml water was added to the obtained residue. The mixture was extracted thrice with 70 ml chloroform. The combined organic phase was washed with 70 ml water, 70 ml of a concentrated solution of sodium bicarbonate, and again with 70 ml water. The solution was then dried over sodium sulfate, filtered, and evaporated under reduced pressure to give 14 grams of (S)-1-octadecyl-2-(4-methylcarboxy)butyl-glycerol as a white wax.

Synthesis of (R)-1-octadecyl-2-(4-methylcarboxy)butyl-sn-glycero-3-phosphoethanolamine 7 grams of (S)-1-octadecyl-2-(4-methylcarboxy)butyl-glycerol (which was dried by azeotropic distillation with benzene) and 7 ml of triethylamine were dissolved in 60 ml of THF. This solution was added dropwise during the course of 30 minutes to an ice-cooled solution of 4.3 ml of $POCl_3$ in 40 ml of THF. The stirring was continued for an additional 15 minutes with cooling, and for an additional 45 minutes at room temperature. The reaction mixture was then cooled in an ice bath, and a solution of 3 ml ethanolamine and 13 ml triethylamine in 60 ml THF was then added dropwise over the course of 30 minutes. The stirring was continued for 15 minutes in the ice bath, and then at room temperature overnight. The reaction mixture was filtered and the solvent was removed under reduced pressure. The obtained residue was dissolved in a mixture of 72 ml acetic acid and 30 ml water, and heated to a temperature of 70° C. for 1 hour. The mixture was extracted thrice with 80 ml chloroform, and washed twice with 100 ml water. Removal of the solvent under reduced pressure yielded 10 grams of (R)-1-octadecyl-2-(4 methylcarboxy)butyl-sn-glycero-3-phosphoethanolamine as a yellow oil.

Synthesis of (R)-1-octadecyl-2-(4-carboxy)butyl-sn-glycero-3-phosphoethanolamine (CI-216)

3 grams of (R)-1-octadecyl-2-(4-methylcarboxy)butyl-sn-glycero-3-phosphoethanolamine was dissolved in 100 ml of an 8:2 (v/v) mixture of methanol:aqueous 10% sodium hydroxide, and the reaction mixture was stirred at room temperature for 5 hours. The pH of the reaction mixture was then adjusted to approximately 4 by addition of formic acid. 100 ml water and 100 ml chloroform were then added. The phases were separated and the solvent from the organic phase was removed under reduced pressure. The obtained residue was dissolved in chloroform, dried over sodium sulfate and filtered, and the solvent was then removed under reduced pressure. The obtained residue (3 grams) was purified by chromatography on silica gel (55 grams). A mixture of chloroform and hexane, followed by mixtures of chloroform and methanol, and finally mixtures of chloroform, methanol and water, were used to elute 760 mg of (R)-1-octadecyl-2-(4-carboxy)butyl-sn-glycero-3-phosphoethanolamine from the column.

NMR characterization of 1-octadecyl-2-(4-carboxy)butyl-glycero-3-phosphoethanolamine The sample was dissolved in deuterated chloroform ($CDCl_3$) with a few drops of deuterated methanol. $^1H$ NMR and $^{13}C$ NMR spectra were measured at 600 MHz.

The results showed the expected signals for the structural elements of 1-octadecyl-2-(4-carboxy)butyl-glycero-3-phosphoethanolamine and thus fully supported the structure.

The assignment of the observed $^1H$ peaks according to the structure of 1-octadecyl-2-(4-carboxy)butyl-glycero-3-phosphoethanolamine was as follows:

$^1H$ NMR

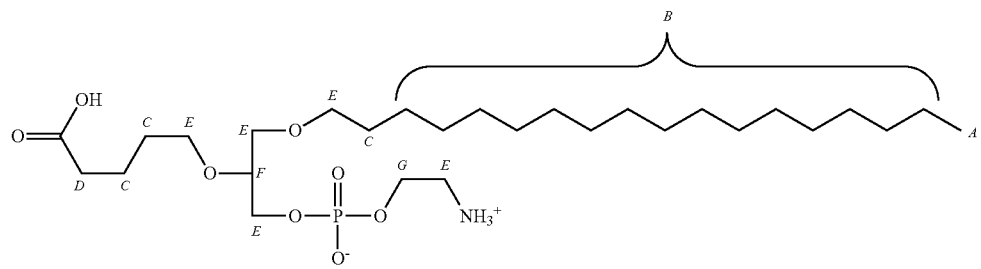

$^1H$ NMR (600 MHz, reference solvent ($CDCl_3$)=7.341 ppm)

| δ [ppm] | Description | Assignment (see formula above) |
| --- | --- | --- |
| 4.113 | 2 H, br s | G |
| 3.858 | 1 H, m | F |
| 3.670 | 2 H, m, $CH_2$ | E |
| 3.614 | 2 H, m, $CH_2$ | E |
| 3.562 | 2 H, m, $CH_2$ | E |
| 3.480 | 2 H, t, J = 5.7 Hz, $CH_2$ | E |
| 3.422 | 2 H, m, $CH_2$ | E |
| 2.334 | 2 H, t, J = 7.2 Hz, $CH_2$ | D |
| 1.692 | 2 H, tt, J = 7.2 Hz, $CH_2$ | C |
| 1.604 | 2 H, tt, J = 6.6 Hz, $CH_2$ | C |
| 1.545 | 2 H, tt, J = 6.6 Hz, $CH_2$ | C |
| 1.259-1.312 | 30 H, m, 15 × $CH_2$ | B |
| 0.881 | 3 H, t, J = 7.2 Hz, $CH_3$ | A |

The assignment of the observed $^{13}C$ peaks according to the structure of 1-octadecyl-2-(4-carboxy)butyl-glycero-3-phosphoethanolamine was as follows:

$^{13}C$ NMR $^{13}C$ NMR (600 MHz, reference solvent ($CDCl_3$)=77.281 ppm)

| δ [ppm] | Assignment (see formula above) |
| --- | --- |
| 177.251 | E |
| 78.072 | D |
| 71.962 | |
| 70.306 | |
| 70.005 | |
| 66.007 | |
| 61.995 | |
| 40.537 | C |
| 34.061 | B |
| 32.030 | |
| 29.815 | |
| 29.764 | |
| 29.727 | |
| 29.645 | |
| 29.459 | |

-continued

| δ [ppm] | Assignment (see formula above) |
| --- | --- |
| 29.314 | |
| 26.178 | |
| 22.778 | |
| 21.877 | |
| 14.140 | A |

Mass spectrometry characterization of 1-octadecyl-2-(4-carboxy)butyl-glycero-3-phosphoethanolamine The calculated mass for 1-octadecyl-2-(4-carboxy)butyl-glycero-3-phosphoethanolamine ($C_{28}H_{58}NO_8P$) was 567.

The mass spectrum obtained using Electrospray Ionization Mass Spectrometry (ESI-MS), showed a molecular ion with m/z=566 corresponding to the deprotonated molecular ion $[M-H]^-$. Positive Electrospray Ionization Mass Spectrometry (ESI+-MS) showed a molecular ion with m/z=590 corresponding to the cationated molecular ion $[M+Na]^+$. The mass spectrometry spectrum is thus in agreement with the

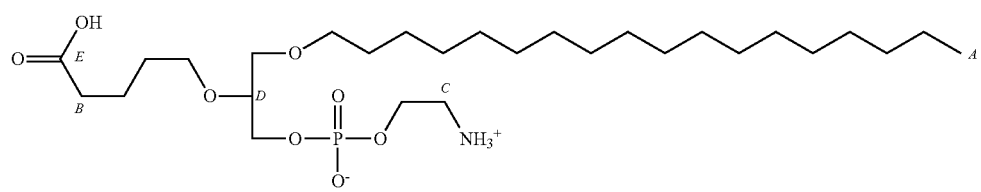

chemical structure of 1-octadecyl-2-(4-carboxy)butyl-glycero-3-phosphoethanolamine (CI-216).

Synthesis of (R)-1-octadecyl-2-(4-methylcarboxy)butyl-sn-glycero-3-phosphocholine 6 grams of (R)-1-octadecyl-2-(4-methylcarboxy)butyl-sn-glycero-3-phosphoethanolamine was dissolved in a mixture of 50 ml isopropanol and 18 ml dichloromethane, and the mixture heated to a temperature in the range if 35-40° C. A solution of 7.5 grams potassium carbonate in 10 ml water was added dropwise while the temperature was kept at 35-40° C. A solution of 5 ml dimethylsulfate in 10 ml isopropanol was then added dropwise at a temperature of 40° C. The reaction was kept at 40° C. for 2 hours and then at room temperature overnight. 100 ml water was added, followed by extraction of the mixture thrice with 100 ml dichloromethane. The organic phase was washed with 100 ml water and the solvent was removed under reduced pressure to give 6 grams of (R)-1-octadecyl-2-(4-methylcarboxy)butyl-sn-glycero-3-phosphocholine as a yellow oil.

Synthesis of (R)-1-octadecyl-2-(4-carboxy)butyl-sn-glycero-3-phosphocholine (CI-215)

6 grams of (R)-1-octadecyl-2-(4-methylcarboxy)butyl-sn-glycero-3-phosphocholine was dissolved in 100 ml of a mixture of an 8:2 (v/v) methanol:aqueous 10% sodium hydroxide, and the reaction mixture was stirred at room temperature for 5 hours. The pH of the reaction mixture was then adjusted to approximately 4 by addition of formic acid. 100 ml water and 100 ml chloroform were then added. The phases were separated and the solvent from the organic phase was removed under reduced pressure. The residue was dissolved in chloroform, dried over sodium sulfate and filtered, and the solvent was then removed under reduced pressure. The obtained residue (5.3 grams) was purified by chromatography on silica gel (112 grams). A mixture of chloroform and hexane, followed by mixtures of chloroform and methanol, and finally mixtures of chloroform, methanol and water, were used to elute the product. Removal of the solvent under reduced pressure from fractions containing the product yielded 2.8 grams of (R)-1-octadecyl-2-(4-carboxy)butyl-sn-glycero-3-phosphocholine (CI-215) as white wax.

NMR characterization of 1-octadecyl-2-(4-carboxy)butyl-glycero-3-phosphocholine The sample was dissolved in deuterated chloroform ($CDCl_3$) with a few drops of deuterated methanol. $^1H$ NMR and $^{13}C$ NMR spectra were measured at 600 MHz.

The results showed the expected signals for the structural elements of 1-octadecyl-2-(4-carboxy)butyl-glycero-3-phosphocholine and thus fully supported the structure.

The assignment of the observed $^1H$ peaks according to the structure of 1-octadecyl-2-(4-carboxy)butyl-glycero-3-phosphocholine was as follows:

$^1H$ NMR:

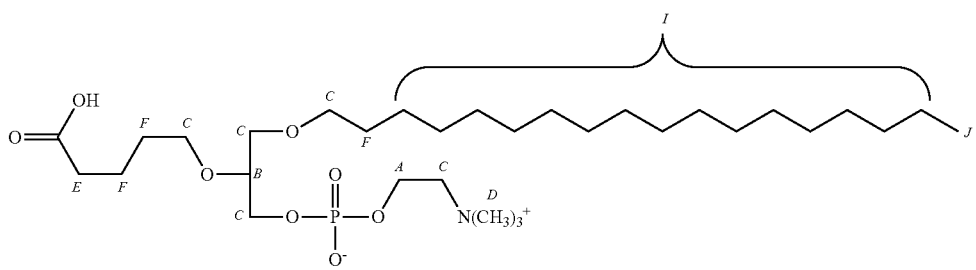

$^1H$ NMR (600 MHz, reference solvent ($CDCl_3$)=7.343 ppm)

| δ [ppm] | Description | Assignment (see formula above) |
|---|---|---|
| 4.267 | 2 H, br, s | A |
| 3.775 | 1 H, m | B |
| 3.657 | 2 H, m, $CH_2$ | C |
| 3.623 | 2 H, m, $CH_2$ | C |
| 3.505-3.562 | 4 H, m, $CH_2$ | C |
| 3.413 | 2 H, m, $CH_2$ | C |
| 3.227 | 9 H, s, 3 × $CH_3$ | D |
| 2.358 | 2 H, dt, $J_1$ = 7.2 Hz, $J_2$ = 3 Hz | E |
| 1.699 | 2 H, tt $CH_2$ | F |
| 1.602 | 2 H, tt $CH_2$ | F |
| 1.542 | 2 H, tt $CH_2$ | F |
| 1.259-1.312 | 30 H, m, 15 × $CH_2$ | I |
| 0.881 | 3 H, t, 1 × $CH_3$, J = 7.2 Hz | J |

The assignment of the observed $^{13}C$ peaks according to the structure of 1-octadecyl-2-(4-carboxy)butyl-glycero-3-phosphocholine was as follows:

$^{13}C$ NMR:

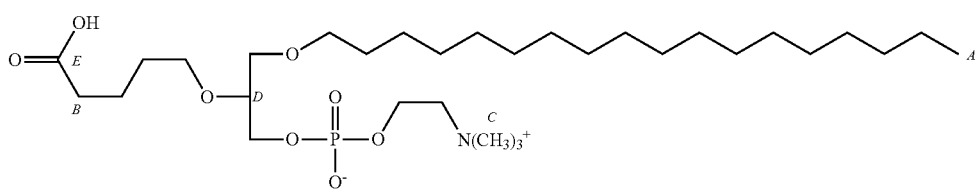

$^{13}$C NMR (600 MHz, reference solvent (CDCl$_3$)=77.285 ppm)

| δ [ppm] | Assignment (see formula above) |
|---|---|
| 176.580 | E |
| 78.216 | D |
| 71.936 | |
| 70.477 | |
| 69.961 | |
| 66.613 | |
| 65.926 | |
| 59.155 | |
| 54.424 | C |
| 34.117 | B |
| 32.026 | |
| 29.802 | |
| 29.767 | |
| 29.750 | |
| 29.717 | |
| 29.625 | |
| 29.452 | |
| 29.346 | |
| 26.164 | |
| 22.774 | |
| 22.073 | |
| 14.133 | A |

Mass spectrometry characterization of 1-octadecyl-2-(4-carboxy)butyl-glycero-3-phosphocholine The calculated mass for 1-octadecyl-2-(4-carboxy)butyl-glycero-3-phosphocholine (C$_{31}$H$_{64}$NO$_8$P) was 609.

The mass spectrum obtained using Electrospray Ionization Mass Spectrometry (ESI+MS), showed a molecular ion with m/z=610 corresponding to the protonated molecular ion [M+H]$^-$. The mass spectrometry spectrum is thus in agreement with the chemical structure of 1-octadecyl-2-(4-carboxy)butyl-glycero-3-phosphocholine (CI-215).

In Vitro IL12/23 p40 Production:

The effect of CI-216 on in vitro production of IL12/23 p40 was determined as described hereinabove in the Materials and Methods section.

As shown in FIG. 16, 20 μg/ml of CI-216 inhibited production of IL12/23 p40 by bone marrow-derived cells.

Tyrosine Phosphorylation:

The effects of CI-215 and CI-216 on in vitro tyrosine phosphorylation in primary macrophages cells were determined as described hereinabove in the Materials and Methods section.

As shown in FIG. 17, treatment with 10 μg/ml (17 μM) of CI-215 induced an increase in phosphotyrosine levels, whereas treatment with 20 μg/ml (34 μM) of CI-215 caused a decrease in phosphotyrosine levels.

Similarly, as shown in FIG. 18, treatment with 10 μg/ml (15 μM) CI-216 results in induction of tyrosine phosphorylation, whereas exposure to 20 μg/ml (30 μM) CI-216 causes reduction in phosphotyrosine levels. These changes were very similar to the effect induced respectively by 10 μg/ml (17 μM) and 20 μg/ml (34 μM) of the positive control CI-201.

Example 6

1-hexadecyl-2-(3-carboxy)propyl-glycero-3-phosphoethanolamine (CI-206) and 1-hexadecyl-2-(3-carboxy)propyl-glycero-3-phosphocholine (CI-205)

(R)-1-hexadecyl-2-(3-carboxy)propyl-sn-glycero-3-phosphoethanolamine and (R)-1-hexadecyl-2-(3-carboxy)propyl-sn-glycero-3-phosphocholine were synthesized as described hereinbelow using (R)-(−)-2,2-dimethyl-1,3-dioxolane-4-methanol as a starting material. (S)-1-hexadecyl-2-(3-carboxy)propyl-glycero-3-phosphoethanolamine and (S)-1-hexadecyl-2-(3-carboxy)propyl-glycero-3-phosphocholine are synthesized using the same procedures, but with (S)-(+)-2,2-dimethyl-1,3-dioxolane-4-methanol as the starting material.

Synthesis of (R)-1-hexadecyl-3-trityl-glycerol (R)-1-hexadecyl-3-trityl-glycerol was prepared as described in Example 1, by first preparing (S)-1-hexadecyl-glycerol using (R)-(−)-2,2-dimethyl-1,3-dioxolane-4-methanol.

Synthesis of (R)-1-hexadecyl-2-(4'-pentenyl)-3-trityl-glycerol 7.35 grams of (R)-1-hexadecyl-3-trityl-glycerol and 1.87 ml of 5-bromo-1-pentene were dissolved in 150 ml of benzene. 3 grams of powdered KOH was added, and the reaction mixture was stirred and refluxed for 10 hours, while removing the water formed by azeotropic distillation. The benzene was distilled until almost dry. The reaction mixture was cooled to room temperature, 100 ml diethyl ether was added, and the mixture was washed with water (3×50 ml) and dried over sodium sulfate. The solvent was removed under reduced pressure. The obtained residue (7.8 grams) was dissolved in 20 ml hexane and cooled to 4° C. overnight. The precipitated byproduct was filtered off, and the solvent was removed under reduced pressure to give 7.75 grams of the product as a yellow oil.

Synthesis of (R)-1-hexadecyl-2-(3-carboxy)propyl-3-trityl-glycerol 7.75 grams of (R)-1-hexadecyl-2-(4'-pentenyl)-3-trityl-glycerol was dissolved in 280 ml t-butanol. A solution of 3.2 grams potassium carbonate in 90 ml water was added. 50 ml of a solution of 34 grams sodium periodate in 250 ml water and 2 ml of a solution of 470 mg potassium permanganate in 10 ml water were then added. The mixture was stirred and the remaining portions of the periodate solution was added over a period of 10 minutes. Additional amounts of the permanganate solution were added as needed to maintain a pink color. The mixture was warmed to 40° C. for 4.5 hours, cooled to room temperature, and stirred at room temperature overnight. Sodium bisulfite was added in portions, and the color of the mixture turned brown, then the solids disappeared and the color turned yellow. The mixture was then stirred for 30 minutes, and 25 ml of a 10% sulfuric acid solution was added dropwise. The solution was extracted with diethyl ether (3×100 ml). The combined organic phase was washed with 50 ml water, twice with 20 ml of a solution of sodium bisulfite (prepared from 5 grams sodium bisulfite in 20 ml water), and twice with 50 ml water, then dried over sodium sulfate, filtered and evaporated under reduced pressure to give 11 grams of the product as a yellow wax.

Synthesis of (S)-1-hexadecyl-2-(3-carboxy)propyl-glycerol 11 grams of 1-hexadecyl-2-(3-carboxy)propyl-3-trityl-glycerol was dissolved in 100 ml formic acid and the mixture was stirred at room temperature for 2 hours. The formic acid was then removed under reduced pressure. 100 ml of a 1:1 solution of toluene:hexane was added, and the mixture was stirred at room temperature. The solution was extracted twice with 100 ml of an 8:2 (v/v) mixture of methanol:aqueous 10% solution of NaOH. The basic solution was acidified with sodium dihydrogen phosphate until a pH in the range of 4-5 was obtained. 100 ml diethyl ether and 100 ml water were added, the phases were separated, and the aqueous phase was washed twice with 100 ml diethyl ether. The combined organic phase was then washed with 100 ml water and 100 ml brine, dried over sodium sulfate, filtered, and the solvent was removed under reduced pressure to give 8 grams of the product. The product was crystallized from a 1:9 mixture of acetone:hexane to give 2.4 grams of (S)-1-hexadecyl-2-(3-carboxy)propyl-glycerol.

Synthesis of (S)-1-hexadecyl-2-(3-methylcarboxy)propyl-glycerol 2.4 grams of (S)-1-hexadecyl-2-(3-carboxy)propyl-glycerol was dissolved in 50 ml of methanol. 1 ml of concentrated HCl was added, and the mixture was stirred at room temperature for 6 hours and then left at 4° C. overnight. The solvent was removed under reduced pressure, 50 ml water was added, and the mixture was extracted thrice with 50 ml chloroform. The organic phase was washed with 50 ml water, 50 ml concentrated sodium bicarbonate, and again with 50 ml water. The mixture was dried over sodium sulfate, filtered, and the solvent was removed under reduced pressure to give 2.9 grams of the product, which was dried under reduced pressure with phosphorus pentoxide.

Synthesis of (R)-1-hexadecyl-2-(3-methylcarboxy)propyl-sn-glycero-3-phosphoethanolamine 2.9 grams of (S)-1-hexadecyl-2-(3-methylcarboxy)propyl-glycerol and 3 ml of triethylamine were dissolved in 30 ml of THF. This solution was added dropwise during the course of 15 minutes to an ice-cooled solution of 2 ml POCl$_3$ in 20 ml THF. The stirring was continued for an additional 10 minutes with cooling and for an additional 45 minutes at room temperature. A solution of 1.3 ml ethanolamine and 6 ml triethylamine in 50 ml THF was added dropwise over the course of 15 minutes to the ice-cooled reaction mixture. The stirring was continued for 10 minutes at 0° C. and then overnight at room temperature. The reaction mixture was filtered and the solvent was removed under reduced pressure. The residue was dissolved in a mixture of 24 ml acetic acid and 10 ml water and heated to 70° C. for 1 hour. The mixture was extracted thrice with 50 ml chloroform and washed twice with 50 ml water. Removal of the solvent under reduced pressure gave 3.8 grams of (R)-1-hexadecyl-2-(3-methylcarboxy)propyl-sn-glycero-3-phosphoethanolamine as a brown oil.

Synthesis of (R)-1-hexadecyl-2-(3-carboxy)propyl-sn-glycero-3-phosphoethanolamine (CI-206)

0.8 gram (R)-1-hexadecyl-2-(3-methylcarboxy)propyl-sn-glycero-3-phosphoethanolamine was dissolved in 20 ml of an 8:2 (v/v) methanol:aqueous 10% sodium hydroxide solution. 10% sodium hydroxide solution was added, and the mixture stirred at room temperature overnight. The pH of the reaction mixture was adjusted to a range of 4-5 by adding sodium dihydrogen phosphate. 50 ml water and 50 ml chloroform were added. The phases were separated and the solvent from the organic phase was removed under reduced pressure. The obtained residue was dissolved in chloroform, dried over sodium sulfate and filtered, and the solvent was removed under reduced pressure to give 684 mg of the crude product as a residue. This residue was purified by chromatography on silica gel (30 grams). The product was eluted with a mixture of chloroform:methanol:water at a 60:35:5 volumetric ratio. The solvent was removed under reduced pressure, the residue dissolved in chloroform and dried over sodium sulfate, and the solvent was removed under reduced pressure to give 314 mg of (R)-1-hexadecyl-2-(3 carboxy)propyl-sn-glycero-3-phosphoethanolamine as a white wax, which was dried under reduced pressure with phosphorus pentoxide.

NMR characterization of 1-hexadecyl-2-(3-carboxy)propyl-glycero-3-phosphoethanolamine The sample was dissolved in deuterated chloroform (CDCl$_3$). $^1$H NMR and $^{13}$C NMR spectra were measured at 300 MHz.

The results showed the expected signals for the structural elements of 1-hexadecyl-2-(3-carboxy)propyl-glycero-3-phosphoethanolamine (CI-206) and thus fully supported the structure.

The assignment of the observed $^1$H peaks according to the structure of CI-206 was as follows:

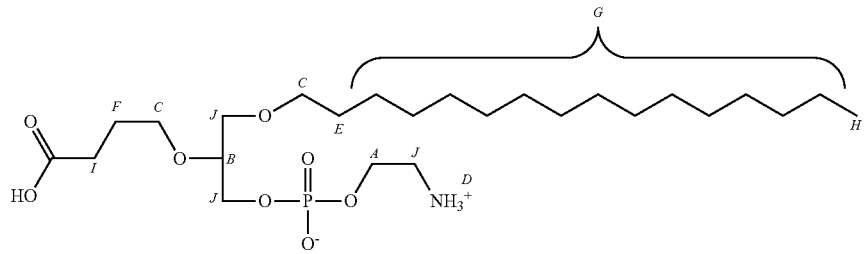

$^1$H NMR (300 MHz, reference solvent (CDCl$_3$)=7.338 ppm)

| δ [ppm] | Description | Assignment (see formula above) |
|---|---|---|
| 4.137 | 2H, br, s | A |
| 3.828-3.900 | 1H, m | B |
| 3.620-3.726 | 6H, m | J |
| 3.371-3.489 | 4 H, m, 2 × CH2 | C |
| 2.302-2.518 | 2H, m | I |
| 1.838-1895 | 2 H, m | F |
| 1.525-1.574 | 2H, m | E |
| 1.258 | 26 H, m, 13 × CH2 | G |
| 0.881 | 3 H, t, 1 × CH3, J = 6.75 Hz | H |

The assignment of the observed $^{13}C$ peaks according to the structure of CI-206 was as follows:

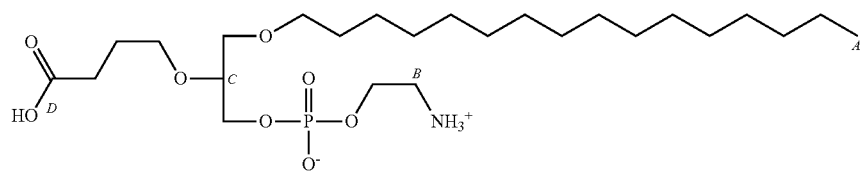

$^{13}C$ NMR (300 MHz, reference solvent (CDCl$_3$)=77.256 ppm)

| δ [ppm] | Assignment (see formula above) |
|---|---|
| 176.760 | D |
| 77.850-77.951 | C |
| 71.938 | |
| 70.268 | |
| 69.376 | |
| 66.045 | |
| 62.068 | |
| 40.408 | B |
| 35.035 | |
| 32.017 | |
| 30.886 | |
| 29.803 | |
| 29.698 | |
| 29.631 | |
| 29.456 | |
| 26.150 | |
| 25.231 | |
| 22.774 | |
| 22.149 | |
| 14.160 | A |

Mass spectrometry characterization of 1-hexadecyl-2-(3-carboxy)propyl-glycero-3-phosphoethanolamine The calculated mass for 1-hexadecyl-2-(3-carboxy)propyl-glycero-3-phosphoethanolamine (C$_{25}$H$_{52}$NO$_8$P) was 525.6560.

The mass spectrum obtained using Electrospray Ionization Mass Spectrometry (ESI-MS), showed a molecular ion with m/z=524, corresponding to the deprotonated molecular ion [M–H]$^-$. The mass spectrometry spectrum is thus in agreement with the chemical structure of 1-hexadecyl-2-(3-carboxy)propyl-glycero-3-phosphoethanolamine (CI-206).

Synthesis of (R)-1-hexadecyl-2-(3-methylcarboxy)propyl-sn-glycero-3-phosphocholine 2.8 grams of (R)-1-hexadecyl-2-(3-methylcarboxy)propyl-sn-glycero-3-phosphoethanolamine was dissolved in mixture of 50 ml isopropanol and 18 ml dichloromethane. A solution of 3.7 grams potassium carbonate in 10 ml water was added dropwise while the reaction mixture was kept at a temperature in the range of 35-40° C. A solution of 2.52 ml dimethylsulfate in 10 ml isopropanol was added dropwise at 40° C. during the course of 5 minutes. The reaction mixture was then kept at 40° C. for 90 minutes, cooled to room temperature, and stirred at room temperature overnight. Water was added and the mixture was extracted thrice with 50 ml chloroform. The organic phase was washed with 50 ml water and the solvent was removed under reduced pressure to give 3 grams of (R)-1-hexadecyl-2-(3-methylcarboxy)propyl-sn-glycero-3-phosphocholine as a brown oil.

Synthesis of (R)-1-hexadecyl-2-(3-carboxy)propyl-sn-glycero-3-phosphocholine (CI-205)

3 grams of (R)-1-hexadecyl-2-(3-methylcarboxy)propyl-sn-glycero-3-phosphocholine was dissolved in 50 ml of an 8:2 (v/v) mixture of methanol:aqueous 10% sodium hydroxide solution, and the mixture was stirred at room temperature overnight. The pH of the reaction was adjusted to a range of 4-5 by adding sodium dihydrogen phosphate. 50 ml water and 50 ml chloroform were added and the obtained solution was transferred to a separatory funnel. The phases were separated, and the solvent from the organic phase was removed under reduced pressure. The obtained residue was dissolved in chloroform, dried over sodium sulfate and filtered, and the solvent was removed under reduced pressure to give 2.3 grams of crude product as a residue. This residue was purified by chromatography on silica gel (110 grams). The product was eluted with chloroform:methanol:water at a 60:35:5 volumetric ratio. After removal of the solvent under reduced pressure, the residue was dissolved in chloroform and dried over sodium sulfate, and the solvent was removed under reduced pressure to give 677 mg of (R)-1-hexadecyl-2-(3 carboxy) propyl-sn-glycero-3-phosphocholine (CI-205) as a white wax, which was dried under reduced pressure with phosphorus pentoxide.

NMR characterization of 1-hexadecyl-2-(3-carboxy)propyl-glycero-3-phosphocholine The sample was dissolved in deuterated chloroform (CDCl$_3$). $^1$H NMR and $^{13}$C NMR spectra were measured at 300 MHz.

The results showed the expected signals for the structural elements of 1-hexadecyl-2-(3-carboxy)propyl-glycero-3-phosphocholine and thus fully supported the structure.

The assignment of the observed $^1$H peaks according to the structure of 1-hexadecyl-2-(3-carboxy)propyl-glycero-3-phosphocholine was as follows:

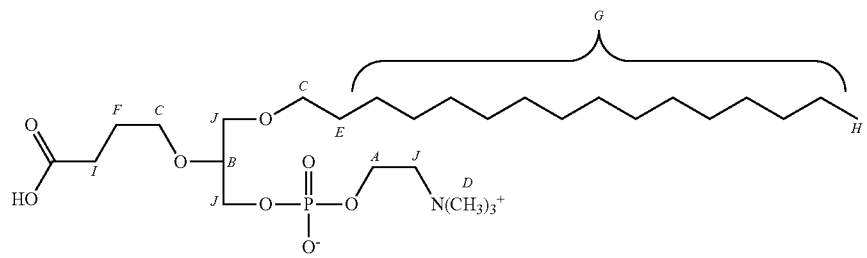

¹H NMR (300 MHz, reference solvent (CDCl₃)=7.338 ppm)

| δ [ppm] | Description | Assignment (see formula above) |
|---|---|---|
| 4.272 | 2H, br, s | A |
| 3.940-3.995 | 1H, m | B |
| 3.583-3.728 | 6H, m | J |
| 3.377-3.482 | 4 H, m, 2 × CH₂ | C |
| 3.241 | 9H, s, 3 × CH₃ | D |
| 2.304-2.510 | 2H, m | I |
| 1.801-1904 | 2 H, m | F |
| 1.517-1.560 | 2H, m | E |
| 1.256 | 26 H, m, 13 × CH2 | G |
| 0.880 | 3 H, t, 1 × CH3, J = 6.75 Hz | H |

The assignment of the observed $^{13}$C peaks according to the structure of 1-hexadecyl-2-(3-carboxy)propyl-glycero-3-phosphoethanolamine was as follows:

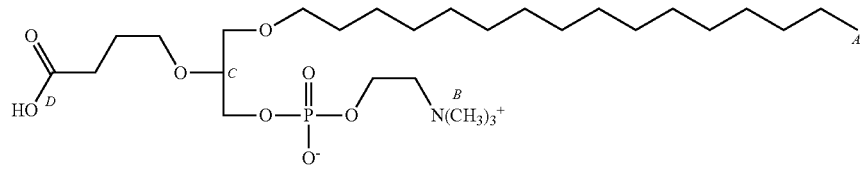

$^{13}$C NMR (300 MHz, reference solvent (CDCl₃)=77.231 ppm)

| δ [ppm] | Assignment (see formula above) |
|---|---|
| 176.790 | D |
| 78.082-78.186 | C |
| 71.888 | |
| 70.389 | |
| 69.298 | |
| 66.494 | |
| 65.922 | |
| 59.115-59.178 | |
| 54.327 | B |
| 31.992 | |
| 31.280 | |
| 29.772 | |
| 29.732 | |
| 29.673 | |
| 29.598 | |
| 29.431 | |
| 26.115 | |
| 25.462 | |
| 22.753 | |
| 14.148 | A |

Mass spectrometry characterization of 1-hexadecyl-2-(3-carboxy)propyl-glycero-3-phosphoethanolamine The calculated mass for 1-hexadecyl-2-(3-carboxy)propyl-glycero-3-phosphoethanolamine ($C_{28}H_{58}NO_8P$) was 567.7358.

The mass spectrum performed using Electrospray Ionization Mass Spectrometry (ESI-MS) showed a molecular ion with m/z=566, corresponding to the deprotonated molecular ion [M–H]⁻. The mass spectrometry spectrum is thus in agreement with the chemical structure of 1-hexadecyl-2-(3-carboxy)propyl-glycero-3-phosphocholine.

Tyrosine Phosphorylation:

The effects of CI-205 and CI-206 on in vitro tyrosine phosphorylation in primary macrophages were determined as described hereinabove in the Materials and Methods section.

As shown in FIG. 19, treatment with 20 μg/ml CI-206 causes reduction in phosphotyrosine levels.

Similarly, as shown in FIG. 20, treatment with 20 μg/ml of CI-205 causes reduction in phosphotyrosine levels, as did treatment with 20 μg/ml of the positive control, CI-201.

Toxicity of CI-205 and CI-206:

The toxicities of CI-205 and CI-206 were evaluated as described hereinabove in the Materials and Methods section.

As shown in FIGS. 21A and 21B, significant toxicity of CI-206 was detected at doses of 50 μg/ml or higher, with the $LD_{50}$ of CI-206 lying between 50 and 100 μg/ml.

As shown in FIGS. 22A and 22B, significant toxicity of CI-205 was detected at a dose of 100 μg/ml in two experiments and at a dose of 20-50 μg/ml in only one experiment, with the $LD_{50}$ of CI-205 lying between 50 and 100 μg/ml.

Example 7

1-octyl-2-(4-carboxy)butyl-glycero-3-phosphocholine (CI-207) and 1-octyl-2-(4-carboxy)butyl-glycero-3-phosphoethanolamine (R)-1-octyl-2-(4-carboxy)butyl-sn-glycero-3-phosphocholine and (R)-1-octyl-2-(4 carboxy)butyl-sn-glycero-3-phosphoethanolamine were synthesized as described hereinbelow using (R)-(–)-2,2-dimethyl-1,3-dioxolane-4-methanol as a starting material. (S)-1-octyl-2-(4-carboxy)butyl-glycero-3-phosphocholine and (S)-1-octyl-2-(4 carboxy)butyl-glycero-3-phosphoethanolamine synthesized using the same procedures, but with (S)-(+)-2,2-dimethyl-1,3-dioxolane-4-methanol as the starting material.

Synthesis of (S)-1-octyl-glycerol 21 ml of (R)-(−)-2,2-dimethyl-1,3-dioxolane-4-methanol, 29 grams of powdered potassium hydroxide and 32 ml of 1-bromooctane were stirred in 150 ml benzene and refluxed for 6 hours, while removing the water formed by azeotropic distillation. The volume of the solvent was gradually reduced to about 100 ml. The reaction mixture was then cooled to room temperature and 200 ml water was added. The reaction mixture was then extracted thrice with 150 ml diethyl ether, the combined organic phase was washed with 100 ml water, and the solvent was then removed under reduced pressure. The obtained residue was dissolved in 100 ml of a 90:10:5 (v/v) mixture of methanol:water:concentrated hydrochloric acid, and the resulting solution was refluxed for 2 hours, followed by cooling to room temperature and addition of 100 ml water. The product was extracted thrice with 150 ml chloroform, washed consecutively with 150 ml water, 150 ml of saturated aqueous solution of sodium bicarbonate, and again with 100 ml water. The solvent was dried over anhydrous $Na_2SO_4$, filtered, and removed under reduced pressure, yielding 34 grams of (S)-1-octyl-glycerol.

Synthesis of (R)-1-octyl-3-trityl-glycerol 34 grams of (S)-1-octyl-glycerol and 61 grams of triphenylchloromethane were added to a mixture of 500 ml of dry THF and 130 ml of dry acetonitrile. 46 ml of dry triethylamine was added, and the reaction mixture was refluxed for 17 hours. The reaction mixture was then cooled to room temperature and poured on ice (1 kilogram). The mixture was transferred to a separatory funnel and extracted thrice with 200 ml diethyl ether. The organic phase was washed consecutively with 150 ml water, twice with 100 ml dilute (1.5%) $H_2SO_4$, 200 ml water, 200 ml concentrated aqueous sodium bicarbonate, and again with 200 ml water. The solution was then dried over anhydrous $Na_2SO_4$ and the solvent was removed under reduced pressure. The obtained residue, 80 grams of a brown oil, was dissolved in 500 ml hot hexane and kept at a temperature of 4° C. overnight. The precipitate was filtered off and the solvent from the filtrate was removed under reduced pressure. The obtained residue was purified by chromatography on silica gel. The resulting pure (R)-1-octyl-3-trityl-glycerol was eluted by mixtures of chloroform with 10% hexane, chloroform with 5% hexane, followed by chloroform with ethyl acetate (5% and 10%). The yield was 73%.

Synthesis of (R)-1-octyl-2-(5'-hexenyl)-3-tritylglycerol 18.7 grams of (R)-1-octyl-3-trityl-glycerol, 5.5 grams of 6-bromo-1-hexene and 22 grams of powdered potassium hydroxide were stirred in 100 ml benzene and refluxed for 9 hours, while removing the water formed by azeotropic distillation. The volume of the solvent was gradually reduced to about 30 ml. The reaction mixture was cooled to room temperature and 100 ml water was added. The obtained mixture was transferred to a separatory funnel and extracted with diethyl ether. The combined organic phase was washed twice with 200 ml water and the solvent was removed under reduced pressure, yielding 20.2 grams of (R)-1-octyl-2-(5'-hexenyl)-3-tritylglycerol.

Synthesis of (S)-1-octyl-2-(5'-hexenyl)-sn-glycerol 20.2 grams of (R)-1-octyl-2-(5'-hexenyl)-3-tritylglycerol was dissolved in 100 ml methanol, 10 ml concentrated hydrochloric acid (32%) was added, and the obtained reaction mixture was refluxed for 4 hours. The reaction mixture was cooled to room temperature and stirred at room temperature overnight. 100 ml water was added, and the solution was extracted twice with 100 ml diethyl ether. The combined organic phase was washed with 100 ml water, 100 ml saturated aqueous sodium bicarbonate solution, and again with 100 ml water. The solvent was removed under reduced pressure. The obtained residue (20.1 grams) was dissolved in 250 ml hexane, and the obtained solution was stored at a temperature of 4° C. for 96 hours, causing most of the triphenyl carbinol to precipitate. After filtration and removal of the solvent from the filtrate, the remaining product (12 grams) was purified by chromatography over silica gel (91.4 grams). The pure (S)-1-octyl-2-(5'-hexenyl)-sn-glycerol (5.7 grams) was eluted with chloroform followed by chloroform with 5% acetone. The yield was 52%.

Synthesis of (R)-1-octyl-2-(5'-hexenyl)-sn-glycero-3-phosphoethanolamine 4.9 grams of (S)-1-octyl-2-(5'-hexenyl)-sn-glycerol (which was dried in a desiccator over $P_2O_5$) and 2.65 ml of triethylamine were dissolved in 40 ml THF. This solution was added dropwise during the course of 30 minutes to an ice-cooled solution of 1.4 ml $POCl_3$ in 20 ml THF while stirring. The stirring was continued for an additional 30 minutes with cooling and for and additional 45 minutes at room temperature. The reaction mixture was then cooled in an ice-bath, and a solution of 1.1 ml ethanolamine and 2.8 ml triethylamine in 30 ml THF was then added dropwise over the course of 15 minutes while stirring. The stirring was continued for 35 minutes in the ice-bath and then at room temperature overnight. The reaction mixture was filtered, the solid washed twice with 15 ml THF, and the solvent from the filtrate was removed under reduced pressure. The obtained residue (5.6 grams) was dissolved in a mixture of 36 ml acetic acid and 15 ml water and heated to a temperature of 70° C. for 1 hour. After cooling to room temperature, the solution was transferred to a separatory funnel and extracted twice with a 2:1 (v/v) mixture of chloroform:methanol and washed with dilute sodium bicarbonate solution, and the solvent was then removed under reduced pressure, yielding 4.6 grams of crude (R)-1-octyl-2-(5'-hexenyl)-sn-glycero-3-phosphoethanolamine. The crude product was purified by chromatography over silica gel (59 grams). 2.6 grams of the pure product was eluted with chloroform followed by mixtures of chloroform with 10%-40% methanol. The yield was 75.9%.

Synthesis of (R)-1-octyl-2-(5'-hexenyl)-sn-glycero-3-phosphocholine 2.1 grams of (R)-1-octyl-2-(5'-hexenyl)-sn-glycero-3-phosphoethanolamine was dissolved in a solution of 100 ml ethanol with 6 grams of potassium carbonate. 8 ml of dimethylsulfate was added, and the reaction mixture was heated to a temperature of 40° C. for 6 hours. The reaction mixture was cooled to room temperature and 100 ml water was added. The mixture was then extracted twice with 100 ml chloroform. The solvent from the organic phase was removed under reduced pressure. The obtained residue was dissolved in chloroform and dried over anhydrous $Na_2SO_4$, and the solvent was removed under reduced pressure. The crude product was purified by chromatography over silica gel (59 grams). 2.0 grams of pure (R)-1-octyl-2-(5'-hexenyl)-sn-glycero-3-phosphocholine was eluted with chloroform followed by mixtures of chloroform with 20%-60% methanol. The yield was 86.4%.

Synthesis of (R)-1-octyl-2-(4-carboxy)butyl-sn-glycero-3-phosphocholine (CI-207)

A solution of 172 mg of sodium bicarbonate in 17 ml water was added to a solution of 700 mg of (R)-1-octyl-2-(5'-hexenyl)-sn-glycero-3-phosphocholine in 28 ml water. A solution of 3.0 grams of sodium periodate in 28 ml water was then added. A solution of 40 mg of potassium permanganate in 12 ml water was placed in a dropping funnel and added dropwise to the reaction mixture as needed to maintain a pink color of the reaction mixture. Approximately half of the permanganate solution was added during the reaction. After stirring at room temperature for 3 hours, 6 grams of sodium dihydrogen phosphate was added, and the reaction mixture was extracted thrice with 50 ml of a 2:1 (v/v) mixture of chloroform:methanol. The combined organic phase was dried over anhydrous $Na_2SO_4$ and the solvent was removed under reduced pressure, yielding 360 mg of crude product. The crude product was purified by chromatography over silica gel (12.23 grams). 119 mg of pure (R)-1-octyl-2-(4-carboxy)butyl-sn-glycero-3-phosphocholine was eluted with chloroform followed by chloroform with 10%-60% methanol.

An alternative synthesis, using (S)-1-octyl-2-(5'-hexenyl)-3-trityl-glycerol prepared as described hereinabove, was performed as follows:

Synthesis of (S)-1-octyl-2-(4-carboxy)butyl-sn-glycerol 77 grams of $NaIO_4$ was dissolved in 300 ml water. To this solution, 9 grams of $NaHCO_3$ and 1.26 gram of $KMnO_4$ were added, and the suspension was heated to 40° C. A solution of 21 grams of (S)-1-octyl-2-(5'-hexenyl)-3-trityl-glycerol in 300 ml tert-butanol was added dropwise to the reaction mixture during the course of 1 hour, and the mixture was heated for an additional 3 hours. Additional amounts of $KMnO_4$ solution were added as needed to maintain a pink color. The reaction mixture was cooled to room temperature, filtered via celite, and the celite was washed with tert-butanol. 100 ml of 10% sulfuric acid solution was added dropwise, and the solution was transferred to a separatory funnel and extracted thrice with 200 ml hexane. The organic phase was washed with a solution of 20 grams of $Na_2S_2O_5$ in 100 ml water and then with 200 ml water. The organic phase was concentrated by removal of solvent under reduced pressure until the volume was reduced to about 150 ml. 15 ml of water and 2 ml concentrated HCl were added to the remaining solution and the obtained mixture was refluxed for 6 hours, then cooled to room temperature and concentrated again by removal of solvent under reduced pressure. The pH of the residue was adjusted to 12 by addition of 100 ml water and 10 ml 30% NaOH solution. The precipitate was filtered off and washed with four times with 20 ml water. The filtrate was extracted with 100 ml of a 1:1 (v/v) mixture of hexane:ethyl acetate. The aqueous phase was acidified to a pH of 1 by addition of 10 ml concentrated HCl and extracted thrice with 100 ml hexane. Drying over anhydrous $NaSO_4$ and removal of the solvent under reduced pressure gave 7.4 grams of crude product as a yellow oil. The crude product was purified by chromatography over silica gel (100 grams). 4.8 grams of pure (S)-1-octyl-2-(4-carboxy)butyl-sn-glycerol was eluted with chloroform followed by chloroform with 5-50% ethyl acetate. The yield was 39.7%.

Synthesis of (S)-1-octyl-2-(4-benzhydrylcarboxy)butyl-sn-glycerol 1.14 grams of (S)-1-octyl-2-(4-carboxy)butyl-sn-glycerol was dissolved in 20 ml dichloromethane. 748 mg of diphenyldiazomethane, prepared as described in J. Organic Chem. (1959) 24: 560-561, was added and the dark red reaction mixture was stirred at room temperature for about 3 hours until the solution turned colorless. The solvent was removed under reduced pressure. The residue (1.9 grams) was purified by chromatography on silica gel (43 grams). 1.08 gram of pure (S)-1-octyl-2-(4-benzhydrylcarboxy)butyl-sn-glycerol was eluted with chloroform followed by chloroform with 5-20% ethyl acetate. The yield was 61.4%.

Synthesis of (R)-1-octyl-2-(4-benzhychylcarboxy)butyl-sn-glycero-3-phosphoethanolamine 1 gram of (S)-1-octyl-2-(4-benzhydrylcarboxy)butyl-sn-glycerol (which was dried by azeotropic distillation with benzene) and 0.885 ml of triethylamine were dissolved in 30 ml THF. This solution was added dropwise during the course of 15 minutes to an ice-cooled solution of 0.235 ml $POCl_3$ in 20 ml THF while stirring. The stirring was continued for an additional 15 minutes with cooling and for an additional 45 minutes at room temperature. The reaction mixture was then cooled in an ice-bath, and a solution of 0.154 ml ethanolamine and 0.885 ml triethylamine in 50 ml THF was then added dropwise over the course of 15 minutes while stirring. The stirring was continued for 15 minutes in the ice-bath, and then at room temperature overnight. The reaction mixture was filtered and the solvent was removed under reduced pressure. The obtained residue was dissolved in a mixture of 24 ml acetic acid and 10 ml water and heated to 70° C. for 1 hour. The mixture was extracted thrice with 80 ml chloroform and washed twice with 50 ml water. Removal of the solvent under reduced pressure resulted in 1.12 gram of (R)-1-octyl-2-(4 benzhydrylcarboxy)butyl-sn-glycero-3-phosphoethanolamine as a yellow oil.

Synthesis of (R)-1-octyl-2-(4-benzhychylcarboxy)butyl-sn-glycero-3-phosphocholine 1.12 gram of (R)-1-octyl-2-(4-benzhydrylcarboxy)butyl-sn-glycero-3-phosphoethanolamine was dissolved in a mixture of 65 ml methanol and 18 ml dichloromethane and the mixture was heated to a temperature in the range of 35-40° C. A solution of 1.3 gram potassium carbonate in 10 ml water was added dropwise while the reaction mixture was kept at a temperature of 35-40° C. A solution of 7.2 ml dimethylsulfate in 10 ml methanol was then added dropwise at 40° C. The reaction mixture was kept at a temperature of 40° C. for 2 hours and then at room temperature overnight. 50 ml water was added, and the mixture was then extracted thrice with 50 ml chloroform. The organic phase was washed with 50 ml water and the solvent was removed under reduced pressure to give 1 gram of (R)-1-octyl-2-(4-benzhydrylcarboxy)butyl-sn-glycero-3-phosphocholine as a yellow oil.

Synthesis of (R)-1-octyl-2-(4-carboxy)butyl-sn-glycero-3-phosphocholine (CI-207)

Gaseous HCl was bubbled for 90 minutes through an ice-cooled solution of 1 gram of (R)-1-octyl-2-(4-benzhydrylcarboxy)butyl-sn-glycero-3-phosphocholine in 40 ml chloroform. The resulting solution was stirred in an ice-bath for an additional 2 hours. The pH of the reaction mixture was then adjusted to approximately 6 by adding sodium dihydrogen phosphate. 50 ml water was added and the mixture was extracted thrice with 60 ml chloroform. The combined organic phase was washed with 60 ml water, and the solvent was removed under reduced pressure, yielding 0.370 gram of (R)-1-octyl-2-(4 carboxy)butyl-sn-glycero-3-phosphocholine. The yield was 50.2%.

Synthesis of (R)-1-octyl-2-(4-carboxy)butyl-sn-glycero-3-phosphoethanolamine

Gaseous HCl was bubbled through an ice-cooled solution of 5 grams (R)-1-octyl-2-(4 benzhydrylcarboxy)butyl-sn-glycero-3-phosphoethanolamine, prepared as described hereinabove, in 40 ml chloroform for 90 minutes. After completion of the addition of HCl, the reaction mixture was stirred in an ice-cooled bath for an additional 2 hours. The pH of the reaction mixture was adjusted to 6 by addition of an aqueous solution of disodium hydrogen phosphate. The mixture was extracted with chloroform (3×50 ml) and the combined organic phase was washed with water (100 ml). The solvent was removed under reduced pressure, yielding 3.5 grams of a brown oil. This oil was purified by chromatography on silica gel (68.5 grams). The product was eluted with chloroform followed by an 8:2 (v/v) mixture of chloroform: methanol, and then by a 700:26:45 (v/v) mixture of chloroform:methanol:$H_2O$. After removal of the solvent under reduced pressure from the fractions containing the desired product, the obtained residue was dissolved in chloroform, dried over sodium sulfate and the solvent was removed under reduced pressure, yielding 150 mg of (R)-1-octyl-2-(4-carboxy)butyl-sn-glycero-3-phosphocholine as a yellow wax.

NMR characterization of 1-octyl-2-(4-carboxy)butyl-glycero-3-phosphocholine (CI-207)

The sample was dissolved in deuterated chloroform ($CDCl_3$) with few drops of deuterated methanol ($CD_3OD$). The spectra were then measured at 300 MHz. Samples were measured by both $^1H$ and $^{13}C$ NMR spectroscopy.

The results showed the expected signals for the structural elements of 1-octyl-2-(4-carboxy)butyl-glycero-3-phosphocholine and thus fully supported the structure.

The assignment of the observed $^1H$ peaks according to the structure of 1-octyl-2-(4-carboxy)butyl-glycero-3-phosphocholine was as follows:

$^1H$ NMR

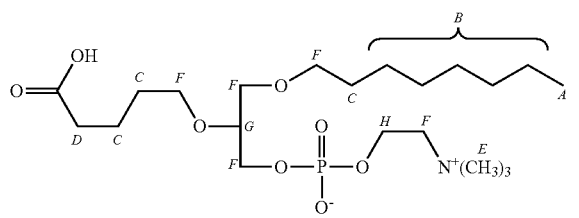

$^1H$ NMR (300 MHz, reference solvent ($CDCl_3$)=7.33 ppm)

| δ [ppm] | Description | Assignment (see formula above) |
|---|---|---|
| 4.268 | 2 H, br s | H |
| 3.942-3.969 | 1H, m | G |
| 3.394-3.673 | 10 H, m, 5 × $CH_2$ | F |
| 3.234 | 9 H, s, 3 × $CH_3$ | E |
| 2.307 | 2 H, t, J = 7.2 Hz | D |
| 1.518-1.652 | 6 H, m, 3 × $CH_2$ | C |
| 1.270 | 10 H, m, 5 × $CH_2$ | B |
| 0.879 | 3 H, t, 1 × $CH_3$, J = 6.75 Hz | A |

$^{13}C$ NMR

The assignment of the observed $^{13}C$ peaks according to the structure of 1-octyl-2-(4-carboxy)butyl-glycero-3-phosphocholine was as follows:

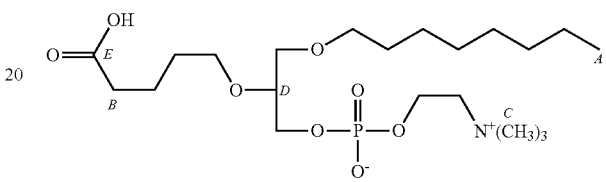

$^{13}C$ NMR (300 MHz, reference solvent ($CDCl_3$)=76.99 ppm)

| δ [ppm] | Assignment (see formula above) |
|---|---|
| 177.530 | E |
| 77.895 | D |
| 71.646 | |
| 69.964 | |
| 69.762 | |
| 65.207 | |
| 65.642 | |
| 59.013 | |
| 54.080 | C |
| 34.629 | B |
| 31.664 | |
| 29.404 | |
| 29.273 | |
| 29.179 | |
| 29.101 | |
| 25.856 | |
| 22.482 | |
| 22.009 | |
| 13.890 | A |

Mass spectrometry characterization of 1-octyl-2-(4-carboxy)butyl-glycero-3-phosphocholine The calculated mass for 1-octyl-2-(4-carboxy)butyl-glycero-3-phosphocholine ($C_{21}H_{44}NO_8P$) was 469.

The mass spectrum performed using Electrospray Ionization Mass Spectrometry (ESI-MS) showed a molecular ion with m/z=468, corresponding to the deprotonated molecular ion $[M-H]^-$. The mass spectrometry spectrum is thus in agreement with the chemical structure of 1-octyl-2-(4-carboxy)butyl-glycero-3-phosphocholine.

NMR characterization of 1-octyl-2-(4-carboxy)butyl-glycero-3-phosphoethanolamine The sample was dissolved in deuterated chloroform ($CDCl_3$) with a few drops of deuterated methanol ($CD_3OD$). The spectra were then measured at 600 MHz. Samples were measured by both $^1H$ and $^{13}C$ NMR spectroscopy.

The results showed the expected signals for the structural elements of 1-octyl-2-(4-carboxy)butyl-glycero-3-phosphoethanolamine and thus fully supported the structure.

The assignment of the observed $^1$H peaks according to the structure of 1-octyl-2-(4-carboxy)butyl-glycero-3-phosphoethanolamine was as follows:

$^1$H NMR

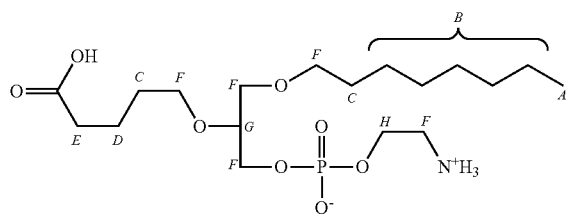

$^1$H NMR (300 MHz, reference solvent (CDCl$_3$)=7.361 ppm)

| δ [ppm] | Description | Assignment (see formula above) |
|---|---|---|
| 4.136 | 2 H, br s | H |
| 3.883-3.901 | 1H, m | G |
| 3.420--3.766 | 10 H, m, 5 × CH$_2$ | F |
| 2.344 | 2 H, t, J = 7.2 Hz | E |
| 1.673-1.719 | 2H, m, CH$_2$ | D |
| 1.588-1.632 | 2H, m, CH$_2$ | C |
| 1.527-1.561 | 2H, m, CH$_2$ | C |
| 1.272-1.290 | 10 H, m, 5 × CH$_2$ | B |
| 0.882 | 3 H, t, 1 × CH$_3$, J = 6.9 Hz | A |

$^{13}$C NMR

The assignment of the observed $^{13}$C peaks according to the structure of 1-octyl-2-(4-carboxy)butyl-glycero-3-phosphoethanolamine was as follows:

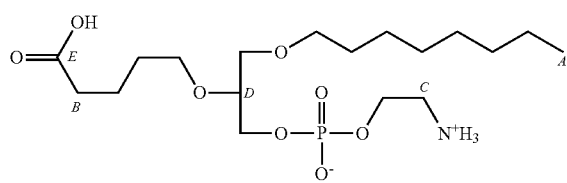

$^{13}$C NMR (300 MHz, reference solvent (CDCl$_3$)=79.344 ppm)

| δ [ppm] | Assignment (see formula above) |
|---|---|
| 178.820 | E |
| 77.895 | D |
| 79.996 | |
| 73.980 | |
| 72.367 | |
| 72.066 | |
| 68.205 | |
| 64.103 | |
| 42.529 | C |
| 35.874 | B |
| 33.953 | |
| 32.948 | |
| 31.699 | |
| 31.557 | |
| 31.471 | |
| 31.383 | |
| 31.327 | |
| 28.162 | |
| 27.320 | |
| 24.785 | |
| 23.819 | |
| 23.691 | |
| 16.123 | A |

Mass spectrometry characterization of 1-octyl-2-(4-carboxy)butyl-glycero-3-phosphoethanolamine The calculated mass for 1-octyl-2-(4-carboxy)butyl-glycero-3-phosphoethanolamine (C$_{18}$H$_{38}$NO$_8$P) was 427.

The mass spectrum performed using Electrospray Ionization Mass Spectrometry (ESI-MS) showed a molecular ion with m/z=426, corresponding to the deprotonated molecular ion [M−H]$^−$. The mass spectrum performed using Positive Electrospray Ionization Mass Spectrometry (ESI+-MS) showed a molecular ion with m/z=428 corresponding to the protonated molecular ion [M+H]$^−$ and an ion with m/z=450 corresponding to the cationated molecular ion [M+Na]$^+$. The MS spectrum is thus in agreement with the chemical structure of 1-octyl-2-(4-carboxy)butyl-glycero-3-phosphoethanolamine Example 8

1-hexadecyl-2-(4-methylcarboxy)butyl-glycero-3-phosphocholine (CI-208)

(R)-1-hexadecyl-2-(4-methylcarboxy)butyl-sn-glycero-3-phosphocholine was synthesized as described hereinbelow from (S)-1-hexadecyl-2-(4-methylcarboxy)butyl-sn-glycerol. (S)-1-hexadecyl-2-(4-methylcarboxy)butyl-glycero-3-phosphocholine is synthesized from (R)-1-hexadecyl-2-(4-methylcarboxy)butyl-glycerol, using the same procedures.

The synthesis of (S)-1-hexadecyl-2-(4-methylcarboxy)butyl-sn-glycerol and (R)-1-hexadecyl-2-(4-methylcarboxy)butyl-glycerol is described in Example 1.

Synthesis of (R)-1-hexadecyl-2-(4-methylcarboxy)butyl-sn-glycero-3-phosphocholine (CI-208)

A solution of 8.60 grams (19.97 mmol) (S)-1-hexadecyl-2-(4 methylcarboxy)butyl-glycerol (prepared as described in Example 1) and 2.63 grams (26 mmol) triethylamine in 500 ml THF was added dropwise, over the course of 25 minutes, to an ice-cooled solution of 3.90 grams (26 mmol) POCl$_3$ in 100 ml THF. Stirring was continued for an additional 10 minutes in an ice-bath and for an additional 45 minutes at room temperature. A solution of 1.6 ml ethanolamine and 6.4 ml triethylamine in 500 ml THF was added dropwise under vigorous stirring to the ice-cooled reaction mixture. The stirring was continued for an additional 10 minutes in the ice-bath and continued overnight at room temperature. The reaction mixture was filtered and the solvent was removed under reduced pressure. The residue was dissolved in a mixture of 24 ml acetic acid and 100 ml water and heated to 70° C. for 1 hour. The reaction mixture was cooled to room temperature and extracted twice with 250 ml dichloromethane. The solvent was then removed under reduced pressure. The residue was dissolved in a mixture of 500 ml isopropanol and 180 ml dichloromethane. A solution of 50 grams of potassium carbonate in 100 ml water was added so as to obtain a pH above 11. The solution was kept at a temperature in the range of 35-40° C. during the dropwise addition of 11.15 grams methyltosylate in 100 ml isopropanol during a time period of 45 minutes. After an additional 90 minutes, the mixture was acidified with hydrochloric acid. 100 ml water and 550 ml dichloromethane were added and the phases were separated. The organic phase was washed with 100 ml water and the solvent was removed under reduced pressure. The crude product was purified by chromatography on a silica gel column. 11.0 grams (18.46 mmol) of (R)-1-hexadecyl-2-(4-methylcarboxy)butyl-glycero-3-phosphocholine was eluted by chloroform followed by a mixture of chloroform, methanol and water. The yield was 92.45%.

NMR characterization of 1-hexadecyl-2-(4-methylcarboxy)butyl-glycero-3-phosphocholine (CI-208)

The sample was dissolved in deuterated chloroform ($CDCl_3$) with a few drops of deuterated methanol ($CD_3OD$). The spectra were then measured at 300 MHz. Samples were measured by both $^1H$ and $^{13}C$ NMR spectroscopy.

The results showed the expected signals for the structural elements of 1-hexadecyl-2-(4-methylcarboxy)butyl-glycero-3-phosphocholine and thus fully supported the structure.

The assignment of the observed $^1H$ peaks according to the structure of 1-hexadecyl-2-(4-methylcarboxy)butyl-glycero-3-phosphocholine was as follows:

$^1H$ NMR $^1H$ NMR (300 MHz, reference solvent ($CDCl_3$)=7.27 ppm)

| δ [ppm] | Description | Assignment (see formula above) |
|---|---|---|
| 4.303 | 2 H, br s | I |
| 3.821-3.840 | 1H, m | H |
| 3.648 | 3H, s, 1 × $CH_3$ | G |
| 3.383-3.606 | 10 H, m, 5 × $CH_2$ | F |
| 3.340 | 9 H, s, 3 × $CH_3$ | E |
| 2.334 | 2 H, t, J = 7.5 Hz | D |
| 1.530-1.657 | 6 H, m, 3 × $CH_2$ | C |
| 1.253 | 26 H, m, 13 × $CH_2$ | B |
| 0.879 | 3 H, t, 1 × $CH_3$, J = 6.3 Hz | A |

$^{13}C$ NMR

The assignment of the observed $^{13}C$ peaks according to the structure of 1-exadecyl-2-(4-methylcarboxy)butyl-glycero-3-phosphocholine was as follows:

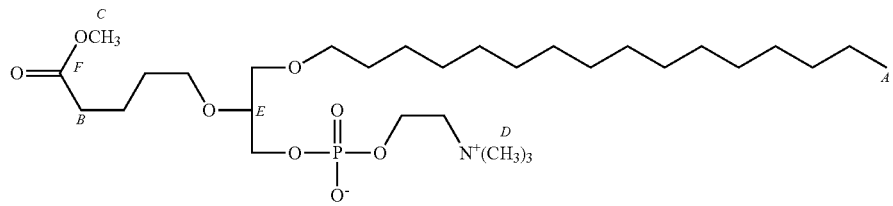

$^{13}C$ NMR (300 MHz, reference solvent ($CDCl_3$)=77.03 ppm)

| δ [ppm] | Assignment (see formula above) |
|---|---|
| 174.23 | F |
| 77.97 | E |
| 71.74 | |
| 70.65 | |
| 69.84 | |
| 66.16 | |
| 65.40 | |
| 59.44 | |
| 54.35 | D |
| 51.51 | C |
| 33.66 | B |
| 31.93 | |
| 29.74 | |
| 29.62 | |
| 29.47 | |
| 29.38 | |
| 26.14 | |
| 22.70 | |
| 21.68 | |
| 14.13 | A |

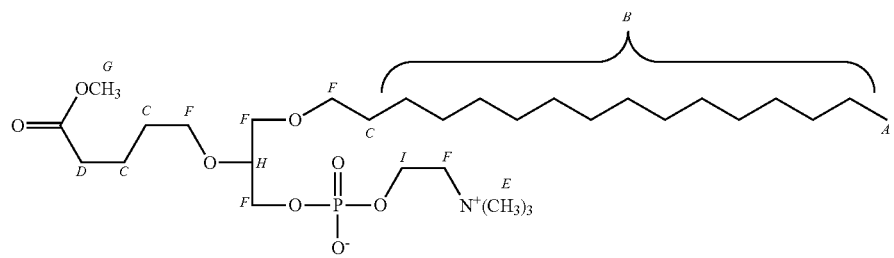

Mass spectrometry characterization of 1-hexadecyl-2-(4-methylcarboxy)butyl-glycero-3-phosphocholine (CI-208):

The calculated mass for 1-hexadecyl-2-(4-methylcarboxy) butyl-glycero-3-phosphocholine ($C_{30}H_{62}NO_8P$) was 595.79.

The mass spectrum performed using Fast Atom Bombardment (FAB+) showed a molecular ion with m/z=596.324, corresponding to the protonated molecular ion $[M+H]^+$. The MS spectrum is in agreement with the chemical structure of 1-hexadecyl-2-(4-methylcarboxy)butyl-glycero-3-phosphocholine.

Tyrosine Phosphorylation:

The effect of CI-208 on in vitro tyrosine phosphorylation in primary macrophages was determined as described hereinabove in the Materials and Methods section.

As shown in FIG. 23, treatment with 20 ng/ml CI-208 causes a reduction in phosphotyrosine levels, which is stronger than the reduction caused by treatment with 20 ng/ml of the CI-201 control.

Toxicity of CI-208:

The toxicity of CI-208 was evaluated as described hereinabove in the Materials and Methods section.

As shown in FIGS. 24A and 24B, toxicity of CI-208 was detected at doses of 50 ng/ml or higher, with toxicity at a dose of 20 µg/ml being detected in only one of two experiments. The $LD_{50}$ of CI-208 appeared to lie between 50 and 100 µg/ml.

Example 9

1-(15'-carboxy)pentadecyl-2-(4-carboxy)butyl-glycero-3-phosphocholine (CI-213) and 1-(15'-carboxy) pentadecyl-2-(4-carboxy)butyl-glycero-3-phosphoethanolamine (CI-214)

(R)-1-(15'-carboxy)pentadecyl-2-(4-carboxy)butyl-sn-glycero-3-phosphocholine and (R)-1-(15'-carboxy)pentadecyl-2-(4-carboxy)butyl-sn-glycero-3-phosphoethanolamine were synthesized as described hereinbelow using (R)-(+)-3-benzyloxy-1,2-propanediol as a starting material. (S)-1-(15'-carboxy)pentadecyl-2-(4-carboxy)butyl-glycero-3-phosphocholine and (S)-1-(15'-carboxy)pentadecyl-2-(4-carboxy)butyl-glycero-3-phosphocholine are synthesized using the same procedures, but with (S)-1-(15'-carboxy)pentadecyl-2-(4-carboxy)butyl-glycero-3-1,2-propanediol as the starting material.

Synthesis of 1-trityl-3-benzyl-sn-glycerol 5 grams (27.44 mmol) of (R)-(+)-3-benzyloxy-1,2-propanediol and 10 grams (35.87 mmol) of triphenylchloromethane were added to 100 ml dry THF and 25 ml dry acetonitrile. 8 ml of dry triethylamine were added and the reaction mixture was refluxed for 17 hours. The reaction mixture was cooled to room temperature, poured on ice (100 grams), transferred to a separatory funnel and extracted thrice with 100 ml diethyl ether. The organic phase was washed consecutively with 100 ml water, twice with 100 ml dilute (1.5%) sulfuric acid, 100 ml water, 100 ml concentrated sodium bicarbonate solution, and again with 100 ml water. The organic phase was dried over anhydrous sodium sulfate and the solvent was removed under reduced pressure, yielding 11 grams of 1-trityl-3-benzyl-sn-glycerol as a yellow oil. The yield was 94%.

Synthesis of 1-trityl-2-(5'-hexenyl)-3-benzyl-sn-glycerol 11 grams of 1-trityl-3-benzyl-sn-glycerol and 5.7 grams of 5-hexenyl-1-methane sulfonate were dissolved in 110 ml benzene. 6 grams of powdered KOH was added and the reaction mixture was stirred and refluxed for 12 hours while removing the water formed in the reaction by azeotropic distillation. The reaction mixture was cooled to room temperature and washed thrice with 100 ml water. The organic phase was dried over anhydrous $Na_2SO_4$ and the solvent was removed under reduced pressure. The residue was dissolved in 150 ml of hot hexane, cooled and kept at 4° C. overnight, during which precipitation of byproducts occurred. Filtration and removal of the solvent from the filtrate under reduced pressure yielded 13 grams of 1-trityl-2-(5'-hexenyl)-3-benzyl-sn-glycerol as a brown oil.

Synthesis of 2-(5'-hexenyl)-3-benzyl-sn-glycerol 13 grams of 1-trityl-2-(5'-hexenyl)-3-benzyl-sn-glycerol was dissolved in 100 ml methanol. 4 ml concentrated hydrochloric acid (37%) was added and the solution was refluxed for 4 hours. The reaction mixture was cooled to room temperature, poured on ice (100 grams), transferred to a separatory funnel and extracted thrice with 100 ml diethyl ether. The organic phase was washed consecutively with 100 ml water, 100 ml saturated sodium bicarbonate solution, and again with 100 ml water. The organic phase was dried over anhydrous sodium sulfate and the solvent was removed under reduced pressure to give 14.5 grams of crude product. The crude product was purified by chromatography on a silica gel (150 grams) column. 3.17 grams of 2-(5'-hexenyl)-3-benzyl-sn-glycerol was eluted by dichloromethane followed by a mixture of dichloromethane and ethyl acetate. The yield was 46.8%.

Synthesis of 1-(15'-carboxy)pentadecyl-2-(5'-hexenyl)-3-benzyl-sn-glycerol 3 grams of 2-(5'-hexenyl)-3-benzyl-sn-glycerol was dissolved in 100 ml benzene. 3 grams of KOH was added, and the reaction mixture was dried by azeotropic distillation for 2 hours. To this mixture, a solution of 5.35 grams tert-butyl-16-bromohexadecanoate in 100 ml benzene was added dropwise during the course of 3 hours. After completion of addition the reaction, the mixture was refluxed for additional 12 hours. The volume of the solvent was gradually reduced to about 20 ml. The reaction mixture was cooled to room temperature, 100 ml water and 100 ml tert-butanol were added. The pH of the reaction mixture was adjusted to approximately 1 by adding concentrated HCl. The mixture was stirred at room temperature for 2 hours and extracted thrice with 100 ml diethyl ether. The combined organic phase was washed with 100 ml portions of water until the pH was neutral. Drying over anhydrous $Na_2SO_4$ and removal of solvent under reduced pressure yielded 6 grams of a brown oil. This oil was dissolved in 100 ml of a 1:1 (v/v) mixture of hexane:ethyl acetate. The solution was extracted twice with 100 ml of an 8:2 (v/v) mixture of methanol:aqueous 10% NaOH. The basic solution was acidified to a pH of 4-5 by adding $NaH_2PO_4$. 100 ml diethyl ether and 100 ml water were added and the phases were then separated. The aqueous phase was extracted twice with 100 ml diethyl ether and combined with the organic phase. The organic phase was washed with 100 ml water and 100 ml brine. Drying over anhydrous $Na_2SO_4$ and removal of the solvent under reduced pressure yielded 5.3 grams of 1-(15'-carboxy)pentadecyl-2-(5'-hexenyl)-3-benzyl-sn-glycerol as a yellow oil. The yield was 90%.

Synthesis of 1-(15'-carboxy)pentadecyl-2-(4-carboxy)butyl-3-benzyl-sn-glycerol 5.3 grams of 1-(15'-carboxy)pentadecyl-2-(5'-hexenyl)-3-benzyl-sn-glycerol was dissolved in 130 ml tert-butanol and a solution of 1.2 gram sodium bicarbonate in 40 ml water was added. 54 mg of $KMnO_4$ in 1 ml of water was then added. 20 grams of $NaIO_4$ were dissolved in 115 ml of water and this solution was then added to the reaction mixture during the course of 10 minutes. Additional amounts of a solution of 216 mg $KMnO_4$ in 4 ml water were added as needed to maintain the pink color of the reaction. Stirring was continued at room temperature for 6 hours and then the reaction mixture was kept at 4° C. over night. Sodium bisulfite was added until the color of the reaction mixture turned light yellow. The mixture was stirred for 30 minutes, 25 ml of 10% sulfuric acid solution was added dropwise, and the mixture was extracted thrice with 100 ml diethyl ether. The combined organic phase was washed consecutively with 100 ml water, twice with 100 ml of a solution containing 25 grams sodium bisulfite in 100 ml water, and twice with 100 ml water. Drying over anhydrous $Na_2SO_4$ and removal of the solvent under reduced pressure yielded 5.3 grams of crude 1-(15'-carboxy)pentadecyl-2-(4-carboxy)butyl-3-benzyl-sn-glycerol as a yellow wax.

Synthesis of (S)-1-(15'-carboxy)pentadecyl-2-(4-carboxy)butyl-sn-glycerol 5.0 grams of 1-(15'-carboxy)pentadecyl-2-(4-carboxy)butyl-3-benzyl-sn-glycerol was dissolved in 50 ml methanol, and 10 ml of 85% formic acid was added. 5 grams of palladium black was added, and the reaction mixture heated to 60° C. under nitrogen for 24 hours. The reaction mixture was cooled to room temperature and filtered through Celite. The Celite was washed with methanol and then with water. The washing solutions were combined with the filtrate and the solvent from the filtrate was removed under reduced pressure. The residue (5 grams) was dissolved in a mixture of 10 ml of 10% aqueous sodium hydroxide solution and 40 ml methanol, and the obtained mixture was stirred at room temperature for 2 hours. The reaction mixture was washed with 50 ml of a 1:1 (v/v) mixture of hexane:toluene. The pH of the reaction mixture was adjusted to 5 by addition of sodium dihydrogen phosphate, and the mixture was then extracted thrice with 50 ml chloroform. The organic phase was washed with 50 ml brine and dried over anhydrous $Na_2SO_4$, and the solvent was removed under reduced pressure. The crude product (4 grams) was recrystallized from a 9:1 (v/v) hexane:acetone mixture, yielding 3 grams of (S)-1-(15'-carboxy)pentadecyl-2-(4-carboxy)butyl-sn-glycerol as a colorless solid. The yield was 72%.

Synthesis of (S)-1-(15'-methylcarboxy)pentadecyl-2-(4-methylcarboxy)butyl-sn-glycerol 3 grams of (S)-1-(15'-carboxy)pentadecyl-2-(4-carboxy)butyl-sn-glycerol was dissolved in 50 ml methanol. 1 ml of concentrated hydrochloric acid (37%) was added, and the reaction mixture was stirred at room temperature overnight. The reaction mixture was concentrated to about 10 ml under reduced pressure, 50 ml water was added, and the mixture was then extracted thrice with 50 ml chloroform. The combined organic phase was washed consecutively with 50 ml water, 50 ml concentrated sodium bicarbonate solution, and 50 ml water. Drying over anhydrous $Na_2SO_4$ and removal of the solvent under reduced pressure yielded 3 grams of (S)-1-(15'-methylcarboxy)pentadecyl-2-(4 methylcarboxy)butyl-sn-glycerol as a yellow oil.

Synthesis of (R)-1-(15'-methylcarboxy)pentadecyl-2-(4-methylcarboxy)butyl-sn-glycero-3-phosphoethanolamine 2.8 grams of (S)-1-(15'-methylcarboxy)pentadecyl-2-(4 methylcarboxy)butyl-sn-glycerol and 2.5 ml dry triethylamine were dissolved in 30 ml THF. This solution was added dropwise, over the course of 20 minutes, to an ice-cooled solution of 1.65 ml $POCl_3$ in 20 ml THF while stirring. The stirring was continued for an additional 10 minutes in an ice-bath and for an additional 45 minutes at room temperature. A solution of 1.1 ml ethanolamine and 5 ml triethylamine in 50 ml THF was added dropwise over the course of 60 minutes to the ice-cooled reaction mixture while stirring. The stirring was continued for an additional 10 minutes in an ice-bath and continued at room temperature overnight. The reaction mixture was filtered and the solvent was removed under reduced pressure. The obtained residue was dissolved in a mixture of 24 ml acetic acid and 100 ml water and heated to 70° C. for 1 hour. The reaction mixture was cooled to room temperature, extracted thrice with 50 ml chloroform, and the organic phase was washed twice with 50 ml water. Removal of solvent under reduced pressure yielded 4 grams of crude (R)-1-(15'-methylcarboxy)pentadecyl-2-(4-methylcarboxy)butyl-sn-glycero-3-phosphoethanolamine as a brown oil.

Synthesis of (R)-1-(15'-carboxy)pentadecyl-2-(4-carboxy)butyl-sn-glycero-3-phosphoethanolamine (CI-214)

1.5 grams of (R)-1-(15'-methylcarboxy)pentadecyl-2-(4 methylcarboxy)butyl-sn-glycero-3-phosphoethanolamine was dissolved in 50 ml of a 8:2 (v/v) mixture of methanol:aqueous 10% sodium hydroxide solution, and the obtained mixture was stirred at room temperature for 5 hours. The pH of the reaction was adjusted to 4 by adding sodium dihydrogen phosphate and formic acid. 100 ml water and 100 ml chloroform were added. After extraction, the phases were separated and the solvent from the organic phase was removed under reduced pressure. The obtained residue was dissolved in chloroform and dried over anhydrous $Na_2SO_4$, and the solvent was removed under reduced pressure to give 500 mg of crude (R)-1-(15'-carboxy)pentadecyl-2-(4-carboxy)butyl-phosphoethanolamine. The crude product was purified by chromatography on silica gel (15 grams). The elution was performed with 100 ml chloroform, followed by 100 ml of chloroform:methanol mixtures (9:1 and 8:2 by volumetric ratio), and then 200 ml of chloroform:methanol:water mixtures (70:26:4, and 60:35:5 by volumetric ratio). The solvent from fractions containing the desired product was removed under reduced pressure, the residue was dissolved in chloroform and dried over anhydrous $Na_2SO_4$, and the solvent was removed by reduced pressure to give 88 mg of pure (R)-1-(15'-carboxy)pentadecyl-2-(4-carboxy)butyl-sn-glycero-3-phosphoethanolamine (CI-214) as a yellow wax.

NMR characterization of 1-(15'-carboxy)pentadecyl-2-(4-carboxy)butyl-glycero-3-phosphoethanolamine The sample was dissolved in deuterated chloroform ($CDCl_3$) with a few drops of deuterated methanol. The spectra were then measured at 300 MHz.

The results showed the expected signals for the structural elements of 1-(15'-carboxy)pentadecyl-2-(4-carboxy)butyl-glycero-3-phosphoethanolamine and thus fully supported the structure.

$^1$H NMR

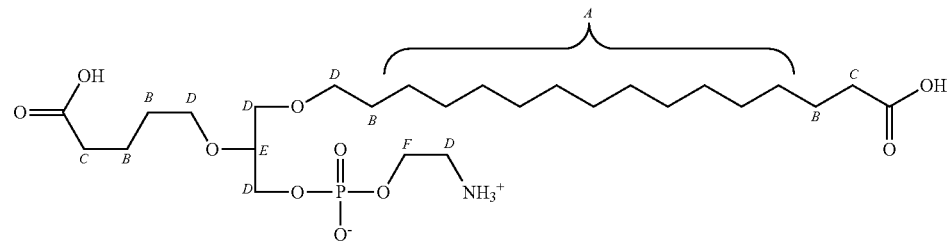

87

¹H NMR (300 MHz, reference solvent (CDCl₃)=7.44 ppm)

| δ [ppm] | Description | Assignment (see formula above) |
|---|---|---|
| 4.37 | 2 H, br, s | F |
| 3.93-3.98 | 1 H, m | E |
| 3.42-3.85 | 10 H, m, 5 × CH₂ | D |
| 2.27-2.36 | 4 H, m, 2 × CH₂ | C |
| 1.54-1.70 | 8 H, m, 4 × CH₂ | B |
| 1.27 | 22 H, m, 11 × CH₂ | A |

¹³C NMR

The assignment of the observed ¹³C peaks according to the structure of 1-(15'-carboxy)pentadecyl-2-(4-carboxy)butyl-glycero-3-phosphoethanolamine was as follows:

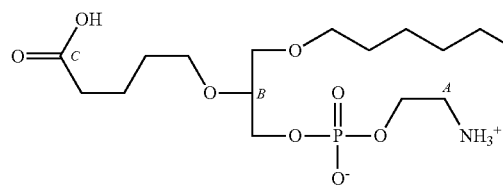

¹³C NMR (300 MHz, reference solvent (CDCl₃)=77.614 ppm)

| δ [ppm] | Assignment (see formula above) |
|---|---|
| 177.250 | C |
| 177.125 | C |
| 78.174 | B |
| 72.097 | |
| 70.388 | |
| 70.199 | |
| 65.850 | |
| 61.841 | |
| 40.788 | A |
| 34.424 | |
| 34.228 | |
| 29.851 | |
| 29.698 | |
| 29.527 | |
| 29.392 | |
| 26.289 | |
| 25.198 | |
| 21.945 | |

Mass spectrometry characterization of 1-(15'-carboxy)pentadecyl-2-(4-carboxy)butyl-glycero-3-phosphoethanolamine The calculated mass for 1-(15'-carboxy)pentadecyl-2-(4-carboxy)butyl-glycero-3-phosphoethanolamine ($C_{26}H_{52}NO_{10}P$) was 569.6655.

The mass spectrum performed using Electrospray Ionization Mass Spectrometry (ES⁻MS) showed a molecular ion with m/z=568, corresponding to the deprotonated molecular ion [M−H]⁻.

In addition, a molecular cation with m/z=570 was observed by Positive Electrospray Ionization Mass Spectrometry (ES+-MS), corresponding to the protonated molecular ion [M+H]⁺.

The MS spectrum is thus in agreement with the chemical structure of 1-(15'-carboxy)pentadecyl-2-(4-carboxy)butyl-glycero-3-phosphoethanolamine.

88

Synthesis of (R)-1-(15'-methylcarboxy)pentadecyl-2-(4-methylcarboxy)butyl-sn-glycero-3-phosphocholine 1.2 gram of (R)-1-(15'-methylcarboxy)pentadecyl-2-(4 methylcarboxy)butyl-sn-glycero-3-phosphoethanolamine was dissolved in a mixture of 60 ml methanol and 20 ml dichloromethane. A solution of 2 grams potassium carbonate in 10 ml water was added, and the solution was heated and kept at a temperature in the range of 35-40° C. A solution of 1.25 ml dimethylsulfate in 10 ml methanol was added dropwise. After completion of addition, the reaction mixture was stirred at 40° C. for an additional 90 minutes, then cooled to room temperature and stirred at room temperature overnight. 100 ml water was added and extraction with 100 ml chloroform was performed three times. The combined organic phase was washed with 100 ml water and the solvent was removed under reduced pressure, yielding 900 mg of (R)-1-(15'-methylcarboxy)pentadecyl-2-(4 methylcarboxy)butyl-sn-glycero-3-phosphocholine as a brown oil.

Synthesis of (R)-1-(15'-carboxy)pentadecyl-2-(4-carboxy)butyl-sn-glycero-3-phosphocholine (CI-213)

1.88 grams of (R)-1-(15'-methylcarboxy)pentadecyl-2-(4 methylcarboxy)butyl-sn-glycero-3-phosphocholine was dissolved in 50 ml of an 8:2 (v/v) mixture of methanol:aqueous 10% sodium hydroxide solution, and the obtained mixture was stirred at room temperature for 5 hours. The pH of the reaction was adjusted to 4 by adding sodium dihydrogen phosphate and formic acid. 100 ml water and 100 ml chloroform were added. The phases were separated, and the solvent from the organic phase was removed under reduced pressure. The obtained residue was dissolved in chloroform and dried over anhydrous Na₂SO₄, and the solvent was removed under reduced pressure to give 860 mg of crude (R)-1-(15'-carboxy)pentadecyl-2-(4-carboxy)butyl-phosphocholine. The crude product was purified by chromatography on silica gel (20 grams). The elution was performed with 100 ml chloroform, followed by 100 ml of chloroform:methanol mixtures (9:1 and 8:2 by volumetric ratio), and then 200 ml of chloroform:methanol:water mixtures (70:26:4, and 60:35:5 by volumetric ratio). The solvent from fractions containing the desired product was removed under reduced pressure, the residue was dissolved in chloroform and dried over anhydrous Na₂SO₄, and the solvent was removed under reduced pressure to yield 105 mg of pure (R)-1-(15'-carboxy)pentadecyl-2-(4-carboxy)butyl-sn-glycero-3-phosphocholine (CI-213) as a yellow wax.

NMR characterization of 1-(15'-carboxy)pentadecyl-2-(4-carboxy)butyl-glycero-3-phosphocholine The sample was dissolved in deuterated chloroform (CDCl₃) with a few drops of deuterated methanol. The spectra were measured at 300 MHz.

The results showed the expected signals for the structural elements of 1-(15'-carboxy)pentadecyl-2-(4-carboxy)butyl-glycero-3-phosphocholine and thus fully supported the structure.

¹H NMR

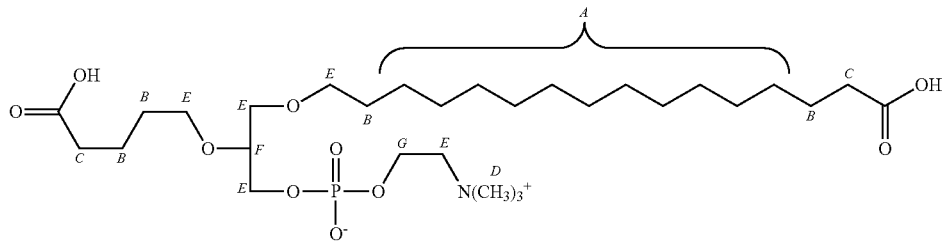

¹H NMR (300 MHz, reference solvent (CDCl3)=7.38 ppm)

| δ [ppm] | Description | Assignment (see formula above) |
|---|---|---|
| 4.27 | 2 H, br, s | G |
| 3.94-4.00 | 1 H, m | F |
| 3.36-3.89 | 10 H, m, 5 × $CH_2$ | E |
| 3.23 | 9 H, s, 3 × $CH_3$ | D |
| 2.26-2.37 | 4 H, m, 2 × $CH_2$ | C |
| 1.52-1.72 | 8 H, m, 4 × $CH_2$ | B |
| 1.26 | 22 H, m, 11 × $CH_2$ | A |

¹³C NMR

The assignment of the observed ¹³C peaks according to the structure of 1-(15'-carboxy)pentadecyl-2-(4-carboxy)butyl-glycero-3-phosphocholine was as follows:

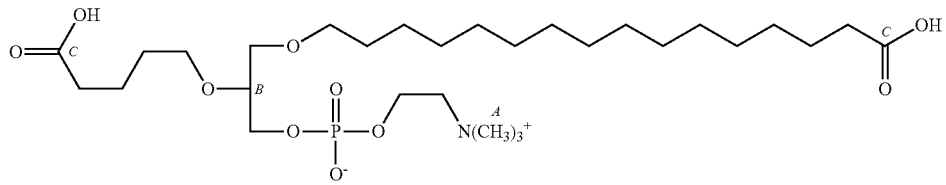

¹³C NMR (300 MHz, reference solvent ($CDCl_3$)=77.35 ppm)

| δ [ppm] | Assignment (see formula above) |
|---|---|
| 176.90 | C |
| 176.72 | C |
| 78.21 | B |
| 71.92 | |
| 70.37 | |
| 70.01 | |
| 66.58 | |
| 65.87 | |
| 59.14 | |
| 54.34 | A |
| 34.31 | |
| 34.07 | |
| 29.66 | |
| 29.56 | |
| 29.52 | |
| 29.36 | |
| 29.24 | |
| 26.12 | |
| 25.06 | |
| 21.98 | |

Mass spectrometry characterization of 1-(15'-carboxy)pentadecyl-2-(4-carboxy)butyl-glycero-3-phosphoethanolamine The calculated mass for 1-(15'-carboxy)pentadecyl-2-(4-carboxy)butyl-glycero-3-phosphocholine ($C_{29}H_{58}NO_{10}P$) was 611.7453.

The mass spectrum performed using Electrospray Ionization Mass Spectrometry (ES⁻MS) showed a molecular ion with m/z=610, corresponding to ion $[M-H]^-$.

In addition, Positive Electrospray Ionization Mass Spectrometry (ES+-MI) showed a molecular ion with m/z=612, corresponding to the protonated molecular ion $[M+H]^+$, accompanied by a molecular cation with m/z=634, corresponding to the cationated ion $[M+Na]^+$.

The MS spectrum is thus in agreement with the chemical structure of 1-(15'-carboxy)pentadecyl-2-(4-carboxy)butyl-glycero-3-phosphocholine.

Toxicity of CI-213 and CI-214:

The toxicities of CI-213 and CI-214 were evaluated as described hereinabove in the Materials and Methods section.

As shown in FIGS. 25A and 25B, CI-213 did not clearly exhibit significant toxicity within the range of tested doses (i.e., up to 150 μg/ml, 245.2 μM). A statistically significant decrease in cell number was detected in only one experiment, at a dose of 100 μg/ml (163.5 μM).

Similarly, as shown in FIGS. 26A and 26B, CI-214 did not clearly exhibit significant toxicity within the range of tested doses (i.e., up to 150 μg/ml, 263.3 μM). A statistically significant decrease in cell number was detected in only one experiment, at a dose of 100 μg/ml (175.5 μM).

These results indicate that the $LD_{50}$ of both CI-213 and CI-214 is higher than 150 μg/ml.

Example 10

1-Hexadecyl-2-(2-carboxy)ethyl-glycero-3-phosphocholine (CI-217)

(R)-1-Hexadecyl-2-(2-carboxy)ethyl-sn-glycero-3-phosphocholine was synthesized as described hereinbelow using (R)-(−)-2,2-dimethyl-1,3-dioxolane-4-methanol as a starting material. (S)-1-Hexadecyl-2-(2-carboxy)ethyl-glycero-3-phosphocholine is synthesized using the same procedures, but with (S)-(+)-2,2-dimethyl-1,3-dioxolane-4-methanol as the starting material.

Synthesis of (S)-1-hexadecyl-sn-glycerol 40 grams of (R)-(−)-2,2-dimethyl-1,3-dioxolane-4-methanol, 80 grams of powdered potassium hydroxide and 100 grams of hexadecyl bromide were stirred in 350 ml benzene and refluxed for 7 hours, while removing the water formed by azeotropic distillation. The volume of the solvent was gradually reduced to about 50 ml. The reaction mixture was cooled to room temperature, 300 ml of ice-cooled water was added, and the mixture was extracted 4 times with 150 ml dichloromethane. The combined organic phase was washed with water and the solvent was removed under reduced pressure. The obtained residue was dissolved in 500 ml of a 90:10:5 (v/v) mixture of methanol:water:concentrated hydrochloric acid, and the resulting solution was refluxed for 2 hours. After cooling to room temperature, 200 ml water was added. The product was extracted thrice with 200 ml chloroform, and washed consecutively with 200 ml water, 200 ml of a saturated aqueous sodium carbonate solution, and again with 200 ml water. The solvent was removed under reduced pressure and the product was crystallized from 450 ml petroleum ether at 4° C., yielding 69.93 grams of pure (S)-1-hexadecyl-sn-glycerol. The yield was 73%.

Synthesis of 1-hexadecyl-3-trityl-glycerol 18.47 grams of (S)-1-hexadecyl-sn-glycerol and 19 grams of triphenylchloromethane were dissolved in a mixture of 250 ml dry THF and 58 ml dry acetonitrile. 17 ml of triethylamine was added and the reaction mixture was refluxed for 17 hours. The reaction mixture was cooled to room temperature, poured on ice (20 grams) and triethylamine (5 ml), transferred to a separatory funnel and extracted with diethyl ether. The organic phase was washed consecutively with 200 ml water, twice with 200 ml dilute (1.5%) sulfuric acid, 200 ml water, 200 ml saturated aqueous sodium bicarbonate, and again with 200 ml water. The organic phase was dried over anhydrous sodium sulfate and the solvent was removed under reduced pressure to yield 41.79 grams of crude product as a residue. This residue was dissolved in 300 ml ethyl acetate and cooled at −20° C. overnight. The mixture was centrifuged (3,500 rotations per minute) at −10° C., and the mother liquid was poured of. The obtained solid melted and was dissolved in hexane and refrigerated (5±3° C.) overnight. Filtration of the precipitate yielded 18.97 grams of pure (R)-1-hexadecyl-3-trityl-sn-glycerol as an off-white solid.

Synthesis of 3-hexenyl-1-methane sulfonate

A mixture of 20 ml cis-3-hexene-1-ol and 40 ml dry triethylamine in 100 ml dry dichloromethane was cooled in an ice bath. A solution of 20 ml methanesulfonyl chloride in 50 ml dichloromethane was added dropwise over the course of 75 minutes, and the mixture was then kept at 4° C. for 2 hours. Ice (50 grams) was added and the mixture was stirred at room temperature for 30 minutes, and then extracted twice with 100 ml chloroform. The organic phase was washed with 50 ml water, 50 ml 10% aqueous sulfuric acid, 50 ml water, 50 ml 10% aqueous sodium bicarbonate, and then twice with 50 ml water. The solvent was dried over anhydrous $Na_2SO_4$ and removed under reduced pressure. The obtained residue (34.90 grams) was purified by chromatography over silica gel (85.37 grams). 18.83 grams of 3-hexenyl-1-methane sulfonate was obtained by elution with a 1:1 (v/v) mixture of chloroform and hexane.

Synthesis of (S)-1-hexadecyl-2-(3'-hexenyl)-glycerol 10.60 grams of (R)-1-hexadecyl-3-trityl-sn-glycerol was dissolved in a mixture of 50 ml benzene and 50 ml petroleum ether. 16.65 grams of powdered KOH was added, and the reaction mixture was heated to reflux under nitrogen. A solution of 10 ml 3-hexenyl-1-methane sulfonate in 50 ml benzene and 200 ml petroleum ether was added dropwise to the refluxing reaction mixture over the course of over 10 hours while removing the water formed in the reaction by azeotropic distillation. After completion of the addition, stirring was continued for 2 hours. The reaction mixture was cooled to room temperature and 200 ml water was added. The mixture was extracted thrice with 200 ml diethyl ether, the combined organic phase was washed thrice with 200 ml water, and the solvent was removed under reduced pressure, yielding 11.88 grams of crude (R)-1-hexadecyl-2-(3 hexenyl)-3-trityl-sn-glycerol. The 1-hexadecyl-2-(3-hexenyl)-3-trityl-glycerol was dissolved in 100 ml methanol, 4 ml concentrated HCl was added, and the resulting solution was refluxed for 4 hours. 100 ml water was added and the mixture extracted four times with 100 ml diethyl ether. The combined organic phase was washed with 100 ml water and dried over anhydrous $Na_2SO_4$, and the solvent was removed under reduced pressure. The obtained residue was dissolved in hexane and stored at 4° C. overnight. Filtration of the precipitate and removal of the solvent under reduced pressure yielded 10.08 grams of crude product. This product was purified by chromatography on silica gel (95.91 grams). 3.71 grams of the product, (S)-1-hexadecyl-2-(3'-hexenyl)-sn-glycerol, was eluted with a 1:1 (v/v) mixture of hexane and chloroform, followed by chloroform and then chloroform with 2% acetone.

Synthesis of (R)-1-hexadecyl-2-(3'-hexenyl)-sn-glycero-3-phosphoethanolamine 2.08 grams of (S)-1-hexadecyl-2-(3'-hexenyl)-sn-glycerol (which was dried in a desiccator over $P_2O_5$) and 1.2 ml of triethylamine were dissolved in 60 ml THF. This solution was added dropwise during the course of 55 minutes to an ice-cooled solution of 0.84 ml $POCl_3$ and 0.7 ml triethylamine in 40 ml THF while stirring. The stirring was continued for an additional 10 minutes with cooling and for an additional 45 minutes at room temperature. The reaction mixture was then cooled in an ice bath, and a solution of 0.55 ml ethanolamine and 2.0 ml triethylamine in 15 ml THF was then added dropwise over the course of 25 minutes. The stirring was continued for 30 minutes in the ice bath and then at room temperature overnight. An additional 0.18 nl ethanolamine was added, and the reaction mixture was stirred at room temperature for 2 hours. The reaction mixture was filtered and the solvent from the filtrate was removed under reduced pressure. The obtained residue was dissolved in a mixture of 48 ml acetic acid and 20 ml water, heated to 77° C. for 1 hour, and cooled to room temperature. The solution was extracted thrice with 100 ml of a 2:1 (v/v) mixture of chloroform: methanol, washed with dilute sodium bicarbonate solution, and 100 ml water, and the solvent was removed under reduced pressure. The obtained residue was dissolved in chloroform, dried over anhydrous $Na_2SO_4$, and the solvent was removed under reduced pressure, yielding 2.57 grams of (R)-1-hexadecyl-2-(3'-hexenyl)-sn-glycero-3-phosphoethanolamine.

Synthesis of (R)-1-hexadecyl-2-(3'-hexenyl)-sn-glycero-3-phosphocholine 6.8 grams of potassium carbonate was added to a solution of 2.54 grams of (R)-1-hexadecyl-2-(3'-hexenyl)-sn-glycero-3-phosphoethanolamine in 100 ml methanol and 100 ml dichloromethane. 3 ml dimethylsulfate was then added dropwise, and the reaction mixture was stirred at room temperature for 7 hours. An additional 1 ml of dimethylsulfate was added and the reaction mixture was stirred at room temperature overnight. 26.4 grams of sodium dihydrogen phosphate was added to the reaction mixture, 100 ml water was then added, and the mixture was then extracted thrice with 100 ml of a 2:1 (v/v) mixture of chloroform:methanol. The combined organic phase was washed with 100 ml water and the solvent was removed under reduced pressure, yielding 3.44 grams of crude (R)-1-hexadecyl-2-(3'-hexenyl)-sn-glycero-3-phosphocholine.

The results showed the expected signals for the structural elements of 1-hexadecyl-2-(2-carboxy)ethyl-glycero-3-phosphocholine and thus fully supported the structure.

$^1$H NMR

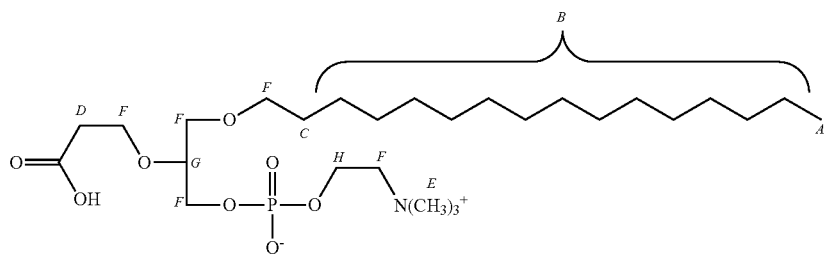

Synthesis of (R)-1-hexadecyl-2-(2-carboxy)ethyl-sn-glycero-3-phosphocholine (CI-217)

A solution of 3.4 grams (R)-1-hexadecyl-2-(3'-hexenyl)-sn-glycero-3-phosphocholine in 200 ml water was heated to 35° C., and 4.33 grams of sodium bicarbonate were added. A solution of 13.5 grams sodium periodate in 90 ml water was then placed in a dropping funnel and added dropwise. A solution of 180 mg potassium permanganate in 10 ml water was placed in a second dropping funnel and added dropwise as needed to maintain a pink color of the reaction mixture. A total of about 4 ml of the permanganate solution was added. The reaction mixture was stirred for 5 hours at 35-40° C. and then at room temperature overnight. The pH of the reaction was adjusted to approximately 3 by adding sodium dihydrogen phosphate and then phosphoric acid (80%). The reaction mixture was extracted thrice with 100 ml chloroform, and the solvent from the organic phase was removed under reduced pressure. The obtained residue was dissolved in chloroform and washed twice with 50 ml sodium bisulfite solution and then with 50 ml water. The organic solution was dried over anhydrous $Na_2SO_4$, and the solvent was removed under reduced pressure, yielding 2.78 grams of crude product. The crude product was purified by chromatography over silica gel (30.89 grams). 1.98 grams of pure (R)-1-hexadecyl-2-(2-carboxy)ethyl-sn-glycero-3-phosphocholine was eluted with mixtures of hexane with 20%-50% chloroform, followed by chloroform and then mixtures of chloroform with 10%-80% methanol.

NMR characterization of 1-hexadecyl-2-(2-carboxy)ethyl-glycero-3-phosphocholine

The sample was dissolved in deuterated chloroform ($CDCl_3$) with a few drops of deuterated methanol. The spectra were measured at 600 MHz.

$^1$H NMR (600 MHz, reference solvent $(CDCl_3)$=7.27 ppm)

| δ [ppm] | Description | Assignment (see formula above) |
|---|---|---|
| 4.052 | 2 H, br, s | H |
| 3.72 | 1 H, m | G |
| 3.66 | 2 H, m, $CH_2$ | F |
| 3.469 | 2 H, m, $CH_2$ | F |
| 3.400 | 2 H, m, $CH_2$ | F |
| 3.299 | 2 H, m, $CH_2$ | F |
| 3.227 | 2 H, m, $CH_2$ | F |
| 3.012 | 9 H, s, 3 × $CH_3$ | E |
| 2.351 | 2 H, m, $CH_2$ | D |
| 1.347 | 2 H, m, $CH_2$ | C |
| 1.059 | 26 H, m, 13 × $CH_2$ | B |
| 0.675 | 3 H, t, J = 7.2 Hz, $CH_3$ | A |

$^{13}$C NMR

The assignment of the observed $^{13}$C peaks according to the structure of 1-hexadecyl-2-(2-carboxy)ethyl-glycero-3-phosphocholine was as follows:

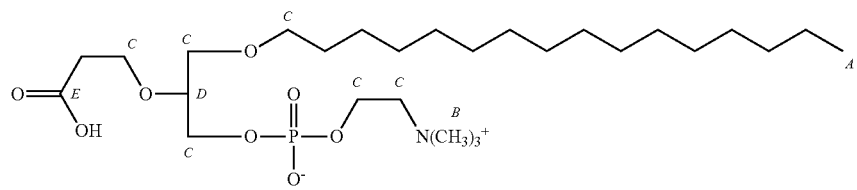

$^{13}$C NMR (600 MHz, reference solvent $(CDCl_3)$=77.817 ppm)

| δ [ppm] | Assignment (see formula above) |
|---|---|
| 173.126 | E |
| 78.990 | D |
| 72.220 | C |
| 70.695 | C |
| 66.932 | C |
| 66.584 | C |
| 66.271 | C |
| 59.509 | C |

-continued

| δ [ppm] | Assignment (see formula above) |
|---------|-------------------------------|
| 54.487  | B |
| 35.945  |   |
| 35.651  |   |
| 32.291  |   |
| 30.040  |   |
| 29.880  |   |
| 29.707  |   |
| 26.432  |   |
| 23.013  |   |
| 14.211  | A |

Mass spectrometry characterization of 1-hexadecyl-2-(2-carboxy)ethyl-glycero-3-phosphocholine The calculated mass for 1-hexadecyl-2-(2-carboxy)ethyl-glycero-3-phosphocholine ($C_{27}H_{56}NO_8P$) was 554.

The mass spectrum performed using Electrospray Ionization Mass Spectrometry ($ES^-MS$) showed a molecular ion with m/z=553, corresponding to the deprotonated molecular ion $[M-H]^-$.

In addition, the mass spectrum performed by Positive Electrospray Ionization Mass Spectrometry (ESI+-MS) showed a molecular ion with m/z=555, corresponding to the protonated molecular ion $[M+H]^+$, accompanied by a molecular ion with m/z=577, corresponding to the cationated molecular ion $[M+Na]^+$.

The MS spectrum is thus in agreement with the chemical structure of 1-hexadecyl-2-(2-carboxy)ethyl-glycero-3-phosphocholine.

Tyrosine Phosphorylation:

The effect of CI-217 on in vitro tyrosine phosphorylation in primary macrophages was determined as described hereinabove in the Materials and Methods section.

As shown in FIG. 27, treatment with 20 μg/ml (36 μM) CI-217 caused a reduction in phosphotyrosine levels, whereas treatment with 10 μg/ml (18 μM) CI-217 had little effect. These results were very similar to the results of the respective treatments with 20 μg/ml (34 μM) and 10 μg/ml (17 μM) of the positive control CI-201.

Example 11

1-eicosanyl-2-(4-carboxy)butyl-glycero-3-phosphocholine (CI-219) and 1-eicosanyl-2-(4-carboxy)butyl-glycero-3-phosphoethanolamine (CI-220)

(R)-1-eicosanyl-2-(4-carboxy)butyl-sn-glycero-3-phosphocholine and (R1-eicosanyl-2-(4-carboxy)butyl-sn-glycero-3-phosphoethanolamine were synthesized as described hereinbelow using (R)-(−)-2,2-dimethyl-1,3-dioxolane-4-methanol as a starting material. (S)-1-eicosanyl-2-(4-carboxy)butyl-glycero-3-phosphocholine and (S)-1-eicosanyl-2-(4-carboxy)butyl-glycero-3-phosphoethanolamine are synthesized using the same procedures, but with (S)-(+)-2,2-dimethyl-1,3-dioxolane-4-methanol as the starting material.

Synthesis of (S)-1-eicosanyl-sn-glycerol 8.6 ml (76.08 mmol) of (R)-(−)-2,2-dimethyl-1,3-dioxolane-4-methanol, 15 grams of powdered potassium hydroxide and 27.5 grams (76.08 mmol) of 1-bromoeicosane were stirred in 150 ml benzene and refluxed for 6 hours, while removing the water formed by azeotropic distillation. The volume of the solvent was gradually reduced to about 70 ml. The reaction mixture was then cooled to room temperature and 150 ml of water was added. The reaction mixture was then extracted thrice with 150 ml diethyl ether, the combined organic phase was washed with 100 ml water, and the solvent was then removed under reduced pressure. The obtained residue was dissolved in 105 ml of a 90:10:5 (v/v) methanol:water:concentrated hydrochloric acid mixture, and the resulting solution was refluxed until the solution became clear. The solution was then cooled to room temperature and 100 ml water was added. The product was extracted with 150 ml chloroform, washed consecutively with 150 ml water, 150 ml saturated aqueous solution of sodium carbonate, and again with 150 ml water. The solvent was then removed under reduced pressure and the product was crystallized from 200 ml hexane, yielding 21.0 grams of pure 1-eicosanyl-sn-glycerol, which was dried in a desiccator under reduced pressure with phosphorus oxide. The yield was 81.5%.

Synthesis of (R)-1-eicosanyl-3-trityl-sn-glycerol 20 grams of 1-eicosanyl-sn-glycerol and 18 grams of triphenylchloromethane were added to a mixture of 400 ml dry tetrahydrofuran (THF) and 100 ml dry acetonitrile. 15 ml of dry triethylamine was added, and the reaction mixture was refluxed for 17 hours. The reaction mixture was then cooled to room temperature, poured on ice (500 grams), transferred to a separatory funnel, and extracted thrice with 200 ml diethyl ether. The organic phase was washed consecutively with 150 ml water, twice with 150 ml dilute (1.5%) $H_2SO_4$, 150 ml water, 150 ml concentrated aqueous sodium bicarbonate, and again with 150 ml water. The solution was then dried over anhydrous sodium sulfate and the solvent was removed under reduced pressure. The obtained residue, a brown oil, was dissolved in 300 ml ethyl acetate, and cooled at −20° C. overnight. The mixture was centrifuged (3,500 rotations per minute) at −10° C., and the mother liquid was poured of. The obtained solid was dissolved in hexane and refrigerated (5±3° C.) overnight. Filtration of the precipitate yielded 26.0 grams of pure (R)-1-eicosanyl-3-trityl-sn-glycerol as an off-white solid. The yield was 79%.

Synthesis of (R)-1-eicosanyl-2-(5'-hexenyl)-3-trityl-sn-glycerol 26 grams of (R)-1-eicosanyl-3-trityl-sn-glycerol and 10 grams of 5-hexenyl-1-methane sulfonate were dissolved in 150 ml benzene. 12 grams of powdered KOH were added, and the reaction mixture was stirred and refluxed for 6 hours while removing the water formed in the reaction by azeotropic distillation. The volume of the solvent was gradually reduced to about 75 ml. The reaction mixture was cooled to room temperature and 200 ml water was added. The mixture was extracted thrice with 150 ml diethyl ether, the combined organic phase was washed thrice with 150 ml water, and the solvent was removed under reduced pressure. The obtained residue, 28 grams of a brown oil, was purified over a silica gel column (200 grams). 28 grams of the product was eluted with chloroform as a light yellow oil. The yield was 87.5%.

Synthesis of (S)-1-eicosanyl-2-(4-carboxy)butyl-sn-glycerol 70 grams of $NaIO_4$ was dissolved in 250 ml water. To this solution, 6 grams of $NaHCO_3$ and 1.2 gram of $KMnO_4$ were added, and the suspension was heated to 40° C. A solution of 25 grams (R)-1-eicosanyl-2-(5'-hexenyl)-3-trityl-sn-glycerol in 250 ml tert-butanol was added dropwise during the course of 90 minutes, and the mixture was heated for an additional 6 hours. Additional amounts of a KMnO$_4$ solution were added as needed to maintain a pink color. The reaction mixture was cooled to room temperature, filtered via celite, and the celite washed then with 50 ml tert-butanol. 100 ml of 10% sulfuric acid solution was added dropwise, and the solution was transferred to separatory funnel and extracted thrice with 200 ml hexane. The organic phase was washed with a solution of 20 grams Na$_2$S$_2$O$_5$ in 100 ml water and then with 100 ml water. The organic phase was concentrated by removal of about 400 ml solvent under reduced pressure. To the remained solution, 15 ml of water and 2 ml concentrated HCl were added, and the obtained mixture was refluxed for 6 hours. The mixture was then cooled to room temperature and concentrated again by removal of solvent under reduced pressure. The pH of the residue was adjusted to 12 by addition of 100 ml water and 10 ml of 30% NaOH solution. The precipitate was filtered off and washed four times with 20 ml water. The filtrate was extracted with 100 ml of a 1:1 (v/v) mixture of hexane:ethyl acetate. The aqueous phase was acidified to a pH of 1 by adding 10 ml concentrated HCl and was then extracted thrice with 100 ml hexane. Drying over anhydrous NaSO$_4$ and removal of the solvent under reduced pressure, followed by overnight recrystallization of the crude product from a 1:9 (v/v) acetone:hexane mixture at 5±3° C., yielded 9.0 grams of pure (S)-1-eicosanyl-2-(4-carboxy)butyl-sn-glycerol. The yield was 53.1%.

Synthesis of (S)-1-eicosanyl-2-(4-methylcarboxy)butyl-sn-glycerol 8.9 grams of 1-eicosanyl-2-(4-carboxy)butyl-sn-glycerol was dissolved in 50 ml methanol. 1 ml of concentrated HCl (32%) was added, and the reaction mixture was stirred at room temperature overnight. The solvent was removed under reduced pressure and 50 ml water was added to the obtained residue. The mixture was extracted thrice with 50 ml chloroform. The combined organic phase washed with 50 ml water, 50 ml saturated sodium bicarbonate solution, and again with 50 ml water. The solution was then dried over sodium sulfate, filtered, and evaporated under reduced pressure, to give 8.9 grams of (S)-1-eicosanyl-2-(4-methylcarboxy)butyl-sn-glycerol as a white wax.

Synthesis of (R)-1-eicosanyl-2-(4-methylcarboxy)butyl-sn-glycero-3-phosphoethanolamine 8.9 grams of 1-eicosanyl-2-(4-methylcarboxy)butyl-sn-glycerol (which was dried by azeotropic distillation with benzene) and 8 ml triethylamine were dissolved in 70 ml THF. This solution was added dropwise during the course of 30 minutes to an ice-cooled solution of 5.36 ml POCl$_3$ in 40 ml THF while stirring. The stirring was continued for an additional 30 minutes with cooling and for an additional 45 minutes at room temperature. The reaction mixture was then cooled in an ice bath, and a solution of 3.5 ml ethanolamine and 16 ml triethylamine in 50 ml THF was then added dropwise over the course of 30 minutes while stirring. The stirring was continued for 30 minutes in the ice bath, and then at room temperature overnight. The reaction mixture was filtered and the solvent was removed under reduced pressure. The obtained residue (14 grams of a yellow oil) was dissolved in a mixture of 72 ml acetic acid and 30 ml water and heated to 70° C. for 1 hour. The obtained mixture was extracted thrice with 150 ml chloroform and washed twice with 150 ml water. Removal of the solvent removed under reduced pressure yielded 13 grams of (R)-1-eicosanyl-2-(4-methylcarboxy)butyl-sn-glycero-3-phosphoethanolamine as a yellow oil.

Synthesis of (R)-1-eicosanyl-2-(4-carboxy)butyl-sn-glycero-3-phosphoethanolamine (CI-220)

4 grams of (R)-1-eicosanyl-2-(4-methylcarboxy)butyl-sn-glycero-3-phosphoethanolamine was dissolved in 100 ml of an 8:2 (v/v) mixture of methanol:aqueous 10% sodium hydroxide, and the reaction mixture was stirred at room temperature overnight. The pH of the reaction mixture was then adjusted to approximately 4 by adding formic acid. 150 ml water and 150 ml chloroform were then added. The phases were separated, and the solvent from the organic phase was removed under reduced pressure. The obtained residue was dissolved in chloroform, dried over sodium sulfate and filtered, and the solvent was then removed under reduced pressure. The obtained residue was purified by chromatography on silica gel (70 grams). A mixture of chloroform and hexane, followed by mixtures of chloroform and methanol, and finally mixtures of chloroform, methanol and water, were used to elute 835 mg of (R)-1-eicosanyl-2-(4 carboxy)butyl-sn-glycero-3-phosphoethanolamine (CI-220) from the column. The yield was 21%.

NMR characterization of 1-eicosanyl-2-(4-carboxy)butyl-glycero-3-phosphoethanolamine The sample was dissolved in deuterated chloroform (CDCl$_3$) with a few drops of deuterated methanol (CD$_3$OD). The spectra were then measured at 600 MHz. Samples were measured by both $^1$H and $^{13}$C NMR spectroscopy.

The results showed the expected signals for the structural elements of 1-eicosanyl-2-(4-carboxy)butyl-glycero-3-phosphoethanolamine and thus fully supported the structure.

The assignment of the observed $^1$H peaks according to the structure of 1-eicosanyl-2-(4-carboxy)butyl-glycero-3-phosphoethanolamine was as follows:

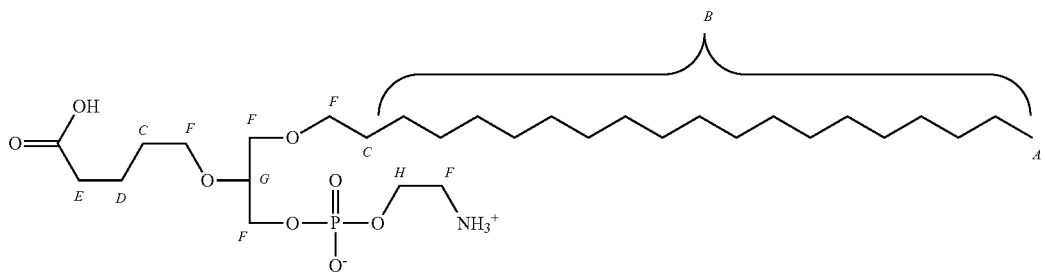

¹H NMR (600 MHz, reference solvent (CDCl₃)=7.357 ppm)

| δ [ppm] | Description | Assignment (see formula above) |
|---|---|---|
| 4.107 | 2 H, br, s | H |
| 3.858-3.876 | 1 H, m | G |
| 3.398-3.745 | 10 H, m, 5 × CH₂ | F |
| 2.346 | 2 H, t, J = 7.2 Hz | E |
| 1.666-1.737 | 2 H, m | D |
| 1.599-1.631 | 2 H, m | C |
| 1.535-1.569 | 2 H, m | C |
| 1.260 | 34 H, m, 17 × CH2 | B |
| 0.882 | 3 H, t, 1 × CH3, J = 6.9 Hz | A |

The assignment of the observed ¹³C peaks according to the structure of 1-eicosanyl-2-(4-carboxy)butyl-glycero-3-phosphoethanolamine was as follows:

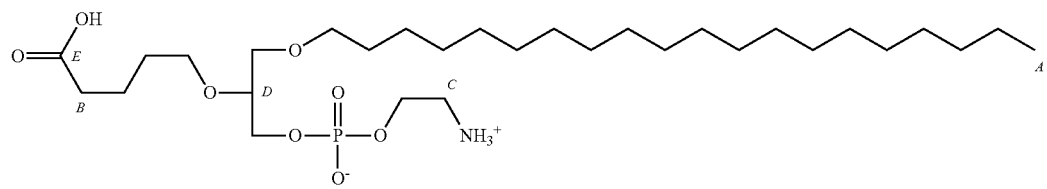

¹³C NMR (600 MHz, reference solvent (CDCl₃)=77.318 ppm)

| δ [ppm] | Assignment (see formula above) |
|---|---|
| 177.352 | E |
| 78.023-78.075 | D |
| 71.977 | |
| 70.293 | |
| 70.019 | |
| 65.968 | |
| 61.913 | |
| 40.525 | C |
| 34.108 | B |
| 32.045 | |
| 29.825 | |
| 29.778 | |
| 29.730 | |
| 29.659 | |
| 29.476 | |
| 29.320 | |
| 26.186 | |
| 22.794 | |
| 21.884 | |
| 14.154 | A |

Mass spectrometry characterization of 1-eicosanyl-2-(4-carboxy)butyl-glycero-3-phosphoethanolamine The calculated mass for 1-eicosanyl-2-(4-carboxy)butyl-glycero-3-phosphoethanolamine ($C_{30}H_{62}NO_8P$) was 595.42.

The mass spectrum performed using Electrospray Ionization Mass Spectrometry (ES⁻MS) showed a molecular ion with m/z=594, corresponding to the deprotonated ion $[M-H]^-$.

The mass spectrum performed using Positive Electrospray Ionization Mass Spectrometry (ESI+-MS) showed a molecular ion with m/z=596, corresponding to the protonated molecular ion $[M+H]^+$, accompanied by a molecular ion with m/z=618, corresponding to the cationated molecular ion $[M+Na]^+$.

The MS spectrum is thus in agreement with the chemical structure of 1-eicosanyl-2-(4-carboxy)butyl-glycero-3-phosphoethanolamine.

Synthesis of (R)-1-eicosanyl-2-(4-methylcarboxy)butyl-sn-glycero-3-phosphocholine 9 grams of (R)-1-eicosanyl-2-(4-methylcarboxy)butyl-sn-glycero-3-phosphoethanolamine was dissolved in a mixture of 40 ml isopropanol and 18 ml dichloromethane, and the mixture heated to 35-40° C. A solution of 10.3 grams potassium carbonate in 20 ml water was added dropwise while the reaction mixture was kept at 35-40° C. A solution of 7.2 ml dimethylsulfate in 10 ml isopropanol (10 ml) was then added dropwise at 40° C. The reaction mixture was kept at 40° C. for 2 hours and then at room temperature overnight. 150 ml water was added, and the mixture was extracted thrice with 150 ml chloroform. The organic phase was washed with 150 ml water and the solvent was removed under reduced pressure to yield 8 grams of (R)-1-eicosanyl-2-(4 methylcarboxy)butyl-sn-glycero-3-phosphocholine as a wax.

Synthesis of (R)-1-eicosanyl-2-(4-carboxy)butyl-sn-glycero-3-phosphocholine (CI-219)

8 grams of (R)-1-eicosanyl-2-(4-methylcarboxy)butyl-sn-glycero-3-phosphocholine was dissolved in 100 ml of an 8:2 (v/v) mixture of methanol:aqueous 10% sodium hydroxide, and the reaction mixture was stirred at room temperature for 5 hours. The pH of the reaction mixture was then adjusted to approximately by adding sodium dihydrogen phosphate and then formic acid. 100 ml water and 150 ml chloroform were then added. The phases were separated, and the solvent from the organic phase was removed under reduced pressure. The obtained residue was dissolved in chloroform, dried over sodium sulfate and filtered, and the solvent was then removed under reduced pressure. The obtained residue (7.5 grams) was purified by chromatography on silica gel (150 grams). Chloroform, followed by mixtures of chloroform and methanol, and finally mixtures of chloroform, methanol and water, were used to elute the product. Removal of the solvent under reduced pressure from fractions containing the product yielded 4 grams of (R)-1-eicosanyl-2-(4-carboxy)butyl-sn-glycero-3-phosphocholine as white solid. The yield was 51.1%.

NMR characterization of 1-eicosanyl-2-(4-carboxy)butyl-glycero-3-phosphocholine

The sample was dissolved in deuterated chloroform (CDCl₃) with a few drops of deuterated methanol (CD₃OD). The spectra were then measured at 600 MHz. Samples were measured by both ¹H and ¹³C NMR spectroscopy.

The results showed the expected signals for the structural elements of 1-eicosanyl-2-(4-carboxy)butyl-glycero-3-phosphocholine and thus fully supported the structure.

The assignment of the observed ¹H peaks according to the structure of 1-eicosanyl-2-(4-carboxy)butyl-glycero-3-phosphocholine was as follows:

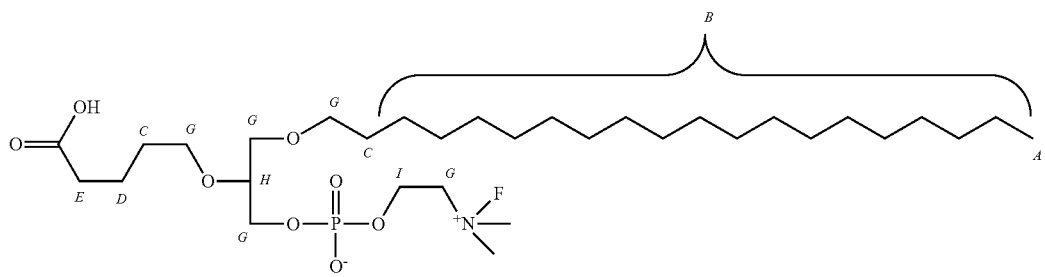

¹H NMR (600 MHz, reference solvent (CDCl₃)=7.246 ppm)

| δ [ppm] | Description | Assignment (see formula above) |
|---|---|---|
| 4.264 | 2 H, br, s | I |
| 3.834-3.872 | 1 H, m | H |
| 3.404-3.679 | 10 H, m, 5 × CH₂ | G |
| 3.224 | 9 H, s, 3 × CH₃ | F |
| 2.188 | 2 H, dt, J₁ = 2.4 Hz, J₂ = 7.2 Hz | E |
| 1.503-1.561 | 2 H, m | D |
| 1.431-1.465 | 2 H, m | C |
| 1.359-1.394 | 2 H, m | C |
| 1.095-1.136 | 34 H, m, 17 × CH₂ | B |
| 0.716 | 3 H, t, 1 × CH₃, J = 7.2 Hz | A |

The assignment of the observed $^{13}$C peaks according to the structure of 1-eicosanyl-2-(4-carboxy)butyl-glycero-3-phosphocholine was as follows:

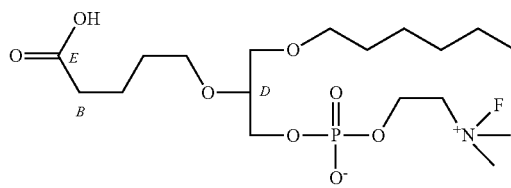

$^{13}$C NMR (600 MHz, reference solvent (CDCl₃)=77.386 ppm)

| δ [ppm] | Assignment (see formula above) |
|---|---|
| 176.589 | E |
| 78.209-78.263 | D |
| 71.974 | |
| 70.467 | |
| 70.034 | |
| 66.615 | |
| 65.856-65.892 | |
| 59.151-59.183 | |
| 54.382 | C |
| 34.053 | B |
| 32.062 | |
| 29.835 | |
| 29.787 | |
| 29.736 | |
| 29.662 | |
| 29.490 | |
| 29.387 | |
| 26.190 | |
| 22.810 | |
| 22.023 | |
| 14.156 | A |

Mass spectrometry characterization of 1-eicosanyl-2-(4-carboxy)butyl-glycero-3-phosphocholine The calculated mass for 1-eicosane-2-(4-carboxy)butyl-glycero-3-phosphocholine ($C_{33}H_{68}NO_8P$) was 637.47.

The mass spectrum performed using Electrospray Ionization Mass Spectrometry (ES⁻MS) showed a molecular ion with m/z=637, corresponding to the deprotonated molecular ion [M−H]⁻.

In addition, the mass spectrum performed using Positive Electrospray Ionization Mass Spectrometry (ESI+-MS) showed a molecular ion with m/z=638, corresponding to the protonated molecular ion [M+H]⁺, accompanied by a molecular ion with m/z=660, corresponding to the cationated molecular ion [M+Na]⁺.

The MS spectrum is thus in agreement with the chemical structure of 1-eicosanyl-2-(4-carboxy)butyl-glycero-3-phosphocholine.

Tyrosine Phosphorylation:

The effects of CI-219 and CI-220 on in vitro tyrosine phosphorylation in primary macrophages were determined as described hereinabove in the Materials and Methods section.

As shown in FIG. 28, treatment with 20 μg/ml CI-219 caused a reduction in phosphotyrosine levels, whereas treatment with 10 μg/ml CI-219 had little effect, if any. The effect of 20 μg/ml CI-219 was similar to that of 20 μg/ml CI-201.

Similarly, as shown in FIG. 29, treatment with 20 μg/ml CI-220 caused a reduction in phosphotyrosine levels, whereas treatment with 10 μg/ml CI-220 had little effect, if any. The effect of 20 μg/ml CI-220 was similar to that of 20 μg/ml CI-201.

Example 12

1-hexadecyl-2-(4-carboxy)butyl-glycero-3-phosphate (CI-201-PA)

(R)-1-hexadecyl-2-(4-carboxy)butyl-sn-glycero-3-phosphate was synthesized as described hereinbelow from (S)-1-hexadecyl-2-(4-methylcarboxy)butyl-sn-glycerol. (S)-1-hexadecyl-2-(4-carboxy)butyl-glycero-3-phosphate is synthesized using the same procedures, but from (R)-1-hexadecyl-2-(4-methylcarboxy)butyl-glycerol.

The synthesis of (S)-1-hexadecyl-2-(4-methylcarboxy)butyl-sn-glycerol and (R)-1-hexadecyl-2-(4-methylcarboxy)butyl-glycerol is described in Example 1.

Synthesis of (R)-1-hexadecyl-2-(4-carboxy)butyl-sn-glycero-3-phosphate

A solution of (S)-1-hexadecyl-2-(4-methylcarboxy)butyl-sn-glycerol (1.44 grams), prepared according to the procedures described in Example 1, and triethylamine (1.5 ml) in THF (15 ml) was added dropwise over the course of 20 minutes to an ice-cooled solution of $POCl_3$ (1 ml) in THF (15 ml) while stirring. The stirring was continued for additional 30 minutes with cooling and at room temperature for an additional 1 hour. The solvent was evaporated under reduced pressure. The obtained residue was dissolved in an ice-cooled solution of saturated sodium bicarbonate (100 ml), and the reaction mixture was stirred in an ice bath for 45 minutes. The pH of the solution was adjusted to a range of 4-5 by addition of HCl (32%). The mixture was extracted with chloroform (3×50 ml), the organic phase was washed with water (50 ml), and the solvent was removed under reduced pressure. The mixture was dissolved in chloroform and purified over silica gel (30 grams). Chloroform, followed by mixtures of chloroform with 10%-50% methanol, were used to elute 470 mg of pure 1-hexadecyl-2-(4-carboxy)butyl-glycero-3-phosphate.

NMR characterization of 1-hexadecyl-2-(4-carboxy)butyl-glycero-3-phosphate (CI-201-PA)

The sample was dissolved in deuterated chloroform ($CDCl_3$). $^1H$ NMR and $^{13}C$ NMR spectra were then measured at 300 MHz.

The results showed the expected signals for the structural elements of 1-hexadecyl-2-(4-carboxy)butyl-glycero-3-phosphate and thus fully supported the structure.

The assignment of the observed $^1H$ peaks according to the structure of 1-hexadecyl-2-(4-carboxy)butyl-glycero-3-phosphate was as follows:

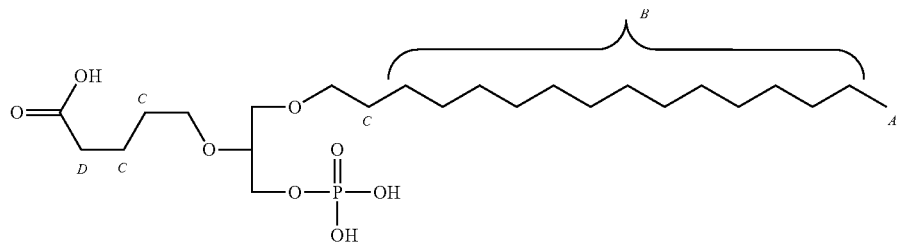

$^1H$ NMR (300 MHz, reference solvent ($CDCl_3$)=7.29 ppm)

| δ [ppm] | Description | Assignment (see formula above) |
|---|---|---|
| 3.900 | 2 H, m | |
| 3.658-3.680 | 3 H, m, $CH_2$ and CH | |
| 3.413 | 4 H, m, 2 × $CH_2$ | |
| 2.336 | 2 H, m | D |
| 1.539-1.609 | 6 H, m, 3 × $CH_2$ | C |
| 1.255 | 26 H, m, 13 × $CH_2$ | B |
| 0.880 | 3 H, t, 1 × $CH_3$, J = 6.75 Hz | A |

The assignment of the observed $^{13}C$ peaks according to the structure of 1-hexadecyl-2-(4-carboxy)butyl-glycero-3-phosphate was as follows:

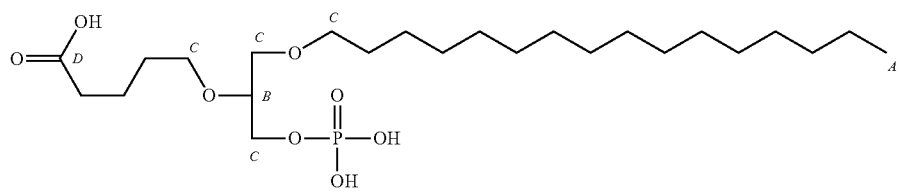

$^{13}$C NMR (300 MHz, reference solvent (CDCl$_3$)=77.113 ppm)

| δ [ppm] | Assignment (see formula above) |
|---------|-------------------------------|
| 178.54  | D |
| 78.057  | B |
| 71.791  | C |
| 70.624  | C |
| 69.837  | C |
| 65.271  | C |
| 33.931  |   |
| 33.766  |   |
| 31.970  |   |
| 30.952  |   |
| 29.775  |   |
| 29.649  |   |
| 29.413  |   |
| 29.048  |   |
| 26.156  |   |
| 22.729  |   |
| 21.571  |   |
| 14.138  | A |

Mass spectrometry characterization of 1-hexadecyl-2-(4-carboxy)butyl-glycero-3-phosphate The calculated mass for 1-hexadecyl-2-(4-carboxy)butyl-glycero-3-phosphate (C$_{24}$H$_{49}$O$_8$P) was 496.3165.

The mass spectrum performed using Electrospray Ionization Mass Spectrometry (ES$^-$MS) showed a molecular ion with m/z=495, corresponding to a deprotonated ion [M–H]$^-$. The MS spectrum is thus in agreement with the chemical structure of 1-hexadecyl-2-(4-carboxy)butyl-glycero-3-phosphate (CI-201-PA).

Toxicity of CI-201-PA:

The toxicity of CI-201-PA was evaluated as described hereinabove in the Materials and Methods section.

As shown in FIGS. 30A and 30B, toxicity was detected for CI-201-PA at doses of 20 μg/ml or higher, with the LD$_{50}$ being approximately 50 μg/ml. At a concentration of 10 μg/ml, toxicity was observed in only one of the two experiments.

Example 13

1-S-hexadecyl-2-(4-carboxy)butyl-glycero-3-phosphocholine (1-S-CI-201) and 1-S-hexadecyl-2-(4-carboxy)butyl-glycero-3-phosphoethanolamine (1-S-CI-202)

1-S-hexadecyl-2-(4-carboxy)butyl-sn-glycero-3-phosphocholine and 1-5-hexadecyl-2-(4-carboxy)butyl-sn-glycero-3-phosphoethanolamine were synthesized as described hereinbelow using (R)-2,2-dimethyl-1,3-dioxolane-4-methanol p-toluenesulfonate as a starting material. 3-S-hexadecyl-2-(4-carboxy)butyl-glycero-1-phosphocholine and 3-S-hexadecyl-2-(4-carboxy)butyl-glycerol-1-phosphoethanolamine are synthesized using the same procedures using (S)-2,2-dimethyl-1,3-dioxolane-4-methanol p-toluenesulfonate as a starting material.

Synthesis of 1-S-hexadecyl-sn-glycerol 48 ml of 1-hexadecanethiol was stirred in 150 ml benzene and refluxed while removing the water by azeotropic distillation. The volume of the solvent was gradually reduced to about 125 ml. 58 ml of sodium ethylate solution in ethanol was added, and the mixture was stirred for 30 minutes under nitrogen. 30 grams of (R)-2,2-dimethyl-1,3-dioxolane-4-methanol p-toluenesulfonate in 100 ml dry benzene was added, and the mixture refluxed for 3 hours. The reaction mixture was cooled to room temperature and stirred at room temperature overnight. The reaction mixture was poured on ice and extracted thrice with 150 ml diethyl ether. The organic phase was washed twice with 150 ml water, dried over sodium sulfate, and the solvent was removed under reduced pressure. The obtained residue was dissolved in 100 ml of a 9:1:0.5 (v/v) methanol:water:concentrated HCl mixture, and the resulting solution was refluxed for 2 hours, then cooled to room temperature. The reaction mixture was poured on ice and extracted thrice with 200 ml chloroform, then washed with 200 ml water, 200 ml saturated sodium carbonate solution, and again with 200 ml water. The solvent was removed under reduced pressure, yielding 70 grams of an orange solid. The residue was recrystallized twice from 400 ml hexane to yield 30 grams 1-S-hexadecyl-sn-glycerol (30 g) as a white solid.

Synthesis of 1-S-hexadecyl-3-trityl-sn-glycerol 28 grams of 1-S-hexadecyl-glycerol and 31 grams chlorotriphenylmethane were placed in a mixture of 370 ml dry THF and 100 ml dry acetonitrile. 25 ml of dry triethylamine was added, and the reaction mixture was refluxed for 17 hours. The reaction mixture was then cooled to room temperature, poured on ice (1 kilogram), transferred to a separatory funnel, and extracted thrice with 200 ml diethyl ether. The organic phase was washed with 200 ml water, twice with 200 ml dilute sulfuric acid (1.5%), 200 ml water, 200 ml concentrated sodium bicarbonate solution, and 200 ml water. The solution was then dried over anhydrous sodium sulfate and the solvent was removed under reduced pressure to give 60 grams of a brown oil. This oil was dissolved in 150 ml ethyl acetate and the obtained solution was kept at −20° C. overnight. The mixture was then centrifuged (at −10° C.) and the mother solution was poured off. The obtained solid was recrystallized from hexane at 4° C. After filtration, 36 grams of 1-S-hexadecyl-3-trityl-sn-glycerol was obtained as a white solid.

Synthesis of 1-S-hexadecyl-2-(4-t-butyl-carboxy) butyl-sn-glycerol 10 grams of 1-S-hexadecyl-3-trityl-sn-glycerol was dissolved in a mixture of 150 ml benzene and 50 ml petroleum ether, and 20.48 grams of powdered KOH were then added. The reaction mixture was stirred and refluxed. A solution of 10 ml t-butyl valerate in 200 ml petroleum ether was added dropwise to the refluxed solution over the course of about 10 hours, while removing the water formed by azeotropic distillation. After completion of the addition, the reaction mixture was refluxed for an additional 1 hour to reduce the volume of the solvents. The reaction mixture was then cooled to room temperature, and mixture of 100 ml ice-cooled water and 20 ml formic acid was added. The reaction mixture was then extracted twice with 100 ml chloroform, dried over sodium sulfate, and the solvent was removed under reduced pressure to give 15.65 grams of a light brown oil. The obtained oil was dissolved in a mixture of 160 ml methyl tert-butyl ether (MTBE) and 20 ml methanol. 3 ml concentrated HCl was added and the resulting solution was refluxed for 4 hours, then cooled to room temperature and stirred at room temperature overnight. The reaction mixture was washed with 100 ml saturated aqueous solution of sodium carbonate and dried over sodium sulfate, and the solvent removed under reduced pressure to give 14.10 grams of a light brown oil. The oil was purified by chromatography on a silica gel column (91 grams). Hexane, followed by mixtures of hexane and chloroform, and then chloroform and acetone, were used to elute the product from the column. The solvent was removed under reduced pressure to yield 6.84 grams of 1-S-hexadecyl-2-(4-t-butyl-carboxy)butyl-sn-glycerol.

Synthesis of 1-S-hexadecyl-2-(4-carboxy)butyl-sn-glycerol 6.84 grams of 1-S-hexadecyl-2-(4-t-butylcarboxy)butyl-sn-glycerol was dissolved in 80 ml ethanol. A solution of 3.7 grams KOH in 5 ml water was added, and the mixture was stirred and refluxed for 6 hours. After cooling the mixture to room temperature, 16 ml water and 100 ml of an 8:2 (v/v) hexane:ethyl acetate mixture were added. The phases were separated, and 50 ml water and 5 ml formic acid were added to the organic phase. Extraction with chloroform, drying over sodium sulfate and removal of the solvents under reduced pressure yielded 3.89 grams of 1-S-hexadecyl-2-(4-carboxy)butyl-sn-glycerol as a light brown oil.

Synthesis of 1-S-hexadecyl-2-(4-methylcarboxy)butyl-sn-glycerol 3.89 grams of 1-S-hexadecyl-2-(4-carboxy)butyl-sn-glycerol was dissolved in 100 ml methanol and 1 ml concentrated hydrochloric acid was added. The reaction mixture was stirred at room temperature overnight and extracted twice with 100 ml chloroform. The organic phase was washed twice with 50 ml water and dried over sodium sulfate, and the solvent was then removed under reduced pressure to give 3.75 grams of a residue. This residue was purified by chromatography on a silica gel column (49 grams). Chloroform, followed by mixtures of chloroform and acetone, were used to elute the product from the column. The solvent was removed under reduced pressure to yield 2.94 grams of pure 1-S-hexadecyl-2-(4 methylcarboxy)butyl-sn-glycerol.

Synthesis of 1-S-hexadecyl-2-(4-methylcarboxy)butyl-sn-glycero-3-phosphoethanolamine 2.83 grams of 1-S-hexadecyl-2-(4-methylcarboxy)butyl-sn-glycerol and 1.7 ml of triethylamine were dissolved in a mixture of 20 ml benzene and 120 ml THF. This solution was added dropwise during the course of 60 minutes to an ice-cooled solution of 1.14 ml POCl$_3$ and 0.98 ml triethylamine in 20 ml THF while stirring. The stirring was continued for an additional 10 minutes with cooling and for an additional 45 minutes at room temperature. A solution of 1.02 ml ethanolamine and 2.8 ml triethylamine in 50 ml THF was then added dropwise over the course of 40 minutes to the ice-cooled reaction mixture. The stirring was continued for 10 minutes at 0° C., and then at room temperature overnight. The reaction mixture was then filtered and the solvent was removed under reduced pressure. The residue (4.23 grams) was dissolved in a mixture of 48 ml acetic acid and 20 ml water and heated to 70° C. for 1 hour. The solution then underwent extraction thrice with 50 ml of a 2:1 (v/v) chloroform:methanol mixture, and the organic solvent was removed under reduced pressure to give 4.05 grams of crude 1-S-hexadecyl-2-(4-methylcarboxy)butyl-sn-glycero-3-phosphoethanolamine.

Synthesis of 1-S-hexadecyl-2-(4-carboxy)butyl-sn-glycero-3-phosphoethanolamine 0.97 grams of 1-S-hexadecyl-2-(4-methylcarboxy)butyl-sn-glycero-3-phosphoethanolamine was dissolved in 50 ml methanol. 7 ml of 10% sodium hydroxide solution was added, and the obtained solution was stirred at room temperature for 8 hours. 2 ml formic acid was added and the mixture was then extracted thrice with 50 ml chloroform. The combined organic solvent was removed under reduced pressure to give 0.70 grams of a waxy residue. This residue was purified by chromatography on silica gel (32 grams). Chloroform, followed by mixtures of chloroform and methanol, were used to elute the product from the column. The solvent was removed under reduced pressure to yield 0.625 gram of pure 1-S-hexadecyl-2-(4-carboxy)butyl-sn-glycero-3-phosphoethanolamine (1-S-CI-202).

NMR characterization of 1-S-hexadecyl-2-(4-carboxy)butyl-glycero-3-phosphoethanolamine (1-S-CI-202)

Samples were measured by $^{13}$C NMR spectroscopy.

The results showed the expected signals for the structural elements of 1-S-hexadecyl-2-(4-carboxy)butyl-glycero-3-phosphoethanolamine (1-S-CI-202), and thus fully supported the structure.

The assignment of the observed $^{13}$C peaks according to the structure of 1-S-hexadecyl-2-(4-carboxy)butyl-glycero-3-phosphoethanolamine (1-S-CI-202) was as follows:

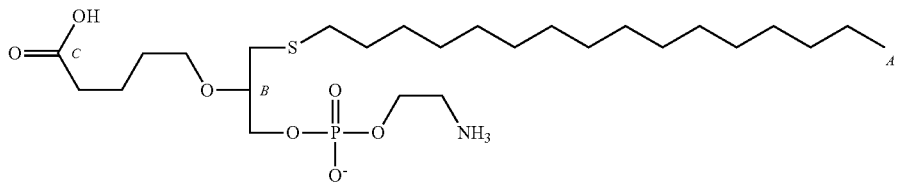

$^{13}$C NMR (300 MHz, reference solvent (CDCl$_3$)=77.724 ppm)

| δ [ppm] | Assignment (see formula above) |
|---------|-------------------------------|
| 179.382 | C |
| 78.616  | B |
| 69.824  |   |
| 66.630  |   |
| 62.304  |   |
| 53.954  |   |
| 40.447  |   |
| 35.308  |   |
| 33.130  |   |
| 32.680  |   |
| 32.072  |   |
| 29.877  |   |
| 29.514  |   |
| 29.165  |   |
| 22.824  |   |
| 22.277  |   |
| 14.179  | A |

Mass spectroscopy characterization of 1-S-hexadecyl-2-(4-carboxy)butyl-glycero-3-phosphocholine (1-S-CI-201)

The calculated mass for 1-S-hexadecyl-2-(4-carboxy)butyl-glycero-3-phosphoethanolamine ($C_{26}H_{54}NO_7PS$) was 555.75.

The mass spectrum performed using Electrospray Ionization Mass Spectrometry (ES⁻MS) showed a molecular ion with m/z=554, corresponding to the deprotonated ion $[M-H]^-$.

The mass spectrum performed using Positive Electrospray Ionization Mass Spectrometry (ESI+-MS) showed a molecular ion with m/z=556 corresponding to the protonated molecular ion $[M+H]^+$, and an ion with m/z=578, corresponding to the cationated molecular ion $[M+Na]^+$.

The MS spectrum is thus in agreement with the chemical structure of 1-S-hexadecyl-2-(4-carboxy)butyl-glycero-3-phosphoethanolamine (1-S-CI-202).

Synthesis of 1-S-hexadecyl-2-(4-methylcarboxy)butyl-sn-glycero-3-phosphocholine 3.48 grams of 1-S-hexadecyl-2-(4-methylcarboxy)butyl-sn-glycero-3-phosphoethanolamine was dissolved in a mixture of 35 ml methanol and 100 ml dichloromethane. A solution of 10 grams potassium carbonate in 20 ml water was added. 3.5 ml dimethylsulfate was then added, and the reaction was stirred at room temperature overnight. The pH of the reaction was adjusted to 4 by addition of 1 ml formic acid. Extracting the mixture thrice with 75 ml of a 2:1 (v/v) chloroform:methanol mixture, followed by removal of the solvent, yielded 3.72 grams of crude 1-S-hexadecyl-2-(4 methylcarboxy)butyl-sn-glycero-3-phosphocholine.

Synthesis of (R)-1-S-hexadecyl-2-(4-carboxy)butyl-sn-glycero-3-phosphocholine 3.72 grams of 1-S-hexadecyl-2-(4-methylcarboxy)butyl-sn-glycero-3-phosphocholine was dissolved in 100 ml methanol. 10 ml of 10% sodium hydroxide solution was added, and the obtained solution was stirred at room temperature overnight. 1.2 ml formic acid was added and the mixture was extracted thrice with 100 ml of a 2:1 (v/v) chloroform:methanol mixture. The combined organic solvent was removed under reduced pressure to give 2.92 grams of a residue. 2.46 grams of this residue was purified by chromatography on silica gel (54 grams). A mixture of chloroform and hexane, followed by chloroform, and then by mixtures of chloroform and methanol, were used to elute the product from the column. The solvent was removed under reduced pressure to yield 1.21 gram of pure 1-S-hexadecyl-2-(4-carboxy)butyl-sn-glycero-3-phosphocholine (1-S-CI-201).

NMR characterization of 1-S-hexadecyl-2-(4-carboxy)butyl-glycero-3-phosphocholine (1-S-CI-201)

Samples were measured by $^{13}C$ NMR spectroscopy.

The results showed the expected signals for the structural elements of 1-S-hexadecyl-2-(4-carboxy)butyl-glycero-3-phosphocholine (1-S-CI-201), and thus fully supported the structure.

The assignment of the observed $^{13}C$ peaks according to the structure of 1-S-hexadecyl-2-(4-carboxy)butyl-glycero-3-phosphocholine (1-S-CI-201) was as follows:

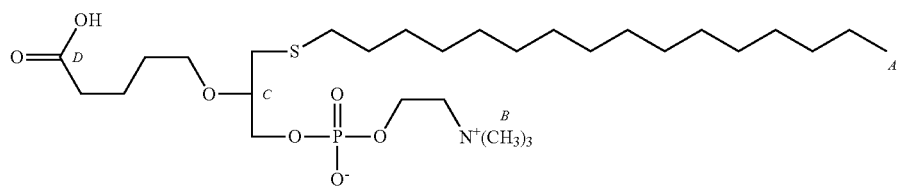

$^{13}C$ NMR (300 MHz, reference solvent ($CDCl_3$)=75.948 ppm)

| δ [ppm] | Assignment (see formula above) |
|---|---|
| 175.904 | D |
| 76.958 | C |
| 68.150 | |
| 64.677-64.749 | |
| 57.613-57.676 | |
| 52.612 | B |
| 52.185 | |
| 33.133 | |
| 31.379 | |
| 31.076 | |
| 30.314 | |
| 28.096 | |
| 27.745 | |
| 27.345 | |
| 21.069 | |
| 20.499 | |
| 12.427 | A |

Mass spectroscopy characterization of 1-S-hexadecyl-2-(4-carboxy)butyl-glycero-3-phosphocholine (1-S-CI-201)

The calculated mass for 1-S-hexadecyl-2-(4-carboxy)butyl-glycero-3-phosphocholine ($C_{29}H_{60}NO_7PS$) was 597.

The mass spectrum performed using Electrospray Ionization Mass Spectrometry (ES⁻MS) showed a molecular ion with m/z=596, corresponding to the deprotonated ion $[M-H]^-$.

The mass spectrum performed using Positive Electrospray Ionization Mass Spectrometry (ESI+-MS) showed a molecular ion with m/z=598 corresponding to the protonated molecular ion $[M+H]^+$, and an ion with m/z=620, corresponding to the cationated molecular ion $[M+Na]^+$.

The MS spectrum is thus in agreement with the chemical structure of 1-S-hexadecyl-2-(4-carboxy)butyl-glycero-3-phosphocholine (1-S-CI-201).

Tyrosine Phosphorylation:

The effects of 1-S-CI-201 and 1-S-CI-202 on in vitro tyrosine phosphorylation in primary macrophages were determined as described hereinabove.

As shown in FIG. 31, treatment with 20 μg/ml (34 μM) 1-S-CI-201 caused a reduction in phosphotyrosine levels, as did 20 μg/ml (34 μM) of the positive control, CI-201. However, treatment with 10 μg/ml (17 μM) 1-S-CI-201 had little effect, if any, whereas 10 μg/ml (34 μM) of CI-201 caused an increase in phosphotyrosine levels.

As shown in FIG. 32, treatment with 20 μg/ml (36 μM) 1-S-CI-202 caused a reduction in phosphotyrosine levels whereas treatment with 10 μg/ml (18 μM) 1-S-CI-202 caused an increase in phosphotyrosine levels. These results are very similar to the results obtained, respectively, for 10 μg/ml and 20 μg/ml of each of CI-201 and CI-202.

Example 14

1-Hexadecyl-2-(5,6-dihydroxy)hexanyl-glycero-3-phosphocholine (di-OH)

(R)-1-Hexadecyl-2-(5,6-dihydroxy)hexanyl-sn-glycero-3-phosphocholine was synthesized as described hereinbelow using (R)-(−)-2,2-dimethyl-1,3-dioxolane-4-methanol as a starting material. (S)-1-Hexadecyl-2-(5,6-dihydroxy)hexanyl-glycero-3-phosphocholine is synthesized using the same procedures, using (S)-(+)-2,2-dimethyl-1,3-dioxolane-4-methanol as a starting material.

Synthesis of 1-hexadecyl-sn-glycerol 19.4 grams of (R)-(−)-2,2-dimethyl-1,3-dioxolane-4-methanol, 49 grams of powdered KOH and 4.8 grams of hexadecyl bromide were stirred in 500 ml toluene (500 ml) were stirred and refluxed for 6 hours, while removing the water formed by azeotropic distillation. The volume of the solvent was gradually reduced to about 100 ml and the reaction mixture was cooled to room temperature. The cooled reaction mixture was dissolved in 500 ml dichloromethane, washed twice with 200 ml water, and the solvent was removed under reduced pressure. The obtained residue was dissolved in 500 ml of a 90:10:5 (v/v) mixture of methanol:water:concentrated $H_2SO_4$, and the resulting solution was refluxed for 30 minutes, cooled to room temperature, and extracted with 500 ml dichloromethane. The extract was washed twice with 100 ml water, 100 ml aqueous 5% sodium carbonate, and again with 100 ml water, until neutral. The solvent was removed under reduced pressure and the crude product was recrystallized from hexane at 4° C., yielding 35.3 grams of pure 1-hexadecyl-sn-glycerol. The yield was 76%.

Synthesis of 1-hexadecyl-3-trityl-sn-glycerol

A solution of 35.3 grams of 1-hexadecyl-sn-glycerol, 37.3 grams of triphenylchloromethane and 22.44 grams of dry triethylamine in a mixture of 470 ml dry tetrahydrofuran and 120 ml dry acetonitrile was refluxed for 15 hours under a nitrogen atmosphere. After cooling to room temperature the reaction mixture was filtered. The filtrate poured on ice (500 grams) and then extracted thrice with 200 ml chloroform. The organic phase was washed successively with 500 ml water, 500 ml of 0.15 N HCl, 500 ml saturated aqueous $NaHCO_3$, and again with water. The extract was dried over $Na_2SO_4$ and the solvent was removed under reduced pressure. The obtained yellow residue was dissolved in 500 ml warm hexane and the obtained clear solution was refrigerated (5±3° C.) overnight. During this time, precipitation occurred. After filtration of the precipitate, the solvent from the filtrate was removed under reduced pressure, yielding 58.3 grams of 1-hexadecyl-3-trityl-sn-glycerol. The yield was 95%.

Synthesis of (S)-1-hexadecyl-2-(5'-hexenyl)-sn-glycerol 36.3 grams of 1-hexadecyl-3-trityl-sn-glycerol and 11.5 grams of 5-hexenyl-methanesulfonate (prepared from 5-hexene-1-ol and methanesulfonyl chloride in dry pyridine) were dissolved in 500 ml toluene. 20 grams of powdered KOH was added, and the reaction mixture was stirred and refluxed for 8 hours, while removing the water formed by azeotropic distillation. The volume of the solvent was gradually reduced to about 100 ml and the reaction mixture was cooled to room temperature. The cooled reaction mixture was dissolved in 500 ml dichloromethane, washed twice with 200 ml water, and the solvent was removed under reduced pressure. The resulting 1-hexadecyl-2-(5'-hexenyl)-3-tritylglycerol was dissolved in 500 ml of a 90:10:5 (v/v) mixture of methanol:water:concentrated (32%) HCl, and the obtained solution was refluxed for 3 hours. The reaction mixture was cooled to room temperature, 500 ml water was added, and then the mixture was extracted thrice with 250 ml dichloromethane. The combined organic phase was washed twice with 100 ml water and the solvent was removed under reduced pressure. The obtained residue was dissolved in 250 ml hexane, and the obtained solution was stored at −20° C. for 48 hours, causing most of the triphenyl carbinol to precipitate. After filtration and removal of the solvent from the filtrate, the remaining product was purified by chromatography over silica gel. 11.65 grams of pure (S)-1-hexadecyl-2-(5'-hexenyl)-sn-glycerol was eluted with 1:1 (v/v) chloroform:petroleum ether. The yield was 45%.

Synthesis of (R)-1-hexadecyl-2-(5'-hexenyl)-sn-glycero-3-phosphoethanolamine 11.65 grams of 1-hexadecyl-2-(5'-hexenyl)-sn-glycerol and 3.23 grams of triethylamine were dissolved in 650 ml dry THF. This solution was added dropwise to an ice-cooled solution of 5.34 grams phosphorous oxychloride in 130 ml THF while stirring. The addition was done at such rate that the temperature in the reaction would not exceed 15° C. The stirring was continued for an additional 10 minutes with cooling and for an additional 45 minutes at room temperature. The reaction mixture was then cooled in an ice bath, and a solution of 2.10 ml ethanolamine and 9.73 ml triethylamine in THF was added dropwise over the course of 30 minutes while stirring. The stirring was continued for 20 minutes in the ice bath and then at room temperature overnight. The reaction mixture was filtered and the solvent was removed under reduced pressure. The obtained residue (15.93 grams) was dissolved in a mixture of 240 ml acetic acid and 100 ml water. The resulting solution was heated at 70° C. for 1 hour, cooled to room temperature, and extracted twice with 250 ml of a 2:1 (v/v) mixture of chloroform:methanol. The solvent from the organic phase was removed under reduced pressure, yielding 12.50 grams of (R)-1-hexadecyl-2-(5'-hexenyl)-sn-glycero-3-phosphoethanolamine.

Synthesis of (R)-1-hexadecyl-2-(5'-hexenyl)-sn-glycero-3-phosphocholine (R)-1-hexadecyl-2-(5'-hexenyl)-3-phosphoethanolamine was dissolved in 650 ml isopropanol and 220 ml dichloromethane. A solution of 66.5 grams K$_2$CO$_3$ in 130 ml water was added, and the reaction mixture heated to 40° C. A solution of 13.3 ml dimethylsulfate in 130 ml isopropanol was added dropwise (over the course of 45 minutes) at such rate that the temperature in the reaction would not exceed 35-40° C. After completion of the addition, stirring was continued at 40° C. for 90 minutes. The reaction mixture was then cooled to room temperature, extracted thrice with 500 ml of a 2:1 (v/v) mixture of chloroform:methanol, and the solvent from the organic phase was removed under reduced pressure, yielding 12.50 grams of (R)-1-hexadecyl-2-(5'-hexenyl)-sn-glycero-3-phosphocholine.

Synthesis of (R)-1-hexadecyl-2-(5,6-dihydroxy-hexyl)-sn-glycero-3-phosphocholine 8.57 grams of (R)-1-hexadecyl-2-(5'-hexenyl)-sn-glycero-3-phosphocholine was dissolved in 80 ml formic acid. 18.7 ml of 30% hydrogen peroxide was added, and the reaction mixture was stirred at room temperature overnight. 250 ml water was added, and the solution was transferred to a separatory funnel and extracted with 5 times with 100 ml of a 2:1 (v/v) a mixture of chloroform:methanol. The solvent from the organic phase was removed under reduced pressure, and the obtained residue was dissolved in 150 ml methanol. 55 ml aqueous sodium hydroxide (10%) was added, and the reaction mixture was stirred at room temperature for 2 hours. 3 ml of a cold mixture of concentrated HCl (32%) in 150 ml water was added, the obtained solution was transferred to a separatory funnel, and the product was extracted 5 times with 100 ml of a 2:1 (v/v) mixture of chloroform:methanol. The solvent from the organic phase was removed under reduced pressure, and the obtained crude product was purified by chromatography over silica gel. 4.5 grams of pure (R)-1-hexadecyl-2-(5,6-dihydroxy-hexyl)-sn-glycero-3-phosphocholine (di-OH) was eluted with mixtures of chloroform and 4-%-60% methanol. The yield was 50%.

NMR characterization of 1-hexadecyl-2-(5,6-dihydroxy-hexyl)-glycero-3-phosphocholine The sample was dissolved in deuterated chloroform (CDCl$_3$). $^1$H NMR and $^{13}$C NMR spectra were measured at 300 MHz.

The results showed the expected signals for the structural elements of 1-hexadecyl-2-(5,6-dihydroxy)hexanyl-glycero-3-phosphocholine and thus fully supported the structure.

The assignment of the observed $^1$H peaks according to the structure of 1-hexadecyl-2-(5,6-dihydroxy)hexanyl-glycero-3-phosphocholine was as follows:

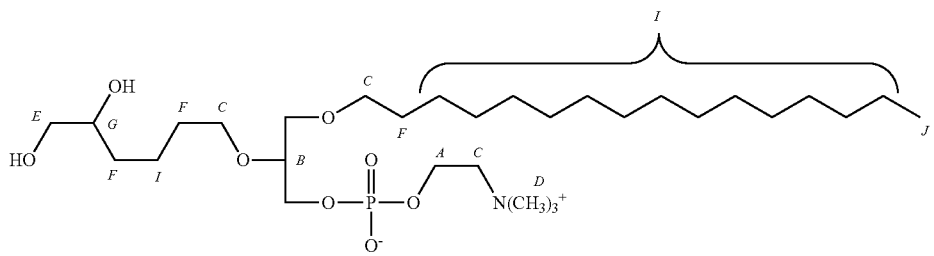

$^1$H NMR (300 MHz, reference solvent (CDCl$_3$)=7.299 ppm)

| δ [ppm] | Description | Assignment (see formula above) |
| --- | --- | --- |
| 4.300 | 2 H, br, s | A |
| 3.930 | 2 H, m | E |
| 3.880-3.898 | 1H, m | B |
| 3.653-3.784 | 2 H, m | G |
| 3.477-3.566 | 10 H, m, 5 × CH$_2$ | C |
| 3.320 | 9 H, s, 3 × CH$_3$ | D |
| 1.506-1.532 | 6H, m 3 × CH$_2$ | F |
| 1.246 | 28 H, m, 14 × CH$_2$ | I |
| 0.872 | 3 H, t, 1 × CH$_3$, J = 6.75 Hz | J |

The assignment of the observed $^{13}$C peaks according to the structure of 1-hexadecyl-2-(5,6-dihydroxy)hexanyl-glycero-3-phosphocholine was as follows:

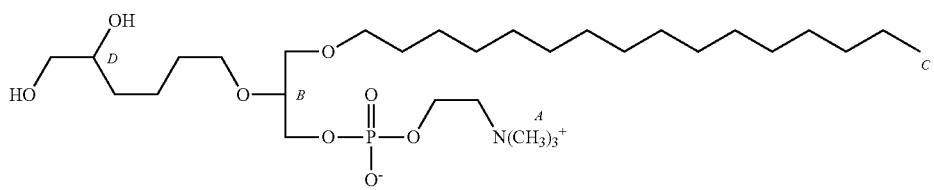

$^{13}$C NMR (300 MHz, reference solvent ($_{CDCl3}$)=77.700 ppm)

| δ [ppm] | Assignment (see formula above) |
| --- | --- |
| 78.691 | B |
| 72.734 | |
| 72.443 | D |
| 70.993 | |
| 70.661 | |
| 67.645 | |
| 66.843 | |
| 66.690 | |
| 60.067 | |
| 55.007 | A |
| 33.669 | |
| 33.512 | |

| δ [ppm] | Assignment (see formula above) |
|---|---|
| 32.612 | |
| 30.586 | |
| 30.411 | |
| 30.258 | |
| 30.051 | |
| 26.779 | |
| 23.373 | |
| 23.176 | |
| 14.800 | C |

Mass spectrometry characterization of 1-hexadecyl-2-(5,6-dihydroxy)hexanyl-glycero-3-phosphocholine The calculated mass for 1-hexadecyl-2-(5,6-dihydroxy)hexanyl-glycero-3-phosphocholine ($C_{30}H_{64}NO_8P$) was 597.4370.

The mass spectrum obtained using Fast Atom Bombardment (FAB+) showed a molecular ion with m/z=598.400, corresponding to the protonated molecular ion $[M+H]^+$. The mass spectrometry spectrum is thus in agreement with the chemical structure of 1-hexadecyl-2-(5,6-dihydroxy)hexanyl-glycero-3-phosphocholine (di-OH).

Toxicity of di-OH:

The toxicity of di-OH was evaluated as described hereinabove.

As shown in FIGS. 33A and 33B, toxicity of di-OH was detected at doses of 20 μg/ml or higher, with the $LD_{50}$ of di-OH being between 20 and 50 μg/ml.

Atherosclerotic Lesion Assay:

The in vivo efficacy of di-OH against atherosclerotic lesions was tested in LDL-RD male mice, as described hereinabove in the Materials and Methods section. Di-OH was administered at a dose of 1 mg per mouse, equivalent to a dose of 60 mg/kg.

As shown in FIG. 34, 1 mg/mouse of di-OH decreased the atherosclerotic lesion area by 25% as compared to the control (PBS).

These results indicate that di-OH is effective against atherosclerosis.

Example 15

1-(cis-9-hexadecenyl)-2-(4-carboxy)butyl-glycero-3-phosphocholine (R)-1-(cis-9-hexadecenyl)-2-(4-carboxy)butyl-sn-glycero-3-phosphocholine was synthesized as described hereinbelow using (R)-(−)-2,2-dimethyl-1,3-dioxolane-4-methanol as a starting material. (S)-1-(cis-9-hexadecenyl)-2-(4-carboxy)butyl-glycero-3-phosphocholine is synthesized using the same procedures, using (S)-(+)-2,2-dimethyl-1,3-dioxolane-4-methanol as a starting material.

Synthesis of 1-(cis-9-hexadecenyl)-sn-glycerol 5.32 grams of (R)-(−)-2,2-dimethyl-1,3-dioxolane-4-methanol, 12.26 grams of powdered potassium hydroxide and 10 grams of cis-9-hexadecenyl-methanesulfonate were stirred in 250 ml benzene and refluxed for 10.5 hours, while removing the water formed by azeotropic distillation. The volume of the solvent was gradually reduced to about 50 ml. The reaction mixture was cooled to room temperature, 50 ml water was added, and the mixture was extracted thrice with 100 ml diethyl ether. The combined organic phase was washed with 100 ml water and the solvent was removed under reduced pressure. The residue (12.01 grams) was dissolved in 200 ml of a 90:10:3 (v/v) mixture of methanol:water:concentrated hydrochloric acid, and the resulting solution was stirred at room temperature overnight and then refluxed for 1 hour. After cooling to room temperature, 100 ml water was added. The product was extracted thrice with 75 ml diethyl ether, washed consecutively with 100 ml water, 100 ml saturated aqueous solution of sodium bicarbonate, and again with 100 ml water. After drying on $Na_2SO_4$, the solvent was removed under reduced pressure, yielding 9.104 grams of crude 1-(cis-9-hexadecenyl)-sn-glycerol. The crude product was purified by chromatography on a silica gel (30 grams) column. 9.07 grams of pure 1-(cis-9-hexadecenyl)-glycerol was eluted by chloroform followed by a mixture of chloroform and 5% methanol. The yield was 91.8%.

Synthesis of (S)-1-(cis-9-hexadecenyl)-3-trityl-sn-glycerol 9.07 grams of 1-(cis-9-hexadecenyl)-glycerol was dissolved in a mixture of dry THF (160 ml) and dry acetonitrile (40 ml). 10.52 grams triphenylchloromethane and 10 ml triethylamine were added, and the reaction mixture was refluxed for 15 hours. The reaction mixture was cooled to room temperature, poured on ice (100 grams), transferred to a separatory funnel, and extracted thrice with 100 ml chloroform. The organic phase was washed consecutively with 100 ml water, 100 ml dilute (1.0%) sulfuric acid, 100 ml water, 100 ml saturated aqueous sodium bicarbonate, and again with 100 ml water. The organic phase was dried over anhydrous sodium sulfate and the solvent was removed under reduced pressure. The obtained residue was dissolved in hot hexane (100 ml) and the resulting solution was cooled at 4° C. for 36 hours. Filtration of precipitated by-products and removal of solvent under reduced pressure yielded 14.57 grams of crude product. The crude product was purified by chromatography over silica gel (200 grams). 9.81 grams of pure 1-(cis-9-hexadecenyl)-3-trityl-sn-glycerol was eluted with chloroform. The yield was 61.1%.

Synthesis of (S)-1-(cis-9-hexadecenyl)-2-(4-tert-butyl-carboxy)butyl-sn-glycerol 8.83 grams of 1-(cis-9-hexadecenyl)-3-trityl-sn-glycerol was dissolved in mixture of benzene (170 ml) and petroleum ether (100 ml). Powdered KOH (23.1 grams) was added and the reaction mixture was heated to a gentle reflux. A solution of tert-butyl-valerate (20 ml) in petroleum ether (420 ml) was added dropwise over the course of 25 hours while removing the water formed by azeotropic distillation. After cooling to room temperature, the pH of the reaction mixture was adjusted to approximately 6 by adding formic acid (10 ml). The mixture was extracted with diethyl ether (3×100 ml) and the organic phase washed with water (100 ml). Removal of solvent under reduced pressure yielded 17.72 grams of an oily product. This residue was dissolved in methanol (50 ml), 4 ml concentrated HCl (32%) was added, and the reaction mixture was refluxed for 5.5 hours. After cooling to room temperature, 50 ml water was added and the mixture was extracted with diethyl ether (3×50 ml). The combined organic phase washed with water (50 ml) and the solvent removed under reduced pressure, yielding 14.26 grams of crude product. 2.93 grams of pure 1-(cis-9-hexadecenyl)-2-(4-tert-butyl-carboxy)butyl-sn-glycerol was purified by chromatography on silica gel (110 grams). The product was eluted with mixture of chloroform:hexane (1:1 by volumetric ratio), followed by mixtures of chloroform with up to 3% ethyl acetate. The solvent from fractions containing the desired product was removed under reduced pressure. The yield was 39.2%.

Synthesis of (R)-1-(cis-9-hexadecenyl)-2-(4-carboxy)butyl-sn-glycero-3-phosphocholine 1.59 grams of (S)-1-(cis-9-hexadecenyl)-2-(4-tert-butyl-carboxy)butyl-sn-glycerol (dried by azeotropic distillation with benzene) and 0.7 ml triethylamine were dissolved in THF (45 ml). This solution was added dropwise during the course of 18 minutes to an ice-cooled solution of $POCl_3$ (0.5 ml) and triethylamine (0.05 ml) in THF (20 ml) while stirring. The stirring was continued for an additional 10 minutes with cooling and for an additional 45 minutes at room temperature. The reaction mixture was cooled in an ice bath and a solution of ethanolamine (0.38 ml) and triethylamine (3.25 ml) in THF (54 ml) was added dropwise over the course of 65 minutes while stirring. The stirring was continued for 10 minutes at during cooling and then at room temperature overnight. The reaction mixture was filtered, washed with THF (2×10 ml) and the solvent was removed under reduced pressure. The residue (2.1 grams) was dissolved in mixture of acetic acid (48 ml) and water (20 ml) and heated to 70° C. for 1 hour. Extraction with diethyl ether (2×50 ml), washing with water (2×50 ml) and removal of the solvent under reduced pressure gave 2.15 grams of crude product as a light brown oil. This oil was dissolved in mixture of methanol (35 ml) and dichloromethane (100 ml). A solution of potassium carbonate (10 grams) in water (20 ml) was added, and the reaction mixture was stirred at room temperature for 10 minutes. Dimethylsulfate (2.5 ml) was added, and the reaction mixture was stirred at room temperature for 6 hours. An additional 1 ml of dimethylsulfate was added, and the reaction mixture stirred at room temperature for 48 hours. The mixture was extracted with chloroform (3×50 ml) and the solvent from the combined organic phase was removed under reduced pressure to give 2.48 grams of a waxy product. This residue was dissolved in methanol (100 ml), a solution (pH≈11) of lithium hydroxide (0.19 g) in water (6 ml) was added, and the reaction mixture was stirred at room temperature overnight. The pH of the reaction mixture was adjusted to 4-5 by adding formic acid, and the mixture was then extracted with chloroform (3×100 ml). Solvent from the combined organic phase was removed under reduced pressure. Analysis by thin layer chromatography showed about 60% conversion. The obtained residue was dissolved in ethanol (100 ml), a solution (pH≈11) of lithium hydroxide (0.2 grams) in water (5 ml) was added, and the reaction mixture was stirred at room temperature overnight. The pH of the reaction mixture was adjusted to 4-5 by adding formic acid (0.22 ml), and the mixture was then extracted with 2:1 (v/v) chloroform:methanol (3×100 ml). The combined organic phase was dried over anhydrous $Na_2SO_4$ and the solvent was removed under reduced pressure, yielding 2.18 grams of crude product. 1.14 grams of pure (R)-1-(cis-9-hexadecenyl)-2-(4-carboxy)butyl-sn-glycero-3-phosphocholine was eluted with chloroform followed by mixtures of chloroform with 10%-80% methanol.

NMR characterization of 1-(cis-9-hexadecenyl)-2-(4-carboxy)butyl-glycero-3-phosphocholine The samples were dissolved in deuterated chloroform ($CDCl_3$). $^1H$ NMR and $^{13}C$ NMR spectra were measured at 300 MHz.

The results showed the expected signals for the structural elements of 1-(cis-9-hexadecenyl)-2-(4-carboxy)butyl-glycero-3-phosphocholine and thus fully supported the structure of 1-(cis-9-hexadecenyl)-2-(4-carboxy)butyl-glycero-3-phosphocholine.

The assignment of the observed $^1H$ peaks according to the structure of 1-(cis-9-hexadecenyl)-2-(4-carboxy)butyl-glycero-3-phosphocholine was as follows:

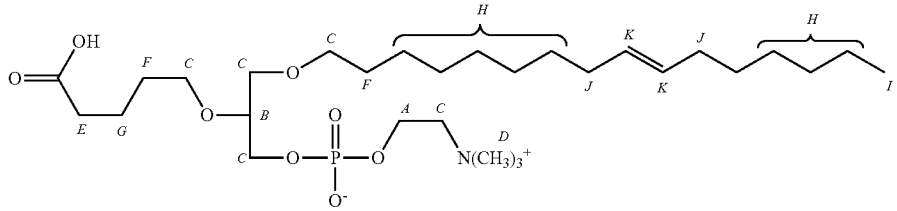

$^1H$ NMR (300 MHz, reference solvent (CDCl3)=7.26 ppm)

| δ [ppm] | Description | Assignment (see formula above) |
|---|---|---|
| 5.340 | 2 H vinyl, dt, $J_1 = 3.9$ Hz, $J_2 = 1.5$ Hz | K |
| 3.896 | 2 H, m | A |
| 3.690 | 1H, m | B |
| 3.400-3.626 | 10 H, m, 5 × $CH_2$ | C |
| 3.307 | 9 H, s, 3 × $CH_3$ | D |
| 2.335 | 2 H, t = 6.9 Hz | E |
| 1.983-2.023 | 4 H, allyl | J |
| 1.6576-1.721 | 2 H, m | G |
| 1.526-1.622 | 4 H, m, 2 × $CH_2$ | F |
| 1.288 | 18 H, m, 9 × $CH_2$ | H |
| 0.884 | 3 H, t, 1 × $CH_3$, J = 7.2 Hz | I |

The assignment of the observed $^{13}C$ peaks according to the structure of 1-(cis-9-hexadecenyl)-2-(4-carboxy)butyl-glycero-3-phosphocholine was as follows:

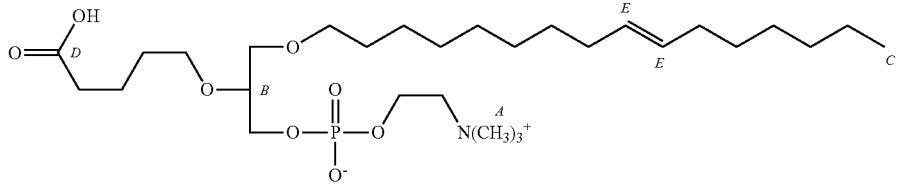

$^{13}C$ NMR (300 MHz, reference solvent (CDCl3)=77.257 ppm)

| δ [ppm] | Assignment (see formula above) |
|---|---|
| 178.41 | D |
| 130.02 | E |
| 129.87 | E |

| δ [ppm] | Assignment (see formula above) |
|---|---|
| 77.876 | B |
| 71.868 | |
| 70.200 | |
| 69.940 | |
| 65.439 | |
| 65.368 | |
| 52.725 | A |
| 33.896 | |
| 31.854 | |
| 29.838 | |
| 29.799 | |
| 29.669 | |
| 29.609 | |
| 29.568 | |
| 29.361 | |
| 29.146 | |
| 29.049 | |
| 27.273 | |
| 26.139 | |
| 22.724 | |
| 21.514 | |
| 14.137 | C |

Mass spectrometry characterization of 1-(cis-9-hexadecenyl)-2-(4-carboxy)butyl-glycero-3-phosphocholine The calculated mass for 1-(cis-9-hexadecenyl)-2-(4-carboxy)butyl-glycero-3-phosphocholine ($C_{29}H_{58}NO_8P$) was 579.3900.

The mass spectrum obtained using Fast Atom Bombardment (FAB+) showed a molecular ion with m/z=580.3995, corresponding to the protonated molecular ion $[M+H]^+$. The mass spectrometry spectrum is thus in agreement with the chemical structure of 1-(cis-9-hexadecenyl)-2-(4-carboxy)butyl-glycero-3-phosphocholine.

Example 16

(S)-1-hexadecyl-2-(4-carboxy)butyl-glycerol (S)-1-hexadecyl-2-(4-carboxy)butyl-sn-glycerol was synthesized as described in Example 1 using (R)-(−)-2,2-dimethyl-1,3-dioxolane-4-methanol as a starting material. The synthesis of (R)-1-hexadecyl-2-(4-carboxy)butyl-glycerol, using (S)-(+)-2,2-dimethyl-1,3-dioxolane-4-methanol as a starting material, is also described in Example 1.

NMR characterization of
(S)-1-hexadecyl-2-(4-carboxy)butyl-glycerol

The sample was dissolved in deuterated chloroform ($CDCl_3$) with a few drops of deuterated methanol ($CD_3OD$). The spectra were then measured at 600 MHz. Samples were measured by both $^1H$ and $^{13}C$ NMR spectroscopy.

The results showed the expected signals for the structural elements of 1-hexadecyl-2-(4-carboxy)butyl-glycerol and thus fully supported the structure.

The assignment of the observed $^1H$ peaks according to the structure of 1-hexadecyl-2-(4-carboxy)butyl-glycerol was as follows:

$^1H$ NMR

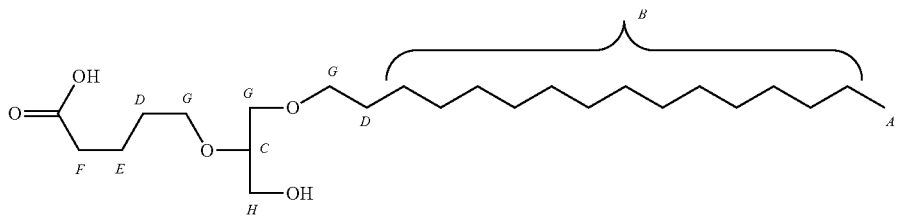

$^1H$ NMR (600 MHz, reference solvent ($CDCl_3$)=7.26 ppm)

| δ [ppm] | Description | Assignment (see formula above) |
|---|---|---|
| 3.721 | 1 H, m | C |
| 3.655 | 2 H, m | H |
| 3.480-3.573 | 4 H, m, 2 × CH2 | G |
| 3.431 | 2 H, m | G |
| 2.403 | 2 H, t, J = 7.2 Hz | F |
| 1.750 | 2 H, tt, CH2 | E |
| 1.653 | 2 H, tt, CH2 | D |
| 1.555 | 2 H, tt, CH2 | D |
| 1.254 | 26 H, m, 13 × CH2 | B |
| 0.880 | 3 H, t, 1 × CH3, J = 7.2 Hz | A |

$^{13}C$ NMR
The assignment of the observed $^{13}C$ peaks according to the structure of 1-hexadecyl-2-(4-carboxy)butyl-glycerol was as follows:

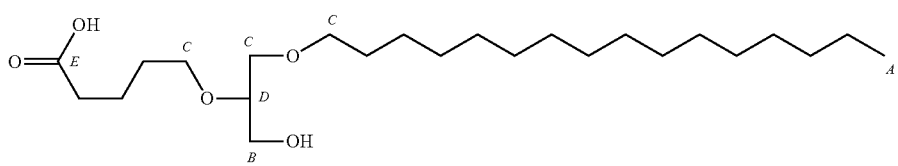

$^{13}$C NMR (600 MHz, reference solvent (CDCl3)=77.014 ppm)

| δ [ppm] | Assignment (see formula above) |
|---|---|
| 176.95 | E |
| 78.495 | D |
| 71.914 | |
| 70.921 | |
| 69.685 | C |
| 63.068 | B |
| 33.302 | |
| 31.937 | |
| 29.708 | |
| 29.682 | |
| 29.633 | |
| 29.609 | |
| 29.473 | |
| 29.372 | |
| 29.242 | |
| 26.099 | |
| 22.701 | |
| 21.609 | |
| 14.127 | A |

Mass spectrometry characterization of 1-hexadecyl-2-(4-carboxy)butyl-glycerol

The calculated mass for 1-hexadecyl-2-(4-carboxy)butyl-glycerol ($C_{24}H_{48}O_5$) was 416.635.

The mass spectrum performed using Electrospray Ionization Mass Spectrometry (ESI+-MS) showed a molecular ion with m/z=417.0, corresponding to the protonated molecular ion [M+H]$^+$. The MS spectrum is thus in agreement with the chemical structure of 1-hexadecyl-2-(4-carboxy)butyl-glycerol.

Example 17

1-hexadecyl-2-(5',5'-dimethoxypentyl)-glycero-3-phosphocholine (diMeAc) and 1-hexadecyl-2-(5',5'-diethoxypentyl)-glycero-3-phosphocholine (diEtAc)

(R)-1-hexadecyl-2-(5',5'-diethoxypentyl)-sn-glycero-3-phosphocholine and (R)-1-hexadecyl-2-(5',5'-dimethoxypentyl)-sn-glycero-3-phosphocholine were prepared from (R)-1-hexadecyl-2-(5,6-dihydroxyhexanyl)-sn-glycero-3-phosphocholine, as described hereinbelow. Using the same procedures, (S)-1-hexadecyl-2-(5',5'-diethoxypentyl)-glycero-3-phosphocholine and (S)-1-hexadecyl-2-(5',5'-dimethoxypentyl)-glycero-3-phosphocholine are prepared from (S)-1-hexadecyl-2-(5,6-dihydroxyhexanyl)-glycero-3-phosphocholine.

The synthesis of (R)-1-hexadecyl-2-(5,6-dihydroxyhexanyl)-sn-glycero-3-phosphocholine and (S)-1-hexadecyl-2-(5,6-dihydroxyhexanyl)-glycero-3-phosphocholine are described in Example 14.

Synthesis of (R)-1-hexadecyl-2-(5'-oxo-pentyl)-sn-glycero-3-phosphocholine 2 grams of sodium periodate was added to an ice-cooled solution of (R)-1-hexadecyl-2-(5',6'-dihydroxyhexanyl)-sn-glycero-3-phosphocholine (2 grams) in water (200 ml), and the reaction mixture stirred for 30 minutes with cooling and at room temperature overnight. The reaction mixture was transferred to a separatory funnel and extracted with a 2:1 (v/v) mixture of chloroform:methanol (3×100 ml), and the solvent from the combined organic phase was removed under reduced pressure. The obtained residue was dissolved in chloroform, dried over anhydrous $Na_2SO_4$ and filtrated, and the solvent was removed under reduced pressure. The obtained crude product was purified by chromatography over silica gel (21 grams). 1.2 grams of pure (R)-1-hexadecyl-2-(5'-oxo-pentyl)-sn-glycero-3-phosphocholine was eluted with chloroform followed by mixtures of chloroform with 40%-60% methanol. The yield was 63%.

Synthesis of (R)-1-hexadecyl-2-(5',5'-diethoxypentyl)-sn-glycero-3-phosphocholine (diEtAc)

The reaction was performed under nitrogen. (R)-1-hexadecyl-2-(5'-oxo-pentyl)-sn-glycero-3-phosphocholine (50 mg, 0.088 mmol) was dissolved in ethanol (10 ml). Triethyl ortho-formate (0.053 ml, 0.0476 grams, 0.32 mmol) and 3 drops of concentrated sulfuric acid (95-97%) were added, and the reaction mixture was stirred at room temperature overnight. The reaction mixture was transferred with the aid of dichloromethane (75 ml) to a separatory funnel. The solution was washed successively with water (75 ml), aqueous 2.5% sodium bicarbonate solution (75 ml), and water (75 ml), and dried over anhydrous sodium sulfate. Filtration and removal of the solvent under reduced pressure yielded 50 mg of (R)-1-hexadecyl-2-(5',5'-diethoxypentyl)-sn-glycero-3-phosphocholine. The yield was 88.4%.

Synthesis of (R)-1-hexadecyl-2-(5',5'-dimethoxypentyl)-sn-glycero-3-phosphocholine (diMeAc)

The reaction was performed under nitrogen. (R)-1-hexadecyl-2-(5'-oxo-pentyl)-sn-glycero-3-phosphocholine (55 mg, 0.097 mmol) was dissolved in methanol (10 ml). Trimethyl ortho-formate (0.043 ml, 0.0414 grams, 0.39 mmol) and 3 drops of concentrated sulfuric acid (95-97%) were added, and the reaction mixture was stirred at room temperature overnight. Dichloromethane (75 ml) was added and the reaction mixture was transferred to a separatory funnel. The solution was washed successively with water (75 ml), aqueous 2.5% sodium bicarbonate solution (75 ml) and again with water (75 ml). Drying over anhydrous sodium sulfate and removal of the solvent under reduced pressure yielded 36.8 mg of (R)-1-hexadecyl-2-(5',5'-dimethoxypentyl)-sn-glycero-3-phosphocholine. The yield was 62%.

NMR characterization of 1-hexadecyl-2-(5',5'-diethoxypentyl)-glycero-3-phosphocholine (DiEtAc)

The sample was dissolved in deuterated chloroform ($CDCl_3$). $^1$H NMR and $^{13}$C NMR spectra were measured at 300 MHz.

The results showed the expected signals for the structural elements of 1-hexadecyl-2-(5',5'-diethoxypentyl)-glycero-3-phosphocholine and thus fully supported the structure.

The assignment of the observed $^1$H peaks according to the structure of 1-hexadecyl-2-(5',5'-diethoxypentyl)-glycero-3-phosphocholine was as follows:

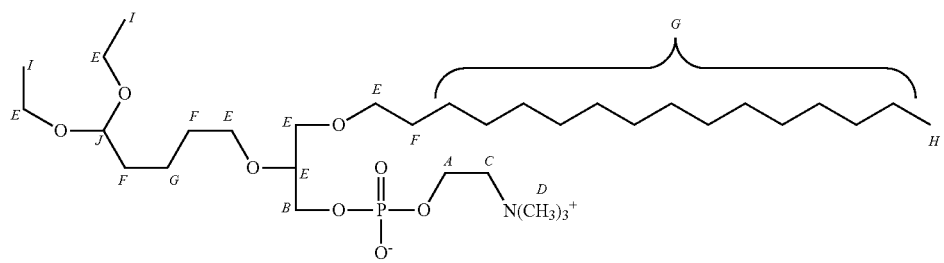

$^1$H NMR (300 MHz, reference solvent (CDCl$_3$)=7.270 ppm)

| δ [ppm] | Description | Assignment (see formula above) |
|---|---|---|
| 4.459 | 1 H, t, J = 5.6 Hz | J |
| 4.309 | 2H, br, s | A |
| 3.859 | 2H, t, J = 5.4 Hz | C |
| 3.808 | 2H, br, s | B |
| 3.430-3.679 | 11H, m, 5 × CH$_2$ + CH | E |
| 3.388 | 9H, s, 3 × CH$_3$ | D |
| 1.509-1.587 | 6H, m | F |
| 1.256 | 28H, 14 × CH$_2$ | G |
| 1.195 | 6H, t, 2 × CH$_3$, J = 7.05 Hz | I |
| 0.881 | 3 H, t, 1 × CH$_3$, J = 6.6 Hz | H |

The assignment of the observed $^{13}$C peaks according to the structure of 1-hexadecyl-2-(5',5'-diethoxypentyl)-glycero-3-phosphocholine was as follows:

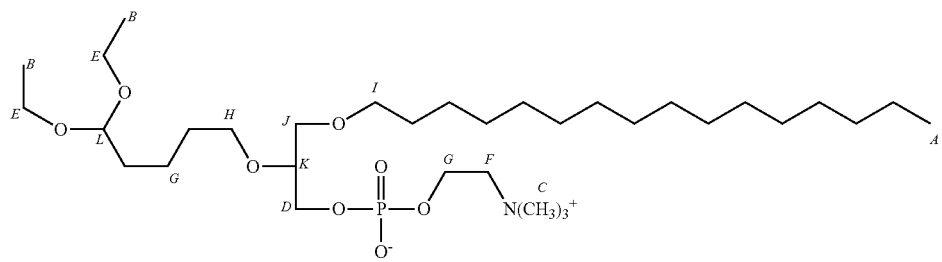

$^{13}$C NMR (300 MHz, reference solvent (CDCl$_3$)=77.0046 ppm)

| δ [ppm] | Assignment (see formula above) |
|---|---|
| 102.980 | L |
| 78.2741 | K |
| 71.7498 | J |
| 71.0295 | I |
| 70.2381 | H |
| 65.5827 | G |
| 64.9656 | F |
| 61.0510 | E |
| 59.1392 | D |
| 54.6214 | C |
| 33.5956 | |
| 31.9161 | |
| 30.0866 | |
| 29.8112 | |
| 29.7010 | |
| 29.3441 | |
| 26.1672 | |
| 22.6671 | |
| 21.3484 | |
| 15.3929 | B |
| 14.0619 | A |

Mass spectrometry characterization of 1-hexadecyl-2-(5',5'-diethoxypentyl)-glycero-3-phosphocholine (DiEtAc)

The calculated mass for 1-hexadecyl-2-(5',5'-diethoxypentyl)-glycero-3-phosphocholine (C$_{33}$H$_{70}$NO$_8$P) was 639.88.

The mass spectrum obtained using Electrospray Ionization Mass Spectrometry (ESI+-MS), showed a molecular ion with m/z=640, corresponding to the protonated molecular ion [M+H]$^+$, accompanied by an ion with m/z=662, corresponding to the cationated molecular ion [M+Na]$^+$, and an ion with m/z=594, corresponding to the de-ethoxylated molecular ion [M−OEt]$^+$. The mass spectrometry spectrum is thus in agreement with the chemical structure of 1-hexadecyl-2-(5',5'-diethoxypentyl)-glycero-3-phosphocholine.

NMR characterization of 1-hexadecyl-2-(5',5'-dimethoxypentyl)-glycero-3-phosphocholine (DiMeAc)

The sample was dissolved in deuterated chloroform (CDCl$_3$). $^1$H NMR and $^{13}$C NMR spectra were measured at 300 MHz.

The results showed the expected signals for the structural elements of 1-hexadecyl-2-(5',5'-dimethoxypentyl)-glycero-3-phosphocholine (DiMeAc) and thus fully supported the structure.

The assignment of the observed $^1$H peaks according to the structure of 1-hexadecyl-2-(5',5'-dimethoxypentyl)-glycero-3-phosphocholine was as follows:

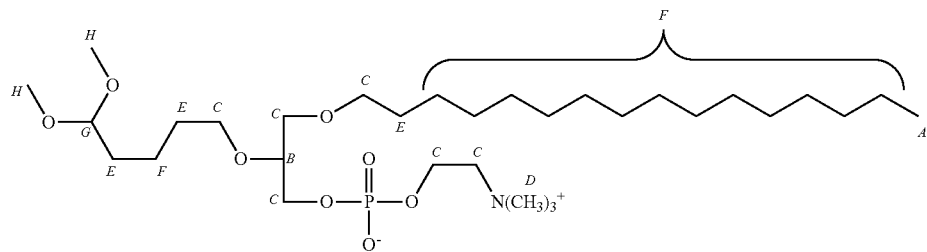

$^1$H NMR (300 MHz, reference solvent (CDCl$_3$)=7.28 ppm)

| δ [ppm] | Description | Assignment (see formula above) |
| --- | --- | --- |
| 4.337 | 1 H, t, J = 5.7 Hz | G |
| 3.855 | 2H, br, s | A |
| 3.834-3.855 | 4H, m, 2 × CH$_2$ | C |
| 3.703 | 1H, m | B |
| 3.529-3.591 | 4H, m | C |
| 3.430-3.464 | 2H, m, CH$_2$ | C |
| 3.388 | 9H, s, 3 × CH$_3$ | D |
| 3.302 | 6H, s, 2 × CH$_3$ | H |
| 1.506-1.605 | 6H, m | E |
| 1.256 | 28H, 14 × CH$_2$ | F |
| 0.880 | 3H, t, 1 × CH$_3$, J = 6.9 Hz | A |

The assignment of the observed $^{13}$C peaks according to the structure of 1-hexadecyl-2-(5',5'-dimethoxypentyl)-glycero-3-phosphocholine was as follows:

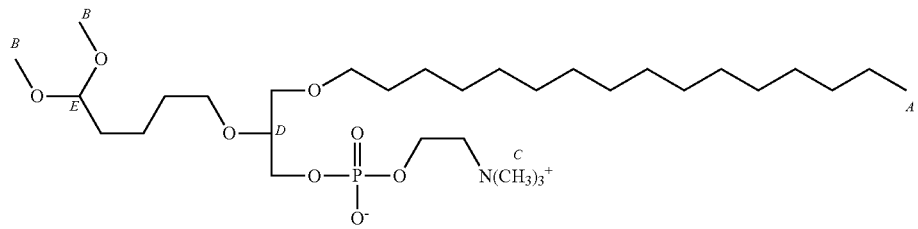

$^{13}$C NMR (300 MHz, reference solvent (CDCl$_3$)=77.000 ppm)

| δ [ppm] | Assignment (see formula above) |
| --- | --- |
| 104.50 | E |
| 78.133 | D |
| 71.686 | |
| 70.845 | |
| 70.121 | |
| 66.330 | |
| 64.974 | |
| 59.187 | |
| 54.411 | C |
| 52.721 | B |
| 52.692 | B |
| 32.324 | |
| 31.884 | |
| 29.963 | |
| 29.756 | |
| 29.554 | |
| 29.320 | |
| 26.112 | |
| 25.348 | |
| 22.646 | |
| 21.165 | |
| 14.071 | A |

Atherosclerotic Lesion Assay:

The in vivo efficacy of diMeAc against atherosclerotic lesions was tested in ApoE KO mice, as described hereinabove in the Materials and Methods section. diMeAc was administered at a dose of 1 mg per mouse, equivalent to a dose of 40 mg/kg.

As shown in FIG. 35, 1 mg/mouse of diMeAc decreased the atherosclerotic lesion area by 23% as compared to the control (PBS).

These results indicate that diMeAc is effective against atherosclerosis.

Toxicity of diEtAc:

The toxicity of diEtAc was evaluated as described hereinabove.

As shown in FIGS. 36A and 36B, diEtAc exhibited toxicity at doses of 20 μg/ml or higher, with the LD$_{50}$ of diEtAc being between 20 and 50 μg/ml. At a concentration of 10 μg/ml, toxicity was observed in only one of two experiments.

Example 18

1-hexadecyl-2-(4-carboxy)butyl-glycero-3-phosphoserine (VB-223)

(R)-1-hexadecyl-2-(4-carboxy)butyl-glycero-3-phosphoserine was prepared from (S)-1-hexadecyl-2-(5'-hexenyl)-sn-glycerol, as described hereinbelow. Using the same procedures, (S)-1-hexadecyl-2-(5' hexenyl)-glycero-3-phosphoserine is prepared from (R)-1-hexadecyl-2-(5'-hexenyl)-glycerol.

The synthesis of (S)-1-hexadecyl-2-(5'-hexenyl)-sn-glycerol and (R)-1-hexadecyl-2-(5'-hexenyl)-glycerol are described in Example 14.

Synthesis of (R)-1-hexadecyl-2-(5'-hexenyl)-sn-glycero-3-phosphate 1.0 gram of (S)-1-hexadecyl-2-(5'-hexenyl)-glycerol (dried by azeotropic distillation with benzene) and dry pyridine (1 ml) were dissolved in THF (60 ml). This solution was added dropwise to an ice-cooled solution of POCl$_3$ (0.3 ml) in THF (12 ml) while stirring. The stirring was continued for an additional 3 hours with cooling. To the cooled reaction mixture, a solution of sodium bicarbonate (2.44 grams) in water (24 ml) was added, and the mixture stirred in an ice bath for an additional 30 minutes. The pH of the reaction mixture was adjusted to approximately 1 by slow addition of 10% hydrochloric acid. Extraction with diethyl ether (3×150 ml), washing of the combined organic phase with water (2×150 ml), drying over anhydrous Na$_2$SO$_4$ and removal of the solvent removed under reduced pressure, yielded 1.43 gram of (R)-1-hexadecyl-2-(5'-hexenyl)-sn-glycero-3-phosphate.

Synthesis of (R)-1-hexadecyl-2-(5'-hexenyl)-sn-glycero-3-phospho-N-Boc-L-serine-benzhydryl ester 1.30 gram of (R)-1-hexadecyl-2-(5'-hexenyl)-sn-glycero-3-phosphate and 0.95 gram of N-Boc-serine-benzhydryl ester (which were dried in a desiccator with P$_2$O$_5$) were dissolved in pyridine (30 ml). 2,4,6-triisopropyl benzene sulfonyl chloride (2.99 grams) was added, and the reaction mixture was stirred under nitrogen at room temperature for 20 hours. Water (50 ml) was added and the mixture was transferred to a separatory funnel. Extraction was done with an 8:2 (v/v) mixture of hexane:ethyl acetate (3×50 ml), the combined organic phase was dried over anhydrous Na$_2$SO$_4$, and the solvent was removed under reduced pressure. The obtained residue is dissolved in an 8:2 (v/v) mixture of hexane:ethyl acetate (50 ml) and washed with cooled dilute acetic acid (5%). The solvent was then removed under reduced pressure, yielding 1.33 gram of crude (R)-1-hexadecyl-2-(5'-hexenyl)-sn-glycero-3-phospho-N-Boc-L-serine-benzhydryl ester.

Synthesis of (R)-1-hexadecyl-2-(4-carboxy)butyl-sn-glycero-3-phospho-N-Boc-L-serine-benzhydryl ester Sodium periodate (3.0 grams), potassium permanganate (0.05 gram), sodium carbonate (0.15 gram) and potassium carbonate (0.03 gram) were dissolved in water (100 ml). To this solution, a solution of (R)-1-hexadecyl-2-(5'-hexenyl)-sn-glycero-3-phospho-N-Boc-L-serine-benzhydryl ester (0.90 gram) in tert-butanol (100 ml) was added dropwise at room temperature over a period of 30 minutes. After the completion of the addition, the reaction mixture was stirred at room temperature for 2 hours. An additional amount of potassium permanganate (0.02 gram) was added, and the reaction mixture was stirred for 90 minutes. A solution of sodium dihydrogen phosphate (10 gram) in water (100 ml) was added, and the reaction mixture was extracted with chloroform (3×100 ml). The combined organic phase was washed with brine (100 ml) and the solvent was removed under reduced pressure, yielding 1.02 gram of crude (R)-1-hexadecyl-2-(4 carboxy)butyl-sn-glycero-3-phospho-N-Boc-L-serine-benzhydryl ester.

Synthesis of (R)-1-hexadecyl-2-(4-carboxy)butyl-sn-glycero-3-phospho-L-serine (VB-223)

1.02 gram of (R)-1-hexadecyl-2-(4-carboxy)butyl-sn-glycero-3-phospho-N-Boc-L-serine-benzhydryl ester was dissolved in dichloromethane (100 ml). The solution was cooled in an ice-bath and saturated with HCl gas for 30 minutes. The reaction mixture was stirred for an additional 1 hour. The reaction mixture was then neutralized by addition of an aqueous solution of sodium dihydrogen phosphate, and then extracted with a 2:1 (v/v) mixture of chloroform:methanol (3×100 ml). The organic phase was dried over anhydrous Na$_2$SO$_4$ and the solvent was removed under reduced pressure. The obtained crude product (0.72 gram) was purified by chromatography over silica gel (12.60 grams). 0.60 gram of pure (R)-1-hexadecyl-2-(4-carboxy)butyl-sn-glycero-3-phospho-L-serine was eluted with a 1:1 (v/v) mixture of hexane:chloroform, followed by chloroform, and then a mixture of chloroform with 10% methanol.

Tyrosine Phosphorylation:

The effect of VB-223 on in vitro tyrosine phosphorylation in primary macrophages was determined as described hereinabove in the Materials and Methods section.

As shown in FIG. 37, treatment with 5, 10 and 20 µg/ml (8.3, 16.7 and 33.3 µM) VB-223, and perhaps also with 1 µg/ml (1.7 µM) VB-223, results in induction of tyrosine phosphorylation.

Example 18

1-(2-octyl)dodecyl-2-(4-carboxy)butyl-glycero-3-phosphocholine (VB-221) and 1-(2-octyl)dodecyl-2-(4-carboxy)butyl-glycero-3-phosphoethanolamine (VB-222)

(R)-1-(2-octyl)dodecyl-2-(4-carboxy)butyl-sn-glycero-3-phosphoethanolamine and (R)-1-(2-octyl)dodecyl-2-(4-carboxy)butyl-sn-glycero-3-phosphocholine were synthesized as described hereinbelow using (R)-(−)-2,2-dimethyl-1,3-dioxolane-4-methanol as a starting material. (S)-1-(2-octyl)dodecyl-2-(4-carboxy)butyl-glycero-3-phosphoethanolamine and (S)-1-(2-octyl)dodecyl-2-(4-carboxy)butyl-glycero-3-phosphocholine are synthesized using the same procedures, but with (S)-(+)-2,2-dimethyl-1,3-dioxolane-4-methanol as the starting material.

Methanesulfonic acid 2-octyl-dodecyl ester

2-Octyl-1-dodecanol (20 ml, 56.14 mmol) and anhydrous triethylamine (16 ml, 112.28 mmol) were dissolved in dry dichloromethane (60 ml). The solution was cooled to 0° C. and methanesulfonyl chloride (5.2 ml, 67.36 mmol) in dry dichloromethane (40 ml) added dropwise. After completion of the addition, the mixture was stirred at 0° C. for 3 hours and then refrigerated (2-8° C.) overnight. The reaction mixture was poured on ice (500 grams), allowed to warm to room temperature, and extracted with ether (3×150 ml). The organic phase was washed consecutively with water (150 ml), 2% H$_2$SO$_4$ (150 ml), water (150 ml), saturated sodium bicarbonate (150 ml) and again with water (150 ml). The organic phase was dried over anhydrous Na$_2$SO$_4$ and the solvent was removed under reduced pressure, yielding 22.8 grams of methanesulfonic acid 2-octyl-dodecyl ester as a yellow oil.

1-(2-octyl)dodecyl-glycerol (R)-(−)-2,2-dimethyl-1,3-dioxolane-4-methanol (8.3 ml, 66.59 mmol), powdered potassium hydroxide (12 grams) and methanesulfonic acid-2-octyl-dodecyl ester (22.77 grams, 60.50 mmol) were stirred in benzene (250 ml) and refluxed for 5 hours, while removing the water formed by azeotropic distillation. The volume of the solvent was gradually reduced to about 150 ml. The reaction mixture was cooled to room temperature and stirred at room temperature overnight. 200 ml water was added, and the mixture was extracted with diethyl ether (3×200 ml). The combined organic phase was washed with water (200 ml) and the solvent was removed under reduced pressure. The obtained residue was dissolved in 105 ml of a 90:10:5 (v/v) mixture of methanol:water: concentrated hydrochloric acid, and the resulting solution was refluxed for 30 minutes. After cooling to room temperature, water (100 ml) was added. The product was extracted with chloroform (3×100 ml), and washed consecutively with water (100 ml), saturated aqueous solution of sodium carbonate (100 ml) and again with water (100 ml). The solvent was removed under reduced pressure, and the crude product was purified by chromatography on a silica gel (400 grams) column. 17 grams of pure 1-(2-octyl)dodecyl-glycerol was eluted by chloroform followed by a mixtures of chloroform and 10%-30% ethyl acetate as a colorless oil. The yield was 75.5%.

(S)-1-(2-octyl)dodecyl-3-trityl-glycerol 17 grams of 1-(2-octyl)dodecyl-glycerol (dried by azeotropic distillation with benzene) was dissolved in a mixture of dry THF (400 ml) and dry acetonitrile (160 ml). Triphenylchloromethane (15.8 grams) and dry triethylamine (14 ml) were added, and the reaction mixture was refluxed for 17 hours. The reaction mixture was cooled to room temperature, poured on ice (1 kilogram), transferred to a separatory funnel and extracted with diethyl ether (3×200 ml). The combined organic phase was washed consecutively with water (200 ml), dilute (1.5%) sulfuric acid (2×100 ml), water (200 ml), concentrated aqueous sodium bicarbonate (200 ml) and again with water (200 ml). The organic phase was dried over anhydrous sodium sulfate, the solvent was removed under reduced pressure, and the obtained crude product was purified by chromatography on a silica gel (350 grams) column. 26 grams of pure (S)-1-(2-octyl)dodecyl-3-trityl-glycerol was eluted by hexane followed by a mixtures of hexane and chloroform (50-100%) as a yellow oil. The yield was 92.7%.

1-(2-octyl)dodecyl-2-(5'-hexenyl)-3-trityl-glycerol 1-(2-octyl)dodecyl-3-trityl-glycerol (26 grams, 42.28 mmol) and 5-hexenyl-1-methane sulfonate (9.4 grams, 50.73 mmol) were dissolved in benzene (150 ml). Powdered KOH (17 grams) was added and the reaction mixture heated to reflux for 5.5 hours, while removing the water formed by azeotropic distillation. The volume of the solvent was gradually reduced to about 50 ml. After cooling of the reaction mixture to room temperature 200 ml water was added, and the mixture was extracted with diethyl ether (3×100 ml). The combined organic phase washed with brine (3×100 ml) and the solvent was removed under reduced pressure, yielding 22.8 grams of crude product. 21 grams of pure 1-(2-octyl) dodecyl-2-(5'-hexenyl)-3-trityl-glycerol was obtained by purifying the crude product by chromatography on silica gel (300 grams). The product was eluted with chloroform as yellow oil. The yield was 71.2%.

(S)-1-(2-octyl)dodecyl-2-(4-carboxy)butyl-glycerol

Sodium periodate (58 grams), potassium permanganate (960 mg) and potassium carbonate (7 grams) were suspended in water (250 ml). A solution of 1-(2-octyl)dodecyl-2-(5'-hexenyl)-3-trityl-glycerol (21 grams) in tert-butanol (250 ml) was added dropwise during the course of 2.5 hours. The reaction mixture was then stirred overnight (permanganate solution was added as needed to maintain a pink color). The mixture was filtered through a pad of celite which was further washed with tert-butanol. 10 ml of dilute sulfuric acid (10%) was added dropwise, and the obtained solution was then extracted with hexane (3×200 ml). The combined organic phase was washed twice with a solution of sodium bisulfite (20 grams) in water (100 ml) and then with water (200 ml). The solvent was concentrated under reduced pressure to a volume of 150 ml. 20 ml water and 5 ml concentrated HCl were added, and the obtained mixture was refluxed for 6 hours. After cooling to room temperature, the solvent was concentrated under reduced pressure and the obtained residue was treated with a mixture of 30% sodium hydroxide (10 ml) and water (100 ml), and the reaction mixture reached a pH of 12. The precipitated triphenyl methanol was filtered and washed with water (4×10 ml). The filtrate was extracted with a 1:1 (v/v) mixture hexane:ethyl acetate (100 ml). The basic solution was acidified with concentrated HCl (10 ml) to a pH of 1 and extracted with hexane (100 ml). The organic solution was dried over anhydrous sodium sulfate and the solvent was removed under reduced pressure, yielding 8.5 grams of (S)-1-(2-octyl)dodecyl-2-(4-carboxy)butyl-glycerol as a yellow oil. The yield was 60%.

(S)-1-(2-octyl)dodecyl-2-(4'-carboxymethyl)butyl-glycerol (S)-1-(2-octyl)dodecyl-2-(4-carboxy)butyl-glycerol (8.39 grams) was dissolved in methanol (100 ml). 2 ml of concentrated HCl (32%) was added, and the solution was stirred at room temperature overnight. Water (100 ml) was added and the mixture was extracted with chloroform (3×100 ml). The combined organic phase was washed consecutively with water (100 ml), concentrated sodium bicarbonate solution (100 ml), and water (100 ml), and then dried over anhydrous sodium sulfate. Removal of the solvent under reduced pressure yielded 8.48 grams of (S)-1-(2-octyl)dodecyl-2-(4-methylcarboxy)butyl-glycerol as a yellow oil. The yield was 98%.

(R)-1-(2-octyl)dodecyl-2-(4-methylcarboxy)butyl-sn-glycero-3-phosphoethanolamine (S)-1-(2-octyl)dodecyl-2-(4'-carboxymethyl)butyl-glycerol (8.48 grams) and triethylamine (7.3 ml) were dissolved in dry THF (50 ml). This solution was added dropwise during the course of 60 minutes to an ice-cooled solution of $POCl_3$ (4.85 ml) in THF (50 ml) while stirring. The stirring was continued for an additional 15 minutes with cooling and for an additional 45 minutes at room temperature. This reaction mixture was cooled in ice, and a solution of ethanolamine (3.2 ml) and triethylamine (15 ml) in dry THF (50 ml) was added dropwise over the course of 60 minutes while stirring. The stirring was continued for 10 minutes in ice and then at room temperature overnight. The reaction mixture was filtered and the solvent was removed under reduced pressure. The obtained residue was dissolved in a mixture of acetic acid (24 ml) and water (10 ml) and heated to 70° C. for 1 hour. The reaction mixture was cooled to room temperature and extracted with chloroform (3×80 ml). The combined organic phase was washed with water (2×50 ml) and the solvent was removed under reduced pressure. The residue (11 grams) was purified by chromatography on silica gel (220 grams). 4.25 grams of pure (R)-1-(2-octyl)dodecyl-2-(4-methylcarboxy)butyl-sn-glycero-3-phosphoethanolamine was eluted with chloroform followed by mixtures of chloroform with 5%-20% methanol and finally with a 70:26:4 chloroform:methanol:water mixture. The yield was 40%.

(R)-1-(2-octyl)dodecyl-2-(4-carboxy)butyl-sn-glycero-3-phosphoethanolamine (VB-222)

(R)-1-(2-octyl)dodecyl-2-(4-methylcarboxy)butyl-sn-glycero-3-phosphoethanolamine (1.2 gram) was dissolved in 100 ml of a 8:2 (v/v) mixture of methanol: 10% sodium hydroxide solution. The reaction mixture was stirred at room temperature overnight. The pH of the reaction was adjusted to 5 by addition of sodium dihydrogen phosphate. Water (100 ml) and chloroform (100 ml) were added. The phases were separated and the solvent from the organic phase was removed under reduced pressure. The obtained residue was dissolved in chloroform, dried over sodium sulfate and filtered, and the solvent was removed under reduced pressure. The crude product (1.2 gram) was purified by chromatography on silica gel (23 grams). The product was eluted with mixtures of 8:2 (v/v) chloroform:methanol followed by mixtures of chloroform:methanol:water at a 70:26:4, and then 60:35:5 volumetric ratio. The solvent from fractions containing the desired product was removed under reduced pressure, the obtained residue was dissolved in chloroform and dried over sodium sulfate, and the solvent was removed by reduced pressure, yielding 500 mg of pure (R)-1-(2-octyl)dodecyl-2-(4 carboxy)butyl-sn-glycero-3-phosphoethanolamine as a wax. The yield was 42.65%.

NMR characterization of 1-(2-octyl)dodecyl-2-(4-carboxy)butyl-glycero-3-phosphoethanolamine The sample was dissolved in deuterated chloroform (CDCl$_3$) with a few drops of deuterated methanol (CD$_3$OD). The spectra were then measured at 600 MHz. Samples were measured by both $^1$H and $^{13}$C NMR spectroscopy.

The results showed the expected signals for the structural elements of 1-(2-octyl)dodecyl-2-(4-carboxy)butyl-glycero-3-phosphoethanolamine and thus fully supported the structure.

The assignment of the observed $^1$H peaks according to the structure of 1-(2-octyl)dodecyl-2-(4-carboxy)butyl-glycero-3-phosphoethanolamine was as follows:

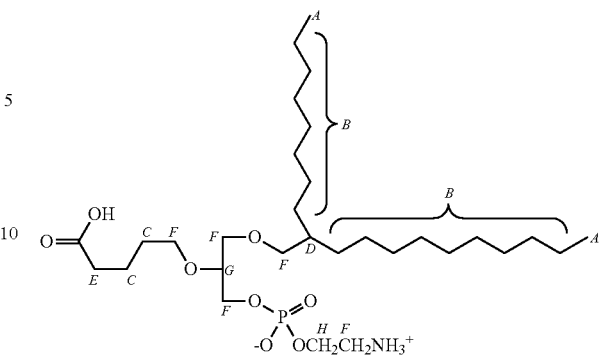

$^1$H NMR (600 MHz, reference solvent (CDCl$_3$)=7.313 ppm)

| δ [ppm] | Description | Assignment (see formula above) |
|---|---|---|
| 4.117 | 2 H, br, s | H |
| 3.835-3.844 | 1 H, m | G |
| 3.394-3.718 | 10 H, m, 5 × CH$_2$ | F |
| 2.329 | 2 H, m | E |
| 1.680-1.700 | 1 H, m | D |
| 1.595-1.606 | 2 H, m | C |
| 1.533 | 2 H, m | C |
| 1.261-1.300 | 32 H, m, 16 × CH$_2$ | B |
| 0.882 | 6 H, t, 2 × CH$_3$, J = 6.9 Hz | A |

The assignment of the observed $^{13}$C peaks according to the structure of 1-(2-octyl)dodecyl-2-(4-carboxy)butyl-glycero-3-phosphoethanolamine was as follows:

$^{13}$C NMR (600 MHz, reference solvent (CDCl$_3$)=77.189 ppm)

| δ [ppm] | Assignment (see formula above) |
|---|---|
| 177.505 | F |
| 78.1013-78.152 | E |
| 75.103 | |
| 71.013 | |
| 70.085 | |
| 66.144 | |
| 61.989 | |
| 40.344 | D |
| 38.229 | C |
| 33.945 | B |
| 31.999 | |

| δ [ppm] | Assignment (see formula above) |
|---|---|
| 31.350 | |
| 31.305 | |
| 31.227 | |
| 30.191 | |
| 29.792 | |
| 29.743 | |
| 29.439 | |
| 29.291 | |
| 26.883 | |
| 22.751 | |
| 21.792 | |
| 21.661 | |
| 14.138 | A |

Mass spectrometry characterization of 1-(2-octyl)dodecyl-2-(4-carboxy)butyl-glycero-3-phosphoethanolamine The calculated mass for 1-(2-octyl)dodecyl-2-(4-carboxy)butyl-glycero-3-phosphoethanolamine ($C_{30}H_{62}NO_8P$) was 595.42.

The mass spectrum performed using Electrospray Ionization Mass Spectrometry (ESI+-MS) showed a molecular ion with m/z=596, corresponding to the protonated molecular ion $[M+H]^+$, accompanied by a molecular ion with m/z=618, corresponding to the cationated ion $[M+Na]^+$.

The MS spectrum is thus in agreement with the chemical structure of 1-(2-octyl)dodecyl-2-(4-carboxy)butyl-glycero-3-phosphoethanolamine.

(R)-1-(2-octyl)dodecyl-2-(4-methylcarboxy)butyl-sn-glycero-3-phosphocholine (R)-1-(2-octyl)dodecyl-2-(4-methylcarboxy)butyl-sn-glycero-3-phosphoethanolamine (2.62 grams) was dissolved in mixture of isopropanol (18 ml) and dichloromethane (40 ml). A solution of potassium carbonate (3 grams) in water (10 ml) was added dropwise while the reaction mixture was kept at a temperature of 35-40° C. A solution of dimethylsulfate (2.1 ml) in isopropanol (10 ml) was added dropwise at 40° C. The reaction mixture was kept at 40° C. for 2 hours, then cooled to room temperature and stirred at room temperature overnight. Water (100 ml) was added and the mixture was extracted with chloroform (3×100 ml). The combined organic phase was washed with water (100 ml) and the solvent was removed under reduced pressure, yielding 2.78 grams of (R)-1-(2-octyl)dodecyl-2-(4 methylcarboxy)butyl-sn-glycero-3-phosphocholine as a white wax.

(R)-1-(2-octyl)dodecyl-2-(4-carboxy)butyl-sn-glycero-3-phosphocholine (VB-221)

(R)-1-(2-octyl)dodecyl-2-(4-methylcarboxy)butyl-sn-glycero-3-phosphocholine (2.78 grams) was dissolved in 100 ml of an 8:2 (v/v) mixture of methanol and 10% aqueous sodium hydroxide solution, and the reaction mixture was stirred at room temperature overnight. The pH of the reaction was adjusted to 5 by adding sodium dihydrogen phosphate. Water (100 ml) and chloroform (100 ml) were added. The phases were separated and the solvent was removed under reduced pressure. The obtained residue was dissolved in chloroform, dried over sodium sulfate and filtered and the solvent was removed under reduced pressure. The residue (2.7 grams) was purified by chromatography on silica gel (50 grams). The non-polar impurities were eluted with 8:2 (v/v) chloroform:methanol. The product was then eluted with mixtures of chloroform:methanol:water at volumetric ratios of 70:26:4, followed by 60:35:5. After removal of the solvent under reduced pressure, the obtained residue was dissolved in chloroform and dried over sodium sulfate, and the solvent was removed under reduced pressure, yielding 800 mg of pure (R)-1-(2-octyl)dodecyl-2-(4-carboxy)butyl-sn-glycero-3-phosphocholine as a white wax. The yield was 29.4%.

NMR characterization of 1-(2-octyl)dodecyl-2-(4-carboxy)butyl-sn-glycero-3-phosphocholine The sample was dissolved in deuterated chloroform ($CDCl_3$) with a few drops of deuterated methanol ($CD_3OD$). The spectra were then measured at 600 MHz. Samples were measured by both $^1H$ and $^{13}C$ NMR spectroscopy.

The results showed the expected signals for the structural elements of 1-(2-octyl)dodecyl-2-(4-carboxy)butyl-sn-glycero-3-phosphocholine and thus fully supported the structure.

The assignment of the observed $^1H$ peaks according to the structure of 1-(2-octyl)dodecyl-2-(4-carboxy)butyl-sn-glycero-3-phosphocholine was as follows:

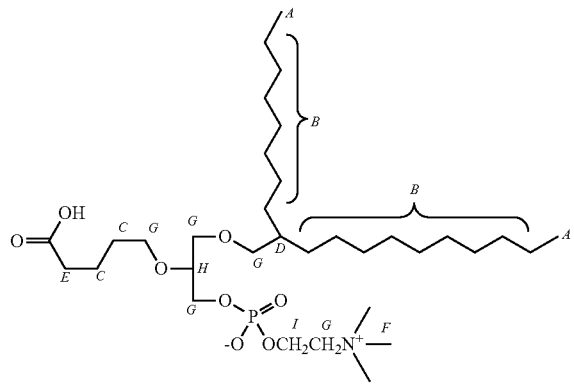

$^1H$ NMR (600 MHz, reference solvent ($CDCl_3$)=7.352 ppm)

| δ [ppm] | Description | Assignment (see formula above) |
|---|---|---|
| 4.259 | 2 H, br, s | I |
| 3.983-3.983 | 1 H, m | H |
| 3.607-3.833 | 6 H, m, 3 × $CH_2$ | G |
| 3.432-3.493 | 2H, m | G |
| 3.304-3.320 | 2H, m | G |
| 3.281 | 9 H, s, 3 × $CH_3$ | F |
| 2.350 | 2 H, m | E |
| 1.875 | 1H, m | D |
| 1.710 | 2 H, m | C |
| 1.602 | 2 H, m | C |
| 1.262-1.313 | 32 H, m, 16 × $CH_2$ | B |
| 0.883 | 6 H, t, 2 × $CH_3$, J = 6.9 Hz | A |

The assignment of the observed $^{13}C$ peaks according to the structure of 1-(2-octyl)dodecyl-2-(4-carboxy)butyl-sn-glycero-3-phosphocholine was as follows:

135

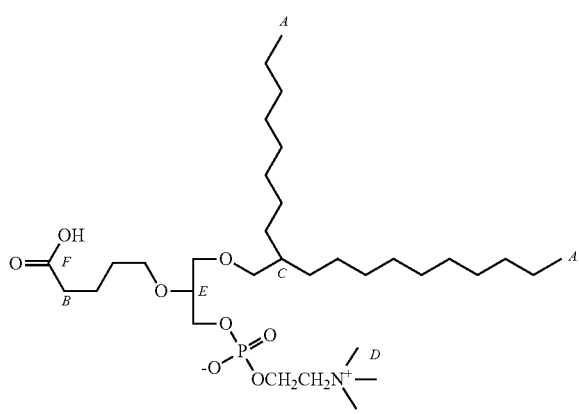

$^{13}$C NMR (600 MHz, reference solvent (CDCl$_3$)=77.308 ppm)

| δ [ppm] | Assignment (see formula above) |
|---|---|
| 176.700 | F |
| 78.289-78.344 | E |
| 75.122 | |
| 71.137 | |
| 70.087 | |
| 66.662 | |
| 66.011-66.046 | |
| 59.052-59.086 | |
| 54.420 | D |
| 38.274 | C |
| 34.150 | B |
| 32.032 | |
| 31.397 | |
| 31.356 | |
| 30.216 | |
| 29.809 | |
| 29.766 | |
| 29.466 | |
| 29.370 | |
| 26.930 | |
| 22.782 | |
| 22.102 | |
| 14.142 | A |

Mass Spectrometry Characterization:

The calculated mass for 1-(2-octyl)dodecyl-2-(4-carboxy)butyl-sn-glycero-3-phosphocholine (C$_{33}$H$_{68}$NO$_8$P) was 637.87.

The mass spectrum obtained using Electrospray Ionization Mass Spectrometry (ES$^-$MS) showed a molecular ion with m/z=636, corresponding to the deprotonated molecular ion [M−H]$^-$.

The mass spectrum obtained using Positive Electrospray Ionization Mass Spectrometry (ESI+-MS) showed a molecular ion with m/z=638, corresponding to the protonated molecular ion [M+H]$^+$, accompanied by an ion with m/z=660, corresponding to the cationated molecular ion [M+Na]$^+$.

The MS spectrum is thus in agreement with the chemical structure of 1-(2-octyl)dodecyl-2-(4-carboxy)butyl-glycero-3-phosphocholine.

Tyrosine Phosphorylation:

The effects of VB-221 and VB-222 on in vitro tyrosine phosphorylation in primary macrophages were determined as described hereinabove in the Materials and Methods section.

As shown in FIG. 38, treatment with 5, 10 and 20 ng/ml (8, 16 and 32 μM) VB-221 results in induction of tyrosine phosphorylation.

Similarly, as shown in FIG. 39, treatment with 10 and 20 μg/ml (16.8 and 33.6 μM) VB-222 results in induction of tyrosine phosphorylation.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A compound having a formula:

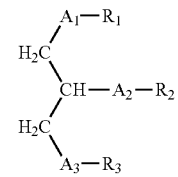

or a stereoisomer, an optical isomer, an enantiomer, a racemic mixture, or a stereoisomeric mixture thereof, or a pharmaceutically acceptable salt thereof, wherein:
(i) A$_1$, A$_2$ and A$_3$ are each independently selected from the group consisting of O and S;
(ii) R$_1$ is selected from the group consisting of eicosanyl and (2-octyl)dodecyl;
(iii) R$_2$ is

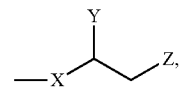

wherein X is a C$_{1-25}$ alkyl, Y is selected from the group consisting of:

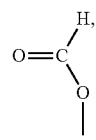

—OH, —H, alkyl, alkoxy, halogen, acetoxy and an aromatic functional group; and
Z is selected from the group consisting of:

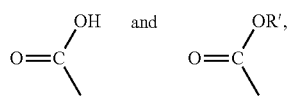

wherein R' is C$_{1-4}$ alkyl;
and
(iv) R$_3$ is selected from the group consisting of H, acyl, alkyl, phosphate, phosphocholine, phosphoethanolamine, phosphoethanolamine-N-glutaric acid, phosphoserine, and phosphoinositol.

2. A pharmaceutical composition comprising a compound of claim 1 and a pharmaceutically acceptable carrier.

3. The pharmaceutical composition of claim 2, packaged in a packaging material and identified in print, in or on said packaging material, for use in the treatment or prevention of an inflammation associated with a disease or disorder selected from the group consisting of an idiopathic inflammatory disease or disorder, a chronic inflammatory disease or disorder, an acute inflammatory disease or disorder, an autoimmune disease or disorder, an infectious disease or disorder, an inflammatory malignant disease or disorder, an inflammatory transplantation-related disease or disorder, an inflammatory degenerative disease or disorder, a disease or disorder associated with a hypersensitivity, an inflammatory cardiovascular disease or disorder, an inflammatory cerebrovascular disease or disorder, a peripheral vascular disease or disorder, an inflammatory glandular disease or disorder, an inflammatory gastrointestinal disease or disorder, an inflammatory cutaneous disease or disorder, an inflammatory hepatic disease or disorder, an inflammatory neurological disease or disorder, an inflammatory musculo-skeletal disease or disorder, an inflammatory renal disease or disorder, an inflammatory reproductive disease or disorder, an inflammatory systemic disease or disorder, an inflammatory connective tissue disease or disorder, an inflammatory tumor, necrosis, an inflammatory implant-related disease or disorder, an inflammatory aging process, an immunodeficiency disease or disorder, a proliferative disease or disorder, and an inflammatory pulmonary disease or disorder.

4. A method of alleviating or ameliorating symptoms of an inflammation associated disease or disorder, the method comprising administering to a subject in need thereof a therapeutically effective amount of the compound of claim 1, thereby treating or preventing the inflammation associated disease or disorder in said subject, wherein the inflammation associated disease or disorder is cancer or atherosclerosis.

5. A method of decreasing a level of a cytokine selected from the group consisting of interleukin-12 and interleukin-23 in a subject, the method comprising administering to the subject an effective amount of the compound of claim 1, thereby decreasing the level of the cytokine.

6. A compound selected from the group consisting of:
1-eicosanyl-2-(4-carboxy)butyl-glycero-3-phosphocholine;
1-eicosanyl-2-(4-carboxy)butyl-glycero-3-phosphoethanolamine;
1-(2-octyl)dodecyl-2-(4-carboxy)butyl-glycero-3-phosphocholine; and
1-(2-octyl)dodecyl-2-(4-carboxyl)butyl-glycero-3-phosphoethanolamine
or a stereoisomer, an optical isomer, an enantiomer, a racemic mixture, or a stereoisomeric mixture thereof, or a pharmaceutically acceptable salt thereof.

7. A pharmaceutical composition comprising a compound of claim 6 and a pharmaceutically acceptable carrier.

8. The pharmaceutical composition of claim 7, packaged in a packaging material and identified in print, in or on said packaging material, for use in the treatment or prevention of an inflammation associated with a disease or disorder selected from the group consisting of an idiopathic inflammatory disease or disorder, a chronic inflammatory disease or disorder, an acute inflammatory disease or disorder, an autoimmune disease or disorder, an infectious disease or disorder, an inflammatory malignant disease or disorder, an inflammatory transplantation-related disease or disorder, an inflammatory degenerative disease or disorder, a disease or disorder associated with a hypersensitivity, an inflammatory cardiovascular disease or disorder, an inflammatory cerebrovascular disease or disorder, a peripheral vascular disease or disorder, an inflammatory glandular disease or disorder, an inflammatory gastrointestinal disease or disorder, an inflammatory cutaneous disease or disorder, an inflammatory hepatic disease or disorder, an inflammatory neurological disease or disorder, an inflammatory musculoskeletal disease or disorder, an inflammatory renal disease or disorder, an inflammatory reproductive disease or disorder, an inflammatory systemic disease or disorder, an inflammatory connective tissue disease or disorder, an inflammatory tumor, necrosis, an inflammatory implant-related disease or disorder, an inflammatory aging process, an immunodeficiency disease or disorder, a proliferative disease or disorder, and an inflammatory pulmonary disease or disorder.

9. A method of alleviating or ameliorating symptoms of an inflammation associated disease or disorder, the method comprising administering to a subject in need thereof a therapeutically effective amount of the compound of claim 6, thereby treating or preventing the inflammation associated disease or disorder in said subject, wherein the inflammation associated disease or disorder is cancer or atherosclerosis.

10. A method of decreasing a level of a cytokine selected from the group consisting of interleukin-12 and interleukin-23 in a subject, the method comprising administering to the subject an effective amount of the compound of claim 6, thereby decreasing the level of the cytokine.

11. The compound of claim 1, wherein $R_2$ is selected from the group consisting of (4-methylcarboxy)butyl, (3-carboxy)propyl, (6-carboxy)hexanyl, and (2-carboxy)ethyl.

12. The compound of claim 1, wherein $R_3$ is selected from the group consisting of H, phosphate, phosphoethanolamine, phosphoethanolamine-N-glutaric acid and phosphoserine.

13. The compound of claim 1, wherein $A_1$ is S and $A_2$ and $A_3$ are each O.

14. 1-eicosanyl-2-(4-carboxy)butyl-glycero-3-phosphocholine.

15. 1-(2-octyl)dodecyl-2-(4-carboxy)butyl-glycero-3-phosphocholine.

16. The compound of claim 1 having the formula:

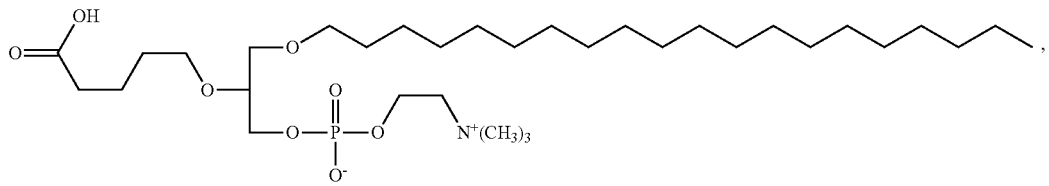

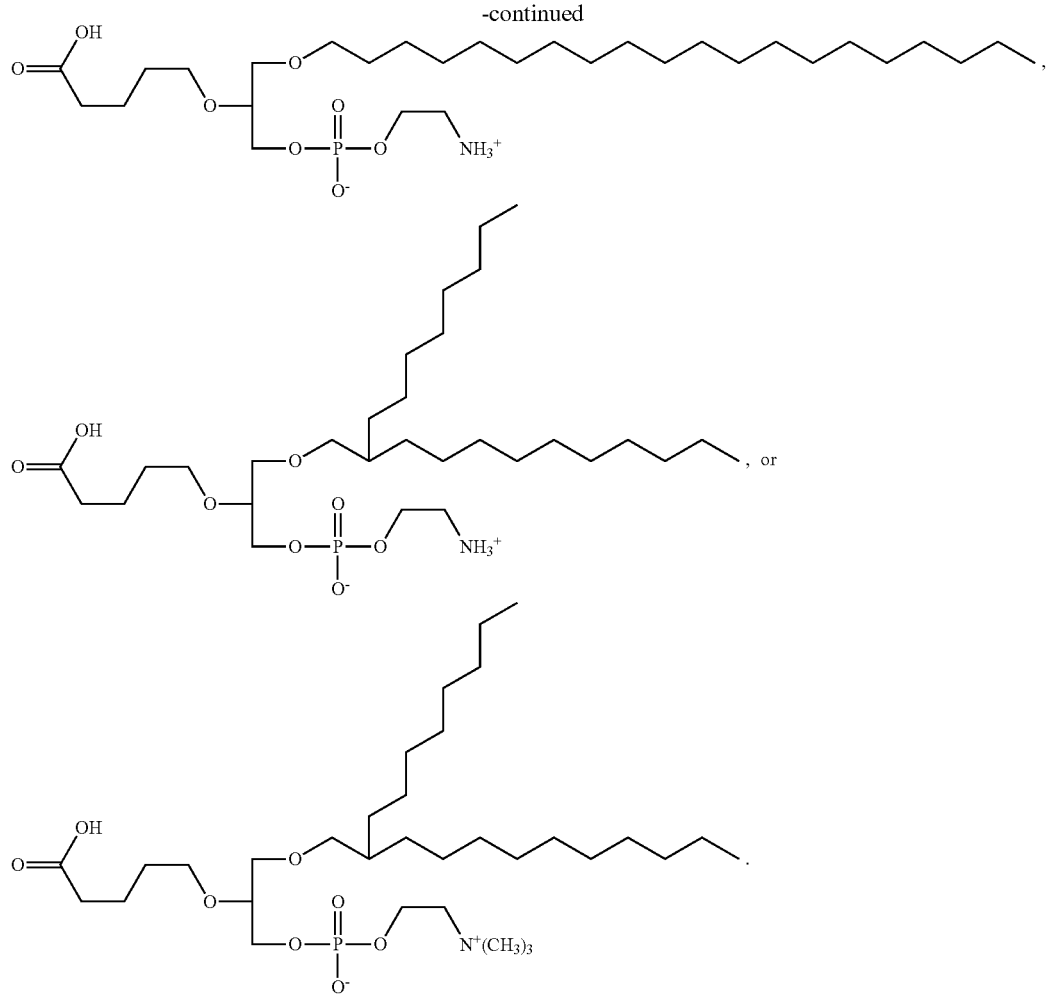

17. The compound of claim 16 having the formula:

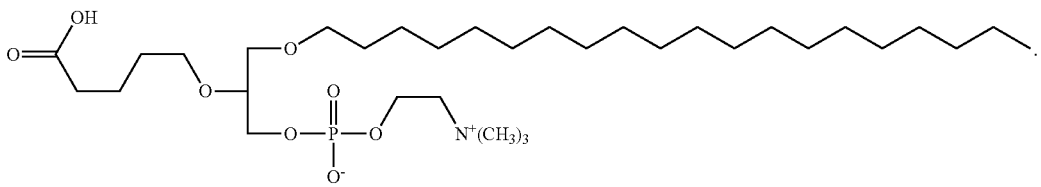

18. The compound of claim 16 having the formula:

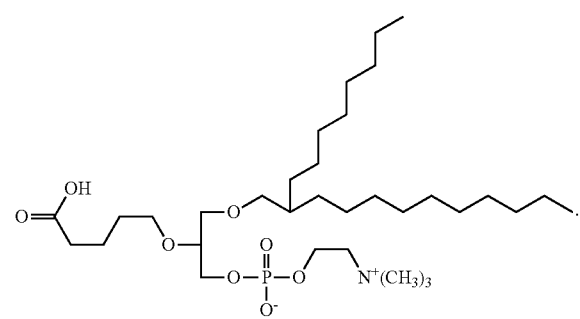

19. The method of claim 4, wherein the subject is a human.
20. The method of claim 5, wherein the subject is a human.
21. The method of claim 9, wherein the subject is a human.
22. The method of claim 10, wherein the subject is a human.
23. The compound of claim 1, wherein $R_2$ is (4-carboxyl) butyl.
24. The pharmaceutical composition of claim 3, identified in print, in or on said packaging material, for use in the treatment or prevention of a proliferative disease or disorder.
25. The pharmaceutical composition of claim 24, identified in print, in or on said packaging material, for use in the treatment or prevention of a proliferative disease or disorder, wherein the proliferative disease or disorder is cancer.

26. The method of claim 4, wherein the inflammation associated disease or disorder is cancer.

27. The pharmaceutical composition of claim 8, identified in print, in or on said packaging material, for use in the treatment or prevention of a proliferative disease or disorder.

28. The method of claim 9, wherein the inflammation associated disease or disorder is cancer.

\* \* \* \* \*

UNITED STATES PATENT AND TRADEMARK OFFICE
CERTIFICATE OF CORRECTION

Page 1 of 1

PATENT NO. : 9,206,206 B2
APPLICATION NO. : 13/127717
DATED : December 8, 2015
INVENTOR(S) : Kovalevski-Ishai et al.

It is certified that error appears in the above-identified patent and that said Letters Patent is hereby corrected as shown below:

In the claims

Column 137

Lines 52 and 53, claim 6, replace "1-(2-octyl)dodecyl-2-(4-carboxyl)butyl-glycero-3-phosphoethanolamine" with --1-(2-octyl)dodecyl-2-(4-carboxy)butyl-glycero-3-phosphoethanolamine;--

Column 140

Lines 59 and 60, claim 23, replace "(4-carboxyl)butyl" with --(4-carboxy)butyl--

Signed and Sealed this
Twenty-ninth Day of March, 2016

Michelle K. Lee
*Director of the United States Patent and Trademark Office*